US008314087B2

(12) United States Patent
Albrecht et al.

(10) Patent No.: US 8,314,087 B2
(45) Date of Patent: Nov. 20, 2012

(54) NITROGEN-CONTAINING HETEROCYCLYL KETONES AND METHODS OF USE

(75) Inventors: Brian K. Albrecht, Cambridge, MA (US); Steven Bellon, Wellesley, MA (US); Shon Booker, Thousand Oaks, CA (US); Alan C. Cheng, Cambridge, MA (US); Derin D'Amico, Newbury Park, CA (US); Noel D'Angelo, Thousand Oaks, CA (US); Jean-Christophe Harmange, Andover, MA (US); Tae-Seong Kim, Thousand Oaks, CA (US); Longbin Liu, Thousand Oaks, CA (US); Mark H. Norman, Thousand Oaks, CA (US); Aaron C. Siegmund, Ventura, CA (US); Markian Stec, Moorpark, CA (US); Ning Xi, Thousand Oaks, CA (US); Kevin Yang, San Gabriel, CA (US)

(73) Assignee: Amgen Inc., South San Francisco, CA (US)

( * ) Notice: Subject to any disclaimer, the term of this patent is extended or adjusted under 35 U.S.C. 154(b) by 764 days.

(21) Appl. No.: 12/070,309

(22) Filed: Feb. 15, 2008

(65) Prior Publication Data
US 2008/0280917 A1 Nov. 13, 2008

Related U.S. Application Data

(60) Provisional application No. 60/902,030, filed on Feb. 16, 2007.

(51) Int. Cl.
C07D 215/233 (2006.01)
C07D 413/14 (2006.01)
C07D 205/08 (2006.01)
C07D 409/14 (2006.01)
C07D 401/14 (2006.01)
C07D 239/36 (2006.01)
A61K 31/4709 (2006.01)
A61K 31/5355 (2006.01)
A61K 31/397 (2006.01)
A61K 31/497 (2006.01)
A61K 31/506 (2006.01)
A61P 35/00 (2006.01)

(52) U.S. Cl. ........... 514/210.02; 514/312; 514/235.2; 514/252.04; 514/255.05; 514/274; 540/200; 544/128; 544/238; 544/405; 544/318; 546/153

(58) Field of Classification Search .......... 544/128, 544/238, 405.318; 546/122, 153, 162; 514/314, 514/210.02, 312, 235.2, 252.04, 255.05, 514/274
See application file for complete search history.

(56) References Cited

U.S. PATENT DOCUMENTS

| | | | | |
|---|---|---|---|---|
| 3,956,287 A | * | 5/1976 | Bambury et al. | 540/225 |
| 4,165,967 A | * | 8/1979 | Buhler et al. | 8/429 |
| 4,673,735 A | * | 6/1987 | Moser et al. | 534/606 |
| 5,360,808 A | * | 11/1994 | Englert et al. | 514/335 |
| 6,451,072 B1 | * | 9/2002 | Tzikas et al. | 8/549 |
| 6,592,634 B1 | * | 7/2003 | Reichert et al. | 8/549 |
| 6,924,292 B2 | * | 8/2005 | Kawano et al. | 514/291 |
| 2006/0205790 A1 | * | 9/2006 | Coe et al. | 514/337 |
| 2007/0161642 A1 | * | 7/2007 | Nishiyama et al. | 514/252.03 |
| 2008/0269235 A1 | * | 10/2008 | Dal Piaz et al. | 514/252.03 |
| 2009/0264434 A1 | * | 10/2009 | Berthel et al. | 514/248 |
| 2009/0281099 A1 | * | 11/2009 | Andres-Gil et al. | 514/235.8 |
| 2009/0312313 A1 | * | 12/2009 | Shimizu et al. | 514/230.5 |
| 2009/0315803 A1 | * | 12/2009 | Wu et al. | 343/872 |

FOREIGN PATENT DOCUMENTS

| | | | |
|---|---|---|---|
| EP | 92520 | * | 10/1983 |
| EP | 0556738 A | | 8/1993 |
| EP | 1270577 A | | 1/2003 |
| WO | WO 92/10483 | | 6/1992 |
| WO | WO 94/12461 | | 6/1994 |
| WO | WO 0170746 | * | 9/2001 |
| WO | WO 2005000818 | * | 6/2003 |
| WO | WO 2007067836 | * | 12/2005 |
| WO | WO 2007083978 | * | 9/2006 |
| WO | WO 2006/108059 | | 10/2006 |
| WO | WO 2006/116713 | | 11/2006 |
| WO | WO 2008079787 | * | 12/2006 |
| WO | WO 2008/017361 | | 2/2008 |
| WO | WO 2008/038841 A1 | | 4/2008 |
| WO | WO 2008072784 | * | 7/2008 |
| WO | WO 2008/116620 | | 10/2008 |

OTHER PUBLICATIONS

Huang, et al., J. Org. Chem. (2002), 67(7), 2382-2385.*
Reiner, et al., Bioorg. & Med. Chem. Letters (1999), 9(6), 895-900.*
Stoss, et al., Nucleosides & Nucleotides (1988), 7(2), 213-25.*
Edwards, et al., J. Med. Chem. (1977), 20(4), 560-3.*
Gancia, et al., J. Computer-Aided Molec. Design (2000), 14(3), 293-306.*
Database Registry, XP 002511806, Mar. 30, 2006.
Database Registry, XP 002511807, Mar. 29, 2006.
Database Registry, XP 002511808, Mar. 28, 2006.
Database Registry, XP 002511809, Feb. 24, 2006.
Database Registry, XP 002511810, Feb. 20, 2006.
Database Registry, XP 002511811, Feb. 20, 2006.
Database Registry, XP 002511812, Feb. 19, 2006.
Database Registry, XP 002511813, Jan. 12, 2006.

(Continued)

Primary Examiner — James O Wilson
Assistant Examiner — Cecilia M Jaisle
(74) Attorney, Agent, or Firm — Olga Mekhovich

(57) ABSTRACT

Selected compounds are effective for prophylaxis and treatment of diseases, such as HGF mediated diseases. The invention encompasses novel compounds, analogs, prodrugs and pharmaceutically acceptable salts thereof, pharmaceutical compositions and methods for prophylaxis and treatment of diseases and other maladies or conditions involving, cancer and the like. The subject invention also relates to processes for making such compounds as well as to intermediates useful in such processes.

6 Claims, No Drawings

OTHER PUBLICATIONS

Database Registry: XP 002511814, Apr. 22, 2007.
Database Registry, XP 002511815, Apr. 17, 2007.
Database Registry, XP 002511816, Mar. 20, 2007.
Database Registry, XP 002511817, Mar. 20, 2007.
Database Registry, XP 02511818, Mar. 20, 2007.
Database Registry, XP 002511819, Mar. 20, 2007.
Database Registry, XP 002511820, Mar. 20, 2007.
Database Registry, XP 002511821, Mar. 20, 2007.
Database Registry, XP 002511822, Mar. 1, 2007.
Kikuchi, Shinichi et al., "Preparation of thiadiazolone derivatives as TNF-, alpha, converting enzyme (TACE) Inhibitors," XP 002511823, Apr. 3, 2008.

* cited by examiner

NITROGEN-CONTAINING HETEROCYCLYL KETONES AND METHODS OF USE

This application claims priority to U.S. Ser. No. 60/902,030, filed Feb. 16, 2007 the entirety of which is incorporated herein by reference.

FIELD OF THE INVENTION

This invention is in the field of pharmaceutical agents and specifically relates to compounds, compositions, uses and methods for treating cancer.

BACKGROUND OF THE INVENTION

Protein kinases represent a large family of proteins, which play a central role in the regulation of a wide variety of cellular processes, maintaining control over cellular function. A partial list of such kinases includes ab1, Akt, bcr-ab1, Blk, Brk, Btk, c-kit, c-Met, c-src, c-fms, CDK1, CDK2, CDK3, CDK4, CDK5, CDK6, CDK7, CDK8, CDK9, CDK10, cRaf1, CSF1R, CSK, EGFR, ErbB2, ErbB3, ErbB4, Erk, Fak, fes, FGFR1, FGFR2, FGFR3, FGFR4, FGFR5, Fgr, flt-1, Fps, Frk, Fyn, Hck, IGF-1R, INS-R, Jak, KDR, Lck, Lyn, MEK, p38, PDGFR, PIK, PKC, PYK2, ros, tie, tie2, TRK, Yes, and Zap70. Inhibition of such kinases has become an important therapeutic target.

The hepatocyte growth factor receptor ("c-Met") is a unique receptor tyrosine kinase shown to be overexpressed in a variety of malignancies. c-Met typically comprises, in its native form, a 190-kDa heterodimeric (a disulfide-linked 50-kDa α-chain and a 145-kDa β-chain) membrane-spanning tyrosine kinase protein (Proc. Natl. Acad. Sci. USA, 84:6379-6383 (1987)). c-Met is mainly expressed in epithelial cells and stimulation of c-Met leads to scattering, angiogenesis, proliferation and metastasis. (See Cytokine and Growth Factor Reviews, 13:41-59 (2002)).

The ligand for c-Met is hepatocyte growth factor (also known as scatter factor, HGF and SF). HGF is a heterodimeric protein secreted by cells of mesodermal origin (Nature, 327: 239-242 (1987); J. Cell Biol., 111:2097-2108 (1990)).

Various biological activities have been described for HGF through interaction with c-met (Hepatocyte Growth Factor-Scatter Factor (HGF-SF) and the c-Met Receptor, Goldberg and Rosen, eds., Birkhauser Verlag-Basel, 67-79 (1993). The biological effect of HGF/SF may depend in part on the target cell. HGF induces a spectrum of biological activities in epithelial cells, including mitogenesis, stimulation of cell motility and promotion of matrix invasion (Biochem. Biophys. Res. Comm., 122:1450-1459 (1984); Proc. Natl. Acad. Sci. U.S.A., 88:415-419 (1991)). It stimulates the motility and invasiveness of carcinoma cells, the former having been implicated in the migration of cells required for metastasis. HGF can also act as a "scatter factor", an activity that promotes the dissociation of epithelial and vascular endothelial cells (Nature, 327:239-242 (1987); J. Cell Biol., 111:2097-2108 (1990); EMBO J., 10:2867-2878 (1991); Proc. Natl. Acad. Sci. USA, 90:649-653 (1993)). Therefore, HGF is thought to be important in tumor invasion (Hepatocyte Growth Factor-Scatter Factor (HGF-SF) and the C-Met Receptor, Goldberg and Rosen, eds., Birkhauser Verlag-Basel, 131-165 (1993)).

HGF and c-Met are expressed at abnormally high levels in a large variety of solid tumors. High levels of HGF and/or c-Met have been observed in liver, breast, pancreas, lung, kidney, bladder, ovary, brain, prostate, gallbladder and myeloma tumors in addition to many others. The role of HGF/c-Met in metastasis has been investigated in mice using cell lines transformed with HGF/c-Met (J. Mol. Med., 74:505-513 (1996)). Overexpression of the c-Met oncogene has also been suggested to play a role in the pathogenesis and progression of thyroid tumors derived from follicular epithelium (Oncogene, 7:2549-2553 (1992)). HGF is a morphogen (Development, 110:1271-1284 (1990); Cell, 66:697-711 (1991)) and a potent angiogenic factor (J. Cell Biol., 119:629-641 (1992)).

Recent work on the relationship between inhibition of angiogenesis and the suppression or reversion of tumor progression shows great promise in the treatment of cancer (Nature, 390:404-407 (1997)), especially the use of multiple angiogenesis inhibitors compared to the effect of a single inhibitor. Angiogenesis can be stimulated by HGF, as well as vascular endothelial growth factor (VEGF) and basic fibroblast growth factor (bFGF).

Angiogenesis, the process of sprouting new blood vessels from existing vasculature and arteriogenesis, the remodeling of small vessels into larger conduit vessels are both physiologically important aspects of vascular growth in adult tissues. These processes of vascular growth are required for beneficial processes such as tissue repair, wound healing, recovery from tissue ischemia and menstrual cycling. They are also required for the development of pathological conditions such as the growth of neoplasias, diabetic retinopathy, rheumatoid arthritis, psoriasis, certain forms of macular degeneration, and certain inflammatory pathologies. The inhibition of vascular growth in these contexts has also shown beneficial effects in preclinical animal models. For example, inhibition of angiogenesis by blocking vascular endothelial growth factor or its receptor has resulted in inhibition of tumor growth and in retinopathy. Also, the development of pathological pannus tissue in rheumatoid arthritis involves angiogenesis and might be blocked by inhibitors of angiogenesis.

The ability to stimulate vascular growth has potential utility for treatment of ischemia-induced pathologies such as myocardial infarction, coronary artery disease, peripheral vascular disease, and stroke. The sprouting of new vessels and/or the expansion of small vessels in ischemic tissues prevents ischemic tissue death and induces tissue repair. Certain diseases are known to be associated with deregulated angiogenesis, for example ocular neovascularization, such as retinopathies (including diabetic retinopathy), age-related macular degeneration, psoriasis, hemangioblastoma, hemangioma, arteriosclerosis, inflammatory disease, such as a rheumatoid or rheumatic inflammatory disease, especially arthritis (including rheumatoid arthritis), or other chronic inflammatory disorders, such as chronic asthma, arterial or post-transplantational atherosclerosis, endometriosis, and neoplastic diseases, for example so-called solid tumors and liquid tumors (such as leukemias). Treatment of malaria and related viral diseases may also be mediated by HGF and cMet.

Elevated levels of HGF and c-Met have also been observed in non-oncological settings, such as hypertension, myocardial infarction and rheumatoid arthritis. It has been observed that levels of HGF increase in the plasma of patients with hepatic failure (Gohda et al., supra) and in the plasma (Hepatol., 13:734-750 (1991)) or serum (J. Biochem., 109:8-13 (1991)) of animals with experimentally induced liver damage. HGF has also been shown to be a mitogen for certain cell types, including melanocytes, renal tubular cells, keratinocytes, certain endothelial cells and cells of epithelial origin (Biochem. Biophys. Res. Commun., 176:45-51 (1991); Biochem. Biophys. Res. Commun., 174:831-838 (1991); Biochem., 30:9768-9780 (1991); Proc. Natl. Acad. Sci. USA, 88:415-419 (1991)). Both HGF and the c-Met proto-oncogene have been postulated to play a role in microglial reactions to CNS injuries (Oncogene, 8:219-222 (1993)).

Metastatic SCC cells overexpress c-Met and have enhanced tumoregenesis and metastasis in vivo [G. Gong et al., Oncogene, 23:6199-6208 (2004)]. C-Met is required for tumor cell survival [N. Shinomiya et al., Cancer Research, 64:7962-7970 (2004)]. For a general review see C. Birchmeier et al., Nature Reviews/Molecular Biology 4:915-925 (2003).

In view of the role of HGF and/or c-Met in potentiating or promoting such diseases or pathological conditions, it would be useful to have a means of substantially reducing or inhibiting one or more of the biological effects of HGF and its receptor. Thus a compound that reduces the effect of HGF would be a useful compound. Compounds of the current invention have not been previously described as inhibitors of angiogenesis such as for the treatment of cancer.

Compounds of the current invention are inhibitors of c-Met.

DESCRIPTION OF THE INVENTION

A class of compounds useful in treating cancer and angiogenesis is defined by Formula I, II, III or IV

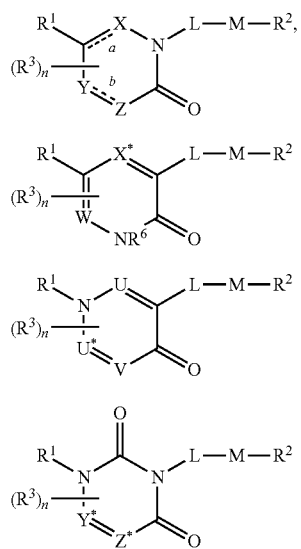

enantiomers, diastereomers, salts and solvates thereof wherein a and b are independently absent or a bond;
n is an integer from 0 to 6 as allowed by valence;
v is an integer from 0 to 2;
when a is a bond X is $CR^{4*}$ or N, and when a is absent X is $CR^4R^5$ or $NR^6$;
when b is a bond Y and Z are independently $CR^{4*}$ or N, and when b is absent one of Y and Z is $CR^4R^5$ and the other is $NR^6$;
$W$, $Y^*$ and $Z^*$ are independently $CR^{4*}$ or N;
V, U and $U^*$ are independently $CR^{4*}$ or N provided that only one of U and $U^*$ is N;
L is absent, $C_{1-6}$alkylene, $C_{3-10}$cycloalkylene, $C_{3-10}$heterocycloalkylene $C_{2-8}$alkenylene or $C_{2-8}$alkynylene any of which may be optionally independently substituted with one or more halo, $-OR^7$ or $-NR^8R^9$ and further wherein any two substituent groups bound to the same tetravalent carbon atom may optionally combine to form a spiro-fused cycloalkyl or heterocyclyl ring;

M is absent, $-O-$, $-S(O)_v-$, $-NR^6-$, $-C(=O)NR^6-$, $-NR^6(C=O)-$, $-SO_2NR^6-$, $-NR^6SO_2-$, provided that L and M are not both simultaneously absent;

or -L-M-$R^2$ may combine to form

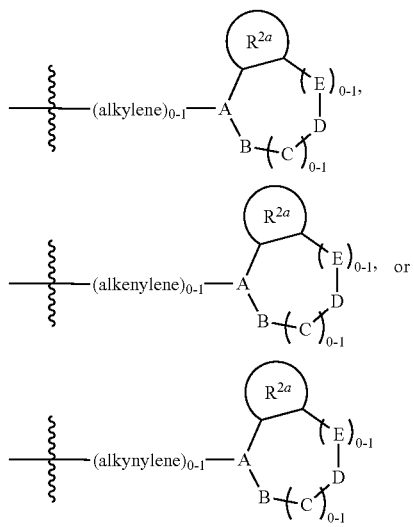

wherein A is CH or N; and B, C, D and E are independently $CH_2$, O, $NR^6$ or $S(O)_v$, provided that only one of A, B, C, D and E can be a heteroatom;

$R^1$ is (1) halo, $-CN$, $-NR^6-(C=O)R^7$, $-NR^6-(C=O)OR^7$, $-NR^6-(C=O)NR^8R^9$, $-(C=O)NR^8R^9$, $-(C=O)OR^7$, $-(C=O)R^7$, $-S(O)_vR^7$, $-SO_2NR^8R^9$, $-NR^8R^9$ or $-OR^7$ (2) cycloalkyl, cycloalkylalkyl, heterocyclyl, heterocyclylalkyl, aryl, arylalkyl, heteroaryl, heteroarylalkyl, $C_{1-6}$ alkyl, $C_{2-6}$ alkenyl, or $C_{2-6}$ alkynyl any of which may be optionally independently substituted with one or more $R^{10}$ as allowed by valance;

$R^2$ is aryl, arylalkyl, heteroaryl, heteroarylalkyl, heterocyclyl, heterocyclylalkyl, cycloalkyl or cycloalkylalkyl any of which may be optionally independently substituted with one or more $R^{10}$ as allowed by valence;

$R^{2a}$ is aryl, heteroaryl, cycloalkyl or heterocyclyl any of which may be optionally independently substituted with one or more $R^{10}$ as allowed by valence;

$R^3$ is an optional substituent independently selected at each occurrence from halo, cyano, optionally substituted alkyl, optionally substituted alkenyl, optionally substituted alkynyl, $-(C=O)_{0-1}OR^7$, $-(C=O)_{0-1}NR^8R^9$, $-S(O)_vR^7$, $-SO_2NR^8R^9$, $-C=OR^7$, $-NR^8C=OR^7$, $-NR^6-C=O-NR^8R^9$ and $-NR^8SO_2R^7$;

$R^{4*}$, $R^4$ and $R^5$ at each occurrence are independently H or one of the optional substituents listed in the definition of $R^3$ provided that $R^4$ and $R^5$ cannot be simultaneously selected from $-OR^7$, $-NR^8R^9$; $-S(O)_vR^7-SO_2NR^8R^9$, $-NR^8C=OR^7$, $-NR^6-C=O-NR^8R^9$ and $-NR^8SO_2R^7$;

$R^6$ at each occurrence is independently
  (1) H, or
  (2) alkyl, alkenyl, alkynyl, cycloalkyl, heteroalkyl, heterocyclyl, aryl, heteroaryl, cycloalkylalkyl, heterocyclylalkyl, arylalkyl or heteroarylalkyl any of which may be optionally independently substituted with one or more $R^{10}$ as allowed by valance;

$R^7$ at each occurrence is independently
  (1) H, or
  (2) alkyl, alkenyl, alkynyl, cycloalkyl, heteroalkyl, heterocyclyl, aryl, heteroaryl, cycloalkylalkyl, heterocyclylalkyl, arylalkyl or heteroarylalkyl any of which may be optionally independently substituted with one or more $R^{10}$ as allowed by valance;

$R^8$ and $R^9$ at each occurrence are independently H, alkyl, cycloalkyl, heteroalkyl, heterocyclyl, aryl, heteroaryl, cycloalkylalkyl, heteralkylalkyl, heterocyclylalkyl, arylalkyl or heteroarylalkyl or $R^8$ and $R^9$ together with the nitrogen atom to which they are attached may combine to form a heterocyclyl ring; and $R^{10}$ is one or more optional substituent independently selected at each occurrence as allowed by valance from halo, oxo, cyano, alkyl, haloalkyl, cycloalkyl, heterocyclyl, heteroaryl, aryl, heterocyclylalkyl, heteroarylalkyl, arylalkyl, $-(CR^4R^5)_{0-3}OR^7$, $-(CR^4R^5)_{0-3}NR^8R^9$, $-(CR^4R^5)_{0-3}N(R^6)C=OR^7$, $-(CR^4R^5)_{0-3}N(R^6)(C=O)OR^7$, $-(CR^4R^5)_{0-3}C=ONR^8R^9$, $-(CR^4R^5)_{0-3}O(C=O)NR^8R^9$, $-(CR^4R^5)_{0-3}C=OR^7$, $-(CR^4R^5)_{0-3}(C=O)OR^7$, $-(CR^4R^5)_{0-3}N(R^6)C=ONR^8R^9$, $-(CR^4R^5)_{0-3}S(O)_xR^7$, $-(CR^4R^5)_{0-3}SO_2NR^8R^9$ or $-(CR^4R^5)_{0-3}NR^6SO_2R^7$.

Preferred compounds of Formulae I-IV include compounds wherein $R^1$ is
  (1) $-NR^8R^9$, $-NR^6CONR^8R^9$, $-NR^6COOR^7$, $-CN$, or $-CONR^8R^9$; or
  (2) aryl, heteroaryl, heterocyclyl, alkenyl or alkynyl any of which may be optionally independently substituted as allowed by valance with one or more $R^{10}$.

Especially preferred compounds are those wherein $R^1$ is aryl, heteroaryl or heterocyclyl any of which may be optionally independently substituted as allowed by valance with one or more $R^{10}$.

Preferred compounds of Formulae I-IV further include compounds wherein M is absent, —O— or —NR$^6$—; and $R^2$ is aryl or heteroaryl either of which may be optionally independently substituted as allowed by valance with one or more $R^{10}$. Especially preferred compounds of this class include compounds the above preferred $R^1$ groups are also present.

Preferred compounds of Formulae I-IV further include compounds wherein $R^1$ is phenyl, naphthyl, naphthyridinyl, thienyl, benzothienyl, furan, benzofuranyl, pyridyl, pyrazinyl, pyrimidinyl, imidazolyl, triazolyl, quinoxalinyl, benzodioxolyl, benzodioxinyl dihydrobenzodioxinyl, indolinyl, indolyl, benzoimidazolyl, benzoisoxazol, benzoisothiozazol, benzoxazole, benzothiazol, thiazolyl, isothiazolyl, oxazolyl, isoxazolyl, morpholinyl, pyrrolidinyl, pyrazolyl, indazolyl, piperazinyl, piperadinyl, azetidinyl, pyranyl, pyridazinyl, dihydropyranyl, tetrahydropyranyl, quinolinyl, quinazolinyl, cinnolinyl, phthalazinyl, dihydroquinolinyl or isoquinolinyl any of which may be optionally independently substituted as allowed by valance with one or more $R^{10}$; and $R^2$ is quinolinyl, isoquinolinyl, naphthyl, pyrrolopyridinyl, naphthyridinyl quinazolinyl, indazolyl, quinoxalinyl, pyridyl, pyrimidinyl, pyridonyl, pyrimidonyl, cinnolinyl, azaindolyl, azabenzothienyl, azaindazolyl, 7H-pyrrolo[2,3-d]pyrimidine, 1H-pyrazolo[3,4-d]pyrimidine or phenyl any of which may be optionally independently substituted as allowed by valance with one or more $R^{10}$. Especially preferred of this class further include compounds wherein M is absent, —O— or —NR$^6$—. Especially preferred compounds further include compounds wherein $R^2$ is quinolinyl, especially quinolinyl groups of the following formula:

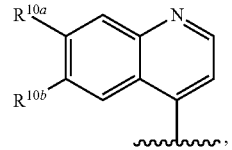

especially wherein $R^{10a}$ and $R^{10b}$ are independently absent or $OR^7$.

Preferred compounds of Formula I include compounds of the following Formula IA

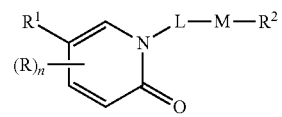

enantiomers, diastereomers, salts and solvates therein. Especially preferred compounds of Formula IA include compounds wherein the above preferred $R^1$, $R^2$, L and M groups are present—either alone, in partial combination, or all together.

Preferred compounds of Formula I include compounds of the following Formula IB

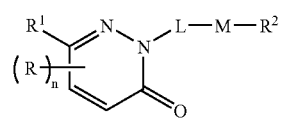

enantiomers, diastereomers, salts and solvates therein. Especially preferred compounds of Formula IB include compounds wherein the above preferred $R^1$, $R^2$, L and M groups are present—either alone, in partial combination, or all together.

Preferred compounds of Formula I include compounds of the following Formula IC

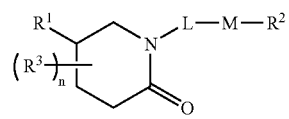

enantiomers, diastereomers, salts and solvates therein. Especially preferred compounds of Formula IC include compounds wherein the above preferred R, $R^2$, L and M groups are present—either alone, in partial combination, or all together.

Preferred compounds of Formula I include compounds of the following Formula ID

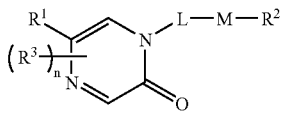

ID enantiomers, diastereomers, salts and solvates therein. Especially preferred compounds of Formula ID include compounds wherein the above preferred R, $R^2$, L and M groups are present—either alone, in partial combination, or all together.

Preferred compounds of Formula II include compounds of the following Formula IIA

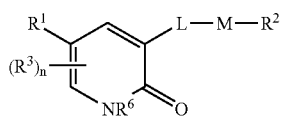

IIA enantiomers, diastereomers, salts and solvates therein. Especially preferred compounds of Formula IIA include compounds wherein the above preferred $R^1$, $R^2$, L and M groups are present—either alone, in partial combination, or all together.

The invention is further directed to compounds of the following Formula V

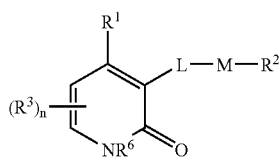

V enantiomers, diastereomers, salts and solvates thereof wherein n is an integer from 0 to 3;
v is an integer from 0 to 2;
L is absent, $C_{1-6}$alkylene, $C_{1-8}$cycloalkylene, $C_{2-6}$alkenylene or $C_{2-6}$alkynylene any of which may be optionally independently substituted with one or more halo, $-OR^7$ or $-NR^8R^9$ and further wherein any two hydrogen or substituent groups bound to the same tetravalent carbon atom may optionally combine to form a spiro-fused cycloalkyl or heterocyclyl ring;
M is absent, $-O-$, $-S(O)_v-$, $-NR^6-$, $-C(=O)NR^6$ or $-NR^6(C=O)-$ provided that L and M are not both simultaneously absent;
$R^1$ is
  (1) halo, $-CN$, $-NR^6-(C=O)R^7$, $-NR^6-(C=O)OR^6$, $-NR^6-(C=O)NR^8R^9$, $-(C=O)NR^8R^9$, $-(C=O)OR^7$, $-(C=O)R^7$, $-S(O)_vR^7-SO_2NR^8R^9$, $-NR^8R^9$ or $-OR^7$
  (2) cycloalkyl, cycloalkylalkyl, heterocyclyl, heterocyclylalkyl, aryl, arylalkyl, heteroaryl, heteroarylalkyl, $C_{2-6}$alkenyl, or $C_{2-6}$ alkynyl any of which may be optionally independently substituted with one or more $R^{10}$ as allowed by valance;
$R^2$ is aryl, arylalkyl, heteroaryl, heteroarylalkyl, heterocyclyl, heterocyclylalkyl, cycloalkyl or cycloalkylalkyl any of which may be optionally independently substituted with one or more $R^{10}$ as allowed by valence;
$R^3$ is an optional substituent independently selected at each occurrence from halo, cyano, optionally substituted alkyl, optionally substituted alkenyl, optionally substituted alkynyl, $-(C=O)_{0-1}OR^7$, $-(C=O)_{0-1}NR^8R^9$, $-S(O)_vR^7$, $-SO_2NR^8R^9$, $-C=OR^7$, $-NR^8C=OR^7$, $-C=ONR^8R^9$, $-NR^6-C=O-NR^8R^9$ and $-NR^8SO_2R^7$;
$R^{4*}$, $R^4$ and $R^5$ at each occurrence are independently H or one of the optional substituents listed in the definition of $R^3$ provided that $R^4$ and $R^5$ cannot be simultaneously selected from $-OR^7$, $-NR^8R^9$; $-S(O)_vR^7$, $-SO_2NR^8R^9$, $-NR^8C=OR^7$, $-NR^6-C=O-NR^8R^9$ and $-NR^8SO_2R^7$;
$R^6$ at each occurrence is independently
  (1) H, or
  (2) alkyl, alkenyl, alkynyl, cycloalkyl, heteroalkyl, heterocyclyl, aryl, heteroaryl, cycloalkylalkyl, heterocyclylalkyl, arylalkyl or heteroarylalkyl any of which may be optionally independently substituted with one or more $R^{10}$ as allowed by valance;
$R^7$ at each occurrence is independently
  (1) H, or
  (2) alkyl, alkenyl, alkynyl, cycloalkyl, heteroalkyl, heterocyclyl, aryl, heteroaryl, cycloalkylalkyl, heterocyclylalkyl, arylalkyl or heteroarylalkyl any of which may be optionally independently substituted with one or more $R^{10}$ as allowed by valance;
$R^8$ and $R^9$ at each occurrence are independently H, alkyl, cycloalkyl, heteroalkyl, heterocyclyl, aryl, heteroaryl, cycloalkylalkyl, heteralkylalkyl, heterocyclylalkyl, arylalkyl or heteroarylalkyl or $R^8$ and $R^9$ together with the nitrogen atom to which they are attached may combine to form a heterocyclyl ring; and
$R^{10}$ is one or more optional substituent independently selected at each occurrence as allowed by valance from halo, oxo, cyano, alkyl, haloalkyl, cycloalkyl, heterocyclyl, heteroaryl, aryl, heterocyclylalkyl, heteroarylalkyl, arylalkyl, $-(CR^4R^5)_{0-3}OR^7$, $-(CR^4R^5)_{0-3}NR^8R^9$, $-(CR^4R^5)_{0-3}N(R^6)C=OR^7$, $-(CR^4R^5)_{0-3}N(R^6)(C=O)OR^7$, $-(CR^4R^5)_{0-3}C=ONR^8R^9$, $-(CR^4R^5)_{0-3}O(C=O)NR^8R^9$, $-(CR^4R^5)_{0-3}C=OR^7$, $-(CR^4R^5)_{0-3}(C=O)OR^7$, $-(CR^4R^5)_{0-3}N(R^6)C=ONR^8R^9$, $-(CR^4R^5)_{0-3}S(O)_vR^7$, $-(CR^4R^5)_{0-3}SO_2NR^8R^9$ or $-(CR^4R^5)_{0-3}NR^6SO_2R^7$.

Especially preferred compounds of Formula V include compounds wherein the above preferred $R^1$, $R^2$, L and M groups are present—either alone, in partial combination, or all together.

The invention also relates to pharmaceutical compositions containing the above compounds, together with a pharmaceutically acceptable vehicle or carrier.

The invention also relates to a method of treating cancer in a subject using the above compounds.

The invention also relates to a method of reducing tumor size in a subject using the above compounds.

The invention also relates to a method of reducing metastasis in a tumor in a subject, using the above compounds.

The invention also relates to a method of treating HGF-mediated disorders in a subject using the above compounds.

Indications

Compounds of the present invention would be useful for, but not limited to, the prevention or treatment of angiogenesis related diseases. The compounds of the invention have c-Met inhibitory activity. The compounds of the invention are useful in therapy as antineoplasia agents or to minimize deleterious effects of HGF.

Compounds of the invention would be useful for the treatment of neoplasia including cancer and metastasis, including, but not limited to: carcinoma such as cancer of the bladder, breast, colon, kidney, liver, lung (including small cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g. soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma).

Preferably, the compounds are useful for the treatment of tumors where c-Met is over-expressed and/or amplified or/and mutated, such as renal cell carcinoma, head and neck tumor, gastric tumor, esophageal tumor, and on HGF-dependent tumor, such as glioblastoma, sarcoma, malignant mesothelioma, gastric tumor, non-small cell lung cancer, breast cancer, renal cell carcinoma.

Additionally, compounds of the present invention can be used to treat conditions such as bladder cancer, small cell lung cancer, colon cancer, sarcoma, ovarian cancer, prostate cancer, and pancreatic cancer.

The compounds also would be useful for treatment of opthalmological conditions such as corneal graft rejection, ocular neovascularization, retinal neovascularization including neovascularization following injury or infection, diabetic retinopathy, retrolental fibroplasia and neovascular glaucoma; retinal ischemia; vitreous hemorrhage; ulcerative diseases such as gastric ulcer; pathological, but non-malignant, conditions such as hemangiomas, including infantile hemaginomas, angiofibroma of the nasopharynx and avascular necrosis of bone; and disorders of the female reproductive system such as endometriosis. The compounds are also useful for the treatment of edema, and conditions of vascular hyperpermeability.

The compounds of the invention are useful in therapy of proliferative diseases. These compounds can be used for the treatment of an inflammatory rheumatoid or rheumatic disease, especially of manifestations at the locomotor apparatus, such as various inflammatory rheumatoid diseases, especially chronic polyarthritis including rheumatoid arthritis, juvenile arthritis or psoriasis arthropathy; paraneoplastic syndrome or tumor-induced inflammatory diseases, turbid effusions, collagenosis, such as systemic Lupus erythematosus, poly-myositis, dermato-myositis, systemic sclerodermia or mixed collagenosis; postinfectious arthritis (where no living pathogenic organism can be found at or in the affected part of the body), seronegative spondylarthritis, such as spondylitis ankylosans; vasculitis, sarcoidosis, or arthrosis; or further any combinations thereof. An example of an inflammation related disorder is (a) synovial inflammation, for example, synovitis, including any of the particular forms of synovitis, in particular bursal synovitis and purulent synovitis, as far as it is not crystal-induced. Such synovial inflammation may for example, be consequential to or associated with disease, e.g. arthritis, e.g. osteoarthritis, rheumatoid arthritis or arthritis deformans. The present invention is further applicable to the systemic treatment of inflammation, e.g. inflammatory diseases or conditions, of the joints or locomotor apparatus in the region of the tendon insertions and tendon sheaths. Such inflammation may be, for example, consequential to or associated with disease or further (in a broader sense of the invention) with surgical intervention, including, in particular conditions such as insertion endopathy, myofasciale syndrome and tendomyosis. The present invention is further especially applicable to the treatment of inflammation, e.g. inflammatory disease or condition, of connective tissues including dermatomyositis and myositis.

These compounds can be used as active agents against such disease states as arthritis, atherosclerosis, psoriasis, hemangiomas, myocardial angiogenesis, coronary and cerebral collaterals, ischemic limb angiogenesis, wound healing, peptic ulcer Helicobacter related diseases, fractures, cat scratch fever, rubeosis, neovascular glaucoma and retinopathies such as those associated with diabetic retinopathy or macular degeneration. In addition, some of these compounds can be used as active agents against solid tumors, malignant ascites, hematopoietic cancers and hyperproliferative disorders such as thyroid hyperplasia (especially Grave's disease), and cysts (such as hypervascularity of ovarian stroma, characteristic of polycystic ovarian syndrome (Stein-Leventhal syndrome)) since such diseases require a proliferation of blood vessel cells for growth and/or metastasis.

Further, some of these compounds can be used as active agents against burns, chronic lung disease, stroke, polyps, anaphylaxis, chronic and allergic inflammation, ovarian hyperstimulation syndrome, brain tumor-associated cerebral edema, high-altitude, trauma or hypoxia induced cerebral or pulmonary edema, ocular and macular edema, ascites, and other diseases where vascular hyperpermeability, effusions, exudates, protein extravasation, or edema is a manifestation of the disease. The compounds will also be useful in treating disorders in which protein extravasation leads to the deposition of fibrin and extracellular matrix, promoting stromal proliferation (e.g. fibrosis, cirrhosis and carpal tunnel syndrome).

The compounds of the present invention are also useful in the treatment of ulcers including bacterial, fungal, Mooren ulcers and ulcerative colitis.

The compounds of the present invention are also useful in the treatment of conditions wherein undesired angiogenesis, edema, or stromal deposition occurs in viral infections such as Herpes simplex, Herpes Zoster, AIDS, Kaposi's sarcoma, protozoan infections and toxoplasmosis, following trauma, radiation, stroke, endometriosis, ovarian hyperstimulation syndrome, systemic lupus, sarcoidosis, synovitis, Crohn's disease, sickle cell anemia, Lyme disease, pemphigoid, Paget's disease, hyperviscosity syndrome, Osler-Weber-Rendu disease, chronic inflammation, chronic occlusive pulmonary disease, asthma, and inflammatory rheumatoid or rheumatic disease. The compounds are also useful in the reduction of subcutaneous fat and for the treatment of obesity.

The compounds of the present invention are also useful in the treatment of ocular conditions such as ocular and macular edema, ocular neovascular disease, scleritis, radial keratotomy, uveitis, vitritis, myopia, optic pits, chronic retinal detachment, post-laser complications, glaucoma, conjunctivitis, Stargardt's disease and Eales disease in addition to retinopathy and macular degeneration.

The compounds of the present invention are also useful in the treatment of cardiovascular conditions such as atherosclerosis, restenosis, arteriosclerosis, vascular occlusion and carotid obstructive disease.

The compounds of the present invention are also useful in the treatment of cancer related indications such as solid tumors, sarcomas (especially Ewing's sarcoma and osteosarcoma), retinoblastoma, rhabdomyosarcomas, neuroblastoma, hematopoietic malignancies, including leukemia and lymphoma, tumor-induced pleural or pericardial effusions, and malignant ascites.

The compounds of the present invention are also useful in the treatment of diabetic conditions such as diabetic retinopathy and microangiopathy.

The compounds of the present invention are also useful in the reduction of blood flow in a tumor in a subject.

The compounds of the present invention are also useful in the reduction of metastasis of a tumor in a subject.

The compounds of this invention may also act as inhibitors of other protein kinases, e.g. tie-2, Ick, src, fgf, c-Met, ron, ckit and ret, and thus be effective in the treatment of diseases associated with other protein kinases.

Besides being useful for human treatment, these compounds are also useful for veterinary treatment of companion animals, exotic animals and farm animals, including mammals, rodents, and the like. More preferred animals include horses, dogs, and cats.

Additionally, appropriately labeled analogues of the compounds of the present invention can be used as imaging agents.

As used herein, the compounds of the present invention include the pharmaceutically acceptable derivatives thereof.

Where the plural form is used for compounds, salts, and the like, this is taken to mean also a single compound, salt and the like.

DEFINITIONS

"Angiogenesis" is defined as any alteration of an existing vascular bed or the formation of new vasculature, which benefits tissue perfasion. This includes the formation of new vessels by sprouting of endothelial cells from existing blood vessels or the remodeling of existing vessels to alter size, maturity, direction or flow properties to improve blood perfusion of tissue.

As used herein, "HGF" refers to hepatocyte growth factor/scatter factor. This includes purified hepatocyte growth factor/scatter factor, fragments of hepatocyte growth factor/scatter factor, chemically synthesized fragments of hepatocyte growth factor/scatter factor, derivatives or mutated versions of hepatocyte growth factor/scatter factor, and fusion proteins comprising hepatocyte growth factor/scatter factor and another protein. "HGF" as used herein also includes hepatocyte growth factor/scatter factor isolated from species other than humans.

As used herein "c-Met" refers to the receptor for HGF. This includes purified receptor, fragments of receptor, chemically synthesized fragments of receptor, derivatives or mutated versions of receptor, and fusion proteins comprising the receptor and another protein. "c-Met" as used herein also includes the HGF receptor isolated from a species other than humans.

As used herein, "HGF" refers to hepatocyte growth factor/scatter factor. This includes purified hepatocyte growth factor/scatter factor, fragments of hepatocyte growth factor/scatter factor, chemically synthesized fragments of hepatocyte growth factor/scatter factor, derivatives or mutated versions of hepatocyte growth factor/scatter factor, and fusion proteins comprising hepatocyte growth factor/scatter factor and another protein. "HGF" as used herein also includes hepatocyte growth factor/scatter factor isolated from species other than humans.

As used herein "c-Met" refers to the receptor for HGF. This includes purified receptor, fragments of receptor, chemically synthesized fragments of receptor, derivatives or mutated versions of receptor, and fusion proteins comprising the receptor and another protein. "c-Met" as used herein also includes the HGF receptor isolated from a species other than humans.

As used herein, the terms "hepatocyte growth factor" and "HGF" refer to a growth factor typically having a structure with six domains (finger, Kringle 1, Kringle 2, Kringle 3, Kringle 4 and serine protease domains). Fragments of HGF constitute HGF with fewer domains and variants of HGF may have some of the domains of HGF repeated; both are included if they still retain their respective ability to bind a HGF receptor. The terms "hepatocyte growth factor" and "HGF" include hepatocyte growth factor from humans ("huHGF") and any non-human mammalian species, and in particular rat HGF. The terms as used herein include mature, pre, pre-pro, and pro forms, purified from a natural source, chemically synthesized or recombinantly produced. Human HGF is encoded by the cDNA sequence published by Miyazawa et al. (1989), supra, or Nakamura et al. (1989), supra. The sequences reported by Miyazawa et al. and Nakamura et al. differ in 14 amino acids. The reason for the differences is not entirely clear; polymorphism or cloning artifacts are among the possibilities. Both sequences are specifically encompassed by the foregoing terms. It will be understood that natural allelic variations exist and can occur among individuals, as demonstrated by one or more amino acid differences in the amino acid sequence of each individual. The terms "hepatocyte growth factor" and "HGF" specifically include the delta 5 huHGF as disclosed by Seki et al., supra.

The terms "HGF receptor" and "c-Met" when used herein refer to a cellular receptor for HGF, which typically includes an extracellular domain, a transmembrane domain and an intracellular domain, as well as variants and fragments thereof which retain the ability to bind HGF. The terms "HGF receptor" and "c-Met" include the polypeptide molecule that comprises the full-length, native amino acid sequence encoded by the gene variously known as p190.sup.MET. The present definition specifically encompasses soluble forms of HGF receptor, and HGF receptor from natural sources, synthetically produced in vitro or obtained by genetic manipulation including methods of recombinant DNA technology. The HGF receptor variants or fragments preferably share at least about 65% sequence homology, and more preferably at least about 75% sequence homology with any domain of the human c-Met amino acid sequence published in Rodrigues et al., Mol. Cell. Biol., 11:2962-2970 (1991); Park et al., Proc. Natl. Acad. Sci., 84:6379-6383 (1987); or Ponzetto et al., Oncogene, 6:553-559 (1991).

The terms "agonist" and "agonistic" when used herein refer to or describe a molecule which is capable of, directly or indirectly, substantially inducing, promoting or enhancing HGF biological activity or HGF receptor activation.

The terms "cancer" and "cancerous" when used herein refer to or describe the physiological condition in mammals that is typically characterized by unregulated cell growth. Examples of cancer include but are not limited to, carcinoma, lymphoma, sarcoma, blastoma and leukemia. More particular examples of such cancers include squamous cell carcinoma, lung cancer, pancreatic cancer, cervical cancer, bladder cancer, hepatoma, breast cancer, colon carcinoma, and head and neck cancer. While the term "cancer" as used herein is not limited to any one specific form of the disease, it is believed that the methods of the invention will be particularly effective for cancers which are found to be accompanied by increased levels of HGF or expression of c-Met in the mammal.

The terms "treating," "treatment," and "therapy" as used herein refer to curative therapy, prophylactic therapy, and preventative therapy.

The term "mammal" as used herein refers to any mammal classified as a mammal, including humans, cows, horses, dogs and cats. In a preferred embodiment of the invention, the mammal is a human.

Given that elevated levels of c-Met and HGF are observed in hypertension, arteriosclerosis, myocardial infarction, and rheumatoid arthritis, nucleic acid ligands will serve as useful therapeutic agents for these diseases.

The term "treatment" includes therapeutic treatment as well as prophylactic treatment (either preventing the onset of disorders altogether or delaying the onset of a pre-clinically evident stage of disorders in individuals).

A "pharmaceutically-acceptable derivative" denotes any salt, ester of a compound of this invention, or any other compound which upon administration to a patient is capable of providing (directly or indirectly) a compound of this invention, or a metabolite or residue thereof, characterized by the ability to inhibit angiogenesis.

The phrase "therapeutically-effective" is intended to qualify the amount of each agent, which will achieve the goal of improvement in disorder severity and the frequency of incidence over treatment of each agent by itself, while avoiding adverse side effects typically associated with alternative therapies. For example, effective neoplastic therapeutic agents prolong the survivability of the patient, inhibit the rapidly proliferating cell growth associated with the neoplasm, or effect a regression of the neoplasm.

The term "H" denotes a single hydrogen atom. This radical may be attached, for example, to an oxygen atom to form a hydroxyl radical.

Where the term "alkyl" is used, either alone or within other terms such as "haloalkyl" and "alkylamino", it embraces linear or branched radicals having one to about twelve carbon atoms. More preferred alkyl radicals are "lower alkyl" radicals having one to about six carbon atoms. Examples of such radicals include methyl, ethyl, n-propyl, isopropyl, n-butyl, isobutyl, sec-butyl, tert-butyl, pentyl, isoamyl, hexyl and the like. Even more preferred are lower alkyl radicals having one or two carbon atoms. The term "alkylenyl" (or "alkylene") embraces bridging divalent strait chain alkyl radicals such as methylenyl, 1,2-ethylenyl, and 1,3-propylenyl, as well as divalent bridged alkyl radicals, such as 1,1-ethylenyl, 1,1-propylenyl, 1-2-isobutylenyl and the like. The term "lower alkyl substituted with $R^2$" does not include an acetal moiety.

The term "alkenyl" embraces linear or branched radicals having at least one carbon-carbon double bond of two to about twelve carbon atoms. More preferred alkenyl radicals are "lower alkenyl" radicals having two to about six carbon atoms. Most preferred lower alkenyl radicals are radicals having two to about four carbon atoms. Examples of alkenyl radicals include ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations. The term "alkenylenyl" (or "alkenylene") embraces bridging divalent strait or branched chain alkyl radicals containing at least one double bond such as 1,2-ethenylen-yl, (E)-1,3-2-methylbut-2-en-yl, (E)-2,3-pent-2-enylen-yl, and the like.

The term "alkynyl" denotes linear or branched radicals having at least one carbon-carbon triple bond and having two to about twelve carbon atoms. More preferred alkynyl radicals are "lower alkynyl" radicals having two to about six carbon atoms. Most preferred are lower alkynyl radicals having two to about four carbon atoms. Examples of such radicals include propargyl, butynyl, and the like. The term "alkynylenyl" (or "alkynylene") embraces bridging divalent strait or branched chain alkyl radicals containing at least one triple bond, such as 1,2-ethynylen-yl, 1,4-but-2ynylen-yl, 2,5-hex-3-ynen-yl, and the like.

The term "cycloalkyl" includes saturated carbocyclic groups. Preferred cycloalkyl groups include $C_3$-$C_6$ rings. More preferred compounds include, cyclopentyl, cyclopropyl, and cyclohexyl. The term "cycloalkylenyl" (or "cycloalkylene") referees to a divalent hydrocarbon linking group containing a cycloalkyl ring with in the backbone. Examples include:

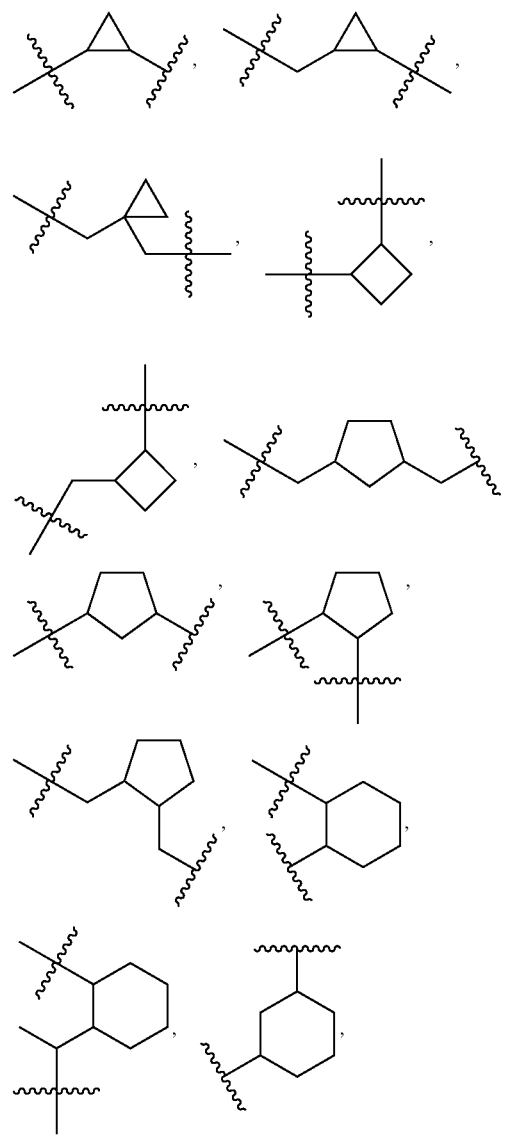

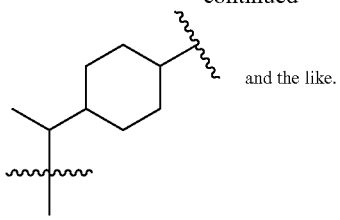 and the like.

The term "cycloalkylalkyl" embraces cycloalkyl-substituted alkyl radicals. Preferable cycloalkylalkyl radicals are "lower cycloalkylalkyl" radicals having cycloalkyl radicals attached to alkyl radicals having one to six carbon atoms. Even more preferred are "5-6-membered cycloalkylalkyl" attached to alkyl portions having one to three carbon atoms. Examples of such radicals include cyclohexylmethyl. The cycloalkyl in said radicals may be additionally substituted with halo, alkyl, alkoxy and hydroxy.

The term "cycloalkenyl" includes carbocyclic groups having one or more carbon-carbon double bonds including "cycloalkyldienyl" compounds. Preferred cycloalkenyl groups include $C_3$-$C_6$ rings. More preferred compounds include, for example, cyclopentenyl, cyclopentadienyl, cyclohexenyl and cycloheptadienyl.

The term "halo" means halogens such as fluorine, chlorine, bromine or iodine atoms.

The term "haloalkyl" embraces radicals wherein any one or more of the alkyl carbon atoms is substituted with halo as defined above. Specifically embraced are monohaloalkyl, dihaloalkyl and polyhaloalkyl radicals including perhaloalkyl. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1-6 carbon atoms. Even more preferred are lower haloalkyl radicals having one to three carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" means alkyl radicals having all hydrogen atoms replaced with fluoro atoms. Examples include trifluoromethyl and pentafluoroethyl.

The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. Even more preferred are lower hydroxyalkyl radicals having one to three carbon atoms.

The term "alkoxy" embraces linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. Even more preferred are lower alkoxy radicals having one to three carbon atoms. Alkoxy radicals may be further substituted with one or more halo atoms, such as fluoro, chloro or bromo, to provide "haloalkoxy" radicals. Even more preferred are lower haloalkoxy radicals having one to three carbon atoms. Examples of such radicals include fluoromethoxy, chloromethoxy, trifluoromethoxy, trifluoroethoxy, fluoroethoxy and fluoropropoxy.

The term "aryl", alone or in combination, means a carbocyclic aromatic system containing one or two rings wherein such rings may be attached together in a fused manner. The term "aryl" embraces aromatic radicals such as phenyl, naphthyl, indenyl, tetrahydronaphthyl, and indanyl. More preferred aryl is phenyl. Said "aryl" group may have 1 to 3 substituents such as lower alkyl, hydroxyl, halo, haloalkyl, nitro, cyano, alkoxy and lower alkylamino. Phenyl substituted with —O—$CH_2$—O— forms the aryl benzodioxolyl substituent.

The term "heterocyclyl" {or "heterocyclo"} embraces saturated, partially saturated and unsaturated heteroatom-containing ring radicals, where the heteroatoms may be selected from nitrogen, sulfur and oxygen. It does not include rings containing —O—O—, —O—S— or —S—S— portions. Said "heterocyclyl" group may have 1 to 3 substituents such as hydroxyl, Boc, halo, haloalkyl, cyano, lower alkyl, lower aralkyl, oxo, lower alkoxy, amino and lower alkylamino.

Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

Examples of unsaturated heterocyclic radicals, also termed "heteroaryl" radicals, include unsaturated 5 to 6 membered heteromonocyclyl group containing 1 to 4 nitrogen atoms, for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- to 6-membered heteromonocyclic group containing an oxygen atom, for example, pyranyl, 2-furyl, 3-furyl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3, 4-thiadiazolyl, 1,2,5-thiadiazolyl].

The term heterocyclyl, (or heterocyclo) 1 also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydrobenzo[1,4]dioxinyl and dihydrobenzofuryl]. Preferred heterocyclic radicals include five to ten membered fused or unfused radicals. More preferred examples of heteroaryl radicals include quinolyl, isoquinolyl, imidazolyl, pyridyl, thienyl, thiazolyl, oxazolyl, furyl, azaindolyl and pyrazinyl. Other preferred heteroaryl radicals are 5- or 6-membered heteroaryl, containing one or two heteroatoms selected from sulfur, nitrogen and oxygen, selected from thienyl, furyl, pyrrolyl, indazolyl, pyrazolyl, oxazolyl, triazolyl, imidazolyl, pyrazolyl, isoxazolyl, isothiazolyl, pyridyl, piperidinyl and pyrazinyl.

Particular examples of non-nitrogen containing heteroaryl include pyranyl, 2-furyl, 3-furyl, 2-thienyl, 3-thienyl, benzofuryl, benzothienyl, and the like.

Particular examples of partially saturated and saturated heterocyclyl include pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydrobenzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1'-benzo[d]isothiazol-6-yl, dihydropyranyl, dihydrofuryl and dihydrothiazolyl, pyridone (or "pyridonyl"), pyrimidone (or "pryimidonyl"), and the like.

The term "sulfonyl", whether used alone or linked to other terms such as alkylsulfonyl, denotes respectively divalent radicals —SO$_2$—.

The terms "sulfamyl," "aminosulfonyl" and "sulfonamidyl," denotes a sulfonyl radical substituted with an amine radical, forming a sulfonamide (—SO$_2$NH$_2$).

The term "alkylaminosulfonyl" includes "N-alkylaminosulfonyl" where sulfamyl radicals are independently substituted with one or two alkyl radical(s). More preferred alkylaminosulfonyl radicals are "lower alkylaminosulfonyl" radicals having one to six carbon atoms. Even more preferred are lower alkylaminosulfonyl radicals having one to three carbon atoms. Examples of such lower alkylaminosulfonyl radicals include N-methylaminosulfonyl, and N-ethylaminosulfonyl.

The terms "carboxy" or "carboxyl", whether used alone or with other terms, such as "carboxyalkyl", denotes —CO$_2$H.

The term "carbonyl", whether used alone or with other terms, such as "aminocarbonyl", denotes —(C=O)—.

The term "aminocarbonyl" denotes an amide group of the formula —C(=O)NH$_2$.

The terms "N-alkylaminocarbonyl" and "N,N-dialkylaminocarbonyl" denote aminocarbonyl radicals independently substituted with one or two alkyl radicals, respectively. More preferred are "lower alkylaminocarbonyl" having lower alkyl radicals as described above attached to an aminocarbonyl radical.

The terms "N-arylaminocarbonyl" and "N-alkyl-N-arylaminocarbonyl" denote aminocarbonyl radicals substituted, respectively, with one aryl radical, or one alkyl and one aryl radical.

The terms "heterocyclylalkylenyl" and "heterocyclylalkyl" embrace heterocyclic-substituted alkyl radicals. More preferred heterocyclylalkyl radicals are "5- or 6-membered heteroarylalkyl" radicals having alkyl portions of one to six carbon atoms and a 5- or 6-membered heteroaryl radical. Even more preferred are lower heteroarylalkylenyl radicals having alkyl portions of one to three carbon atoms. Examples include such radicals as pyridylmethyl and thienylmethyl.

The term "aralkyl" embraces aryl-substituted alkyl radicals. Preferable aralkyl radicals are "lower aralkyl" radicals having aryl radicals attached to alkyl radicals having one to six carbon atoms. Even more preferred are "phenylalkylenyl" attached to alkyl portions having one to three carbon atoms. Examples of such radicals include benzyl, diphenylmethyl and phenylethyl. The aryl in said aralkyl may be additionally substituted with halo, alkyl, alkoxy, halkoalkyl and haloalkoxy.

The term "alkylthio" embraces radicals containing a linear or branched alkyl radical, of one to ten carbon atoms, attached to a divalent sulfur atom. Even more preferred are lower alkylthio radicals having one to three carbon atoms. An example of "alkylthio" is methylthio, (CH$_3$S—).

The term "haloalkylthio" embraces radicals containing a haloalkyl radical, of one to ten carbon atoms, attached to a divalent sulfur atom. Even more preferred are lower haloalkylthio radicals having one to three carbon atoms. An example of "haloalkylthio" is trifluoromethylthio.

The term "alkylamino" embraces "N-alkylamino" and "N,N-dialkylamino" where amino groups are independently substituted with one alkyl radical and with two alkyl radicals, respectively. More preferred alkylamino radicals are "lower alkylamino" radicals having one or two alkyl radicals of one to six carbon atoms, attached to a nitrogen atom. Even more preferred are lower alkylamino radicals having one to three carbon atoms. Suitable alkylamino radicals may be mono or dialkylamino such as N-methylamino, N-ethylamino, N,N-dimethylamino, N,N-diethylamino and the like.

The term "arylamino" denotes amino groups, which have been substituted with one or two aryl radicals, such as N-phenylamino. The arylamino radicals may be further substituted on the aryl ring portion of the radical.

The term "heteroarylamino" denotes amino groups, which have been substituted with one or two heteroaryl radicals, such as N-thienylamino. The "heteroarylamino" radicals may be further substituted on the heteroaryl ring portion of the radical.

The term "aralkylamino" denotes amino groups, which have been substituted with one or two aralkyl radicals. More preferred are phenyl-C$_1$-C$_3$-alkylamino radicals, such as N-benzylamino. The aralkylamino radicals may be further substituted on the aryl ring portion.

The terms "N-alkyl-N-arylamino" and "N-aralkyl-N-alkylamino" denote amino groups, which have been independently substituted with one aralkyl and one alkyl radical, or one aryl and one alkyl radical, respectively, to an amino group.

The term "aminoalkyl" embraces linear or branched alkyl radicals having one to about ten carbon atoms any one of which may be substituted with one or more amino radicals. More preferred aminoalkyl radicals are "lower aminoalkyl" radicals having one to six carbon atoms and one or more amino radicals. Examples of such radicals include aminomethyl, aminoethyl, aminopropyl, aminobutyl and aminohexyl. Even more preferred are lower aminoalkyl radicals having one to three carbon atoms.

The term "alkylaminoalkyl" embraces alkyl radicals substituted with alkylamino radicals. More preferred alkylaminoalkyl radicals are "lower alkylaminoalkyl" radicals having alkyl radicals of one to six carbon atoms. Even more preferred are lower alkylaminoalkyl radicals having alkyl radicals of one to three carbon atoms. Suitable alkylaminoalkyl radicals may be mono or dialkyl substituted, such as N-methylaminomethyl, N,N-dimethyl-aminoethyl, N,N-diethylaminomethyl and the like.

The term "alkylaminoalkoxy" embraces alkoxy radicals substituted with alkylamino radicals. More preferred alkylaminoalkoxy radicals are "lower alkylaminoalkoxy" radicals having alkoxy radicals of one to six carbon atoms. Even more preferred are lower alkylaminoalkoxy radicals having alkyl radicals of one to three carbon atoms. Suitable alkylaminoalkoxy radicals may be mono or dialkyl substituted, such as N-methylaminoethoxy, N,N-dimethylaminoethoxy, N,N-diethylaminoethoxy and the like.

The term "alkylaminoalkoxyalkoxy" embraces alkoxy radicals substituted with alkylaminoalkoxy radicals. More preferred alkylaminoalkoxyalkoxy radicals are "lower alkylaminoalkoxyalkoxy" radicals having alkoxy radicals of one to six carbon atoms. Even more preferred are lower alkylaminoalkoxyalkoxy radicals having alkyl radicals of one to three carbon atoms. Suitable alkylaminoalkoxyalkoxy radicals may be mono or dialkyl substituted, such as N-methylaminomethoxyethoxy, N-methylaminoethoxyethoxy, N,N-dimethylaminoethoxyethoxy, N,N-diethylaminomethoxymethoxy and the like.

The term "carboxyalkyl" embraces linear or branched alkyl radicals having one to about ten carbon atoms any one of which may be substituted with one or more carboxy radicals. More preferred carboxyalkyl radicals are "lower carboxyalkyl" radicals having one to six carbon atoms and one carboxy radical. Examples of such radicals include carboxymethyl, carboxypropyl, and the like. Even more preferred are lower carboxyalkyl radicals having one to three $CH_2$ groups.

The term "halosulfonyl" embraces sulfonyl radicals substituted with a halogen radical. Examples of such halosulfonyl radicals include chlorosulfonyl and fluorosulfonyl.

The term "arylthio" embraces aryl radicals of six to ten carbon atoms, attached to a divalent sulfur atom. An example of "arylthio" is phenylthio.

The term "aralkylthio" embraces aralkyl radicals as described above, attached to a divalent sulfur atom. More preferred are phenyl-$C_1$-$C_3$-alkylthio radicals. An example of "aralkylthio" is benzylthio.

The term "aryloxy" embraces optionally substituted aryl radicals, as defined above, attached to an oxygen atom. Examples of such radicals include phenoxy.

The term "aralkoxy" embraces oxy-containing aralkyl radicals attached through an oxygen atom to other radicals. More preferred aralkoxy radicals are "lower aralkoxy" radicals having optionally substituted phenyl radicals attached to lower alkoxy radical as described above.

The term "heteroaryloxy" embraces optionally substituted heteroaryl radicals, as defined above, attached to an oxygen atom.

The term "heteroarylalkoxy" embraces oxy-containing heteroarylalkyl radicals attached through an oxygen atom to other radicals. More preferred heteroarylalkoxy radicals are "lower heteroarylalkoxy" radicals having optionally substituted heteroaryl radicals attached to lower alkoxy radical as described above.

The term "comprising" is meant to be open ended, including the indicated component but not excluding other elements.

The term "Formulas I, IA, IB, IC, ID, II, IIA, III, IV and V" includes any sub formulas.

The compounds of the invention are endowed with c-Met inhibitory activity.

The present invention also comprises the use of a compound of the invention, or pharmaceutically acceptable salt thereof, in the manufacture of a medicament for the treatment either acutely or chronically of an angiogenesis mediated disease state, including those described previously. The compounds of the present invention are useful in the manufacture of an anti-cancer medicament.

The compounds of the present invention are also useful in the manufacture of a medicament to attenuate or prevent disorders through inhibition of c-Met.

The present invention comprises a pharmaceutical composition comprising a therapeutically effective amount of a compound of Formulas I, IA, II, IIII and IV in association with a least one pharmaceutically acceptable carrier, adjuvant or diluent.

The present invention also comprises a method of treating angiogenesis related disorders in a subject having or susceptible to such disorder, the method comprising treating the subject with a therapeutically effective amount of a compound of Formula I, IA, IB, IC, ID, II, IIA, III, IV and V.

Combinations

While the compounds of the invention can be administered as the sole active pharmaceutical agent, they can also be used in combination with one or more compounds of the invention or other agents. When administered as a combination, the therapeutic agents can be formulated as separate compositions that are administered at the same time or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of neoplasia, such as with radiation therapy or with cytostatic or cytotoxic agents.

If formulated as a fixed dose, such combination products employ the compounds of this invention within the accepted dosage ranges. Compounds of Formula I, IA, IB, IC, ID, II, IIA, III, IV and V may also be administered sequentially with known anticancer or cytotoxic agents when a combination formulation is inappropriate. The invention is not limited in the sequence of administration; compounds of the invention may be administered either prior to, simultaneous with or after administration of the known anticancer or cytotoxic agent.

Currently, standard treatment of primary tumors consists of surgical excision followed by either radiation or IV administered chemotherapy. The typical chemotherapy regime consists of either DNA alkylating agents, DNA intercalating agents, CDK inhibitors, or microtubule poisons. The chemotherapy doses used are just below the maximal tolerated dose and therefore dose limiting toxicities typically include, nausea, vomiting, diarrhea, hair loss, neutropenia and the like.

There are large numbers of antineoplastic agents available in commercial use, in clinical evaluation and in pre-clinical development, which would be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

A first family of antineoplastic agents, which may be used in combination with compounds of the present invention, consists of antimetabolite-type/thymidilate synthase inhibitor antineoplastic agents. Suitable antimetabolite antineoplastic agents may be selected from but not limited to the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, Taiho UFT and uricytin.

A second family of antineoplastic agents, which may be used in combination with compounds of the present invention, consists of alkylating-type antineoplastic agents. Suitable alkylating-type antineoplastic agents may be selected from but not limited to the group consisting of Shionogi 254-S, aldophosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which may be used in combination with compounds of the present invention consists of antibiotic-type antineoplastic agents. Suitable antibiotic-type antineoplastic agents may be selected from but not limited to the group consisting of Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindanycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of antineoplastic agents which may be used in combination with compounds of the present invention consists of a miscellaneous family of antineoplastic agents, including tubulin interacting agents, topoisomerase II inhibitors, topoisomerase I inhibitors and hormonal agents, selected from but not limited to the group consisting of α-carotene, α-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluoron, benzotript, Ipsen-Beaufour BIM-23015, bisantrene, Bristol-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel elliprabin, elliptinium acetate, Tsumura EPMTC, the epothilones, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanlne derivatives, methylanilinoacridine, Molecular Genetics MGI-136, minactivin, mitonafide, mitoquidone mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM-534.

Alternatively, the present compounds may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofuran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

Alternatively, the present compounds may also be used in co-therapies with VEGFR inhibitors including N-(4-chlorophenyl)-4-(4-pyridinylmethyl)-1-phthalazinamine;

4-[4-[[[[4-chloro-3-(trifluoromethyl)phenyl]amino]carbonyl]amino]phenoxy]-N-methyl-2-pyridinecarboxamide;

N-[2-(diethylamino)ethyl]-5-[(5-fluoro-1,2-dihydro-2-oxo-3H-indol-3-ylidene)methyl]-2,4-dimethyl-1H-pyrrole-3-carboxamide;

3-[(4-bromo-2,6-difluorophenyl)methoxy]-5-[[[[4-(1-pyrrolidinyl)butyl]amino]carbonyl]amino]-4-isothiazolecarboxamide;

N-(4-bromo-2-fluorophenyl)-6-methoxy-7-[(1-methyl-4-piperidinyl)methoxy]-4-quinazolinamine;

3-[5,6,7,13-tetrahydro-9-[(1-methylethoxy)methyl]-5-oxo-12H-indeno[2,1-a]pyrrolo[3,4-c]carbazol-12-yl]propyl ester N,N-dimethyl-glycine;

N-[5-[[[5-(1,1-dimethylethyl)-2-oxazolyl]methyl]thio]-2-thiazolyl]-4-piperidinecarboxamide;

N-[3-chloro-4-[(3-fluorophenyl)methoxy]phenyl]-6-[5-[[[2-(methylsulfonyl)ethyl]amino]methyl]-2-furanyl]-4-quinazolinamine 4-[(4-Methyl-1-piperazinyl)methyl]-N-[4-methyl-3-[[4-(3-pyridinyl)-2-pyrimidinyl]amino]-phenyl]benzamide N-(3-chloro-4-fluorophenyl)-7-methoxy-6-[3-(4-morpholinyl)propoxy]-4-quinazolinamine N-(3-ethynylphenyl)-6,7-bis(2-methoxyethoxy)-4-quinazolinamine N-(3-((((2R)-1-methyl-2-pyrrolidinyl)methyl)oxy)-5-(trifluoromethyl)phenyl)-2-((3-(1,3-oxazol-5-yl)phenyl)amino)-3-pyridinecarboxamide;

2-(((4-fluorophenyl)methyl)amino)-N-(3-((((2R)-1-methyl-2-pyrrolidinyl)methyl)oxy)-5-(trifluoromethyl)phenyl)-3-pyridinecarboxamide;

N-[3-(Azetidin-3-ylmethoxy)-5-trifluoromethyl-phenyl]-2-(4-fluorobenzylamino)-nicotinamide.

6-fluoro-N-(4-(1-methylethyl)phenyl)-2-((4-pyridinylmethyl)amino)-3-pyridinecarboxamide;

2-((4-pyridinylmethyl)amino)-N-(3-(((2S)-2-pyrrolidinylmethyl)oxy)-5-(trifluoromethyl)phenyl)-3-pyridinecarboxamide;

N-(3-(1,1-dimethylethyl)-1H-pyrazol-5-yl)-2-((4-pyridinylmethyl)amino)-3-pyridinecarboxamide;

N-(3,3-dimethyl-2,3-dihydro-1-benzofuran-6-yl)-2-((4-pyridinylmethyl)amino)-3-pyridinecarboxamide;

N-(3-((((2S)-1-methyl-2-pyrrolidinyl)methyl)oxy)-5-(trifluoromethyl)phenyl)-2-((4-pyridinylmethyl)amino)-3-pyridinecarboxamide;

2-((4-pyridinylmethyl)amino)-N-(3-((2-(1-pyrrolidinyl)ethyl)oxy)-4-(trifluoromethyl)phenyl)-3-pyridinecarboxamide;

N-(3,3-dimethyl-2,3-dihydro-1H-indol-6-yl)-2-((4-pyridinylmethyl)amino)-3-pyridinecarboxamide;
N-(4-(pentafluoroethyl)-3-(((2S)-2-pyrrolidinylmethyl)oxy)phenyl)-2-((4-pyridinylmethyl)amino)-3-pyridinecarboxamide;
N-(3-((3-azetidinylmethyl)oxy)-5-(trifluoromethyl)phenyl)-2-((4-pyridinylmethyl)amino)-3-pyridinecarboxamide;
N-(3-(4-piperidinyloxy)-5-(trifluoromethyl)phenyl)-2-((2-(3-pyridinyl)ethyl)amino)-3-pyridinecarboxamide;
N-(4,4-dimethyl-1,2,3,4-tetrahydro-isoquinolin-7-yl)-2-(1H-indazol-6-ylamino)nicotinamide;
2-(1H-indazol-6-ylamino)-N-[3-(1-methylpyrrolidin-2-ylmethoxy)-5-trifluoromethyl-phenyl]-nicotinamide;
N-[1-(2-dimethylamino-acetyl)-3,3-dimethyl-2,3-dihydro-1H-indol-6-yl]-2-(1H-indazol-6-ylamino)-nicotinamide;
2-(1H-indazol-6-ylamino)-N-[3-(pyrrolidin-2-ylmethoxy)-5-trifluoromethylphenyl]-nicotinamide;
N-(1-acetyl-3,3-dimethyl-2,3-dihydro-1H-indol-6-yl)-2-(1H-indazol-6-ylamino)nicotinamide;
N-(4,4-dimethyl-1-oxo-1,2,3,4-tetrahydro-isoquinolin-7-yl)-2-(1H-indazol-6-ylamino)-nicotinamide;
N-[4-(tert-butyl)-3-(3-piperidylpropyl)phenyl][2-(1H-indazol-6-ylamino)(3-pyridyl)]carboxamide;
N-[5-(tert-butyl)isoxazol-3-yl][2-(1H-indazol-6-ylamino)(3-pyridyl)]carboxamide; and
N-[4-(tert-butyl)phenyl][2-(1H-indazol-6-ylamino)(3-pyridyl)]carboxamide.

Other compounds described in the following patents and patent applications can be used in combination therapy: U.S. Pat. No. 6,258,812, US 2003/0105091, WO 01/37820, U.S. Pat. No. 6,235,764, WO 01/32651, U.S. Pat. Nos. 6,630,500, 6,515,004, 6,713,485, 5,521,184, 5,770,599, 5,747,498, WO 02/68406, WO 02/66470, WO 02/55501, WO 04/05279, WO 04/07481, WO 04/07458, WO 04/09784, WO 02/59110, WO 99/45009, WO 00/59509, WO 99/61422, U.S. Pat. No. 5,990,141, WO 00/12089 and WO 00/02871.

In some embodiments, the combination comprises a composition of the present invention in combination with at least one anti-angiogenic agent. Agents are inclusive of, but not limited to, in vitro synthetically prepared chemical compositions, antibodies, antigen binding regions, radionuclides, and combinations and conjugates thereof. An agent can be an agonist, antagonist, allosteric modulator, toxin or, more generally, may act to inhibit or stimulate its target (e.g., receptor or enzyme activation or inhibition), and thereby promote cell death or arrest cell growth.

Exemplary anti-tumor agents include HERCEPTIN™ (trastuzumab), which may be used to treat breast cancer and other forms of cancer, and RITUXAN™ (rituximab), ZEVALIN™ (ibritumomab tiuxetan), and LYMPHOCIDE™ (epratuzumab), which may be used to treat non-Hodgkin's lymphoma and other forms of cancer, GLEEVAC™ which may be used to treat chronic myeloid leukemia and gastrointestinal stromal tumors, and BEXXAR™ (iodine 131 tositumomab) which may be used for treatment of non-Hodgkins's lymphoma.

Exemplary anti-angiogenic agents include ERBITUX™ (IMC-C225), KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF, or soluble VEGF receptors or a ligand binding region thereof) such as AVASTIN™ or VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as ABX-EGF (panitumumab), IRESSA™ (gefitinib), TARCEVA™ (erlotinib), anti-Ang1 and anti-Ang2 agents (e.g., antibodies or antigen binding regions specifically binding thereto or to their receptors, e.g., Tie2/Tek), and anti-Tie2 kinase inhibitory agents (e.g., antibodies or antigen binding regions that specifically bind thereto). The pharmaceutical compositions of the present invention can also include one or more agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor "c-met".

Other anti-angiogenic agents include Campath, IL-8, B-FGF, Tek antagonists (Ceretti et al., US Publication No. 2003/0162712; U.S. Pat. No. 6,413,932), anti-TWEAK agents (e.g., specifically binding antibodies or antigen binding regions, or soluble TWEAK receptor antagonists; see, Wiley, U.S. Pat. No. 6,727,225), ADAM distintegrin domain to antagonize the binding of integrin to its ligands (Fanslow et al., US Publication No. 2002/0042368), specifically binding anti-eph receptor and/or anti-ephrin antibodies or antigen binding regions (U.S. Pat. Nos. 5,981,245; 5,728,813; 5,969,110; 6,596,852; 6,232,447; 6,057,124 and patent family members thereof), and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto).

Additional anti-angiogenic/anti-tumor agents include: SD-7784 (Pfizer, USA); cilengitide. (Merck KGBA, Germany, EPO 770622); pegaptanib octasodium, (Gilead Sciences, USA); Alphastatin, (BioActa, UK); M-PGA, (Celgene, USA, U.S. Pat. No. 5,712,291); ilomastat, (Arriva, USA, U.S. Pat. No. 5,892,112); emaxanib, (Pfizer, USA, U.S. Pat. No. 5,792,783); vatalanib, (Novartis, Switzerland); 2-methoxyestradiol, (EntreMed, USA); TLC ELL-12, (Elan, Ireland); anecortave acetate, (Alcon, USA); alpha-D148 Mab, (Amgen, USA); CEP-7055, (Cephalon, USA); anti-Vn Mab, (Crucell, Netherlands) DAC:antiangiogenic, (ConjuChem, Canada); Angiocidin, (InKine Pharmaceutical, USA); KM-2550, (Kyowa Hakko, Japan); SU-0879, (Pfizer, USA); CGP-79787, (Novartis, Switzerland, EP 970070); ARGENT technology, (Ariad, USA); YIGSR-Stealth, (Johnson & Johnson, USA); fibrinogen-E fragment, (BioActa, UK); angiogenesis inhibitor, (Trigen, UK); TBC-1635, (Encysive Pharmaceuticals, USA); SC-236, (Pfizer, USA); ABT-567, (Abbott, USA); Metastatin, (EntreMed, USA); angiogenesis inhibitor, (Tripep, Sweden); maspin, (Sosei, Japan); 2-methoxyestradiol, (Oncology Sciences Corporation, USA); ER-68203-00, (IVAX, USA); Benefin, (Lane Labs, USA); Tz-93, (Tsumura, Japan); TAN-1120, (Takeda, Japan); FR-111142, (Fujisawa, Japan, JP 02233610); platelet factor 4, (RepliGen, USA, EP 407122); vascular endothelial growth factor antagonist, (Borean, Denmark); cancer therapy, (University of South Carolina, USA); bevacizumab (pINN), (Genentech, USA); angiogenesis inhibitors, (SUGEN, USA); XL 784, (Exelixis, USA); XL 647, (Exelixis, USA); MAb, alpha5beta3 integrin, second generation, (Applied Molecular Evolution, USA and MedImmune, USA); gene therapy, retinopathy, (Oxford BioMedica, UK); enzastaurin hydrochloride (USAN), (Lilly, USA); CEP 7055, (Cephalon, USA and Sanofi-Synthelabo, France); BC 1, (Genoa Institute of Cancer Research, Italy); angiogenesis inhibitor, (Alchemia, Australia); VEGF antagonist, (Regeneron, USA); rBPI 21 and BPI-derived antiangiogenic, (XOMA, USA); PI 88, (Progen, Australia); cilengitide (pINN), (Merck KGAA, German; Munich Technical University, Germany, Scripps Clinic and Research Foundation, USA); cetuximab (INN), (Aventis, France); AVE 8062, (Ajinomoto, Japan); AS1404, (Cancer Research Laboratory, New Zealand); SG 292, (Telios, USA); Endostatin, (Boston Childrens Hospital, USA); ATN 161, (Attenuon, USA); ANGIOSTATIN, (Boston Childrens Hospital, USA); 2-methoxyestradiol, (Boston Childrens Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Schering AG, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProlX, USA); METASTATIN, (EntreMed, USA); troponin I, (Harvard University, USA); SU 6668, (SUGEN, USA); OXI 4503, (OXiGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University, USA); AE 941, (Aeterna, Canada); vaccine, angiogenesis, (EntreMed, USA); urokinase plasminogen activator inhibitor, (Dendreon, USA); oglufanide (pINN), (Melmotte, USA); HIF-1alfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithiKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxyestradiol, (EntreMed, USA); anginex, (Maastricht University, Netherlands, and Minnesota University, USA); ABT 510, (Abbott, USA); AAL 993, (Novartis, Switzerland); VEGI, (ProteomTech, USA); tumor necrosis factor-alpha inhibitors, (National Institute on Aging, USA); SU 11248, (Pfizer, USA and SUGEN USA); ABT 518, (Abbott, USA); YH16, (Yantai Rongchang, China); S-3APG, (Boston Childrens Hospital, USA and EntreMed, USA); MAb, KDR, (ImClone Systems, USA); MAb, alpha5 beta1, (Protein Design, USA); KDR kinase inhibitor, (Celltech Group, UK, and Johnson & Johnson, USA); GFB 116, (South Florida University, USA and Yale University, USA); CS 706, (Sankyo, Japan); combretastatin A4 prodrug, (Arizona State University, USA); chondroitinase AC, (IBEX, Canada); BAY RES 2690, (Bayer, Germany); AGM 1470, (Harvard University, USA, Takeda, Japan, and TAP, USA); AG 13925, (Agouron, USA); Tetrathiomolybdate, (University of Michigan, USA); GCS100, (Wayne State University, USA) CV 247, (Ivy Medical, UK); CKD 732, (Chong Kun Dang, South Korea); MAb, vascular endothelium growth factor, (Xenova, UK); irsogladine (INN), (Nippon Shinyaku, Japan); RG 13577, (Aventis, France); WX 360, (Wilex, Germany); squalamine (pINN), (Genaera, USA); RPI 4610, (Sirna, USA); cancer therapy, (Marinova, Australia); heparanase inhibitors, (InSight, Israel); KL 3106, (Kolon, South Korea); Honokiol, (Emory University, USA); ZK CDK, (Schering AG, Germany); ZK Angio, (Schering AG, Germany); ZK 229561, (Novartis, Switzerland, and Schering AG, Germany); XMP 300, (XOMA, USA); VGA 1102, (Taisho, Japan); VEGF receptor modulators, (Pharmacopeia, USA); VE-cadherin-2 antagonists, (ImClone Systems, USA); Vasostatin, (National Institutes of Health, USA); vaccine, Flk-1, (ImClone Systems, USA); TZ 93, (Tsumura, Japan); TumStatin, (Beth Israel Hospital, USA); truncated soluble FLT 1 (vascular endothelial growth factor receptor 1), (Merck & Co, USA); Tie-2 ligands, (Regeneron, USA); and, thrombospondin 1 inhibitor, (Allegheny Health, Education and Research Foundation, USA).

Alternatively, the present compounds may also be used in co-therapies with other anti-neoplastic agents, such as VEGF antagonists, other kinase inhibitors including p38 inhibitors, KDR inhibitors, EGF inhibitors and CDK inhibitors, TNF inhibitors, metallomatrix proteases inhibitors (MMP), COX-2 inhibitors including celecoxib, NSAID's, or $\alpha_v\beta_3$ inhibitors.

The present invention comprises processes for the preparation of a compound of Formula I, IA, IB, IC, ID, II, IIA, III, IV and V. Also included in the family of compounds of Formula I, IA, IB, IC, ID, II, IIA, III, IV and V are the pharmaceutically acceptable salts thereof. The term "pharmaceutically-acceptable salts" embraces salts commonly used to form alkali metal salts and to form addition salts of free acids or free bases. The nature of the salt is not critical, provided that it is pharmaceutically acceptable. Suitable pharmaceutically acceptable acid addition salts of compounds of Formula I, IA, IB, IC, ID, II, IIA, III, IV and V may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, example of which are formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, tartaric, thiocyanic, mesylic, undecanoic, stearic, algenic, β-hydroxybutyric, salicylic, galactaric and galacturonic acid. Suitable pharmaceutically-acceptable base addition salts of compounds of Formula I, IA, IB, IC, ID, II, IIA, III, IV and V include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, aistidine, glucamine, isopropylamine, lysine, morpholine, N-ethyl morpholine, piperazine, piperidine, triethylamine, trimethylamine. All of these salts may be prepared by conventional means from the corresponding compound of the invention by reacting, for example, the appropriate acid or base with the compound of Formula I, IA, IB, IC, ID, II, IIA, III, IV and V. When a basic group and an acid group are present in the same molecule, a compound of Formula I, IA, IB, IC, ID, II, IIA, III, IV and V may also form internal salts.

General Synthetic Procedures

The compounds of the invention can be synthesized according to the following procedures of Schemes 1-10, wherein the substituents are as defined for Formulas I, IA, IB, IC, ID, II, IIA, III, IV and V above, except where further noted.

The following abbreviations are used throughout the specification:
HOAc—acetic acid
MeCN, CH$_3$CN—acetonitrile
NH$_3$—ammonia
NH$_4$Cl—ammonium chloride
Ar—argon
HBTA—O-benzotriazol-1-yl-N,N,N',N'-tetramethyluronium hexafluorophosphate
HATU—O-(7-azabenzotriazol-1-yl)-N,N,N',N'-tetramethyluronium hexafluorophosphate
PyBop—benzotriazol-1-yl-oxy-tripyrrolidino-phosphonium hexafluorophosphate
Pd$_2$(dba)$_3$—bis(dibenzylideneacetone) palladium
BINAP—2,2'-bis(diphenylphosphino)-1,1'-binaphthyl
TEAC—bis(tetra-ethylammonium)carbonate
BBr$_3$—boron tribromide
BSA—bovine serum albumin
Br$_2$–bromine
BOC—butyloxycarbonyl
Cs$_2$CO$_3$—cesium carbonate
CHCl$_3$—chloroform
CDCl$_3$—chloroform deuterated
Cu—copper
CuI—copper(I) iodide
Et$_2$O—diethyl ether
DBU—1,8-diazabicyclo[5.4.0]undec-7-ene
DIBAL—diisobutylaluminum hydride
DIAD—diisopropyl azodicarboxylate
DIEA—diisopropylethylamine
DMF—dimethylformamide
DMAP—4-dimethylaminopyridine
DMSO—dimethylsulfoxide
EDC, EDCI—1-(3-dimethylaminopropyl)-3-ethylcarbodiimide hydrochloride
dppa—diphenylphosphoryl azide
EtOAc—ethyl acetate
FBS—fetal bovine serum
g—gram
h—hour
HBr—hydrobromic acid
HCl—hydrochloric acid
HOBt—1-hydroxybenzotriazole hydrate
H$_2$—hydrogen
H$_2$O$_2$—hydrogen peroxide
Fe—iron
LiHMDS—lithium bis(trimethylsilyl)-amide
LDA—Lithium diisopropylamide
MCPBA—meta-chloroperbenzoic acid
MgSO$_4$—magnesium sulfate
MeOH, CH$_3$OH—methanol
MeI—methyl iodide
CH$_2$Cl$_2$, DCM—methylene chloride
NMP—N-methylpyrrolidinone
ML, ml—milliliter
N$_2$—nitrogen
Pd/C—palladium on carbon
Pd(OAc)$_2$—palladium acetate
Pd(OH)$_2$—palladium hydroxide
Pd(PPh$_3$)$_4$—palladium tetrakis triphenylphosphine
Pd(dppf)Cl$_2$—1,1-bis(diphenylphosphino)ferrocene palladium chloride
PBS—phosphate buffered saline
POCl$_3$—phosphorous oxychloride
K$_2$CO$_3$—potassium carbonate
KOH—potassium hydroxide
RT—room temperature
NaHCO$_3$—sodium bicarbonate
NaBH$_4$—sodium borohydride
NaBH$_3$CN—sodium cyanoborohydride
NaOtBu—sodium tert-butoxide
NaOH—sodium hydroxide
NaClO$_2$—sodium chlorite
NaCl—sodium chloride
NaHPO$_4$—sodium biphospate
NaH—sodium hydride
NaI—sodium iodide
Na$_2$SO$_4$—sodium sulfate
TBTU—O-benzotriazol-1-yl-N,N,N',N'-tetramethyluronium tetrafluoroborate
THF—tetrahydrofuran
Et$_3$N, TEA—triethylamine
TFA—trifluoroacetic acid
P(t-bu)$_3$—tri(tert-butyl)phosphine
H$_2$O—water

EXAMPLE 1

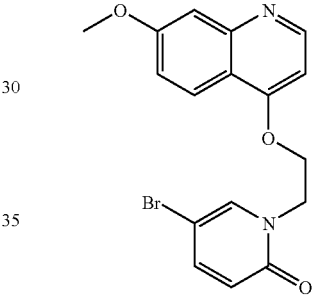

5-Bromo-1-(2-(7-methoxyquinolin-4-yloxy)ethyl) pyridin-2(1H)-one

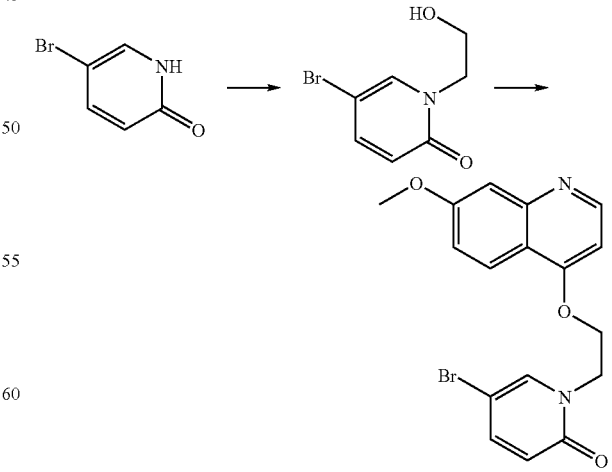

5-Bromo-1-(2-hydroxyethyl)pyridin-2(1H)-one. To a stirring solution of 5-bromo-2(1H)-pyridone (1000 mg, 5.74 mmol) in dry DMF (10 mL) under nitrogen was added sodium hydride (60% dispersion in mineral oil, 264 mg, 11.5 mmol). After 20 min at 23° C., 2-bromoethyl alcohol (448 µl, 6.32 mmol) was added and the reaction mixture was stirred at 23° C. for 3 days. The reaction was quenched with NH₄Cl (sat., 20 mL) and extracted with 9:1 CH₂Cl₂/iPrOH (50 mL; 25 mL×6). The combined organics were dried over MgSO₄, and concentrated to an oil under reduced pressure from toluene. iPrOH (0.5 mL) was added, and the solution was seeded with crystals of the product. The resulting solids were washed with iPrOH (0.5 mL) and ether (2×2 mL). The mother liquor was then purified on silica (12 g) eluting with 0-3% MeOH/CH₂Cl₂. MS (ESI pos. ion) m/z (MH+): 217/219. Calc'd exact mass for $C_7H_8BrNO_2$: 216. ¹HNMR (400 MHz, CDCl₃): δ 3.34 (br. s., 1H) 3.90-3.94 (m, 2H) 4.02-4.10 (m, 2H) 6.49 (d, J=9.59 Hz, 1H) 7.39 (dd, J=9.68, 2.64 Hz, 1H) 7.49-7.53 (m, 1H). ¹³C NMR (101 MHz, CDCl₃) δ ppm 53.11, 61.04, 98.15, 121.80, 138.62, 143.04, 161.89

5-Bromo-1-(2-(7-methoxyquinolin-4-yloxy)ethyl)pyridin-2(1H)-one: To a stirring solution of 5-bromo-1-(2-hydroxyethyl)pyridin-2(1H)-one (3000 mg, 13.7 mmol) in DMF (25 mL) was added sodium hydride (60% dispersion in mineral oil, 632.6 mg, 27.5 µmol) portionwise. After stirred for 30 min at 23° C., additional DMF (20 mL) was added to the thick suspension. To this was added 4-chloro-7-methoxyquinoline (2664 mg, 13.7 mmol). Upon completion, the reaction was quenched with 5% NaHCO₃ (100 mL), and the aqueous was extracted with CH₂Cl₂ (4×75 mL). The combined organics were dried over MgSO₄, concentrated from toluene, and purified on 80 grams of silica eluting with 30-80% of 5% MeOH/CH₂Cl₂. The product was isolated as a white solid. MS (ESI pos. ion) m/z (MH+): 375/377. Calc'd exact mass for $C_{17}H_{15}BrN_2O_3$: 374. ¹³C NMR (101 MHz, CDCl₃) δ ppm 48.66, 54.80, 64.75, 97.11, 98.75, 106.69, 114.92, 118.10, 121.48, 121.78, 137.81, 142.38, 150.57, 151.00, 159.87, 160.24, 160.40

EXAMPLE 1A

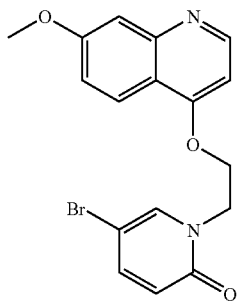

5-Bromo-1-(2-(7-methoxyquinolin-4-yloxy)ethyl)pyridin-2(1H)-one

Alternative Synthesis of 5-Bromo-1-(2-(7-methoxyquinolin-4-yloxy)ethyl)pyridin-2(1H)-one

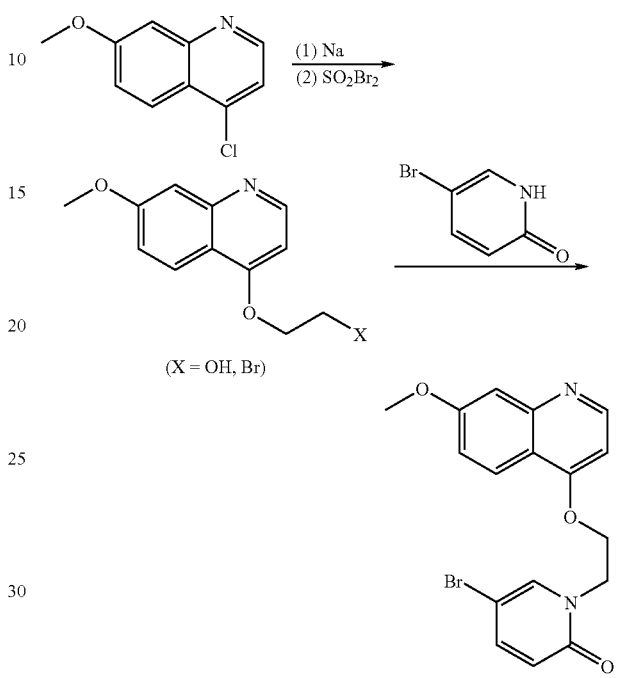

2-(7-Methoxyquinolin-4-yloxy)ethanol. In a 1 L RBF under nitrogen was placed sodium (15 g, 652 mmol) cubes. The flask was cooled in an ice bath and ethane-1,2-diol (150 ml, 2690 mmol) was added slowly through an addition funnel (15 min). The cooling bath was removed and the reaction mixture was allowed to warm to 50° C. until all the sodium disappeared. After 20 min, the mixture was heated to 110° C. and 4-chloro-7-methoxyquinoline (69 g, 356 mmol) was added. After 12 h, the mixture was cooled to room temperature and was diluted with H₂O (250 mL), resulting the formation of a thick sludge. The content was filtered, and washed with H₂O (2×50 mL). After air drying overnight, the solid was heated with benzene (300 mL) under reflux for 3 hr. The mixture was cooled and filtered. The solid was washed with ether (2×50 mL) to give a soft solid (77 g) contaminated with the small amount of bisether dimer. MS (ESI pos. ion) calcd for $C_{12}H_{13}NO_3$: 219.2; found: 220.1 (MH+). ¹H NMR (400 MHz, Chloroform-d) δ ppm 3.94 (s, 3H) 4.13 (t, 2H) 4.32 (t, 2H) 6.64 (d, J=5.28 Hz, 1H) 7.14 (dd, J=9.19, 2.54 Hz, 1H) 7.37 (d, J=2.35 Hz, 1H) 8.08 (d, J=9.19 Hz, 1H) 8.66 (d, J=5.48 Hz, 1H)

4-(2-Bromoethoxy)-7-methoxyquinoline. To a solution of 2-(7-methoxyquinolin-4-yloxy)ethanol (1520 mg, 6.93 mmol) in CH₂Cl₂ (15 mL)-DMF (5 mL) cooled in an ice bath was added SO₂Br₂ (1600 µl, 20.6 mmol). The cooling bath was removed and the orange solution was stirred at room temperature for 2 h. The mixture was concentrated to a sludge and was treated with a solution of NaOH (1.5 N, 20 mL) slowly followed by NaHCO₃ (sat) until pH~8-9. After standing overnight, the mixture was filtered and the yellow solid was washed with H₂O and air dried. The solid was washed with hot hexane (2×20 mL) to give the product as a yellow solid (1.7 g).

MS (ESI pos. ion) calcd for $C_{12}H_{12}BrNO_2$: 282.1; found 282/4 (MH+).

$^1$H NMR (400 MHz, Chloroform-d) δ ppm 3.79 (t, J=6.06 Hz, 2H) 3.95 (s, 3H) 4.51 (t, J=6.06 Hz, 2H) 6.61 (dd, 1H) 7.17 (dd, J=9.10, 2.45 Hz, 1H) 7.38 (s, 1H) 8.14 (d, J=9.19 Hz, 1H) 8.67 (d, J=5.28 Hz, 1H)

5-Bromo-1-(2-(7-methoxyquinolin-4-yloxy)ethyl)pyridin-2(1H)-one. In a 2-L RBF, a mixture of 5-bromopyridin-2(1H)-one (30 g, 172 mmol) in DME (250 mL) and DMF (70 mL) was purged with nitrogen and cooled in an ice bath. NaH (60% dispersion, 8.0 g, 200 mmol) was added in small portions to the mixture (over 2 h), resulting in a yellow suspension. LiBr (35 g, 403 mmol) was added and the mixture was stirred at room temperature for 15 min before 4-(2-bromoethoxy)-7-methoxyquinoline (40.0 g, 142 mmol) was added. The mixture was then heated to 60° C. in an oil bath for 5 days. The mixture was cooled to room temperature. $CH_2Cl_2$ (300 mL) was added and the slurry was filtered through a pad of Celite. The filtrate was washed with NaOH (0.5 N, 3×150 mL), $H_2O$ (100 mL), and dried over $Na_2SO_4$. The solution was concentrated to give a soft sludge which was stirred with a mixture of hexane (150 mL)-THF (150 mL) at reflux. The mixture was let cooled to room temperature overnight. The soft cake was filtered and washed with 1:1 hexane-THF (100 mL) to afford the product as a white solid (35.5 g, 67%).

EXAMPLE 2

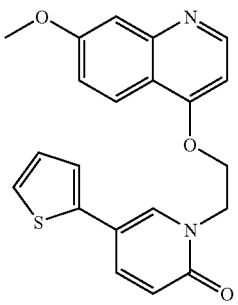

1-(2-(7-Methoxyquinolin-4-yloxy)ethyl)-5-(thiophen-2-yl)pyridin-2(1H)-one

General Scheme:

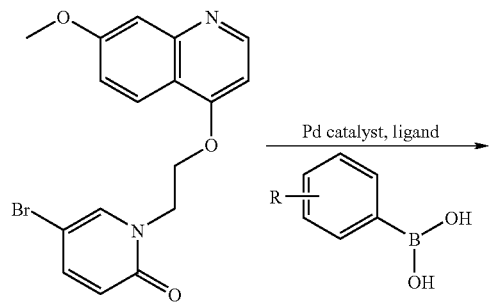

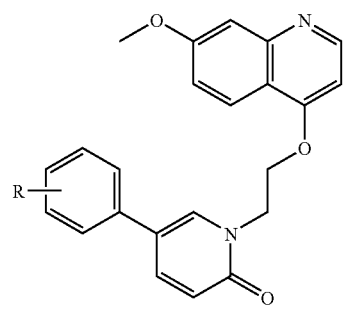

1-(2-(7-Methoxyquinolin-4-yloxy)ethyl)-5-(thiophen-2-yl)pyridin-2(1H)-one: A mixture of 5-bromo-1-(2-(7-methoxyquinolin-4-yloxy)ethyl)pyridin-2(1H)-one (50 mg, 133 μmol), thiophene-2-boronic acid (34 mg, 267 μmol), 1,1'-bis(diphenylphosphino)ferrocene]dichloride palladium(II) (8 mg, 11 μmol), and $Na_2CO_3$ (2M, 200 μl, 400 μmol) in DME (0.5 mL) were heated to 85° C. for 1 h. The reaction mixture was partitioned between $CH_2Cl_2$ (10 mL) and 5% $NaHCO_3$ (5 mL). The aqueous layer was further extracted with $CH_2Cl_2$ (5 mL) and the combined organics were dried with brine and $MgSO_4$. The concentrated organic residue was purified on 4 g silica eluting with 0-2.5% $MeOH/CH_2Cl_2$. The product was isolated as an off white solid. MS (ESI pos. ion) m/z (MH+): 379. Calc'd exact mass for $C_{21}H_{18}N_2O_3S$: 378. $^1$H NMR (400 MHz, Chloroform-d) δ ppm 3.92 (s, 3H) 4.53 (s, 4H) 6.62-6.67 (m, 2H) 7.24-7.28 (m, 1H) 7.34 (d, J=2.54 Hz, 1H) 7.63 (dd, J=9.49, 2.64 Hz, 1H) 7.79 (d, J=2.54 Hz, 1H) 8.00 (d, J=9.19 Hz, 1H) 8.66 (d, J=5.28 Hz, 1H)

EXAMPLE 3

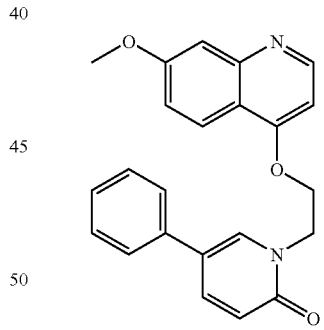

1-(2-(7-Methoxyquinolin-4-yloxy)ethyl)-5-phenylpyridin-2(1H)-one: This compound was prepared according to the procedure described in Example 2. MS (ESI pos. ion) m/z (MH+): 373. Calc'd exact mass for $C_{23}H_{20}N_2O_3$: 372. $^1$H NMR (400 MHz, Chloroform-d) δ ppm 3.90 (s, 3H) 4.49-4.56 (m, 4H) 6.62 (d, J=5.28 Hz, 1H) 6.67 (d, J=9.39 Hz, 1H) 6.99 (dd, J=9.10, 2.45 Hz, 1H) 7.31-7.44 (m, 6H) 7.62 (dd, J=9.39, 2.54 Hz, 1H) 7.68 (d, J=2.35 Hz, 1H) 7.94 (d, J=9.19 Hz, 1H) 8.63 (d, J=5.28 Hz, 1H). $^{13}$C NMR (101 MHz, Chloroform-d) δ ppm 49.45, 55.46, 65.75, 99.50, 107.29, 115.63, 118.48, 120.23, 120.87, 122.56, 125.81, 127.46, 129.09, 136.09, 136.22, 140.01, 151.18, 151.75, 160.70

EXAMPLE 4

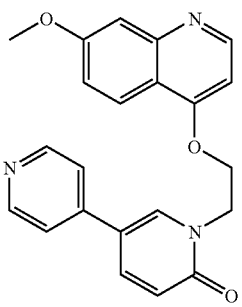

1-(2-(7-Methoxyquinolin-4-yloxy)ethyl)-5-(pyridin-4-yl)pyridin-2(1H)-one: This compound was prepared according to the procedure described in Example 2. MS (ESI pos. ion) m/z (MH+): 374. Calc'd exact mass for $C_{22}H_{19}N_3O_3$: 373. $^1$H NMR (400 MHz, Chloroform-d) δ ppm 3.91 (s, 3H) 4.56 (s, 4H) 6.63 (d, J=5.28 Hz, 1H) 6.71 (d, J=9.59 Hz, 1H) 7.00 (dd, J=9.19, 2.35 Hz, 1H) 7.23-7.29 (m, 2H) 7.33 (d, J=2.35 Hz, 1H) 7.66 (dd, J=9.49, 2.64 Hz, 1H) 7.82 (d, J=2.54 Hz, 1H) 7.91 (d, J=9.19 Hz, 1H) 8.63 (dd, J=11.54, 5.67 Hz, 3H).

EXAMPLE 5

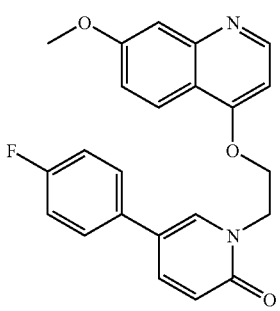

5-(4-Fluorophenyl)-1-(2-(7-methoxyquinolin-4-yloxy)ethyl)pyridin-2(1H)-one. This compound was prepared according to the procedure described in Example 2. MS (ESI pos. ion) m/z (MH+): 391. Calc'd exact mass for $C_{23}H_{19}FN_2O_3$: 390. $^1$H NMR (400 MHz, Chloroform-d) δ ppm 3.92 (s, 3H) 4.50-4.58 (m, 4H) 6.62-6.70 (m, 2H) 7.01 (dd, J=9.19, 2.54 Hz, 1H) 7.06-7.13 (m, 2H) 7.25-7.31 (m, 2H) 7.34 (d, J=2.35 Hz, 1H) 7.57 (dd, J=9.39, 2.54 Hz, 1H) 7.62 (d, J=2.54 Hz, 1H) 7.93 (d, J=9.19 Hz, 1H) 8.64 (d, J=5.28 Hz, 1H).

EXAMPLE 6

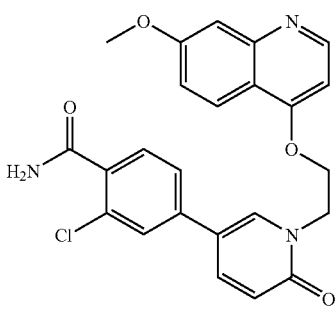

2-Chloro-4-(1-(2-(7-methoxyquinolin-4-yloxy)ethyl)-6-oxo-1,6-dihydropyridin-3-yl)benzamide This compound was prepared according to the procedure described in Example 2. MS (ESI pos. ion)/Z (MH+): 450. Calc'd exact mass for $C_{24}H_{20}ClN_3O_4$: 449. $^1$H NMR (400 MHz, Chloroform-d) δ ppm 3.92 (s, 3H) 4.51-4.62 (m, 4H) 5.96 (br. s., 1H) 6.50 (br. s., 1H) 6.64 (d, J=5.28 Hz, 1H) 6.69 (d, J=9.39 Hz, 1H) 7.06 (dd, J=9.19, 2.35 Hz, 1H) 7.30 (dd, J=8.02, 1.76 Hz, 1H) 7.33-7.38 (m, 2H) 7.59 (dd, J=9.49, 2.64 Hz, 1H) 7.69 (d, J=2.35 Hz, 1H) 7.87 (d, J=8.02 Hz, 1H) 7.95 (d, J=9.19 Hz, 1H) 8.65 (d, J=5.28 Hz, 1H).

EXAMPLE 7

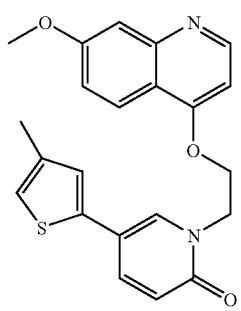

1-(2-(7-Methoxyquinolin-4-yloxy)ethyl)-5-(4-methylthiophen-2-yl)pyridin-2(1H)-one This compound was prepared according to the procedure described in Example 2. MS (ESI pos. ion) m/z (MH+): 393. Calc'd exact mass for $C_{22}H_{20}N_2O_3S$: 392. $^1$H NMR (400 MHz, Chloroform-d) δ ppm 2.26 (s, 3H) 3.92 (s, 3H) 4.47-4.56 (m, 4H) 6.59-6.66 (m, 2H) 6.83 (s, 2H) 7.07 (dd, J=9.19, 2.35 Hz, 1H) 7.34 (d, J=2.54 Hz, 1H) 7.58 (dd, J=9.39, 2.54 Hz, 1H) 7.73 (d, J=2.54 Hz, 1H) 8.01 (d, J=9.19 Hz, 1H) 8.65 (d, J=5.28 Hz, 1H).

EXAMPLE 8

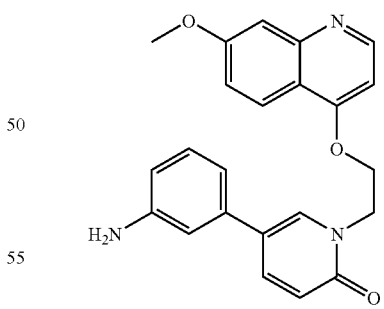

5-(3-Aminophenyl)-1-(2-(7-methoxyquinolin-4-yloxy)ethyl)pyridin-2(1H)-one. This compound was prepared according to the procedure described in Example 2. MS (ESI pos. ion) m/z (MH+): 388. Calc'd exact mass for $C_{23}H_{21}N_3O_3$: 387. $^1$H NMR (400 MHz, DMSO-d6) δ ppm 3.87 (s, 3H) 4.52 (s, 4H) 5.10 (s, 2H) 6.41-6.57 (m, 2H) 6.63-6.76 (m, 2H) 6.92 (d, J=4.70 Hz, 1H) 7.01-7.14 (m, 2H) 7.29 (s, 1H) 7.69 (d, J=9.19 Hz, 1H) 7.99 (d, J=9.00 Hz, 1H) 8.14 (s, 1H) 8.61 (d, J=4.50 Hz, 1H).

EXAMPLE 9

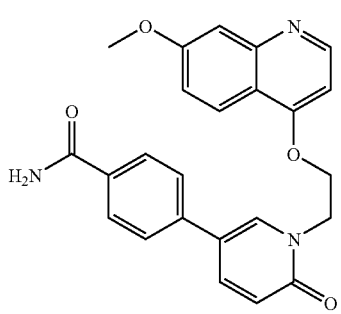

4-(1-(2-(7-Methoxyquinolin-4-yloxy)ethyl)-6-oxo-1,6-dihydropyridin-3-yl)benzamide This compound was prepared according to the procedure described in Example 2. MS (ESI pos. ion) m/z (MH+): 416. Calc'd exact mass for $C_{24}H_{21}N_3O_4$: 415. $^1$H NMR (400 MHz, DMSO-d) δ ppm 3.87 (s, 3H) 4.54 (s, 4H) 6.54 (d, J=9.54 Hz, 1H) 6.93 (d, J=5.52 Hz, 1H) 7.01 (d, J=9.04 Hz, 1H) 7.29 (s, 1H) 7.66 (d, J=8.03 Hz, 2H) 7.88-8.04 (m, 5H) 8.44 (d, J=2.51 Hz, 1H) 8.62 (d, J=5.02 Hz, 1H).

EXAMPLE 10

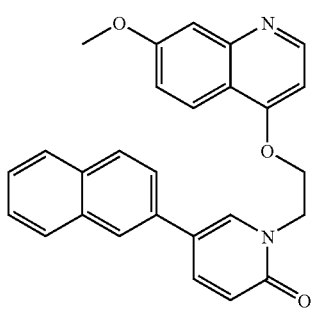

1-(2-(7-Methoxyquinolin-4-yloxy)ethyl)-5-(naphthalen-2-yl)pyridin-2(1H)-one

This compound was prepared according to the procedure described in Example 2. MS (ESI pos. ion) m/z (MH+): 423. Calc'd exact mass for $C_{27}H_{22}N_2O_3$: 422. $^1$H NMR (400 MHz, Chloroform-d) δ ppm 3.89 (s, 3H) 4.59 (dd, J=11.05, 4.01 Hz, 4H) 6.66 (d, J=5.28 Hz, 1H) 6.72 (d, J=9.19 Hz, 1H) 7.00 (dd, J=9.10, 2.25 Hz, 1H) 7.34 (d, J=2.15 Hz, 1H) 7.71-7.82 (m, 4H) 7.87 (t, J=8.22 Hz, 2H) 8.01 (d, J=9.19 Hz, 1H) 8.65 (d, J=5.28 Hz, 1H).

EXAMPLE 11

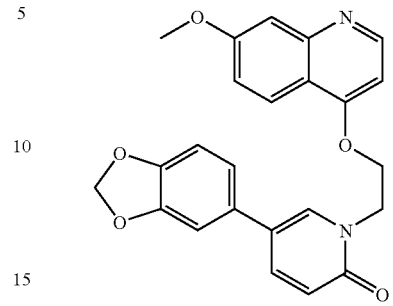

5-(Benzo[d][1,3]dioxol-5-yl)-1-(2-(7-methoxyquinolin-4-yloxy)ethyl)pyridin-2(1H)-one This compound was prepared according to the procedure described in Example 2. MS (ESI pos. ion) m/z (MH+): 417. Calc'd exact mass for $C_{24}H_{20}N_2O_5$: 416. $^1$H NMR (400 MHz, Chloroform-d) δ ppm 3.93 (s, 3H) 4.49-4.60 (m, 4H) 6.01 (s, 2H) 6.64 (dd, J=7.34, 2.05 Hz, 2H) 6.74-6.85 (m, 3H) 7.06 (dd, J=9.19, 2.54 Hz, 1H) 7.35 (d, J=2.54 Hz, 1H) 7.54 (dd, J=9.39, 2.54 Hz, 1H) 7.58 (d, J=2.35 Hz, 1H) 7.97 (d, J=9.00 Hz, 1H) 8.65 (d, J=5.28 Hz, 1H).

EXAMPLE 12

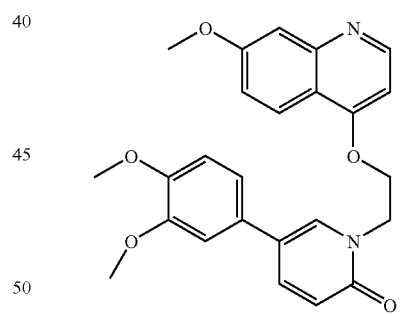

5-(3,4-Dimethoxyphenyl)-1-(2-(7-methoxyquinolin-4-yloxy)ethyl)pyridin-2(1H)-one

This compound was prepared according to the procedure described in Example 2. MS (ESI pos. ion) m/z (MH+): 433. Calc'd exact mass for $C_{25}H_{24}N_2O_5$: 432. $^1$H NMR (400 MHz, Chloroform-d) δ ppm 3.86 (s, 3H) 3.92 (s, 6H) 4.56 (dd, J=16.56, 4.52 Hz, 4H) 6.61-6.70 (m, 2H) 6.81 (s, 1H) 6.89 (s, 2H) 7.01 (dd, J=9.03, 2.51 Hz, 1H) 7.34 (d, J=2.51 Hz, 1H) 7.55-7.64 (m, 2H) 7.95 (d, J=9.03 Hz, 1H) 8.65 (d, J=5.02 Hz, 1H).

EXAMPLE 13

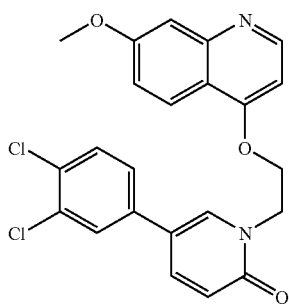

5-(3,4-Dichlorophenyl)-1-(2-(7-methoxyquinolin-4-yloxy)ethyl)pyridin-2(1H)-one

This compound was prepared according to the procedure described in Example 2. MS (ESI pos. ion) m/z (MH+): 441. Calc'd exact mass for $C_{23}H_{18}Cl_2N_2O_3$: 440. $^1$H NMR (400 MHz, Chloroform-d) δ ppm 3.91-3.94 (m, 3H) 4.50-4.55 (m, 2H) 4.56-4.61 (m, 2H) 6.64 (d, J=5.28 Hz, 1H) 6.68 (d, J=9.59 Hz, 1H) 7.09 (dd, J=9.10, 2.45 Hz, 1H) 7.14 (dd, J=8.31, 2.25 Hz, 1H) 7.36 (d, J=2.35 Hz, 1H) 7.39 (d, J=2.15 Hz, 1H) 7.46 (d, J=8.41 Hz, 1H) 7.55 (dd, J=9.49, 2.64 Hz, 1H) 7.63 (d, J=2.54 Hz, 1H) 7.95 (d, J=9.19 Hz, 4H) 8.65 (d, J=5.28 Hz, 1H).

EXAMPLE 14

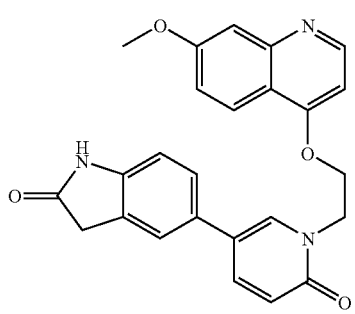

5-(1-(2-(7-Methoxyquinolin-4-yloxy)ethyl)-6-oxo-1,6-dihydropyridin-3-yl)indolin-2-one This compound was prepared according to the procedure described in Example 2. MS (ESI pos. ion) calc'd for $C_{25}H_{21}N_3O_4$: 427.2; found: 428.2 (MH+) $^1$H NMR (400 MHz, DMSO-d6) δ ppm 3.50 (s, 2H) 3.87-3.90 (m, 3H) 4.47-4.57 (m, 4H) 6.49 (d, J=9.39 Hz, 1H) 6.84 (d, J=8.02 Hz, 1H) 6.92 (dd, 1H) 7.08 (dd, J=9.10, 2.45 Hz, 1H) 7.25-7.37 (m, 3H) 7.74 (dd, 1H) 8.02 (d, J=9.00 Hz, 1H) 8.14 (s, 1H) 8.62 (d, J=5.28 Hz, 1H) 10.44 (s, 1H)

EXAMPLE 15

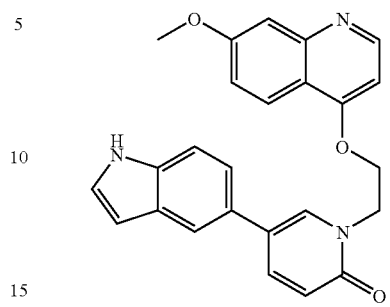

5-(1H-Indol-5-yl)-1-(2-(7-methoxyquinolin-4-yloxy)ethyl)pyridin-2(1H)-one

This compound was prepared according to the procedure described in Example 2. MS (ESI pos. ion) calc'd for $C_{25}H_{21}N_3O_3$: 411.5; found: 412.2 (MH+), ~95% pure. $^1$H NMR (400 MHz, Chloroform-d) δ ppm 3.92 (s, 3H) 4.53-4.62 (m, 4H) 6.55-6.58 (m, 1H) 6.65-6.70 (m, 2H) 7.04 (dd, J=9.19, 2.54 Hz, 1H) 7.19 (dd, J=8.41, 1.76 Hz, 1H) 7.28 (t, 1H) 7.35 (d, J=2.35 Hz, 1H) 7.43 (d, J=8.41 Hz, 1H) 7.58 (s, 1H) 7.67-7.73 (m, 2H) 8.05 (d, J=9.00 Hz, 1H) 8.32 (s, 1H) 8.66 (d, J=5.28 Hz, 1H)

EXAMPLE 16

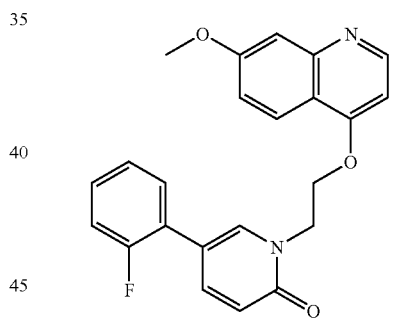

5-(2-Fluorophenyl)-1-(2-(7-methoxyquinolin-4-yloxy)ethyl)pyridin-2(1H)-one

General Scheme:

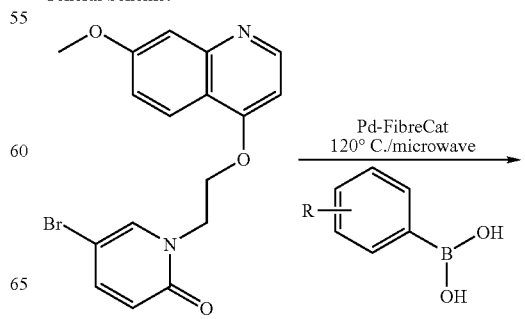

-continued

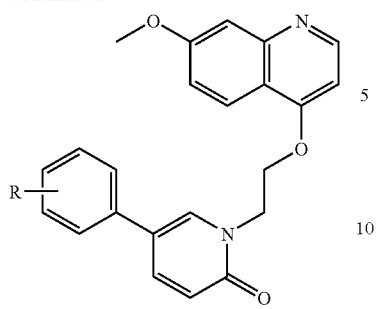

To a microwave tube was added 5-bromo-1-(2-(7-methoxyquinolin-4-yloxy)ethyl)pyridin-2(1H)-one (0.1 g, 0.3 mmol), 2-fluorophenylboronic acid (0.1 g, 1 mmol), palladium fibrecatalyst (0.010 mg, 10% wt), potassium carbonate (0.4 ml, 0.8 mmol), and dioxane (2 mL). The vial was sealed and placed in a CEM microwave for 20 min. at 120° C., with 50 Watts of power in Powermax mode. The reaction mixture was partitioned between water/$CH_2Cl_2$. The aqueous layer was extracted more with $CH_2Cl_2$. The combined organic layers were dried over $MgSO_4$ and concentrated. The crude product was purified using $SiO_2$ chromatography with $CH_2Cl_2$:EtOAc:MeOH=90%:5%:5% solvent system to afford the product as white solid (75 mg). MS (ESI pos. ion) m/z (MH+): 391.2. Calc'd exact mass for $C_{23}H_{19}FN_2O_3$: 390.1. $^1$H NMR (300 MHz, Chloroform-d) δ ppm 3.94 (s, 3H) 4.50-4.62 (m, 4H) 6.63-6.72 (m, 2H) 7.04 (dd, J=9.13, 2.56 Hz, 1H) 7.12-7.20 (m, 2H) 7.20-7.25 (m, 1H) 7.28-7.33 (m, 1H) 7.35 (d, J=2.48 Hz, 1H) 7.54-7.64 (m, 1H) 7.79 (d, J=2.63 Hz, 1H) 7.99 (d, J=9.21 Hz, 1H) 8.66 (d, J=5.26 Hz, 1H).

EXAMPLE 17

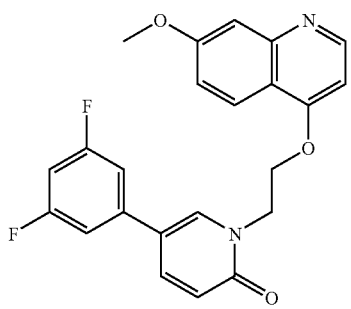

5-(3,5-Difluorophenyl)-1-(2-(7-methoxyquinolin-4-yloxy)ethyl)pyridin-2(1H)-one

This compound was prepared according to the procedure described in Example 16. MS (ESI pos. ion) m/z (MH+): 409.3. Calc'd exact mass for $C_{23}H_{18}F_2N_2O_3$: 408.1. $^1$H NMR (300 MHz, Chloroform-d)δ ppm 3.94 (s, 3H) 4.50-4.64 (m, 4H) 6.65 (d, J=5.41 Hz, 1H) 6.69 (d, J=9.50 Hz, 1H) 6.73-6.79 (m, 1H) 6.80-6.84 (m, 1H) 6.86 (s, 1H) 7.08 (dd, J=9.13, 2.56 Hz, 1H) 7.37 (d, J=2.48 Hz, 1H) 7.56 (dd, J=9.50, 2.63 Hz, 1H) 7.69 (d, J=2.19 Hz, 1H) 7.97 (d, J=9.06 Hz, 1H) 8.66 (d, J=5.41 Hz, 1H).

EXAMPLE 18

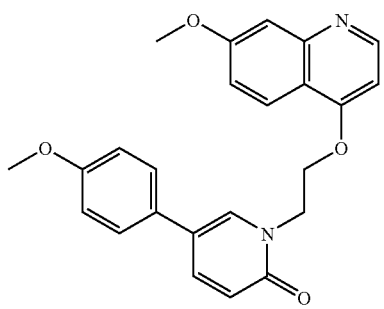

5-(4-Methoxyphenyl)-1-(2-(7-methoxyquinolin-4-yloxy)ethyl)pyridin-2(1H)-one

This compound was prepared according to the procedure described in Example 16. MS (ESI pos. ion) m/z (MH+): 403.5. Calc'd exact mass for $C_{23}H_{18}F_2N_2O_3$: 402.2. $^1$H NMR (300 MHz, Chloroform-d) δ ppm 3.86 (s, 3H) 3.94 (s, 3H) 4.48-4.62 (m, 4H) 6.63-6.70 (m, 2H) 6.89-6.98 (m, 2H) 7.04 (dd, J=9.21, 2.48 Hz, 1H) 7.26 (s, 2H) 7.29 (s, 1H) 7.35 (d, J=2.48 Hz, 1H) 7.61 (s, 1H) 7.97 (d, J=9.06 Hz, 1H) 8.66 (d, J=5.26 Hz, 1H).

EXAMPLE 19

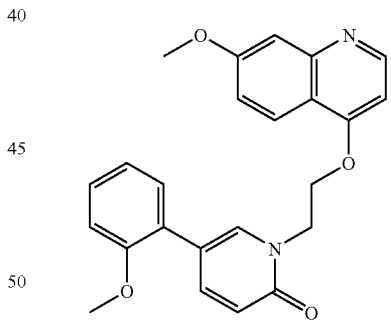

5-(2-Methoxyphenyl)-1-(2-(7-methoxyquinolin-4-yloxy)ethyl)pyridin-2(1H)-one

This compound was prepared according to the procedure described in Example 16. MS (ESI pos. ion) m/z (MH+): 403.5. Calc'd exact mass for $C_{23}H_{18}F_2N_2O_3$: 402.2. $^1$H NMR (300 MHz, Chloroform-d) δ ppm 3.78 (s, 3H) 3.94 (s, 3H) 4.55 (dd, J=11.40, 4.38 Hz, 4H) 6.60-6.69 (m, 2H) 6.94-7.05 (m, 3H) 7.16 (dd, J=7.45, 1.61 Hz, 1H) 7.30-7.35 (m, 1H) 7.36 (d, J=2.48 Hz, 1H) 7.61 (dd, J=9.43, 2.56 Hz, 1H) 7.70 (d, J=2.19 Hz, 1H) 7.99 (d, J=9.06 Hz, 1H) 8.66 (d, J=5.26 Hz, 1H).

EXAMPLE 20

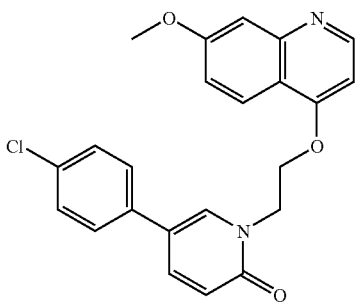

5-(4-chlorophenyl)-1-(2-(7-methoxyquinolin-4-yloxy)ethyl)pyridin-2(1H)-one. This compound was prepared according to the procedure described in Example 16. MS (ESI pos. ion) m/z (MH+): 407.5. Calc'd exact mass for $C_{23}H_{19}ClN_2O_3$: 406.1. $^1$H NMR (300 MHz, Chloroform-d) δ ppm 3.94 (s, 3H) 4.50-4.63 (m, 4H) 6.60-6.73 (m, 2H) 7.03 (dd, J=9.21, 2.48 Hz, 1H) 7.23-7.29 (m, 2H) 7.33-7.38 (m, 2H) 7.39 (s, 1H) 7.58 (dd, J=9.43, 2.70 Hz, 1H) 7.65 (d, J=2.19 Hz, 1H) 7.94 (d, J=9.21 Hz, 1H) 8.66 (d, J=5.26 Hz, 1H).

EXAMPLE 21

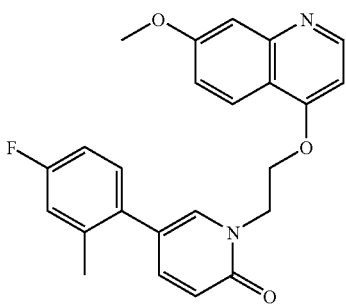

5-(4-Fluoro-2-methylphenyl)-1-(2-(7-methoxyquinolin-4-yloxy)ethyl)pyridin-2(1H)-one This compound was prepared according to the procedure described in Example 16. MS (ESI pos. ion) m/z (MH+): 405.3. Calc'd exact mass for $C_{24}H_{21}FN_2O_3$: 404.1. $^1$H NMR (300 MHz, Chloroform-d) δ ppm 2.18 (s, 3H) 3.95 (s, 3H) 4.47-4.63 (m, 4H) 6.58-6.69 (m, 2H) 6.87-6.97 (m, 2H) 6.98-7.07 (m, 3H) 7.39 (dd, J=12.20, 2.27 Hz, 2H) 7.91 (d, J=9.21 Hz, 1H) 8.66 (d, J=5.26 Hz, 1H).

EXAMPLE 22

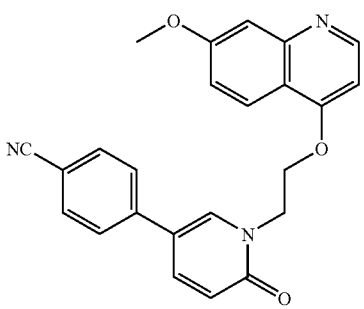

4-(1-(2-(7-Methoxyquinolin-4-yloxy)ethyl)-6-oxo-1,6-dihydropyridin-3-yl)benzonitrile This compound was prepared according to the procedure described in Example 16. MS (ESI pos. ion) m/z (MH+): 399.3. Calc'd exact mass for $C_{24}H_{22}N_2O_3$: 398.1. $^1$H NMR (300 MHz, Chloroform-d) δ ppm 3.94 (s, 3H) 4.51-4.65 (m, 4H) 6.66 (d, J=5.41 Hz, 1H) 6.72 (d, J=9.50 Hz, 1H) 7.00 (dd, J=9.13, 2.56 Hz, 1H) 7.35 (d, J=2.48 Hz, 1H) 7.41 (d, J=8.62 Hz, 2H) 7.62 (dd, J=9.50, 2.78 Hz, 1H) 7.65-7.74 (m, 3H) 7.92 (d, J=9.06 Hz, 1H) 8.66 (d, J=5.26 Hz, 1H).

EXAMPLE 23

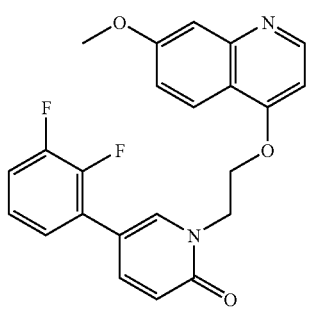

5-(2,3-Difluorophenyl)-1-(2-(7-methoxyquinolin-4-yloxy)ethyl)pyridin-2(1H)-one

This compound was prepared according to the procedure described in Example 16. MS (ESI pos. ion) m/z (MH+): 409.3. Calc'd exact mass for $C_{23}H_{18}F_2N_2O_3$: 408.1. $^1$H NMR (300 MHz, Chloroform-d) δ ppm 3.94 (s, 1H) 4.50-4.62 (m, 4H) 6.65 (d, J=5.41 Hz, 1H) 6.69 (d, J=9.50 Hz, 1H) 6.97-7.09 (m, 2H) 7.09-7.22 (m, 2H) 7.35 (d, J=2.48 Hz, 1H) 7.54-7.61 (m, 1H) 7.79 (d, J=2.63 Hz, 1H) 7.98 (d, J=9.06 Hz, 1H) 8.66 (d, 1H).

EXAMPLE 24

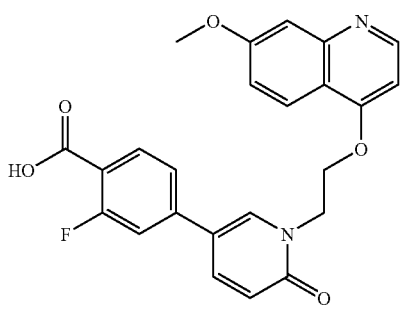

2-Fluoro-4-(1-(2-(7-methoxyquinolin-4-yloxy)ethyl)-6-oxo-1,6-dihydropyridin-3-yl)benzoic acid This compound was prepared according to the procedure described in Example 16. MS (ESI pos. ion) m/z (MH+): 435.3. Calc'd exact mass for $C_{24}H_{19}FN_2O_5$: 434.1. $^1$H NMR (300 MHz, MeOH-$d_4$) δ ppm 4.01 (s, 3H) 4.72 (t, J=4.90 Hz, 2H) 4.94 (t, J=4.90 Hz, 2H) 6.68 (d, J=9.50 Hz, 1H) 7.27-7.46 (m, 5H) 7.89-7.97 (m, 1H) 7.98-8.03 (m, 1H) 8.29 (d, J=9.50 Hz, 1H) 8.34 (d, J=2.48 Hz, 1H) 8.83 (d, J=6.87 Hz, 1H).

EXAMPLE 25

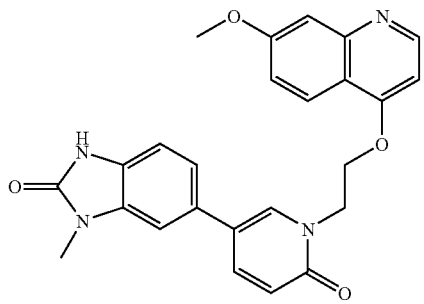

6-(1-(2-(7-Methoxyquinolin-4-yloxy)ethyl)-6-oxo-1,6-dihydropyridin-3-yl)-1-methyl-1H-benzo[d]imidazol-2(3H)-one This compound was prepared according to the procedure described in Example 16. MS (ESI pos. ion) m/z (MH+): 443.5. Calc'd exact mass for $C_{24}H_{19}FN_2O_5$: 442.1. $^1$H NMR (300 MHz, Chloroform-d) δ ppm 3.94 (s, 3H) 4.51-4.65 (m, 4H) 6.66 (d, J=5.41 Hz, 1H) 6.72 (d, J=9.50 Hz, 1H) 7.00 (dd, J=9.13, 2.56 Hz, 1H) 7.35 (d, J=2.48 Hz, 1H) 7.41 (d, J=8.62 Hz, 2H) 7.62 (dd, J=9.50, 2.78 Hz, 1H) 7.65-7.74 (m, 3H) 7.92 (d, J=9.06 Hz, 1H) 8.66 (d, J=5.26 Hz, 1H).

EXAMPLE 26

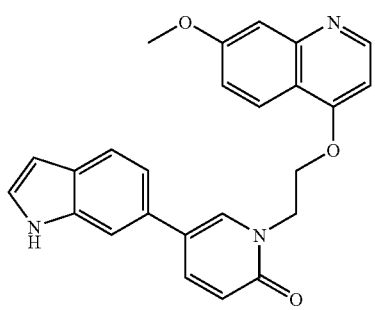

5-(1H-Indol-6-yl)-1-(2-(7-methoxyquinolin-4-yloxy)ethyl)pyridin-2(1H)-one. This compound was prepared according to the procedure described in Example 16. MS (ESI pos. ion) m/z (MH+): 412.5. Calc'd exact mass for $C_{25}H_{21}N_3O_3$: 411.1. $^1$HNMR (300 MHz, Chloroform-d) δ ppm 3.92 (s, 3H) 4.58 (dd, J=14.76, 4.68 Hz, 4H) 6.59 (s, 1H) 6.68 (t, J=7.09 Hz, 2H) 7.03 (d, J=9.21 Hz, 1H) 7.13 (d, J=8.33 Hz, 1H) 7.20 (s, 1H) 7.27 (d, J=5.55 Hz, 1H) 7.37 (d, J=2.48 Hz, 1H) 7.66 (s, 2H) 7.67-7.71 (m, 1H) 8.04 (d, J=9.21 Hz, 1H) 8.31 (s, 1H) 8.66 (d, J=5.26 Hz, 1H).

EXAMPLE 27

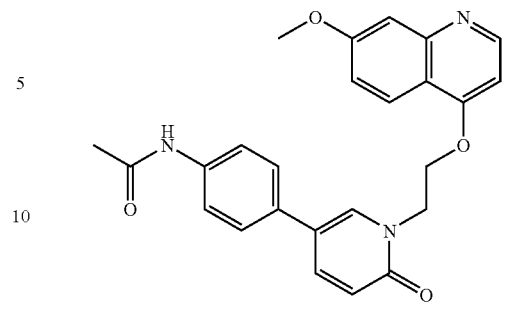

N-(4-(1-(2-(7-Methoxyquinolin-4-yloxy)ethyl)-6-oxo-1,6-dihydropyridin-3-yl)phenyl)acetamide This compound was prepared according to the procedure described in Example 16. MS (ESI pos. ion) m/z (MH+): 430.5. Calc'd exact mass for $C_{25}H_{23}N_3O_4$: 429.2. $^1$H NMR (300 MHz, MeOH-d$_4$) δ ppm 2.15 (s, 3H) 3.90 (s, 3H) 4.64 (s, 4H) 6.64 (d, J=9.35 Hz, 1H) 6.87 (d, J=5.41 Hz, 1H) 6.99 (dd, J=9.21, 2.48 Hz, 1H) 7.23 (d, J=2.34 Hz, 1H) 7.38 (d, J=8.77 Hz, 2H) 7.61 (d, J=8.77 Hz, 2H) 7.83 (dd, J=9.43, 2.70 Hz, 1H) 8.01 (d, J=9.21 Hz, 1H) 8.05 (d, J=2.34 Hz, 1H) 8.54 (d, J=5.41 Hz, 1H).

EXAMPLE 28

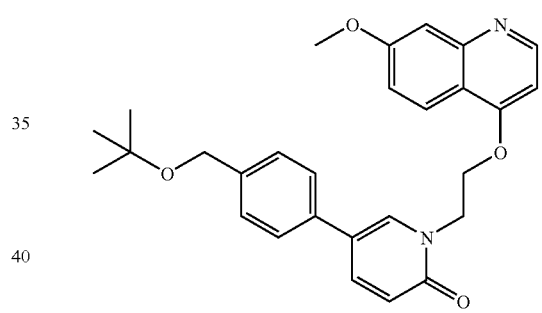

5-(4-(tert-Butoxymethyl)phenyl)-1-(2-(7-methoxyquinolin-4-yloxy)ethyl)pyridin-2(1H)-one This compound was prepared according to the procedure described in Example 16. MS (ESI pos. ion) m/z (MH+): 459.1. Calc'd Exact Mass for C28H30N2O4: 458.22.

EXAMPLE 29

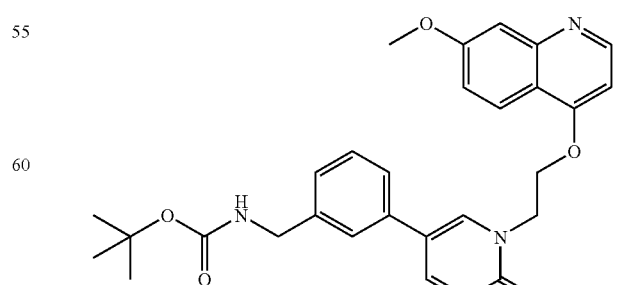

tert-Butyl (3-(1-(2-(7-methoxyquinolin-4-yloxy)ethyl)-6-oxo-1,6-dihydropyridin-3-yl)phenyl)methylcarbamate This compound was prepared according to the procedure described in Example 16. MS (ESI pos. ion) m/z (MH+): 502.1. Calc'd Exact Mass for C29H31N3O5: 501.23.

EXAMPLE 30

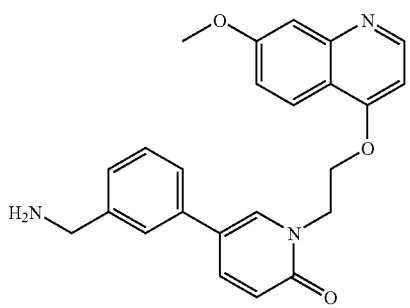

5-(3-(Aminomethyl)phenyl)-1-(2-(7-methoxyquinolin-4-yloxy)ethyl)pyridin-2(1H)-one This compound was prepared according to the procedure described in Example 16. A solution of tert-butyl (3-(1-(2-(7-methoxyquinolin-4-yloxy)ethyl)-6-oxo-1,6-dihydropyridin-3-yl)phenyl)methylcarbamate (0.3 g, 0.6 mmol) in 10 mL of saturated HCl in EtOAc was stirred at rt for 2 hours. The mixture was then concentrated in vacuo. The residue was washed with 50% Hex/EtOAc to give the desired product (0.2 g, 83% yield) as light yellow solid. MS (ESI pos. ion) m/z (MH+): 402.1. Calc'd Exact Mass for $C_{24}H_{23}N_3O_3$: 401.17.

EXAMPLE 31

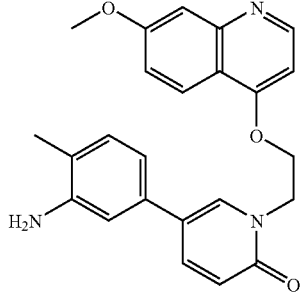

5-(3-Amino-4-methylphenyl)-1-(2-(7-methoxyquinolin-4-yloxy)ethyl)pyridin-2(1H)-one This compound was prepared according to the procedure described in Example 16. MS (ESI pos. ion) m/z (MH+): 402.1. Calc'd Exact Mass for $C_{24}H_{23}N_3O_3$: 401.17.

EXAMPLE 32

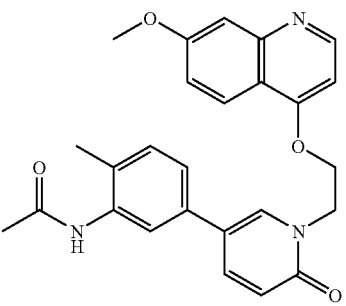

N-(3-(1-(2-(7-Methoxyquinolin-4-yloxy)ethyl)-6-oxo-1,6-dihydropyridin-3-yl)prop-2-ynyl)-2-(pyrrolidin-1-yl)acetamide To a solution of 5-(3-amino-4-methylphenyl)-1-(2-(7-methoxyquinolin-4-yloxy)ethyl)pyridin-2(1H)-one (0.12 g, 0.30 mmol) in 10 mL of CH$_2$Cl$_2$ at rt was added triethylamine (0.083 ml, 0.60 mmol) followed by acetic anhydride (0.042 ml, 0.45 mmol). The reaction was stirred at rt for 4 hours and was then concentrated in vacuo. The residue was dissolved in 50 mL of EtOAc and the resulted organic phase was washed with 20 mL of satd. NaHCO$_3$ followed by 20 mL of brine. The organic solution was dried over Na$_2$SO$_4$ and concentrated in vacuo. The residue was washed with 50% hex/EtOAc to give white solid as desired product (0.10 g, 75% yield). MS (ESI pos. ion) m/z (MH+): 444.1. Calc'd Exact Mass for $C_{26}H_{25}N_3O_4$: 443.18.

EXAMPLE 33

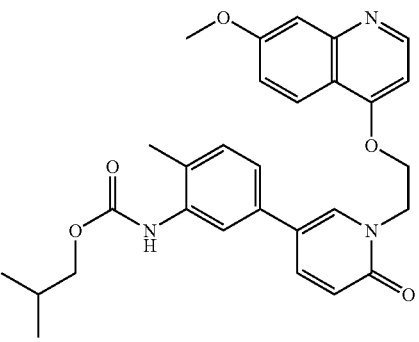

Isobutyl 5-(1-(2-(7-methoxyquinolin-4-yloxy)ethyl)-6-oxo-1,6-dihydropyridin-3-yl)-2-methylphenylcarbamate To a solution of 5-(3-amino-4-methylphenyl)-1-(2-(7-methoxyquinolin-4-yloxy)ethyl)pyridin-2(1H)-one (0.10 g, 0.25 mmol) in 10 mL of CH$_2$Cl$_2$ at rt was added triethylamine (0.083 ml, 0.60 mmol) followed by isobutyl chlorocarbonate (0.048 ml, 0.37 mmol). The reaction was stirred at rt for 4 hours and was then concentrated in vacuo. The residue was dissolved in 50 mL of EtOAc and the resulted organic phase was washed with 20 mL of satd. NaHCO$_3$ followed by 20 mL of brine. The organic solution was dried over $Na_2SO_4$ and concentrated in vacuo. The residue was washed with 50% hex/EtOAc to give white solid as desired product (0.0879 g, 70% yield). MS (ESI pos. ion) m/z (MH+): 502.1. Calc'd Exact Mass for $C_{29}H_{31}N_3O_5$: 501.23.

EXAMPLE 34

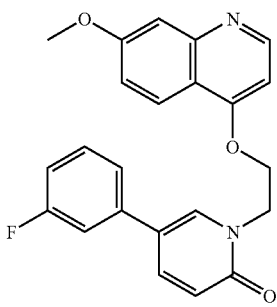

5-(3-Fluorophenyl)-1-(2-(7-methoxyquinolin-4-yloxy)ethyl)pyridin-2(1H)-one

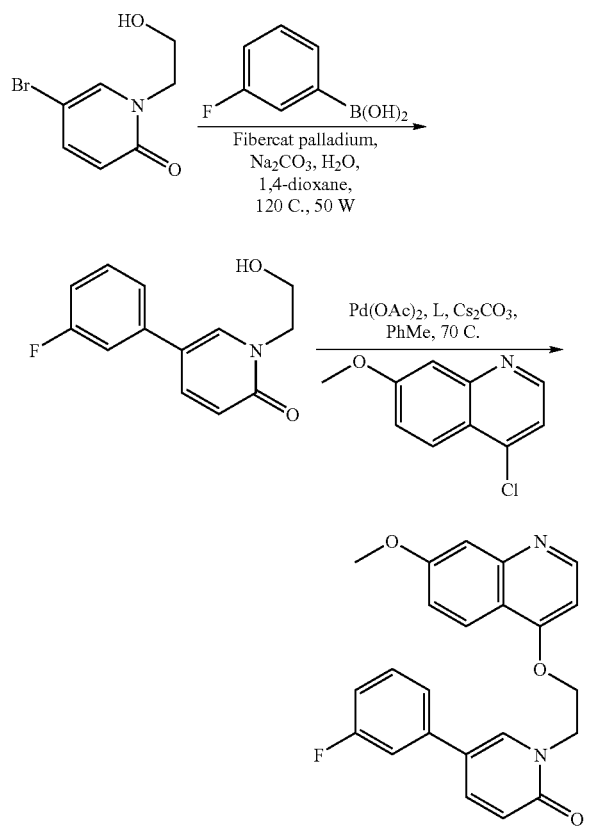

5-(3-Fluorophenyl)-1-(2-hydroxyethyl)pyridin-2(1H)-one. 5-Bromo-1-(2-hydroxyethyl)pyridin-2(1H)-one (100.7 mg, 462 µmol), 3-fluorophenylboronic acid (121.5 mg, 868 µmol), palladium fibercat catalyst (4.11%, 14.1 mg), and sodium carbonate (0.48 ml, 2.0 M in water, 960 µmol) were put in a microwave vial, and then 1,4-dioxane (0.69 ml) was added. The microwave vial was sealed and heated in the CEM microwave at 120° C. and 50 Watts for a 5 minute ramp time and then a 20-minute run time. The reaction was then cooled to room temperature, diluted with water, and extracted with 3:1 $CH_2Cl_2$/MeOH. The organic phases were combined, dried over sodium sulfate, filtered, concentrated, and dried under vacuum. The material was used for the next step. MS (ESI pos. ion) m/z (MH+): 234. Calc'd exact mass for $C_{13}H_{12}FNO_2$: 233.

5-(3-Fluorophenyl)-1-(2-(7-methoxyquinolin-4-yloxy)ethyl)pyridin-2(1H)-one. The crude 5-(3-fluorophenyl)-1-(2-hydroxyethyl)pyridin-2(1H)-one, 4-chloro-7-methoxyquinoline (107 mg, 553 µmol), cesium carbonate (191.2 mg, 587 µmol), palladium(II) acetate (24.6 mg, 110 µmol), and racemic-2-(di-t-butylphosphino)-1,1'-binaphthyl (50.2 mg, 126 µmol) were suspended in a microwave vial in toluene (3.0 ml) and sealed under argon. The tube was heated in a preheated oil bath (70° C.) and stirred for about 2 hours. The reaction was then cooled to room temperature and filtered through a silica gel filter [5:1 $CH_2Cl_2$/(2 N ammonia in MeOH)]. The filtrate was concentrated and purified on reverse phase HPLC (10%->95% MeCN/water with 0.1% TFA over 40 minutes on Shimatzu HPLC). The fractions with product were collected, concentrated, washed with $Et_2O$, and then purified on a silica gel column (25:1->10:1 $CH_2Cl_2$/MeOH->10:1 $CH_2Cl_2$/2 N ammonia in MeOH) to afford the desired product (22.8 mg, 58.4 µmol, 13% yield over two steps). MS (ESI pos. ion) m/z (MH+): 391. Calc'd exact mass for $C_{23}H_{19}FN_2O_3$: 390. $^1$H NMR (400 MHz, $CDCl_3$): 8.67 (d, J=5.0 Hz, 1H), 7.97 (d, J=9.0 Hz, 1H), 7.70 (d, J=2.0 Hz, 1H), 7.61 (dd, J=9.0 Hz, 2.0 Hz, 1H), 7.40-7.36 (m, 2H), 7.13 (d, J=8.0 Hz, 1H), 7.07-7.02 (m, 3H), 6.70 (d, J=9.0 Hz, 1H), 6.67 (d, J=5.2 Hz, 1H), 4.62-4.54 (m, 4H), 3.94 (s, 3H).

EXAMPLE 35

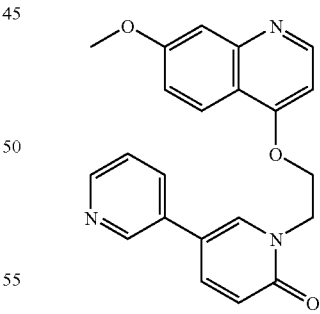

1-(2-(7-Methoxyquinolin-4-yloxy)ethyl)-5-(pyridin-3-yl)pyridin-2(1H)-one. This compound was prepared according to the procedure described in Example 34. MS (ESI pos. ion) m/z (MH+): 374. Calc'd exact mass for $C_{22}H_{19}N_3O_3$: 373. $^1$H NMR (400 MHz, $CDCl_3$): 8.69 (d, J=2.0 Hz, 1H), 8.66 (d, J=5.0 Hz, 1H), 8.61 (dd, J=5.0 Hz, 2.0 Hz, 1H), 7.93 (d, J=9.0 Hz, 1H), 7.71 (d, J=3.0 Hz, 1H), 7.65-7.59 (m, 2H), 7.36-7.32 (m, 2H), 7.04 (dd, J=9.0 Hz, 2.8 Hz, 1H), 6.73 (d, J=9.0 Hz, 1H), 6.66 (d, J=5.0 Hz, 1H), 4.62-4.55 (m, 4H), 3.93 (s, 3H).

EXAMPLE 36

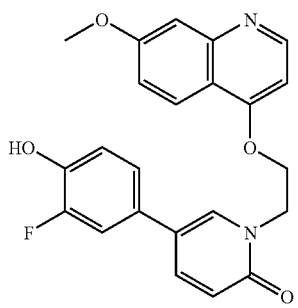

5-(3-Fluoro-4-hydroxyphenyl)-1-(2-(7-methoxyquinolin-4-yloxy)ethyl)pyridin-2(1H)-one This compound was prepared according to the procedure described in Example 34. MS (ESI pos. ion) m/z (MH+): 407. Calc'd exact mass for $C_{23}H_{19}FN_2O_4$: 406. $^1$H NMR (400 MHz, CDCl$_3$): 8.66 (d, J=5.0 Hz, 1H), 7.98 (d, J=9.0 Hz, 1H), 7.59 (d, J=3.0 Hz, 1H), 7.55 (dd, J=9.0 Hz, 3.0 Hz, 1H), 7.37 (d, J=2.6 Hz, 1H), 7.09-6.98 (m, 4H), 6.68 (d, J=7.0 Hz, 1H), 6.66 (d, J=2.0 Hz, 1H), 4.61-4.52 (m, 4H), 3.93 (s, 3H), 3.50 (s, 1H).

EXAMPLE 37

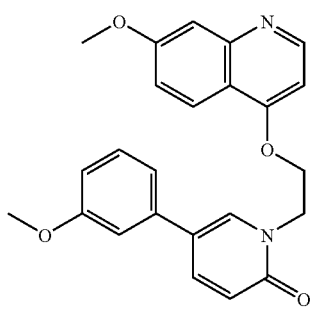

5-(3-Methoxyphenyl)-1-(2-(7-methoxyquinolin-4-yloxy)ethyl)pyridin-2(1H)-one

This compound was prepared according to the procedure described in Example 34. MS (ESI pos. ion) m/z (MH+): 403. Calc'd exact mass for $C_{24}H_{22}N_2O_4$: 402. $^1$H NMR (400 MHz, CDCl$_3$): 8.65 (d, J=5.5 Hz, 1H), 7.97 (d, J=9.5 Hz, 1H), 7.70 (d, J=3.0 Hz, 1H), 7.63 (dd, J=9.0 Hz, 3.0 Hz, 1H), 7.36-7.30 (m, 2H), 7.03 (dd, J=9.0 Hz, 3.0 Hz, 1H), 6.95 (d, J=8.0 Hz, 1H), 6.90-6.87 (m, 2H), 6.67 (d, J=9.5 Hz, 1H), 6.65 (d, J=5.0 Hz, 1H), 4.60-4.52 (m, 4H), 3.93 (s, 3H), 3.83 (s, 3H).

EXAMPLE 38

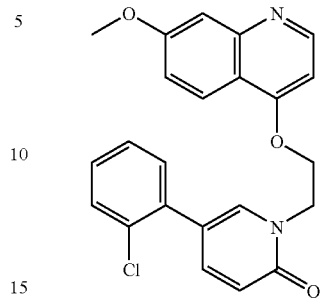

5-(2-Chlorophenyl)-1-(2-(7-methoxyquinolin-4-yloxy)ethyl)pyridin-2(1H)-one

This compound was prepared according to the procedure described in Example 34. MS (ESI pos. ion) m/z (MH+): 407. Calc'd exact mass for $C_{23}H_{19}ClN_2O_3$: 406. $^1$H NMR (400 MHz, CDCl$_3$): 8.67 (d, J=5.5 Hz, 1H), 7.97 (d, J=9.0 Hz, 1H), 7.58 (d, J=3.0 Hz, 1H), 7.53-7.47 (m, 2H), 7.37 (d, J=2.0 Hz, 1H), 7.35-7.28 (m, 2H), 7.17 (dd, J=7.0 Hz, 2.0 Hz, 1H), 7.06 (dd, J=9.0 Hz, 3.0 Hz, 1H), 6.66 (dd, J=6.0 Hz, 3.0 Hz, 2H), 4.60 (t, J=5.0 Hz, 2H), 4.53 (t, J=5.0 Hz, 2H), 3.95 (s, 3H).

EXAMPLE 39

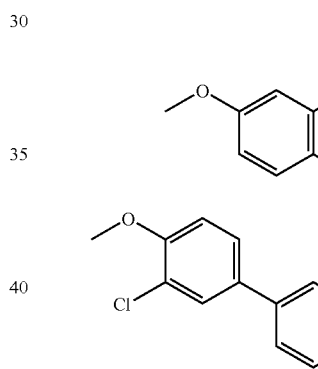

5-(3-Chloro-4-methoxyphenyl)-1-(2-(7-methoxyquinolin-4-yloxy)ethyl)pyridin-2(1H)-one This compound was prepared according to the procedure described in Example 34. MS (ESI pos. ion) m/z (MH+): 437. Calc'd exact mass for $C_{24}H_{21}ClN_2O_4$: 436.

EXAMPLE 40

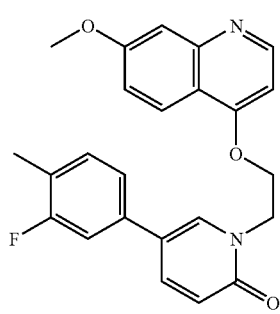

5-(3-Fluoro-4-methylphenyl)-1-(2-(7-methoxyquinolin-4-yloxy)ethyl)pyridin-2(1H)-one This compound was prepared according to the procedure described in Example 34. MS (ESI pos. ion) m/z (MH+): 405. Calc'd exact mass for $C_{24}H_{21}FN_2O_3$: 404.

EXAMPLE 41

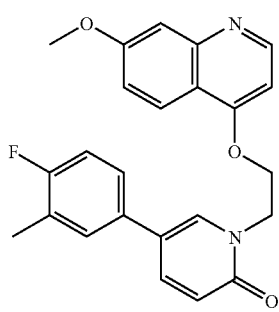

5-(4-Fluoro-3-methylphenyl)-1-(2-(7-methoxyquinolin-4-yloxy)ethyl)pyridin-2(1H)-one This compound was prepared according to the procedure described in Example 34C. MS (ESI pos. ion) m/z (MH+): 405. Calc'd exact mass for $C_{24}H_{21}FN_2O_3$: 404.

EXAMPLE 42

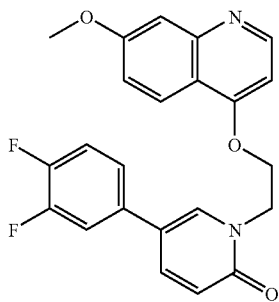

5-(3,4-Difluorophenyl)-1-(2-(7-methoxyquinolin-4-yloxy)ethyl)pyridin-2(1H)-one

This compound was prepared according to the procedure described in Example 34. MS (ESI pos. ion) m/z (MH+): 409. Calc'd exact mass for $C_{23}H_{18}F_2N_2O_3$: 408.

EXAMPLE 43

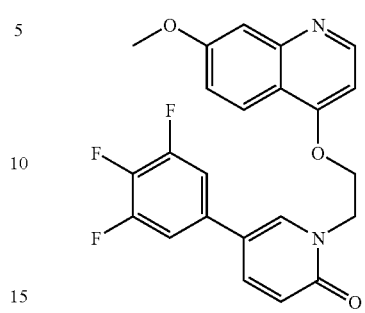

1-(2-(7-Methoxyquinolin-4-yloxy)ethyl)-5-(3,4,5-trifluorophenyl)pyridin-2(1H)-one This compound was prepared according to the procedure described in Example 2. MS (ESI pos. ion) m/z (MH+): 427. Calc'd exact mass for $C_{23}H_{17}F_3N_2O_3$: 426. $^1$HNMR (300 MHz, CDCl$_3$): δ 8.66 (d, J=6 Hz, 1H), 7.96 (d, J=9 Hz, 1H), 7.59 (d, J=3, 1H), 7.50 (dd, J=3, 9 Hz, 1H), 7.39 (m, 1H), 7.09 (dd, J=3, 9 Hz, 1H), 6.89 (m, 2H), 6.67 (m, 2H), 4.57 (m, 4H), 3.93 (s, 3H).

EXAMPLE 44

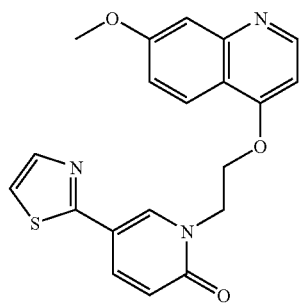

2-(2-(7-Methoxyquinolin-4-yloxy)ethyl)-6-(thiazol-2-yl)pyridazin-3(2H)-one

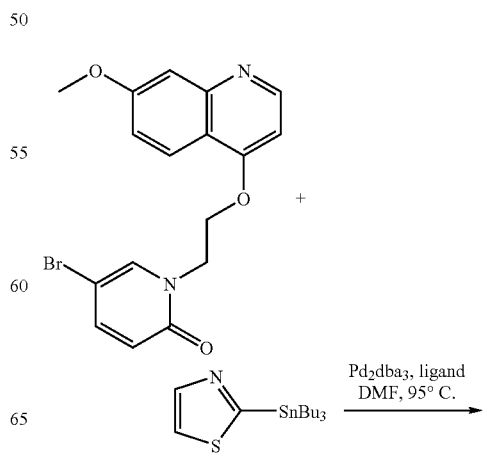

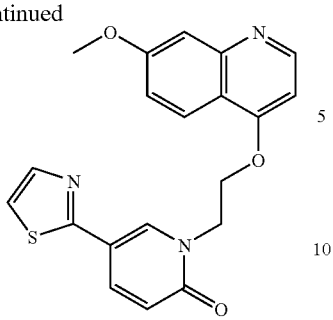

To a microwave tube was added 6-chloro-2-(2-(7-methoxyquinolin-4-yloxy)ethyl)pyridazin-3(2H)-one (0.1 g, 0.3 mmol), 2-tributylstannylthiazole (0.2 g, 0.6 mmol), tris(dibenzylideneacetone)dipalladium (0.01 g, 0.02 mmol), 2-(dicyclohexylphosphino)-2',6'-dimenthoxy-1,1'biphenyl (0.02 g, 0.05 mmol), and DMF (3 mL). The vial was sealed and heated at 90° C. for 20 h. The reaction mixture was partitioned between water/CH$_2$Cl$_2$. The aqueous layer was extracted with CH$_2$Cl$_2$. The combined organic layers were dried over MgSO$_4$ and concentrated. The crude product was purified using SiO$_2$ chromatography with CH$_2$Cl$_2$:MeOH=97%:3% solvent system to afford the product as light brownish solid (40 mg). MS (ESI pos. ion) m/z (MH+): 381.4. Calc'd exact mass for C$_{19}$H$_{16}$N$_4$O$_3$S: 380.1. $^1$H NMR (300 MHz, Chloroform-d) δ ppm 3.92 (s, 3H) 4.63 (t, J=5.26 Hz, 2H) 4.80 (t, J=5.26 Hz, 2H) 6.67 (d, J=5.26 Hz, 1H) 7.02 (dd, J=9.13, 2.56 Hz, 1H) 7.07 (d, J=9.65 Hz, 1H) 7.32 (d, J=2.48 Hz, 1H) 7.44 (d, J=3.22 Hz, 1H) 7.88 (d, J=3.22 Hz, 1H) 8.06 (d, J=9.06 Hz, 1H) 8.13 (d, J=9.65 Hz, 1H) 8.66 (d, J=5.26 Hz, 1H).

EXAMPLE 45

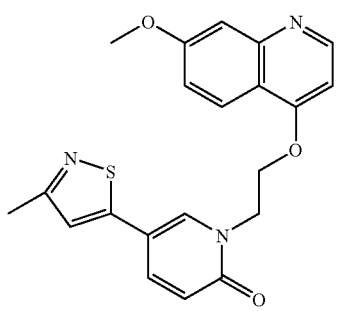

1-(2-(7-Methoxyquinolin-4-yloxy)ethyl)-5-(3-methylisothiazol-5-yl)pyridin-2(1H)-one Prepared similarly using 3-methyl-5-(trimethylstannyl)isothiazole according to the procedure described in Example 44. MS (ESI pos. ion) m/z (MH+): 394.3. Calc'd exact mass for C$_{21}$H$_{19}$N$_3$O$_3$S: 393.1. $^1$H NMR (300 MHz, Chloroform-d) δ ppm 2.51 (s, 3H) 3.94 (s, 3H) 4.55 (q, J=2.87 Hz, 4H) 6.60-6.67 (m, 1H) 6.69 (s, 1H) 6.92 (s, 1H) 7.11 (dd, J=9.06, 2.48 Hz, 1H) 7.38 (d, J=2.48 Hz, 1H) 7.54 (dd, J=9.35, 2.63 Hz, 1H) 7.82 (d, J=2.48 Hz, 1H) 7.97 (d, J=9.06 Hz, 1H) 8.66 (d, J=5.41 Hz, 1H).

EXAMPLE 46

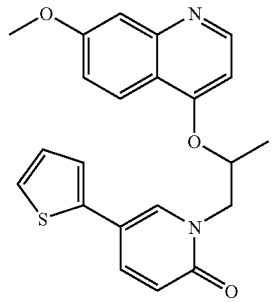

1-(2-(7-Methoxyquinolin-4-yloxy)propyl)-5-(thiophen-2-yl)pyridin-2(1H)-one

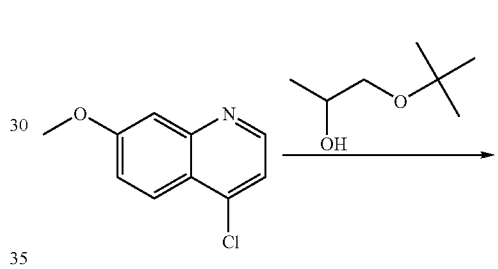

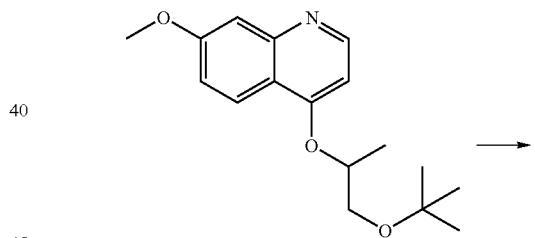

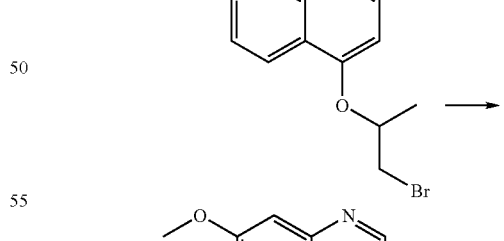

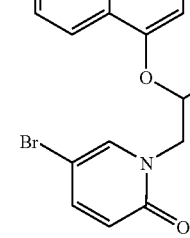

-continued

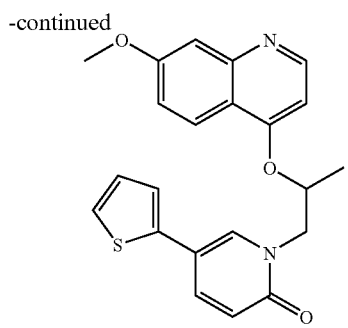

4-(1-tert-Butoxypropan-2-yloxy)-7-methoxyquinoline. To a stirring solution of 1-tert-butoxypropan-2-ol (293 μl, 1937 μmol) in DMF (2.5 mL) under nitrogen was added NaH (93 mg, 3873 μmol) at 23° C. After 10 min, 4-chloro-7-methoxyquinoline (250 mg, 1291 μmol) was added. The mixture was heated to 37° C. for 18 h. The reaction was partioned between 5% NaHCO$_3$ (10 mL) and CH$_2$Cl$_2$ (15%). The aqueous was extracted with CH$_2$Cl$_2$ (10 mL). The combined organics were dried with brine and MgSO$_4$, concentrated under reduced pressure from toluene, and purified on silica (12 g) eluting with 0-30% of 5% (MeOH/CH$_2$Cl$_2$). MS (ESI pos. ion) m/z (MH+): 290. Calc'd exact mass for C$_{17}$H$_{23}$NO$_3$: 291. $^1$H NMR (400 MHz, Chloroform-d) δ ppm 1.19 (s, 9H) 1.44 (d, J=6.26 Hz, 3H) 3.46-3.54 (m, 2H) 3.69 (dd, J=9.49, 5.77 Hz, 1H) 3.93 (s, 3H) 4.69-4.77 (m, 1H) 6.70 (d, J=5.28 Hz, 1H) 7.12 (dd, J=9.19, 2.54 Hz, 1H) 7.34 (d, J=2.54 Hz, 1H) 8.10 (d, J=9.19 Hz, 1H) 8.63 (d, J=5.48 Hz, 1H). $^{13}$C NMR (101 MHz, Chloroform-d) δ ppm 17.15, 27.45, 50.29, 55.40, 65.09, 73.31, 74.06, 100.45, 106.89, 116.62, 118.04, 123.38, 151.26, 151.58, 160.89, 161.07

2-(7-Methoxyquinolin-4-yloxy)propan-1-ol. A solution of 4-(1-tert-butoxypropan-2-yloxy)-7-methoxyquinoline in TFA (10 mL) was stirred for 45 min at 23° C. The solvent was removed under reduced pressure and the residue was partitioned between CH$_2$Cl$_2$ and 10% Na$_2$CO$_3$. The aqueous layer was extracted with CH$_2$Cl$_2$ (5 mL×4) and the combined organics were dried over MgSO$_4$. The mixture was purified on 12 grams of silica eluting with 0-100% of 5% MeOH/CH$_2$Cl$_2$. MS (ESI pos. ion) m/z (MH+): 234. Calc'd exact mass for C$_{13}$H$_{15}$NO$_3$: 233.

4-(1-Bromopropan-2-yloxy)-7-methoxyquinoline. To a stirred solution of 1-(7-methoxyquinolin-4-yloxy)propan-2-ol (235 mg, 1007 μmol) and 2-(7-methoxyquinolin-4-yloxy)propan-1-ol (235 mg, 1007 μmol) (mixture of isomers) in CH$_2$Cl$_2$ (3 mL) was added phosphorus tribromide (94.7 μl, 1007 μmol). The mixture was heated to reflux for 18 h. The mixture was quenched with 5% NaHCO$_3$, and was extracted with CH$_2$Cl$_2$ (3×5 mL). The combined organics were dried over MgSO$_4$ and concentrated to a white solid (150 mg) under reduced pressure. MS (ESI pos. ion) m/z (MH+): 296/298. Calc'd exact mass for C$_{13}$H$_{14}$BrNO$_2$: 295.

5-Bromo-1-(2-(7-methoxyquinolin-4-yloxy)propyl)pyridin-2(1H)-one.

To a stirring solution of 5-bromo-2(1H)-pyridone (100 mg, 575 μmol) in DMF (1 mL) under nitrogen was added sodium hydride (60% dispersion in mineral oil; 27.6 mg, 1149 μmol) and stirred for 10 min. To this suspension was added 4-(2-bromopropoxy)-7-methoxyquinoline (170 mg, 575 μmol) and 4-(1-bromopropan-2-yloxy)-7-methoxyquinoline (170 mg, 575 μmol) mixture in DMF (1 mL). The mixture was stirred at 40° C. for 48 h. The reaction was quenched with 5% NaHCO$_3$ and extracted with CH$_2$Cl$_2$ (4×10 mL). The combined organics were dried over MgSO$_4$, concentrated to a residue from toluene, and purified on 12 grams of silica eluting with 30-60% of 5% (MeOH/CH$_2$Cl$_2$). MS (ESI pos. ion) m/z (MH+): 389/391. Calc'd exact mass for C$_{18}$H$_{17}$BrN$_2$O$_3$: 388. $^1$H NMR (400 MHz, Chloroform-d) δ ppm 1.52 (d, J=6.26 Hz, 3H) 3.90-4.01 (m, 4H) 4.48 (dd, J=13.60, 3.23 Hz, 1H) 5.05-5.14 (m, 1H) 6.45 (d, J=9.59 Hz, 1H) 6.67 (d, J=5.48 Hz, 1H) 7.18 (dd, J=9.19, 2.54 Hz, 1H) 7.24-7.31 (m, 1H) 7.37 (d, J=2.15 Hz, 1H) 7.53 (d, J=2.54 Hz, 1H) 8.01 (d, J=9.19 Hz, 1H) 8.61 (d, J=5.48 Hz, 1H). $^{13}$C NMR (101 MHz, Chloroform-d) δ ppm 17.29, 54.82, 55.55, 71.78, 97.82, 100.08, 107.03, 116.03, 118.81, 121.93, 122.66, 138.56, 143.08, 151.11, 151.41, 160.12, 161.17.

1-(2-(7-Methoxyquinolin-4-yloxy)propyl)-5-(thiophen-2-yl)pyridin-2(1H)-one. A suspension of 5-bromo-1-(2-(7-methoxyquinolin-4-yloxy)propyl)pyridin-2(1H)-one (20 mg, 51 μmol), thiophen-2-ylboronic acid (13 mg, 103 μmol), 1,1'-bis(diphenylphosphino)ferrocene-palladium dichloride (2 mg, 3 μmol), and Na$_2$CO$_3$ (77 μl, 154 μmol) in DME (0.5 mL) was heated to 80° C. for 2 h. The mixture was purified on RP-HPLC and the product was netralized with CH$_2$Cl$_2$/NaOH (1 M). The product was lyophilized from 1:1 acetonitrile/water (1 mL) to give a white fluffy powder. MS (ESI pos. ion) m/z (MH+): 393. Calc'd exact mass for C$_{22}$H$_{20}$N$_2$O$_3$S: 392. $^1$H NMR (400 MHz, Chloroform-d) δ ppm 1.55 (d, J=6.02 Hz, 3H) 3.49 (d, J=3.01 Hz, 1H) 3.91 (s, 3H) 4.03 (dd, J=13.55, 8.03 Hz, 1H) 4.58 (dd, J=13.55, 3.01 Hz, 1H) 5.10-5.22 (m, 1H) 6.58 (d, J=9.54 Hz, 1H) 6.66 (d, J=5.02 Hz, 1H) 6.88 (d, J=3.01 Hz, 1H) 6.96-7.01 (m, 1H) 7.05 (dd, J=9.03, 2.51 Hz, 1H) 7.19 (d, J=5.02 Hz, 1H) 7.30 (d, J=2.01 Hz, 1H) 7.52 (dd, J=9.54, 2.51 Hz, 1H) 7.63 (d, J=2.51 Hz, 1H) 8.05 (d, J=9.03 Hz, 1H) 8.59 (d, J=5.52 Hz, 1H). $^{13}$C NMR (101 MHz, Chloroform-d) δ ppm 17.37, 53.44, 55.03, 55.49, 71.85, 100.05, 107.33, 114.41, 116.10, 118.50, 120.89, 122.78, 124.20, 127.97, 135.11, 138.95, 139.26, 151.43, 151.71, 160.01, 160.98, 161.84.

EXAMPLE 47

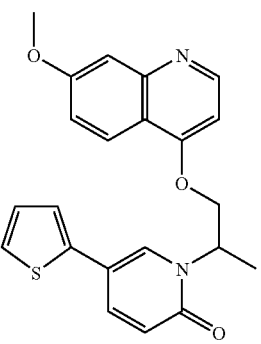

1-(1-(7-Methoxyquinolin-4-yloxy)propan-2-yl)-5-(thiophen-2-yl)pyridin-2(1H)-one

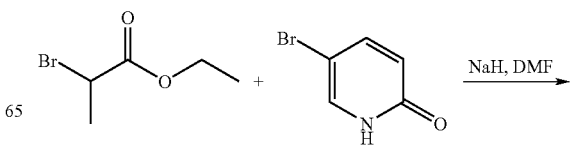

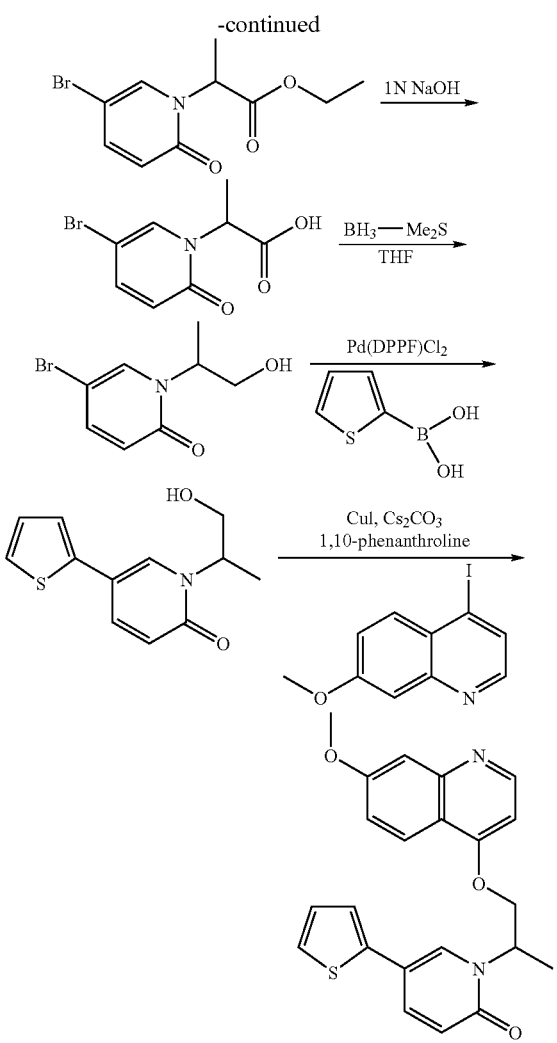

Ethyl 2-(5-bromo-2-oxopyridin-1(2H)-yl)propanoate. To a solution of 5-bromo-2(1H)-pyridone (7.8 g, 45 mmol) in 80 mL of DMF at 0° C. was added sodium hydride (60% dispersion in mineral oil, 2.1 g, 90 mmol). The mixture was stirred at 0° C. for 45 minutes. Ethyl 2-bromopropionate (9.7 g, 54 mmol) was then added via a syringe. The reaction was warmed up to rt and let stir for 16 hours. The reaction mixture was then poured into an ice-HCl (2N) solution until pH~2. The aqueous mixture was extracted with 2×100 mL of EtOAc. The combined organic phases were dried over Na$_2$SO$_4$ and concentrated in vacuo. The residue was chromatographed on a silica gel column (30% EtOAc/hexane to EtOAC) to give yellow oil (9.0 g, 73% yield) as desired product. MS (ESI pos. ion) m/z (MH+): 273.9. Calc'd Exact Mass for C$_{10}$H$_{12}$BrNO$_3$: 273.00.

2-(5-Bromo-2-oxopyridin-1(2H)-yl)propanoic acid. To a solution of ethyl 2-(5-bromo-2-oxopyridin-1(2H)-yl)propanoate (5.0 g, 18 mmol) in 40 mL of 1:1 THF/MeOH are rt was added 25 mL of 1N NaOH. The reaction was stirred at rt for 5 hours and was then acidified with 2N HCl to pH~2. The solid formed was collected and was washed with water and EtOAc to give white solid (4.2 g, 94% yield) as desired product. MS (ESI pos. ion) m/z (MH+): 245.9. Calc'd Exact Mass for C$_8$H$_8$BrNO$_3$: 244.97.

5-Bromo-1-(1-hydroxypropan-2-yl)pyridin-2(1H)-one. To a solution of 2-(5-bromo-2-oxopyridin-1(2H)-yl)propanoic acid (3.36 g, 13.7 mmol) in 50 mL of THF was added borane-dimethyl sulfide (3.89 ml, 41.0 mmol) via a syringe. The reaction was stirred at rt for 16 hours and was quenched with 10 mL of 1N HCl. The mixture was extracted with 70 mL of EtOAc twice. The combined organic phases were washed with brine and dried over Na$_2$SO$_4$. The solution was concentrated in vacuo to give a light yellow oil (2.50 g, 78.9% yield) which was used in the next step without further purification. MS (ESI pos. ion) m/z (MH+): 231.9. Calc'd Exact Mass for C$_8$H$_{10}$BrNO$_2$: 230.99.

1-(1-Hydroxypropan-2-yl)-5-(thiophen-2-yl)pyridin-2(1H)-one. To a solution of 5-bromo-1-(1-hydroxypropan-2-yl)pyridin-2(1H)-one (0.51 g, 2.2 mmol) and 2-thiopheneboronic acid (0.28 g, 2.2 mmol) in 30 mL of dioxane was added 6 mL of 1N Na$_2$CO$_3$ followed by 1,1'-bis(diphenylphosphino)ferrocene-palladium dichloride (0.16 g, 0.22 mmol). The reaction was heated to 90° C. for 12 hours. The mixture was then diluted with 30 mL of water and 80 mL of EtOAc. The organic phase was separated, washed with 40 mL of brine, dried over Na$_2$SO$_4$ and concentrated in vacuo. The residue was obtained as a greenish semi-solid (0.15 g, 29% yield). MS (ESI pos. ion) m/z (MH+): 236.0. Calc'd Exact Mass for C$_{12}$H$_{13}$NO$_2$S: 235.07.

1-(1-(7-Methoxyquinolin-4-yloxy)propan-2-yl)-5-(thiophen-2-yl)pyridin-2(1H)-one. To a solution of 1-(1-hydroxypropan-2-yl)-5-(thiophen-2-yl)pyridin-2(1H)-one (0.052 g, 0.22 mmol) and 4-iodo-7-methoxyquinoline (0.063 g, 0.22 mmol) in 3.0 mL of DMF was added cesium carbonate (Cs$_2$CO$_3$, 0.072 g, 0.22 mmol), 1,10-phenanthroline (0.020 g, 0.11 mmol) followed by copper iodide (CuI) (0.021 g, 0.11 mmol) in a microwave vial. The mixture was heated to 140° C. for 45 minutes. The mixture was then diluted with 40 mL of water and 60 mL of EtOAc. The organic phase was separated, washed with 30 mL of brine, dried over Na$_2$SO$_4$ and concentrated in vacuo. The crude product was purified by a MS-triggered Prep-HPLC to give light organic film 1-(1-(7-methoxyquinolin-4-yloxy)propan-2-yl)-5-(thiophen-2-yl)pyridin-2(1H)-one (0.015 g, 17% yield). MS (ESI pos. ion) m/z (MH+): 393.1. Calc'd Exact Mass for C$_{22}$H$_{20}$N$_2$O$_3$S: 392.12.

EXAMPLE 48

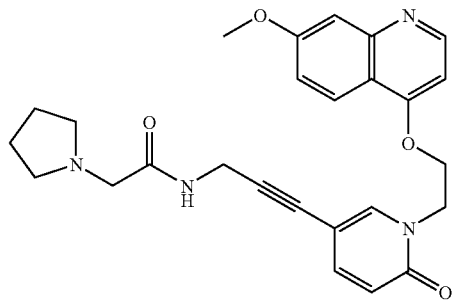

N-(3-(1-(2-(7-Methoxyquinolin-4-yloxy)ethyl)-6-oxo-1,6-dihydropyridin-3-yl)prop-2-ynyl)-2-(pyrrolidin-1-yl)acetamide To a 50 mL round bottom flask was charged with the 5-bromo-1-(2-(7-methoxyquinolin-4-yloxy)ethyl)pyridin-2(1H)-one (0.136 g, 0.4 mmol), trans-dichlorobis(triphenylphosphine)palladium (II) (0.005 g, 0.007 mmol), and copper (I) iodide (0.0002 ml, 0.007 mmol) along with a magnetic stirring bar and degassed and back-filled three times with $N_2$. Triethylamine (0.2 ml, 1 mmol) was introduced into the reaction flask using a syringe under the gaseous mixture atmosphere. Then N-(prop-2-ynyl)-2-(pyrrolidin-1-yl)acetamide (0.06 g, 0.4 mmol) was added to the reaction flask. After refluxing for 16 hours, the solvent was evaporated and the residue was shaken with 20 mL of saturated aqueous sodium bicarbonate solution and 50 mL of EtOAc. The organic layer was washed with 20 mL of brine and then dried over anhydrous sodium sulfate. The organic solution was concentrated in vacuo and the residue was purified by a Prep-HPLC to give a yellow solid (0.04 g, 24% yield). MS (ESI pos. ion) m/z (MH+): 461.1. Calc'd Exact Mass for $C_{26}H_{28}N_4O_4$: 460.21.

EXAMPLE 49

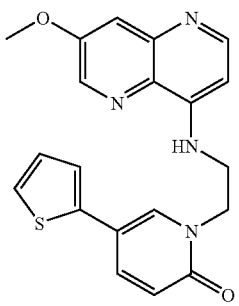

1-(2-(7-methoxy-1,5-naphthyridin-4-ylamino)ethyl)-5-(thiophen-2-yl)pyridin-2(1H)-one

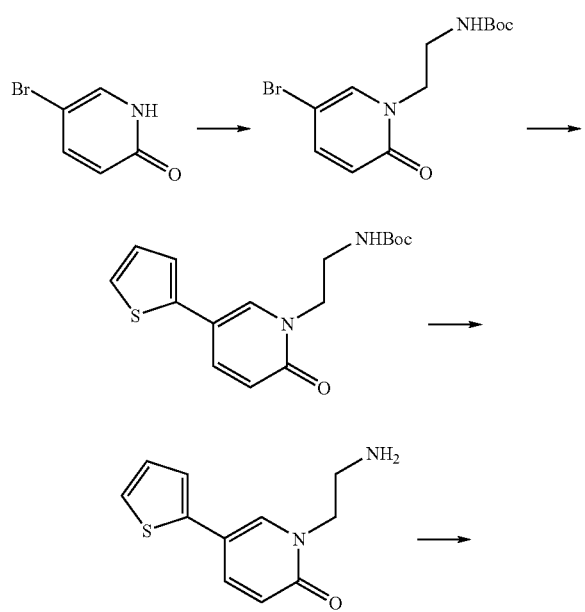

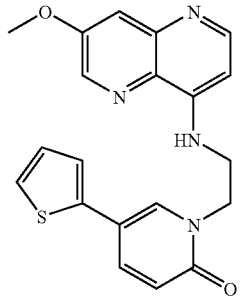

tert-Butyl 2-(5-bromo-2-oxopyridin-1(2H)-yl)ethylcarbamate. To a stirring solution of 5-bromo-2(1h)-pyridone (550 mg, 3161 μmol) in DMF (5 mL) under nitrogen was added NaH (60% dispersion in mineral oil; 152 mg, 6322 μmol). After for 10 min, 2-(boc-amino) ethyl bromide (779 mg, 3477 μmol) was added. The mixture was stirred for 18 h at 23° C. The mixture was partitioned between $CH_2Cl_2$ and 5% $NaHCO_3$. The aqueous was extracted with $CH_2Cl_2$ (10 mL) twice. The combined organics were dried over MgSO then concentrated to a solid from toluene under reduced pressure. The residue was purified on silica (40 g) eluting with 0-30% of 5% MeOH/$CH_2Cl_2$ to give the product as a white solid. MS (ESI pos. ion) m/z (MH+): 317/319. Calc'd exact mass for $C_{12}H_{17}BrN_2O_3$: 316. $^1$H NMR (400 MHz, Chloroform-d) δ ppm 1.44 (s, 9H) 3.45 (q, J=6.02 Hz, 2H) 4.03-4.09 (m, 2H) 4.92 (br. s., 1H) 6.48 (d, J=10.04 Hz, 1H) 7.34-7.39 (m, 2H). $^{13}$C NMR (101 MHz, Chloroform-d) δ ppm 26.08, 37.26, 47.20, 95.56, 119.79, 135.87, 140.53 tert-Butyl 2-(2-oxo-5-(thiophen-2-yl)pyridin-1(2H)-yl)ethylcarbamate. A suspension of tert-butyl 2-(5-bromo-2-oxopyridin-1(2H)-yl)ethylcarbamate (166 mg, 523 μmol), 2-thiopheneboronic acid (134 mg, 1047 μmol), $Na_2CO_3$ (785 μl, 1570 μmol) [2M], and 1,1'-bis(diphenylphosphino)ferrocene-palladium dichloride (31 mg, 42 μmol) in DME (2 mL) was heated to 85° C. for 45 min. The mixture was partitioned between $CH_2Cl_2$ and 10% $Na_2CO_3$ and the aqueous was extracted with $CH_2Cl_2$ (10 mL). The combined organics were dried over $MgSO_4$ and purified on silica (12 g) eluting with 0>50% of 5% MeOH/$CH_2Cl_2$, and isolated as orange crystals from ACN. MS (ESI pos. ion) m/z (MH+): 321 (MH+). Calc'd exact mass for $C_{16}H_{20}N_2O_3S$: 320. $^1$H NMR (400 MHz, Chloroform-d) δ ppm 1.42 (s, 9H) 3.51 (q, J=6.00 Hz, 2H) 4.14 (t, J=5.67 Hz, 2H) 4.96 (br. s., 1H) 6.63 (d, J=9.39 Hz, 1H) 7.01-7.09 (m, 2H) 7.23 (dd, J=4.99, 1.27 Hz, 1H) 7.47-7.51 (m, 1H) 7.61 (dd, J=9.39, 2.54 Hz, 1H).

1-(2-Aminoethyl)-5-(thiophen-2-yl)pyridin-2(1H)-one. To a solution of tert-butyl 2-(2-oxo-5-(thiophen-2-yl)pyridin-1(2H)-yl)ethylcarbamate (125 mg, 390 μmol) in $CH_2Cl_2$ (1 mL) was added TFA (5 mL) and stirred for 30 min at 23° C. Solvents removed under reduced pressure and residue partioned between $CH_2Cl_2$ (10 mL) and 1M NaOH (5 mL). The organic layer was dried over $MgSO_4$ and reduced to a brown oil under reduced pressure. MS (ESI pos. ion) m/z (MH+): 221 (MH+). Calc'd exact mass for $C_{11}H_{12}N_2OS$: 220.

1-(2-(7-methoxy-1,5-naphthyridin-4-ylamino)ethyl)-5-(thiophen-2-yl)pyridin-2(1H)-one. A suspension of 8-chloro-3-methoxy-1,5-naphthyridine (35 mg, 182 μmol) and 1-(2-aminoethyl)-5-(thiophen-2-yl)pyridin-2(1H)-one (40 mg, 182 μmol) in iPrOH (0.5 mL) was heated to 100° C. overnight. The mixture was partitioned between $CH_2Cl_2$ (10 mL) and 1M NaOH (5 mL). The aqueous was further extracted with $CH_2Cl_2$ (2×5 mL) and combined organics dried over MgSO4 then purified on silica (12 g) eluting with 15-60% of 5% (MeOH/CH$_2$Cl$_2$). MS (ESI pos. ion) m/z (MH+): 379. Calc'd exact mass for C$_{20}$H$_{18}$N$_4$O$_2$S: 378. $^1$H NMR (400 MHz, Chloroform-d) δ ppm 3.09 (br. s., 1H) 3.85 (q, J=6.13 Hz, 2H) 3.93 (s, 3H) 4.28 (t, J=5.97 Hz, 2H) 6.57 (d, J=5.48 Hz, 1H) 6.65 (d, J=9.59 Hz, 1H) 6.81 (d, J=2.74 Hz, 1H) 6.91-7.00 (m, 2H) 7.10-7.15 (m, 1H) 7.34 (d, J=2.54 Hz, 1H) 7.50-7.58 (m, 2H) 8.40 (d, J=2.74 Hz, 1H) 8.45 (d, J=5.48 Hz, 1H).

EXAMPLE 50

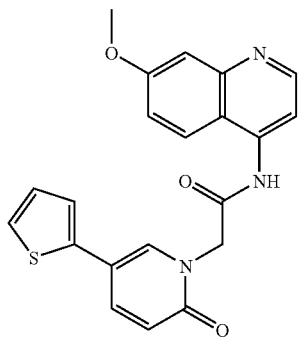

N-(7-Methoxyquinolin-4-yl)-2-(2-oxo-5-(thiophen-2-yl)pyridin-1(2H)-yl)acetamide

To a solution of 7-methoxyquinolin-4-amine (0.13 g, 0.77 mmol) and 2-(2-oxo-5-(thiophen-2-yl)pyridin-1(2H)-yl)acetic acid (0.15 g, 0.64 mmol) in 5 mL of DMF at rt was added triethylamine (0.13 ml, 0.96 mmol) followed by HATU (0.44 g, 1.1 mmol) solid. The reaction was then heated up to 40° C. for 8 hours and was cooled to rt and diluted with 60 mL of EtOAc and 30 mL of satd. NaHCO$_3$ (aq.) solution. The organic phase was separated, washed with 30 mL of brine and dried over Na$_2$SO$_4$ and concentrated in vacuo. The residue was purified by a silica gel column chromatography (EtOAc to 10% MeOH/EtOAc) to give white (0.10 g, 40% yield). MS (ESI pos. ion) m/z (MH+): 392.1. Calc'd Exact Mass for C$_{21}$H$_{17}$N$_3$O$_3$S: 391.1.

EXAMPLE 51

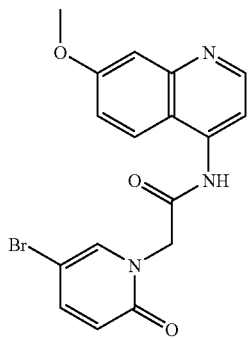

2-(5-Bromo-2-oxopyridin-1(2H)-yl)-N-(7-methoxyquinolin-4-yl)acetamide. To a solution of 7-methoxyquinolin-4-amine (0.275 g, 2 mmol) and 2-(5-bromo-2-oxopyridin-1(2H)-yl)acetic acid (0.273 g, 1 mmol) in 5 mL of DMF at rt was added triethylamine (0.2 ml, 2 mmol) followed by HATU (0.7 g, 2 mmol) solid. The reaction was then heated up to 40° C. for 8 hours and was cooled to rt and diluted with 60 mL of EtOAc and 30 mL of satd. NaHCO$_3$ solution. The organic phase was separated, washed with 30 mL of brine and dried over Na$_2$SO$_4$ and concentrated in vacuo. The residue was purified by a silica gel column chromatography (EtOAc to 10% MeOH/EtOAc) to give a white solid (0.05 g, 11% yield). MS (ESI pos. ion) m/z (MH+): 388.0. Calc'd Exact Mass for C$_{17}$H$_{14}$BrN$_3$O$_3$: 387.02.

EXAMPLE 52

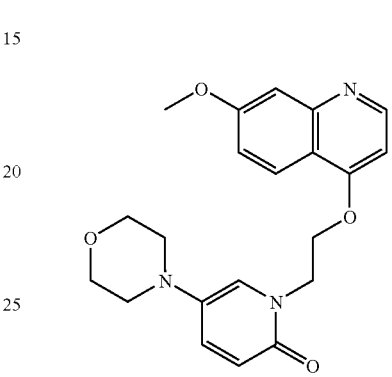

1-(2-(7-Methoxyquinolin-4-yloxy)ethyl)-5-morpholinopyridin-2(1H)-one

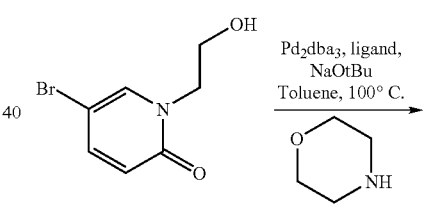

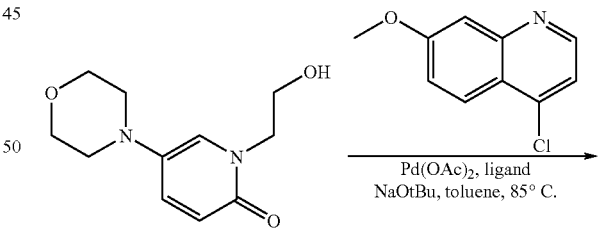

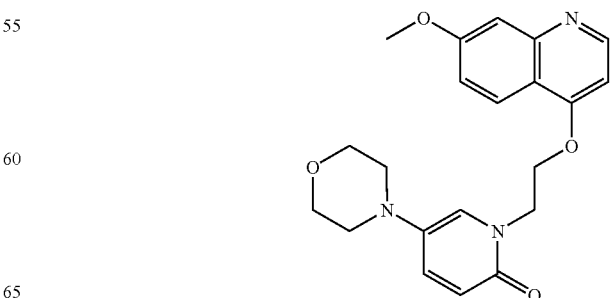

1-(2-Hydroxyethyl)-5-morpholinopyridin-2(1H)-one. To a flame-dry round bottomed flask was added 5-bromo-1-(2-hydroxyethyl)pyridin-2(1H)-one (0.1 g, 0.5 mmol), morpholine (0.1 g, 1 mmol), tris(dibenzylideneacetone)dipalladium (0) (0.004 g, 0.005 mmol), Ru-Phos (13 mg, 0.0275 mmol), sodium 2-methylpropan-2-olate (0.002 g, 0.02 mmol) and toluene (0.8 mL). The resulting mixture was heated at 100° C. for 20 h. The mixture was cooled to rt and passed through the celite to separate the inorganic solid. The filtrate was partitioned between EtOAc/water. The organic layer was washed with brine, dried over $MgSO_4$ and concentrated. The crude product was purified using $SiO_2$ chromatography with $CH_2Cl_2$:MeOH=95%:5% solvent system to afford the product as brown liquid (15 mg). MS (ESI pos. ion) m/z (MH+): 225.3. Calc'd exact mass for $C_{11}H_{16}N_2O_3$: 224.2. $^1$H NMR (400 MHz, Chloroform-d) δ ppm 2.85-2.93 (m, 4H) 3.80-3.87 (m, 4H) 3.94-4.01 (m, 2H) 4.10-4.16 (m, 2H) 6.61 (d, J=9.54 Hz, 1H) 6.74 (d, J=2.51 Hz, 1H) 7.31 (dd, J=9.79, 2.76 Hz, 1H).

1-(2-(7-Methoxyquinolin-4-yloxy)ethyl)-5-morpholinopyridin-2(1H)-one. To a solution of 1-(2-hydroxyethyl)-5-morpholinopyridin-2(1H)-one (0.06 g, 0.3 mmol) in toluene (3 mL) was added 7-methoxyquinoline (0.09 g, 0.5 mmol), racemic-2-(di-t-butylphosphino)-1,1'-binaphthyl (0.03 g, 0.08 mmol), sodium tert-butoxide (0.05 g, 0.5 mmol), and palladium(II) acetate (0.06 g, 0.3 mmol). The reaction mixture was heated to 80° C. under $N_2$ overnight. The reaction was cooled to rt and passed through a pad of celite. The celite pad was rinsed with $CH_2Cl_2$ and the solvent was removed. The crude product was purified using $SiO_2$ chromatography with $CH_2Cl_2$:MeOH=95%:5% solvent system to afford the product as green solid (12 mg). MS (ESI pos. ion) m/z (MH+): 382.3. Calc'd exact mass for $C_{21}H_{23}N_3O_4$: 381.4. $^1$H NMR (300 MHz, Chloroform-d) δ ppm 2.76-2.84 (m, 4H) 3.76-3.84 (m, 4H) 3.95 (s, 3H) 4.41-4.47 (m, 2H) 4.53-4.59 (m, 2H) 6.59 (d, J=9.79 Hz, 1H) 6.64 (d, J=5.41 Hz, 1H) 6.87 (d, J=2.92 Hz, 1H) 7.13 (dd, J=9.06, 2.48 Hz, 1H) 7.29 (d, J=3.07 Hz, 1H) 7.37 (d, J=2.34 Hz, 1H) 8.01 (d, J=9.21 Hz, 1H) 8.65 (d, J=5.26 Hz, 1H).

EXAMPLE 53

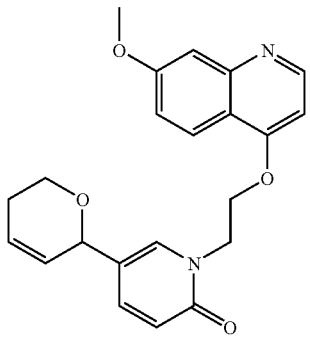

5-(5,6-dihydro-2H-pyran-2-yl-1-(2-(7-Methoxyquinolin-4-yloxy)ethyl)pyridin-2(1H)-one

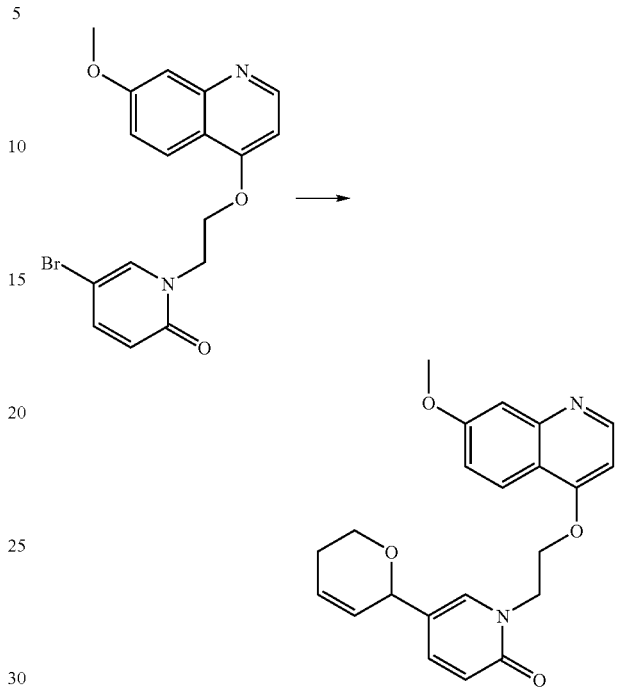

A 10 mL Schlenk-type flask was charged with tris(dibenzylideneacetone)dipalladium (0) (0.036 g, 0.039 mmol), 2 mL dioxane, and swept with Ar. To the solution was added tri-tert-butylphosphine (0.16 g, 0.079 mmol), N-methyldicyclohexylamine (0.077 g, 0.39 mmol) and a stirrer bar. The solution was stirred for 15 min, and treated with 5-bromo-1-(2-(7-methoxyquinolin-4-yloxy)ethyl)pyridin-2(1H)-one (0.0295 g, 0.079 mmol) followed by 2H-3,4-dihydropyran (0.14 mL, 1.6 mmol). The solution was heated to 100° C. for 72 h, and cooled. To the solution was added Silica carbonate (Silicycle, Inc., 0.23 g, 0.16 mmol). The slurry was stirred for 15 min, diluted with 2 mL $CH_2Cl_2$ and filtered. The silica was washed with 20 mL $CH_2Cl_2$, and the filtrate was concentrated in vacuo. The residue was dissolved in 2 mL THF and treated with Silica Propyl sulfonic acid (Silicycle, Inc., 0.37 g, 0.27 mmol). The slurry was stirred for 20 min, and filtered. The Silica was washed with THF (5 mL), and EtOH (5 mL). The filtrates were discarded. The silica was eluted with 2N $NH_3$ in EtOH (5 mL), followed by 10 mL EtOH. The filtrate was concentrated in vacuo. The residue was loaded onto a 19×150 mm Waters Xterra Prep C18 OBD column (100 Å pore diameter, 5 μm particle size, spherical shape, PN 186002381; Gradient: 0→5 min@20 mL/min, 25% B; 5.0→35 min@20 mL/min, linear gradient to 55% B; 35→45@20 mL/min, isocratic at 55% B, 45→55 min@20 mL/min, step to 100% B; 55→60 min@20 mL/min, step to 25% B; 60 min end). A=10 mM $NH_4$ Carbonate in water, pH 8.6, B=ACN. A band that eluted from 4.6-5.1 minutes was isolated. The solvent was removed in vacuo to afford 5-(5,6-dihydro-2H-pyran-2-yl-1-(2-(7-methoxyquinolin-4-yloxy)ethyl)pyridin-2(1H)-one.
$^1$H NMR (400 MHz, $CDCl_3$) δ ppm 1.97 (br. s., 1 H) 3.94 (s, 3H) 4.46 (td, J=5.18, 1.27 Hz, 2H) 4.53 (td, J=5.18, 1.27 Hz, 2H) 6.21 (td, J=6.70, 1.37 Hz, 1H) 6.60 (ddd, J=9.17, 1.25, 0.73 Hz, 1H) 6.64 (d, J=5.38 Hz, 1H) 7.14 (dd, J=9.10, 2.54 Hz, 1H) 7.35 (ddd, J=9.17, 6.77, 1.96 Hz, 1H) 7.37 (d, J=2.35

Hz, 1H) 7.96 (d, J=9.10 Hz, 1H) 8.65 (d, J=5.28 Hz, 1H). $^{13}$C NMR (101 MHz, CDCl$_3$) δ ppm 49.49 (s, 1 C) 55.48 (s, 1 C) 65.74 (s, 1 C) 99.46 (s, 1 C) 105.95 (s, 1 C) 107.20 (s, 1 C) 115.66 (s, 1 C) 118.61 (s, 1 C) 121.11 (s, 1 C) 122.56 (s, 1 C) 138.49 (s, 1 C) 140.07 (s, 1 C) 151.07 (s, 1 C) 151.63 (s, 1 C) 160.86 (s, 1 C) 161.04 (s, 1 C) 162.60 (s, 1 C). MS (ESI pos. ion) m/z (MH+): 297.1, calcd for C$_{17}$H$_{16}$F$_3$N$_2$O$_3$+H$^+$=297.1.

EXAMPLE 54

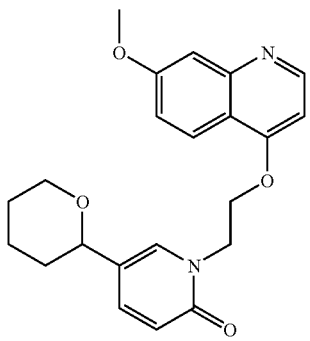

1-(2-(7-Methoxyquinolin-4-yloxy)ethyl)-5-(tetrahydro-2H-pyran-2-yl)pyridin-2(1H)-one A 15 mL, 1-neck round bottom flask was charged with 5-(5,6-dihydro-2H-pyran-2-yl)-1-(2-(7-methoxyquinolin-4-yloxy)ethyl)pyridin-2(1H)-one (0.006 g, 0.02 mmol), 2 mL dry THF, and a stirbar. The solution was cooled to 0° C., and carefully evacuated and refilled with N$_2$ (three times). To the stirring solution was added Platinum oxide (0.004 g, 0.02 mmol). The solution was carefully evacuated and refilled with hydrogen from a balloon. The cooling bath was removed, and the reaction was stirred overnight. The solution was filtered through a 0.22 uM frit, and the filtrate was concentrated in vacuo. The residue was dissolved in 1 mL EtOH and treated with Silica propyl sulfonic acid (Silicycle, Inc., 0.04 g, 0.03 mmol). The slurry was swirled occasionally for 15 min, filtered and washed with EtOH (2×2 mL). The silica was then eluted with 1 mL of 2N NH$_3$ in EtOH, followed by 2 mL of EtOH. The ammonia solution was concentrated in vacuo to afford 1-(2-(7-methoxyquinolin-4-yloxy)ethyl)-5-(tetrahydro-2H-pyran-2-yl)pyridin-2(1H)-one. $^1$H NMR (400 MHz, CDCl$_3$) δ ppm 1.36-1.49 (m, 1H) 1.55-1.70 (m, 3H) 1.70-1.78 (m, 1H) 1.89-1.97 (m, 1H) 3.54-3.64 (m, 1H) 3.94 (s, 3H) 4.07-4.18 (m, 2H) 4.43-4.54 (m, 4H) 6.56 (d, J=9.29 Hz, 1H) 6.62 (d, J=5.28 Hz, 1H) 7.11 (dd, J=9.19, 2.54 Hz, 1H) 7.30 (dd, J=9.34, 2.49 Hz, 1H) 7.36 (d, J=2.54 Hz, 1H) 7.55 (d, J=2.54 Hz, 1H) 8.05 (d, J=9.10 Hz, 1H) 8.64 (d, J=5.28 Hz, 1H). $^{13}$C NMR (101 MHz, CDCl$_3$) δ ppm 23.59 (s, 1 C) 25.71 (s, 1 C) 33.10 (s, 1 C) 49.18 (s, 1 C) 55.47 (s, 1 C) 65.75 (s, 1 C) 69.01 (s, 1 C) 76.55 (s, 1 C) 99.42 (s, 1 C) 107.11 (s, 1 C) 115.71 (s, 1 C) 118.42 (s, 1 C) 120.46 (s, 1 C) 121.23 (s, 1 C) 122.95 (s, 1 C) 135.65 (s, 1 C) 138.91 (s, 1 C) 151.13 (s, 1 C) 151.70 (s, 1 C) 160.84 (s, 1 C) 160.98 (s, 1 C) 162.22 (s, 1 C). MS (ESI pos. ion) m/z (MH+): 381.2, calcd for C$_{22}$H$_{24}$N$_2$O$_4^+$H$^+$=381.2.

EXAMPLE 55

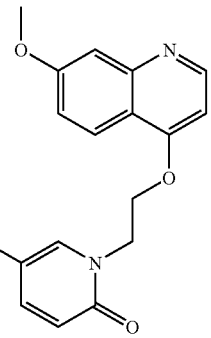

5-((2R,3S,4S)-, 5-((2S,3R,4R)-, 5-((2S,3S,4S) and 5-((2R,3R,4R)-3,4-Dihydroxy-tetrahydro-2H-pyran-2-yl)-1-(2-(7-methoxyquinolin-4-yloxy)ethyl)pyridin-2(1H)-one A dry HPLC vial was charged with 5-(5,6-dihydro-2H-pyran-2-yl)-1-(2-(7-methoxyquinolin-4-yloxy)ethyl)pyridin-2(1H)-one (0.0113 g, 0.030 mmol), and a spin vane. To the vial was added 200 μL t-butanol, 200 μL acetone, and 100 μL water. The solution was cooled to 0° C., and treated with OsO$_4$ (0.011 mL, 0.0030 mmol). The reaction was stirred for 24 h at 0° C., and then 8 h at room temperature. The slurry was treated with Si-diphenylphosphine (Silicycle, Inc., 0.12 g, 0.12 mmol). The slurry was stirred for 4 h, filtered and concentrated in vacuo. The solids were washed with MeOH (2×1 mL), and the filtrates were concentrated in vacuo. The solids were heated into 1 mL 30% aqueous Methanol, and filtered. The solution was concentrated in vacuo to afford the anti-diol.

Spectral data for anti-diols 5-((2R,3S,4S)-, 5-((2S,3R,4R)-3,4-dihydroxy-tetrahydro-2H-pyran-2-yl)-1-(2-(7-methoxyquinolin-4-yloxy)ethyl)pyridin-2(1H)-one: $^1$H NMR (600 MHz, D$_2$O) δ ppm 1.83-1.87 (m, 1H) 1.94-1.98 (m, 1H) 1.99 (s, 3H) 3.64 (dd, J=10.01, 3.02 Hz, 1H) 3.69 (dd, J=11.52, 5.10 Hz, 1H) 3.77 (ddd, J=13.03, 11.52, 2.08 Hz, 1H) 3.97 (s, 3H) 4.20 (q, J=2.83 Hz, 1H) 4.28 (d, J=10.01 Hz, 1H) 4.56 (ddd, J=14.73, 6.42, 4.34 Hz, 1H) 4.65 (ddd, J=14.73, 4.44, 4.25 Hz, 1H) 4.83 (d, J=4.34 Hz, 1H) 4.84 (dd, J=3.59, 1.13 Hz, 1H) 6.65 (d, J=9.25 Hz, 1H) 7.14 (d, J=6.80 Hz, 1H) 7.22 (d, J=2.46 Hz, 1H) 7.34 (dd, J=9.35, 2.36 Hz, 1H) 7.63 (dd, J=9.44, 2.45 Hz, 1H) 7.90 (d, J=2.46 Hz, 1H) 8.14 (d, J=9.25 Hz, 1H) 8.62 (d, J=6.80 Hz, 1H). $^{13}$C NMR (151 MHz, D$_2$O) δ ppm 21.50 (s, 2 C) 31.66 (s, 1 C) 49.15 (s, 1 C) 56.18 (s, 1 C) 62.22 (s, 1 C) 66.70 (s, 1 C) 67.84 (s, 1 C) 70.34 (s, 1 C) 74.62 (s, 1 C) 99.25 (s, 1 C) 100.67 (s, 1 C) 115.12 (s, 1 C) 119.48 (s, 1 C) 119.62 (s, 1 C) 120.74 (s, 1 C) 124.80 (s, 1 C) 139.61 (s, 1 C) 141.28 (s, 1 C) 141.31 (s, 1 C) 145.00 (s, 1 C) 163.85 (s, 1 C) 164.20 (s, 1 C) 167.59 (s, 1 C) 178.55 (s, 1 C). MS (ESI pos. ion) m/z (MH+): 413.2, calcd for C$_{22}$H$_{24}$N$_2$O$_4$+H$^+$=413.2.

Spectral data for syn-diols 5-((2S,3S,4S)-, 5-((2R,3R,4R)-3,4-dihydroxy-tetrahydro-2H-pyran-2-yl)-1-(2-(7-methoxyquinolin-4-yloxy)ethyl)pyridin-2(1H)-one: The filtrate following the isolation on the anti-diol was concentrated in vacuo. The residue was loaded onto a 19×150 mm Waters Xterra Prep C18 OBD column (100 Å pore diameter, 5 μm particle size, spherical shape, PN 186002381; Gradient: 0→5 min@20 mL/min, 10% B; 5.0→35 min@20 mL/min, linear gradient to 40% B; 35→45@20 mL/min, isocratic at 40% B, 45→55 min@20 mL/min, step to 100% B; 55→60 min@20 mL/min, step to 10% B; 60 min end). A=10 mM NH$_4$ Carbonate in water, pH 8.6, B=ACN. A band that eluted from 13.8-14.4 minutes was isolated. The solvent was removed in vacuo to afford syn-diol. $^1$H NMR (600 MHz, D$_2$O) δ ppm 1.89-2.06 (m, 2H) 3.51 (dd, J=9.82, 3.02 Hz, 1H) 3.80 (dd, J=11.99, 5.00 Hz, 1H) 3.91-3.95 (m, J=3.78 Hz, 1H) 3.95 (s, 3H) 4.21 (q, J=2.83 Hz, 1H) 4.35 (d, J=9.82 Hz, 1H) 4.51-4.59 (m, 2H) 4.58-4.66 (m, 2H) 6.65 (d, J=9.25 Hz, 1H) 6.85 (d, J=5.85 Hz, 1H) 7.27 (dd, J=9.25, 2.46 Hz, 1H) 7.32 (d, J=2.08 Hz, 1H) 7.61 (dd, J=9.44, 2.45 Hz, 1H) 7.73 (d, J=2.08 Hz, 1H) 8.18 (d, J=9.25 Hz, 1H) 8.48 (s, 1H). MS (ESI pos. ion) m/z (MH+): 413.2, calcd for C$_{22}$H$_{24}$N$_2$O$_4$+H$^+$=413.2. Noesy and Cosy were recorded, data consistent with assigned syn-structure.

EXAMPLE 56

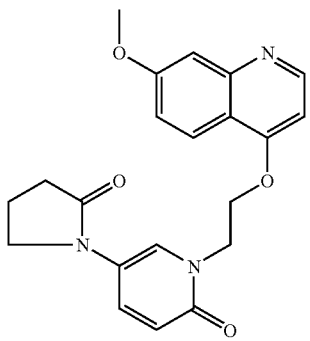

1-(2-(7-Methoxyquinolin-4-yloxy)ethyl)-5-(2-oxopyrrolidin-1-yl)pyridin-2(1H)-one General procedure is described in Klapars, A.; Huang, X.; Buchwald, S. L., A General and Efficient Copper Catalyst for the Amidation of Aryl Halides. *J. Am. Chem. Soc.* 2002, 124, (25), 7421-7428.

A dry 5 mL, 1-neck round bottom flask was charged with 5-bromo-1-(2-(7-methoxyquinolin-4-yloxy)ethyl)pyridin-2 (1H)-one (0.0476 g, 0.13 mmol), copper(I)iodide (0.0033 mL, 0.098 mmol), 1 mL toluene, N,N'-dimethylethylenediamine (0.017 g, 0.20 mmol), 2-pyrrolidone (0.048 mL, 0.63 mmol), cesium carbonate (0.12 g, 0.38 mmol), a stirbar and a reflux condenser. The solution was placed in a 120° C. bath for 6 h. The solution was cooled and retreated with the same amounts of CuI and diamine. The solution was heated to 120° C. for 16 h, and cooled. The solution was treated with 2 mL 50% concentrated NH$_4$OH, and stirred/sonicated for 2 min. The biphasic solution was loaded onto an unbuffered Varian Chem elute (10 mL, PN 12198007). The column was extracted with CH$_2$Cl$_2$ (5×10 mL), and the extracts were concentrated in vacuo. The residue was taken up in 0.5 mL 20% THF in DCE, and filtered. The solid was washed with 20% THF in DCE (2×0.5 mL). The solid was heated into 2 mL EtOH and filtered hot. The solvent was removed in vacuo to afford 1-(2-(7-methoxyquinolin-4-yloxy)ethyl)-5-(2-oxopyrrolidin-1-yl)pyridin-2(1H)-one. $^1$H NMR (400 MHz, CDCl$_3$) δ ppm 2.11-2.20 (m, 2H) 2.58 (t, J=8.12 Hz, 2H) 3.66 (t, J=6.94 Hz, 2H) 3.93 (s, 3H) 4.47-4.55 (m, 4H) 6.60 (dd, J=9.78, 0.59 Hz, 1H) 6.62 (d, J=5.38 Hz, 1H) 7.13 (dd, J=9.15, 2.59 Hz, 1H) 7.35 (d, J=2.54 Hz, 1H) 7.47 (dd, J=9.78, 2.93 Hz, 1H) 8.10 (d, J=9.10 Hz, 1H) 8.19 (dd, J=2.93, 0.59 Hz, 1H) 8.64 (d, J=5.28 Hz, 1H). $^{13}$C NMR (101 MHz, CDCl$_3$) δ ppm 17.91 (s, 1 C) 31.78 (s, 1 C) 48.39 (s, 1 C) 49.78 (s, 1 C) 55.46 (s, 1 C) 65.70 (s, 1 C) 99.42 (s, 1 C) 107.20 (s, 1 C) 115.69 (s, 1 C) 118.46 (s, 1C) 120.67 (s, 2 C) 123.03 (s, 1 C) 131.19 (s, 1 C) 134.70 (s, 1 C) 151.21 (s, 1 C) 151.76 (s, 1 C) 160.57 (s, 1 C) 160.79 (s, 1 C) 160.99 (s, 1 C) 173.95 (s, 1 C). MS (ESI pos. ion) m/z (MH+): 380.2, calcd for C$_{21}$H$_{21}$N$_3$O$_4$+H$^+$=380.2.

EXAMPLE 57

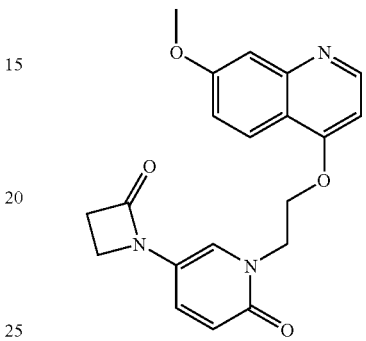

1-(2-(7-Methoxyquinolin-4-yloxy)ethyl)-5-(2-oxoazetidin-1-yl)pyridin-2(1H)-one

This compound was prepared according to the procedure described in Example 56. $^1$H NMR (400 MHz, CDCl$_3$) δ ppm 3.14 (t, J=4.40 Hz, 2H) 3.51 (t, J=4.40 Hz, 2H) 3.94 (s, 3H) 4.46-4.53 (m, 4H) 6.59-6.62 (m, 2H) 7.16 (dd, J=9.19, 2.54 Hz, 1H) 7.36 (dd, J=9.59, 2.93 Hz, 1H) 7.35 (d, J=2.64 Hz, 1H) 7.92 (d, J=2.84 Hz, 1H) 8.12 (d, J=9.10 Hz, 1H) 8.64 (d, J=5.28 Hz, 1H). $^{13}$C NMR (101 MHz, CDCl$_3$) δ ppm 36.80 (s, 1 C) 38.35 (s, 1 C) 49.42 (s, 1 C) 55.46 (s, 1 C) 65.80 (s, 1 C) 99.35 (s, 1 C) 107.25 (s, 1 C) 115.63 (s, 1 C) 118.58 (s, 1 C) 120.69 (s, 1 C) 121.50 (s, 1 C) 123.02 (s, 1 C) 126.62 (s, 1 C) 131.44 (s, 1 C) 151.19 (s, 1 C) 151.73 (s, 1 C) 160.45 (s, 1 C) 160.75 (s, 1 C) 161.04 (s, 1 C) 163.68 (s, 1 C).

EXAMPLE 58

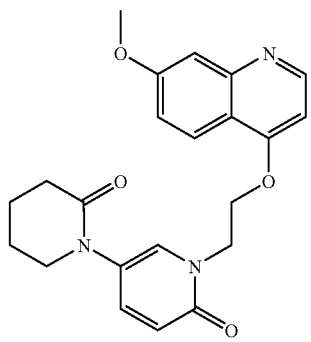

1-(2-(7-Methoxyquinolin-4-yloxy)ethyl)-5-(2-oxopiperidin-1-yl)pyridin-2(1H)-one

This compound was prepared according to the procedure described in Example 56. The crude sample was loaded onto a Waters Spherisorb S5 column (PN PSS830195, 20×250 mm, 60 Å pore, 5 μm particle size); flow=20 mL/min; A=20 mM NH₃ in 99:1 DCE-EtOH, B=EtOH; isocratic at 12% B. A band that eluted from 10.4-13.4 minutes was isolated. The solvent was removed in vacuo to afford the desired product. $^1$H NMR (400 MHz, CDCl₃) δ ppm 1.81-1.95 (m, 4H) 2.53 (t, J=6.46 Hz, 2H) 3.34 (t, J=6.06 Hz, 2H) 3.94 (s, 3H) 4.43 (t, J=4.94 Hz, 2H) 4.55 (t, J=4.94 Hz, 2H) 6.59 (dd, J=9.59, 0.39 Hz, 1H) 6.63 (d, J=5.38 Hz, 1H) 7.11 (dd, J=9.19, 2.54 Hz, 1H) 7.26 (dd, J=9.68, 2.84 Hz, 1H) 7.36 (d, J=2.54 Hz, 1H) 7.45 (dd, J=2.89, 0.54 Hz, 1H) 8.00 (d, J=9.19 Hz, 1H) 8.64 (d, J=5.38 Hz, 1H). $^{13}$C NMR (101 MHz, CDCl₃) δ ppm 21.35 (s, 1 C) 23.44 (s, 1 C) 32.68 (s, 1 C) 49.61 (s, 1 C) 51.85 (s, 1 C) 55.50 (s, 1 C) 65.45 (s, 1 C) 99.44 (s, 1 C) 107.26 (s, 1 C) 115.64 (s, 1 C) 118.44 (s, 1 C) 121.06 (s, 1 C) 122.61 (s, 1 C) 123.52 (s, 1 C) 136.18 (s, 1 C) 139.98 (s, 1 C) 151.20 (s, 1 C) 151.80 (s, 1 C) 160.68 (s, 1 C) 161.01 (s, 1 C) 161.25 (s, 1 C) 170.49 (s, 1 C). MS (ESI pos. ion) m/z (MH+): 394.2, calcd for $C_{21}H_{21}N_3O_5+H^+=394.2$.

EXAMPLE 59

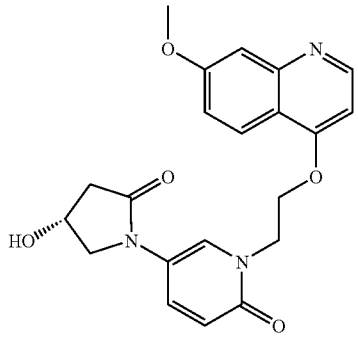

(R)-5-(4-Hydroxy-2-oxopyrrolidin-1-yl)-1-(2-(7-methoxyquinolin-4-yloxy)ethyl)pyridin-2(1H)-one This compound was prepared according to the procedure described in Example 56. The crude sample was loaded onto a Waters Spherisorb S5 column (PN PSS830195, 20×250 mm, 60 Å pore, 5 μm particle size); flow=20 mL/min; A=20 mM NH₃ in 99:1 DCE-EtOH, B=EtOH; isocratic at 20% B. A band that eluted from 9.0-10.7 minutes was isolated. The solvent was removed in vacuo to afford the title product. $^1$H NMR (400 MHz, MeOD) δ ppm 2.48 (ddd, J=17.41, 2.10, 0.54 Hz, 1H) 2.92 (dd, J=17.41, 6.26 Hz, 1H) 3.61 (ddd, J=10.56, 1.71, 0.64 Hz, 1H) 3.97 (s, 3H) 4.05 (dd, J=10.47, 5.18 Hz, 1H) 4.53-4.58 (m, 1H) 4.58-4.68 (m, 4H) 6.63 (d, J=9.88 Hz, 1H) 6.93 (d, J=5.58 Hz, 1H) 7.24 (dd, J=9.19, 2.54 Hz, 1H) 7.30 (d, J=2.54 Hz, 1H) 7.80 (dd, J=9.68, 2.93 Hz, 1H) 8.18 (d, J=9.19 Hz, 1H) 8.28 (d, J=2.84 Hz, 1H) 8.61 (d, J=5.48 Hz, 1H). $^{13}$C NMR (101 MHz, MeOD) δ ppm 42.65 (s, 1 C) 50.92 (s, 1 C) 56.19 (s, 1 C) 59.37 (s, 1 C) 64.97 (s, 1 C) 67.38 (s, 1 C) 101.09 (s, 1 C) 106.74 (s, 1 C) 117.13 (s, 1 C) 120.09 (s, 1 C) 120.75 (s, 1 C) 122.78 (s, 1 C) 124.79 (s, 1 C) 134.48 (s, 1 C) 138.40 (s, 1 C) 151.44 (s, 1 C) 152.49 (s, 1 C) 163.11 (s, 1 C) 163.30 (s, 1 C) 163.49 (s, 1 C) 175.23 (s, 1 C). MS (ESI pos. ion) m/z (MH+): 396.1, calcd for $C_{21}H_{21}N_3O_5+H^+=396.1$.

EXAMPLE 60

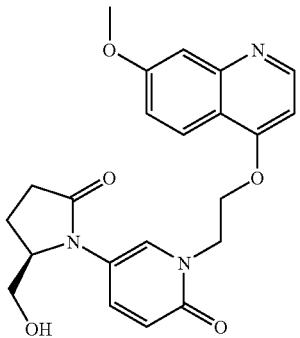

(R)-5-(2-(Hydroxymethyl)-5-oxopyrrolidin-1-yl)-1-(2-(7-methoxyquinolin-4-yloxy)ethyl)pyridin-2(1H)-one This compound was prepared according to the procedure described in Example 56. The sample was loaded onto a Waters Spherisorb S5 column (PN PSS830195, 20×250 mm, 60 Å pore, 5 μm particle size); flow=20 mL/min; A=20 mM NH₃ in 99:1 DCE-EtOH, B=EtOH; isocratic at 20% B. A band that eluted from 8.3-10.4 minutes was isolated. The solvent was removed in vacuo to afford the indicated product. $^1$H NMR (400 MHz, CDCl₃) δ ppm 2.08-2.18 (m, J=12.95, 9.89, 5.38, 4.25 Hz, 1 H) 2.20-2.32 (m, 1 H) 2.50 (ddd, J=17.22, 10.03, 5.33 Hz, 1 H) 2.68 (ddd, J=17.31, 9.93, 7.48 Hz, 1 H) 3.48 (dd, J=11.44, 2.74 Hz, 1 H) 3.57 (dd, J=11.54, 3.52 Hz, 1 H) 3.89 (s, 3 H) 3.94 (dt, J=11.62, 3.63 Hz, 1 H) 4.25-4.34 (m, 1 H) 4.42-4.55 (m, 3 H) 6.51 (d, J=5.38 Hz, 1 H) 6.58 (d, J=9.68 Hz, 1 H) 7.09 (dd, J=9.10, 2.54 Hz, 1 H) 7.20 (d, J=2.54 Hz, 1 H) 7.30 (dd, J=9.73, 2.89 Hz, 1 H) 7.87 (d, J=2.45 Hz, 1 H) 7.98 (d, J=9.10 Hz, 1 H) 8.43 (d, J=5.38 Hz, 1 H). $^{13}$C NMR (101 MHz, CDCl₃) δ ppm 21.17 (s, 1 C) 30.93 (s, 1 C) 50.05 (s, 1 C) 55.42 (s, 1 C) 60.90 (s, 1 C) 62.02 (s, 1 C) 65.43 (s, 1 C) 99.18 (s, 1 C) 106.64 (s, 1 C) 115.41 (s, 1 C) 117.94 (s, 1 C) 118.61 (s, 1 C) 120.76 (s, 1 C) 122.91 (s, 1 C) 136.20 (s, 1 C) 138.10 (s, 1 C) 150.64 (s, 1 C) 151.27 (s, 1 C) 160.90 (s, 1 C) 161.06 (s, 1 C) 161.08 (s, 1 C) 175.45 (s, 1 C). MS (ESI pos. ion) m/z (MH+): 410.1, calcd for $C_{22}H_{23}N_3O_5+H^+=410.1$.

EXAMPLE 61

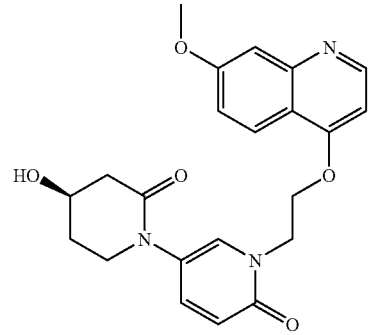

(R)-5-(4-Hydroxy-2-oxopiperidin-1-yl)-1-(2-(7-methoxyquinolin-4-yloxy)ethyl)pyridin-2(1 H)-one This compound was prepared according to the procedure described in Example 56. $^1$H NMR (400 MHz, MeOD) δppm 1.90-2.02 (m, 1 H) 2.06-2.18 (m, 1 H) 2.50 (ddd, J=17.56, 5.33, 1.47 Hz, 1 H) 2.78 (ddd, J=17.56, 4.55, 0.88 Hz, 1 H) 3.42 (ddd, J=11.79, 5.77, 5.53 Hz, 2 H) 3.70 (ddd, J=11.96, 8.58, 4.99 Hz, 1 H) 3.97 (s, 3 H) 4.24-4.31 (m, J=7.13, 4.70, 4.70, 2.84 Hz, 1 H) 4.57 (td, J=4.77, 1.32 Hz, 2 H) 4.61-4.67 (m, 2 H) 6.61 (d, J=9.59 Hz, 1 H) 6.92 (d, J=5.48 Hz, 1H) 7.23 (dd, J=9.19, 2.35 Hz, 1 H) 7.31 (d, J=2.35 Hz, 1 H) 7.50 (dd, J=9.59, 2.84 Hz, 1 H) 7.93 (d, J=2.74 Hz, 1 H) 8.15 (d, J=9.19 Hz, 1 H). $^{13}$C NMR (101 MHz, MeOD) δ ppm 31.41 (s, 1 C) 41.83 (s, 1 C) 48.87 (s, 1 C) 50.67 (s, 1 C) 56.21 (s, 1 C) 64.99 (s, 1 C) 67.23 (s, 1 C) 101.08 (s, 1 C) 106.69 (s, 1 C) 117.15 (s, 1 C) 120.04 (s, 1 C) 120.92 (s, 1 C) 124.78 (s, 1 C) 125.76 (s, 1 C) 139.00 (s, 1 C) 142.79 (s, 1 C) 151.42 (s, 1 C) 152.48 (s, 1 C) 163.30 (s, 1 C) 163.48 (s, 1 C) 163.80 (s, 1 C) 172.24 (s, 1 C). MS (ESI pos. ion) m/z (MH+): 410.2, calcd for $C_{22}H_{23}N_3O_5+H^+=410.2$.

EXAMPLE 62

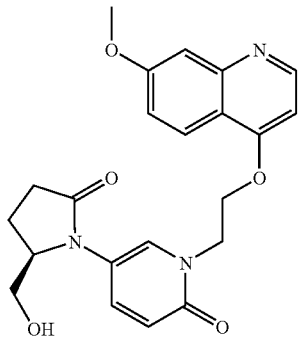

(S)-5-(2-(Hydroxymethyl)-5-oxopyrrolidin-1-yl)-1-(2-(7-methoxyquinolin-4-yloxy)ethyl)pyridin-2(1 H)-one This compound was prepared according to the procedure described in Example 56. $^1$H NMR (400 MHz, MeOD) δ ppm 2.11-2.20 (m, 1 H) 2.28-2.39 (m, J=12.90, 10.18, 8.66, 7.48 Hz, 1 H) 2.52 (ddd, J=17.17, 10.22, 5.18 Hz, 1 H) 2.67 (ddd, J=17.26, 9.98, 7.48 Hz, 1 H) 3.49 (dd, J=12.03, 2.54 Hz, 1 H) 3.56 (dd, J=11.93, 3.42 Hz, 1 H) 3.96 (s, 3 H) 4.07 (ddd, J=11.81, 3.50, 3.28 Hz, 1 H) 4.49-4.68 (m, 4 H) 6.63 (d, J=9.59 Hz, 1 H) 6.91 (d, J=5.58 Hz, 1 H) 7.22 (dd, J=9.15, 2.49 Hz, 1 H) 7.30 (d, J=2.54 Hz, 1 H) 7.59 (dd, J=9.59, 2.84 Hz, 1 H) 8.05 (d, J=2.84 Hz, 1 H) 8.17 (d, J=9.19 Hz, 1 H) 8.59 (d, J=5.48 Hz, 1 H). $^{13}$C NMR (101 MHz, MeOD) δ ppm 22.20 (s, 1 C) 31.97 (s, 1 C) 51.00 (s, 1 C) 56.15 (s, 1 C) 62.53 (s, 1 C) 63.72 (s, 1 C) 67.17 (s, 1 C) 100.99 (s, 1 C) 106.91 (s, 1 C) 117.14 (s, 1 C) 119.97 (s, 1 C) 120.36 (s, 1 C) 120.88 (s, 1 C) 124.81 (s, 1 C) 138.95 (s, 1 C) 141.76 (s, 1 C) 151.72 (s, 1 C) 152.66 (s, 1 C) 163.17 (s, 1 C) 163.29 (s, 1 C) 163.65 (s, 1 C) 178.56 (s, 1 C). MS (ESI pos. ion) m/z (MH+): 410.2, calcd for $C_{22}H_{23}N_3O_5+H^+=410.2$.

EXAMPLE 63

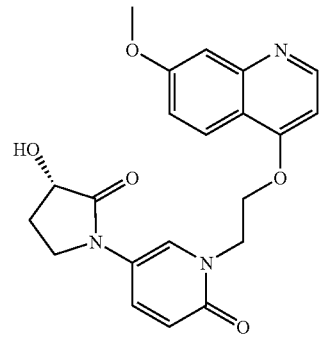

(S)-5-(3-Hydroxy-2-oxopyrrolidin-1-yl)-1-(2-(7-methoxyquinolin-4-yloxy)ethyl)pyridin-2(1 H)-one This compound was prepared according to the procedure described in Example 56. $^1$H NMR (400 MHz, D$_2$O) δ ppm 2.04 (dq, J=12.80, 9.08, 8.95 Hz, 1 H) 2.59-2.68 (m, J=12.53, 8.52, 6.24, 2.35 Hz, 1 H) 3.63-3.74 (m, 2 H) 4.03 (s, 3 H) 4.59 (dd, J=9.05, 8.36 Hz, 1 H) 4.67 (t, J=4.89 Hz, 2 H) 4.93 (t, J=4.70 Hz, 2 H) 6.72 (d, J=9.68 Hz, 1 H) 7.27 (d, J=8.80 Hz, 1 H) 7.28 (d, J=4.40 Hz, 1 H) 7.38 (dd, J=9.39, 2.45 Hz, 1 H) 7.75 (dd, J=9.73, 2.79 Hz, 1 H) 8.18 (d, J=9.39 Hz, 1 H) 8.18 (d, J=2.93 Hz, 1 H) 8.70 (tt, J=7.92, 1.42 Hz, 1 H) 8.73 (d, J=6.95 Hz, 1 H). $^{13}$C NMR (101 MHz, D$_2$O) δ ppm 30.21-30.83 (m, 1 C) 48.23-48.77 (m, 1 C) 52.18 (s, 1 C) 59.03 (s, 1 C) 70.70 (s, 1 C) 72.60 (s, 1 C) 101.84 (s, 1 C) 103.62 (s, 1 C) 117.81 (s, 1 C) 122.33 (s, 1 C) 123.69 (s, 1 C) 124.33 (s, 1 C) 127.51 (s, 1 C) 130.18 (s, 1 C) 136.90 (s, 1 C) 141.02 (s, 1 C) 147.72 (s, 1 C) 165.24 (s, 1 C) 167.08 (s, 1 C) 170.54 (s, 1 C) 178.28 (s, 1 C). MS (ESI pos. ion) m/z (MH+): 396.2, calcd for $C_{21}H_{21}N_3O_5+H^+=396.1$.

EXAMPLE 64

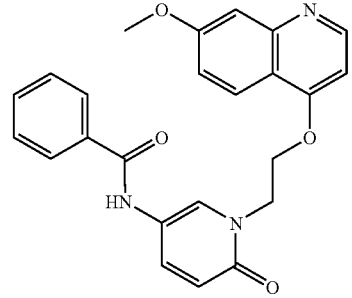

N-(1-(2-(7-Methoxyquinolin-4-yloxy)ethyl)-6-oxo-1,6-dihydropyridin-3-yl)benzamide A suspension of 5-bromo-1-(2-(7-methoxyquinolin-4-yloxy)ethyl)pyridin-2(1 H)-one (220 mg, 586 μmol), benzamide (213 mg, 1759 μmol), n,n'-dimethylethylenediamine (189 μl, 1759 μmol), copper(I) iodide (167 mg, 879 μmol), and cesium carbonate (573 mg, 1759 μmol) in toluene (3 mL) was sparged with argon then heated to 120° C. for 90 min. The mixture was partioned between CH$_2$Cl$_2$ and 5% NaHCO$_3$ and the hazy organic was washed with 30% NH$_4$OH, dried over MgSO$_4$, and concentrated onto silica (10 g) and purified on silica (12 g) eluting with 0 to 6% of 2M NH$_3$ in MeOH/CH$_2$Cl$_2$. A solid crystallized upon evaporation of selected fractions as a white solid. MS (ESI pos. ion) m/z (MH+): 416. Calc'd exact mass for C$_{24}$H$_{21}$N$_3$O$_4$: 415. $^1$H NMR (400 MHz, DMSO-d6) δ ppm 10.07 (s, 1 H) 8.62 (d, J=4.5 Hz, 1 H) 8.19 (d, J=9.0 Hz, 1 H) 7.96 (d, J=7.5 Hz, 2 H) 7.51-7.66 (m, 4 H) 7.28 (d, J=2.5 Hz, 1 H) 7.03 (dd, J=9.0, 2.5 Hz, 1 H) 6.92 (d, J=5.5 Hz, 1 H) 6.48 (d, J=10.0 Hz, 1 H), 4.48 (s, 4 H), 3.86 (s, 3 H).

EXAMPLE 65

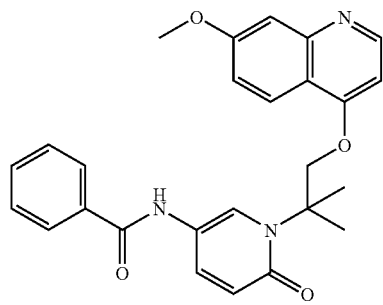

N-(1-(1-(7-Methoxyquinolin-4-yloxy)-2-methylpropan-2-yl)-6-oxo-1,6-dihydropyridin-3-yl)benzamide

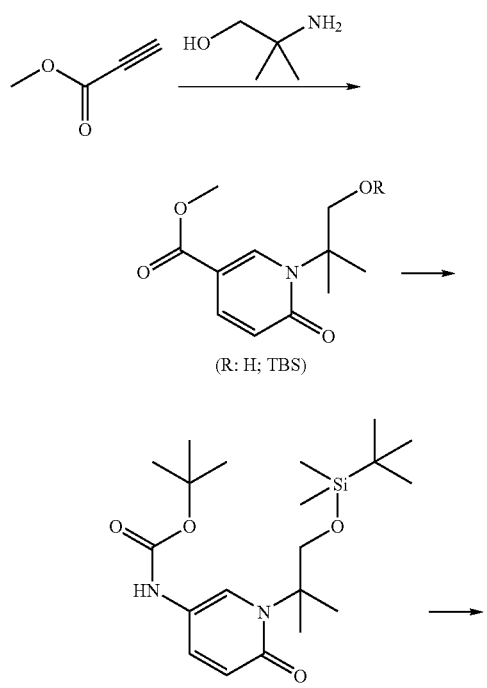

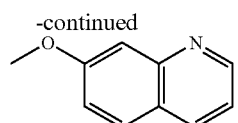

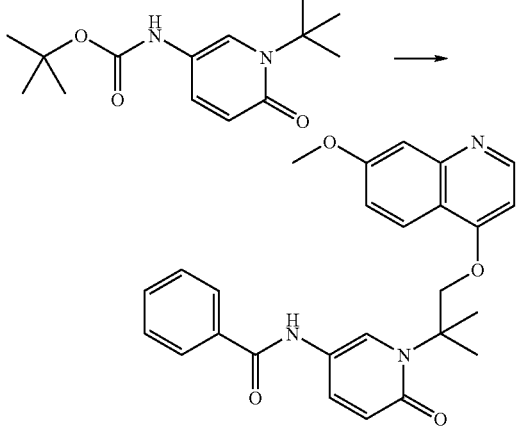

Methyl 1-(1-hydroxy-2-methylpropan-2-yl)-6-oxo-1,6-dihydropyridine-3-carboxylate. A solution of 2-amino-2-methyl-1-propanol (2 mL, 24 mmol) and methyl propiolate (5 mL, 61 mmol) in MeOH (10 mL) was appropriately sealed and heated to 120° C. for 30 min with microwaves. Sodium methoxide (25 wt. % in methanol, 4 mL, 73 mmol) was added and the solution was sealed and heated again to 120° C. for 30 min with microwaves. The mixture was partioned between CH$_2$Cl$_2$ (60 mL) and 10% citric acid (20 mL). The aqueous was repeatedly extracted with CH$_2$Cl$_2$ (4×15 mL). Combined organics dried over MgSO$_4$ then concentrated onto dry silica (20 g). The residue was purified on 120 g silica eluting with 10-40% of 5% MeOH/CH$_2$Cl$_2$, and isolated as a yellow solid. MS (ESI pos. ion) m/z (MH+): 226. Calc'd exact mass for C$_{11}$H$_{15}$NO$_4$: 225. $^1$H NMR (400 MHz, Chloroform-d) δ ppm 1.66 (s, 6 H) 3.86 (s, 3 H) 3.98 (s, 2 H) 6.49 (d, J=9.54 Hz, 1 H) 7.77-7.89 (m, 1 H) 8.42 (s, 1 H). $^{13}$C NMR (101 MHz, Chloroform-d) δ ppm 22.70, 50.08, 65.04, 66.57, 107.88, 119.17, 135.92, 138.43, 162.56, 162.98.

Methyl 1-(1-(tert-butyldimethylsilyloxy)-2-methylpropan-2-yl)-6-oxo-1,6-dihydropyridine-3-carboxylate. A solution of methyl 1-(1-hydroxy-2-methylpropan-2-yl)-6-oxo-1,6-dihydropyridine-3-carboxylate (2000 mg, 8.88 mmol), 1H-imidazole (1.51 mg, 22.2 mmol), and chloro-tert-butyldimethylsilane (1405 mg, 9.32 mmol) in DMF (10 mL) was stirred overnight at 23° C. The mixture was partitioned between CH$_2$Cl$_2$ and 5% NaHCO$_3$. The organic was dried over MgSO$_4$ and reduced to an oil under reduced pressure from toluene. MS (ESI pos. ion) m/z (MH+): 340. Calc'd exact mass for C$_{17}$H$_{29}$NO$_4$Si: 339.

1-(1-(tert-Butyldimethylsilyloxy)-2-methylpropan-2-yl)-6-oxo-1,6-dihydropyridine-3-carboxylic acid. To a solution of methyl 1-(1-(tert-butyldimethylsilyloxy)-2-methylpropan-2-yl)-6-oxo-1,6-dihydropyridine-3-carboxylate (3600 mg, 10.6 mmol) in THF (10 mL) and MeOH (5 mL) was added NaOH (3181 µl, 31.8 mmol). The solution was stirred at 23° C. for 48 h and was partitioned between CH$_2$Cl$_2$ and 10% citric acid (aq. pH~4). The aqueous was extracted with CH$_2$Cl$_2$ (3×50 mL). The combined organics were dried with brine and MgSO$_4$, and concentrated to a yellow solid under reduced pressure. MS (ESI pos. ion) m/z (MH+): 326. Calc'd exact mass for C$_{16}$H$_{27}$NO$_4$Si: 325.

tert-Butyl 1-(1-(tert-butyldimethylsilyloxy)-2-methylpropan-2-yl)-6-oxo-1,6-dihydropyridin-3-ylcarbamate. A stirred solution of 1-(1-(tert-butyldimethylsilyloxy)-2-methylpropan-2-yl)-6-oxo-1,6-dihydropyridine-3-carboxylic acid (2980 mg, 9.15 mmol), DIPEA (3198 µl, 18.3 mmol), diphenylphosphoryl azide (3.97 mL, 18.3 mmol), and t-butanol (8.60 mL, 9.15 mmol) in Dioxane (10 mL) was heated to reflux under nitrogen for 21 h. The reaction mixture was concentrated under reduced pressure and was purified on silica (80 g) eluting with 10-30% EtOAc/hexane. MS (ESI pos. ion) m/z (MH+): 397. Calc'd exact mass for $C_{20}H_{36}N_2O_4Si$: 396. $^1$H NMR (400 MHz, Chloroform-d) δ ppm −0.04 (s, 6 H) 0.81 (s, 9H) 1.49 (s, 9H) 1.63 (s, 6 H) 4.03 (s, 2 H) 5.98 (s, 1 H) 6.41 (d, J=9.54 Hz, 1 H) 7.15 (dd, J=9.54, 2.51 Hz, 1 H) 7.79 (br. s., 1 H).

tert-Butyl 1-(1-hydroxy-2-methylpropan-2-yl)-6-oxo-1,6-dihydropyridin-3-ylcarbamate. To a stirred suspension of tert-butyl 1-(1-(tert-butyldimethylsilyloxy)-2-methylpropan-2-yl)-6-oxo-1,6-dihydropyridin-3-ylcarbamate (800 mg, 2017 µmol) in ACN (10 mL) was added hydrogen fluoride pyridine (484 µl, 24206 µmol). The reaction mixture was stirred for 1 h and quenched with dry silica. The solvent was removed under reduced pressure and the product purified on silica (40 g) eluting with 0-5% MeOH/CH$_2$Cl$_2$. MS (ESI pos. ion) m/z (MH+): 283. Calc'd exact mass for $C_{14}H_{22}N_2O_4$: 282.

tert-Butyl 1-(1-(7-methoxyquinolin-4-yloxy)-2-methylpropan-2-yl)-6-oxo-1,6-dihydropyridin-3-ylcarbamate. A suspension of tert-butyl 1-(1-hydroxy-2-methylpropan-2-yl)-6-oxo-1,6-dihydropyridin-3-ylcarbamate (275 mg, 974 µmol), 1,10-phenanthroline (35 mg, 195 µmol), cesium carbonate (635 mg, 1948 µmol), copper(I) iodide (19 mg, 97 µmol), and 4-iodo-7-methoxyquinoline in DMF (4 mL) was heated to 100° C. for 2 h. The reaction mixture was partitioned between CH$_2$Cl$_2$ (50 mL) and 5% NaHCO$_3$ (25 mL). The aqueous was extracted twice with CH$_2$Cl$_2$ (5 mL). The combined extracts were concentrated onto dry silica (10 g) and purified on 80 grams of silica eluting with 0-6% 2M NH$_3$ in MeOH/CH$_2$Cl$_2$. MS (ESI pos. ion) m/z (MH+): 440. Calc'd exact mass for $C_{24}H_{29}N_3O_5$: 439.

5-Amino-1-(1-(7-methoxyquinolin-4-yloxy)-2-methylpropan-2-yl)pyridin-2(1 H)-one. To a stirred solution of tert-butyl 1-(1-(7-methoxyquinolin-4-yloxy)-2-methylpropan-2-yl)-6-oxo-1,6-dihydropyridin-3-ylcarbamate (55 mg, 125 µmol) in CH$_2$Cl$_2$ (1 mL) was added TFA (3 mL). After 90 min at 23° C., the solvents were removed under reduced pressure. The residue was partitioned between CH$_2$Cl$_2$ and NaOH (1 M). The organic was dried over MgSO$_4$, reduced to a brown solid under reduced pressure. MS (ESI pos. ion) m/z (MH+): 340. Calc'd exact mass for $C_{19}H_{21}N_3O_3$: 339. $^1$H NMR (400 MHz, Chloroform-d) δ ppm 1.65 (s, 6 H) 2.35 (s, 2 H) 3.94 (s, 3 H) 3.99 (s, 2 H) 6.30 (d, J=5.52 Hz, 1 H) 6.64 (d, J=9.03 Hz, 1 H) 7.09-7.20 (m, 4 H) 7.29-7.36 (m, 2 H) 7.64 (s, 1 H) 7.82 (d, J=9.03 Hz, 1 H) 8.31-8.39 (m, 1 H).

N-(1-(1-(7-Methoxyquinolin-4-yloxy)-2-methylpropan-2-yl)-6-oxo-1,6-dihydropyridin-3-yl)benzamide. To a stirred solution of 5-amino-1-(1-(7-methoxyquinolin-4-yloxy)-2-methylpropan-2-yl)pyridin-2(1 H)-one (33 mg, 97 µmol) in CH$_2$Cl$_2$ (3 mL) and tBuOH (1 mL) at 0° C. under nitrogen was added DIEA (17 µl, 97 µmol) followed by a solution of benzoyl chloride (11 µl, 97 µmol) in CH$_2$Cl$_2$ (0.5 mL). The reaction mixture was stirred for 24 h at 23° C. and partitioned between CH$_2$Cl$_2$ (10 mL) and 5% NaHCO$_3$ (5 mL). The organic was dried over MgSO$_4$, concentrated onto dry silica, and purified on silica (12 g) eluting with 0-5% MeOH/CH$_2$Cl$_2$. MS (ESI pos. ion) m/z (MH+): 444. Calc'd exact mass for $C_{26}H_{25}N_3O_4$: 443. $^1$H NMR (400 MHz, Chloroform-d) δ ppm 1.77 (s, 6 H) 3.89 (s, 3 H) 4.97 (s, 2 H) 6.15 (d, J=5.67 Hz, 1 H) 6.60 (d, J=9.59 Hz, 1H) 7.08 (dd, J=9.19, 2.54 Hz, 1 H) 7.29-7.58 (m, 8H) 7.66 (d, J=2.74 Hz, 1 H) 7.85-7.92 (m, 3 H) 8.02-8.18 (m, 2 H).

EXAMPLE 66

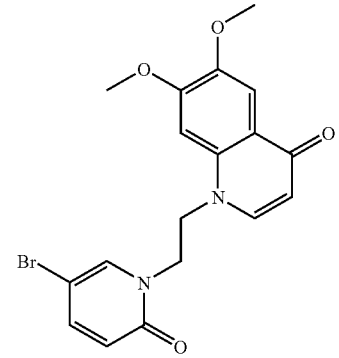

1-(2-(5-Bromo-2-oxopyridin-1(2 H)-yl)ethyl)-6,7-dimethoxyquinolin-4(1 H)-one

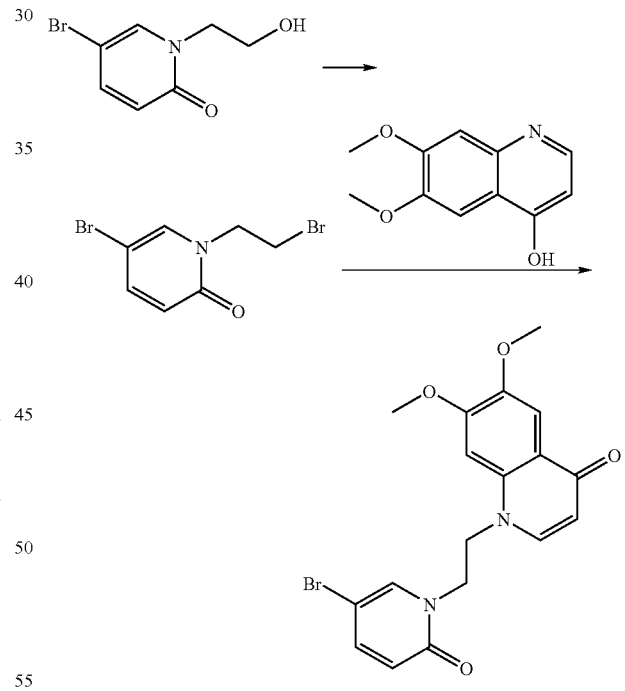

5-Bromo-1-(2-bromoethyl)pyridin-2(1 H)-one. To a solution of 5-bromo-1-(2-hydroxyethyl)pyridin-2(1 H)-one (460 mg, 2110 µmol) in CH$_2$Cl$_2$ (5 mL) at 0° C. under nitrogen was added phosphorous tribromide (595 µL, 6329 µmol). A precipitate formed at 0° C. The reaction mixture was heated at 40° C. for 3 days. The mixture was partitioned between CH$_2$Cl$_2$ and 5% NaHCO$_3$ (vigorous gas evolution). The aqueous was extracted with CH$_2$Cl$_2$ (2×10 mL). The combined organics were dried over MgSO$_4$, and concentrated to a white solid. MS (ESI pos. ion) m/z (MH+): 279/281/283. Calc'd exact mass for $C_7H_7Br_2NO$: 278.

1-(2-(5-Bromo-2-oxopyridin-1(2H)-yl)ethyl)-6,7-dimethoxyquinolin-4(1H)-one. A suspension of 5-bromo-1-(2-bromoethyl)pyridin-2(1H)-one (100 mg, 356 μmol), 6,7-dimethoxyquinolin-4-ol (88 mg, 427 μmol), and cesium carbonate (290 mg, 890 μmol) in DMF (2 mL) was stirred at 23° C. for 18 h. The reaction mixture was partitioned between $CH_2Cl_2$ and 5% $NaHCO_3$. The aqueous was extracted with $CH_2Cl_2$ (2×10 mL) and the combined organics were dried over $MgSO_4$. The solvents were concentrated to an oil from toluene and purified on silica (12 g) eluting with 0-100% of 6% (2M $NH_3$ in $MeOH/CH_2Cl_2$). MS (ESI pos. ion) m/z (MH+): 405/407. Calc'd exact mass for $C_{18}H_{17}BrN_2O_4$: 404. $^1$H NMR (400 MHz, DMSO-d6) δ ppm 3.84 (s, 3 H) 4.00 (s, 3 H) 4.25 (t, J=7.04 Hz, 2 H) 4.47 (t, J=7.04 Hz, 2 H) 5.97 (d, J=7.63 Hz, 1 H) 6.44 (d, J=9.59 Hz, 1 H) 7.41 (s, 1 H) 7.50-7.60 (m, 2 H) 7.74 (d, J=7.63 Hz, 1 H) 7.87 (d, J=2.54 Hz, 1H). $^{13}$C NMR (101 MHz, DMSO-d6) δ ppm 47.43, 49.21, 55.39, 56.01, 96.58, 98.22, 105.09, 108.26, 120.40, 120.95, 135.41, 139.10, 142.58, 142.96, 146.31, 153.03, 160.30, 175.10.

EXAMPLE 67

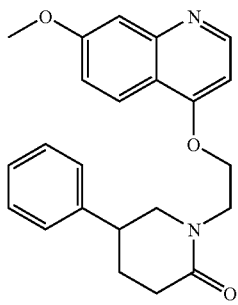

1-(2-(7-Methoxyquinolin-4-yloxy)ethyl)-5-phenylpiperidin-2-one

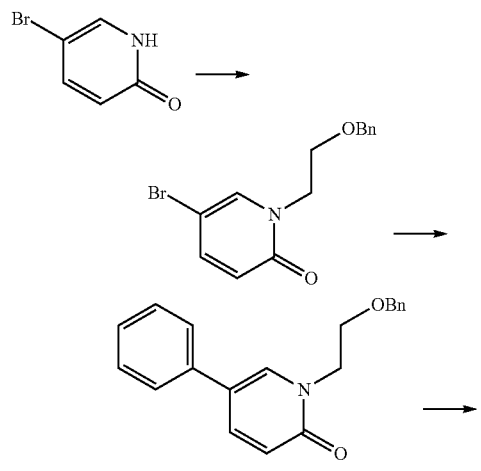

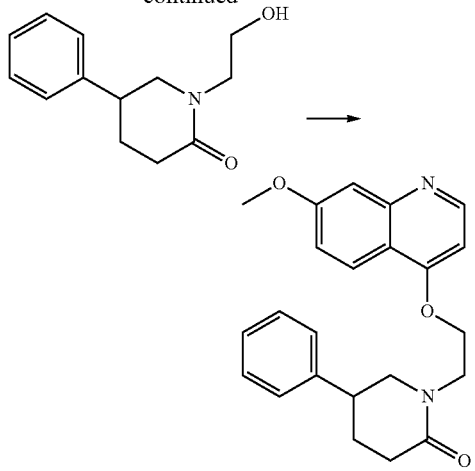

1-(2-(Benzyloxy)ethyl)-5-bromopyridin-2(1H)-one. To a stirring solution of 5-bromo-2(1h)-pyridone (2000 mg, 11.5 mmol) in DMF (15 mL) at 0° C. was added NaH (60% dispersion in mineral oil, 552 mg, 23.0 mmol). After 1 h then 1-((2-bromoethoxy)methyl)benzene (2.00 mL, 12.6 mmol) was added. The reaction mixture was heated to 50° C. for 18 h. $NH_4Cl$ (satd.) was added and the mixture was partitioned between EtOAc and water. The aqueous layer was extracted twice with EtOAc (50 mL) and the combined organic was washed with satd. $NH_4Cl$ and dried over $MgSO_4$. The organic was concentrated to an oil by repeatedly azeotroping with toluene. This residue was purified on 40 grams of silica eluting with 15-30% of EtOAc/hexanes to give a colorless oil that crystallized upon sitting for 2 weeks. MS (ESI pos. ion) m/z (MH+): 308/310. Calc'd exact mass for $C_{14}H_{14}BrNO_2$: 307. $^1$H NMR (400 MHz, Chloroform-d) δ ppm 3.71-3.76 (m, 2 H) 4.08-4.13 (m, 2 H) 4.48 (s, 2 H) 6.46 (d, J=9.78 Hz, 1H) 7.21-7.38 (m, 6 H) 7.54 (d, J=2.74 Hz, 1 H).

1-(2-(Benzyloxy)ethyl)-5-phenylpyridin-2(1H)-one. A suspension of 1-(2-(benzyloxy)ethyl)-5-bromopyridin-2(1H)-one (350 mg, 1.14 mmol), phenylboronic acid (277 mg, 2.27 mmol), 1,1'-bis(diphenylphosphino)ferrocene-palladium dichloride (83 mg, 114 μmol), $Na_2CO_3$ (1.70 mL, 3.41-mmol) [2M], and DME (3 mL) was sparged with argon for 10 min then heated to 85° C. for 60 min. The reaction mixture was partitioned between EtOAc and 5% $NaHCO_3$. The organic residue was purified on 40 grams of silica eluting with 20-60% EtOAc/hexane to give a colorless oil. MS (ESI pos. ion) m/z (MH+): 306. Calc'd exact mass for $C_{20}H_{19}NO_2$: 305. $^1$H NMR (400 MHz, Chloroform-d) δ ppm 3.77-3.89 (m, 2 H) 4.19-4.30 (m, 2 H) 4.50 (s, 2 H) 6.58-6.73 (m, 1 H) 7.17-7.45 (m, 10H) 7.59-7.71 (m, 2 H).

1-(2-Hydroxyethyl)-5-phenylpiperidin-2-one. A solution of 1-(2-(benzyloxy)ethyl)-5-phenylpyridin-2(1H)-one (100 mg, 327 μmol) in MeOH (10 mL) was sparged with argon for 10 min. A portion of palladium hydroxide (46 mg, 327 μmol) was added and the reaction was subjected to 55 psi hydrogen in a Parr shaker for 1 hr. The mixture was filtered through a pad of Celite, and concentrated to a white solid under reduced pressure. MS (ESI pos. ion) m/z (MH+): 220. Calc'd exact mass for $C_{13}H_{17}NO_2$: 219. $^1$H NMR (400 MHz, Chloroform-d) δ ppm 2.00-2.14 (m, 2 H) 2.46-2.67 (m, 2 H) 3.07-3.18 (m, 1H) 3.33 (br. s., 1 H) 3.42-3.56 (m, 3 H) 3.60-3.68 (m, 1 H) 3.83 (t, J=4.89 Hz, 2H) 7.21-7.30 (m, 3 H) 7.35 (t, J=7.24 Hz, 2 H). $^{13}$C NMR (101 MHz, Chloroform-d) δ ppm 27.75, 31.9, 40.37, 51.24, 55.88, 61.79, 126.99, 127.30, 128.85, 141.51, 171.78.

1-(2-(7-Methoxyquinolin-4-yloxy)ethyl)-5-phenylpiperidin-2-one. To a stirring solution of 1-(2-hydroxyethyl)-5-phenylpiperidin-2-one (100 mg, 456 µmol) in DMF (1.5 mL) under nitrogen was added NaH (60% dispersion in mineral oil; 16 mg, 684 µmol). The suspension was stirred for 10 min at 23° C., then 4-chloro-7-methoxyquinoline (132 mg, 684 µmol) was added. After 2 h at 23° C. the reaction mixture was partitioned between $CH_2Cl_2$ (15 mL) and 5% $NaHCO_3$ (10 mL). The aqueous was extracted with $CH_2Cl_2$ (5 mL) twice. The organics were dried over $MgSO_4$, concentrated to a solid from toluene under reduced pressure. Purification on silica (12 g) eluting with 10>40% of 5% MeOH/$CH_2Cl_2$ afforded a white solid from acetonitrile. $^1$H NMR (400 MHz, Chloroform-d) δ ppm 1.95-2.09 (m, 2 H) 2.40-2.64 (m, 2 H) 2.97-3.09 (m, 1H) 3.63 (t, J=11.35 Hz, 1 H) 3.68-3.76 (m, 1 H) 3.88 (t, J=4.99 Hz, 2 H) 3.94 (s, 3 H) 4.36-4.47 (m, 2 H) 6.65 (d, J=5.28 Hz, 1 H) 7.08 (dd, J=9.19, 2.54 Hz, 1 H) 7.16 (d, J=6.85 Hz, 2 H) 7.22-7.34 (m, 3 H) 7.38 (d, J=2.35 Hz, 1 H) 7.96 (d, J=9.00 Hz, 1 H) 8.66 (d, J=5.28 Hz, 1 H).

EXAMPLE 68

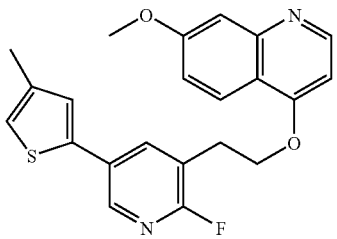

4-(2-(2-Fluoro-5-(4-methylthiophen-2-yl)pyridin-3-yl)ethoxy)-7-methoxyquinoline

To a 5 mL CEM microwave tube was added 2-(2-fluoro-5-(4-methylthiophen-2-yl)pyridin-3-yl)ethanol (0.06 g, 0.3 mmol), 4-chloro-7-methoxyquinoline (0.10 g, 0.5 mmol), racemic-2-(di-t-butylphosphino)-1,1'-binaphthyl (0.04 g, 0.1 mmol), palladium (II) acetate (0.02 g, 0.1 mmol), cesium carbonate (0.2 g, 0.5 mmol), and toluene (4 mL). The vial was sealed and heated at 80° C. in the closed system for 3 h. The reaction mixture was passed through the celite to separate the inorganic salt. Solvent was removed. The crude product was purified using $SiO_2$ chromatography with $CH_2Cl_2$:MeOH (98%:2%) to afford the product as brown solid. MS (ESI pos. ion) m/z (MH+): 395.3. Calc'd exact mass for $C_{22}H_{19}FN_2O_2S$: 394.1. $^1$H NMR (300 MHz, Chloroform-d) δ ppm 2.30 (s, 3 H) 3.31 (t, J=6.21 Hz, 2 H) 3.94 (s, 3 H) 4.46 (t, J=6.21 Hz, 2 H) 6.65 (d, J=5.41 Hz, 1 H) 6.94 (s, 1 H) 7.07 (s, 1 H) 7.12 (dd, J=9.13, 2.56 Hz, 1 H) 7.36 (d, J=2.48 Hz, 1 H) 7.95 (dd, J=8.99, 2.41 Hz, 1 H) 8.05 (d, J=9.06 Hz, 1 H) 8.33 (s, 1 H) 8.67 (d, J=5.26 Hz, 1 H).

EXAMPLE 69

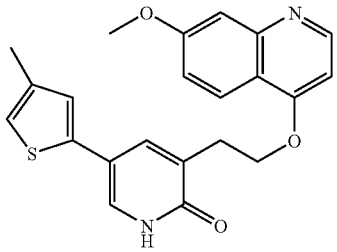

3-(2-(7-Methoxyquinolin-4-yloxy)ethyl)-5-(4-methylthiophen-2-yl)pyridin-2(1 H)-one

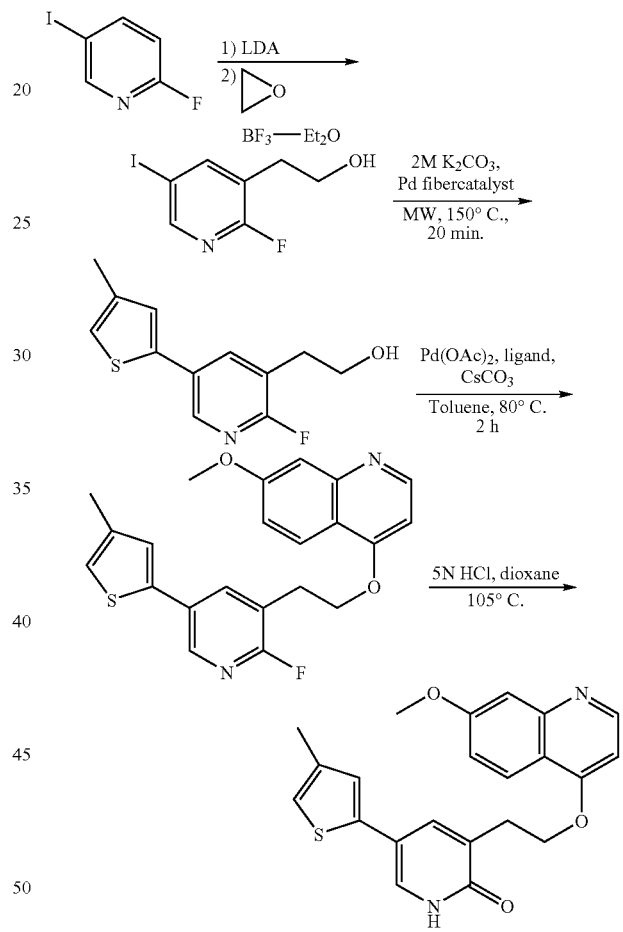

2-(2-Fluoro-5-iodopyridin-3-yl)ethanol. To a stirred solution of diisopropylamine (2 mL, 15 mmol) in THF (15 mL) at −20° C. was added butyllithium (9 mL, 15 mmol) dropwise via an addition funnel (cooled below −10° C.) under $N_2$. The reaction mixture was stirred for 30 min at −20° C. and then cooled to −78° C. A solution of 2-fluoro-5-iodopyridine (3 g, 13 mmol) in THF (15 mL) was added to the reaction mixture dropwise via the addition funnel (cooled at −78° C.). After the addition, the resulting mixture was continued to stir at −78° C. for 1 h. To another round bottom flask cooled to −10° C., was added oxirane (3 g, 67 mmol) by using the cold finger apparatus to condense the oxirane gas into the round bottom flask. THF (10 mL) was then added and cooled to −78° C. The oxirane solution was added in drops to the reaction mixture prepared above via cannulation (cooled under −70° C.). After the addition, boron trifluoride-diethyl etherate (3 mL, 27 mmol) was added via the syringe pump over 1 h. After the addition, the reaction mixture was allowed to slowly warm to rt overnight. The reaction mixture was quenched with satd. NH₄Cl. The solvent was removed. The residue was partitioned between EtOAc/water. The organic layer was washed with water, brine, dried over MgSO₄ and concentrated. The crude product was purified using SiO₂ chromatography with hexane:acetone (95%:5%) to afford the product as light yellow solid (400 mg) along with 1.3 g of starting material. MS (ESI pos. ion) m/z (MH+): 268.3. Calc'd exact mass for C₇H₇FINO: 266.96. ¹H NMR (300 MHz, Chloroform-d) δ ppm 1.49 (t, J=5.33 Hz, 1 H) 2.86 (t, J=6.28 Hz, 2 H) 3.91 (q, J=6.04 Hz, 2 H) 7.99 (d, J=8.77 Hz, 1 H) 8.29 (s, 1 H).

2-(2-Fluoro-5-(4-methylthiophen-2-yl)pyridin-3-yl)ethanol. To a microwave tube was added 2-(2-fluoro-5-iodopyridin-3-yl)ethanol (0.09 g, 0.3 mmol), 4-methylthiophen-2-ylboronic acid (0.2 g, 1 mmol), palladium fibrecatalyst (0.010 mg, 10% wt), potassium carbonate (2 M, 0.3 mL, 0.7 mmol), and dioxane (3 mL). The vial was sealed and placed into CEM microwave for 20 min. at 150° C., with 80 Watts of power via Powermax. The reaction mixture was partitioned between water/CH₂Cl₂. The aqueous layer was extracted with CH₂Cl₂ and the combined organic layers were dried over MgSO₄ and concentrated. The crude product was purified using SiO₂ chromatography with hexane:acetone (90%:10%) to afford the product as colorless liquid (65 mg). MS (ESI pos. ion) m/z (MH+): 238.3. Calc'd exact mass for C₁₂H₁₂FNOS: 237.1. ¹H NMR (300 MHz, Chloroform-d) δ ppm 1.54-1.64 (m, 1 H) 2.30 (s, 3 H) 2.94 (t, J=6.36 Hz, 2 H) 3.95 (q, J=6.24 Hz, 2 H) 6.92 (s, 1 H) 7.11 (s, 1 H) 7.84 (d, J=9.06 Hz, 1 H) 8.27 (s, 1 H).

3-(2-(7-Methoxyquinolin-4-yloxy)ethyl)-5-(4-methylthiophen-2-yl)pyridin-2(1 H)-one. To a 4 mL microwave tube was added 4-(2-(2-fluoro-5-(4-methylthiophen-2-yl)pyridin-3-yl)ethoxy)-7-methoxyquinoline (0.025 g, 0.063 mmol), aq. HCl (5N, 2 mL), and dioxane (3 mL). The resulting mixture was sealed and heated to reflux (105° C.) in closed system for 20 h. The reaction mixture was partitioned between EtOAc/ satd. NaHCO₃. The aqueous layer was extracted with EtOAc and the combined organic layers were dried over MgSO₄ and concentrated. The crude product was purified using SiO₂ chromatography with CH₂Cl₂:EtOAc:MeOH (2M NH₃) (90%:6%:4%) to afford the product as whit solid (15 mg). MS (ESI pos. ion) m/z (MH+): 393.3. Calc'd exact mass for C₂₂H₂₀N₂O₃S: 392.1. ¹H NMR (300 MHz, MeOH-d₄) δ ppm 2.24 (s, 3 H) 3.20 (t, J=6.28 Hz, 2 H) 3.93 (s, 3 H) 4.54 (t, J=6.28 Hz, 2 H) 6.90 (s, 1 H) 6.94 (d, J=5.55 Hz, 1 H) 6.96 (s, 1 H) 7.11 (dd, J=9.21, 2.48 Hz, 1 H) 7.27 (d, J=2.34 Hz, 1 H) 7.55 (d, J=2.63 Hz, 1 H) 7.88 (d, J=2.48 Hz, 1 H) 8.10 (d, J=9.21 Hz, 1 H) 8.57 (d, J=5.55 Hz, 1 H).

EXAMPLE 70

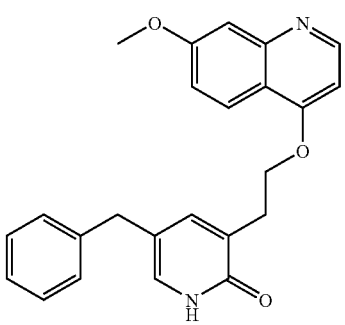

4-Benzyl-3-(2-(7-methoxyquinolin-4-yloxy)ethyl) pyridin-2(1 H)-one

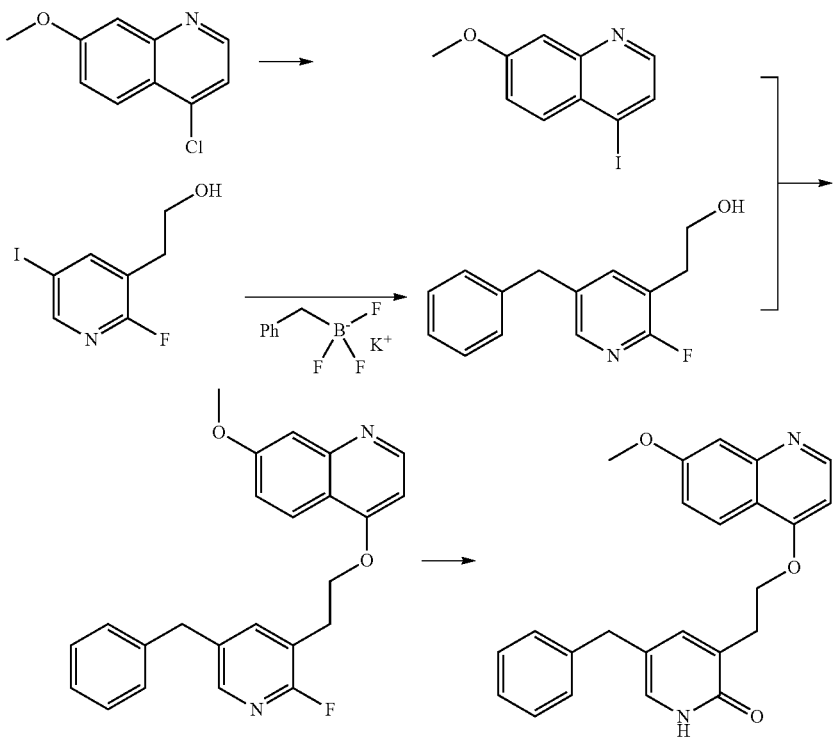

4-Iodo-7-methoxyquinoline: The general procedure is described in Drake, N. L.; Creech, H. J.; Garman, J. A.; Haywood, S. T.; Peck, R. M.; Van Hook, J. O.; Walton, E., Synthetic antimalarials. The preparation of certain 4-aminoquinolines. *Journal of the American Chemical Society* 1946, 68, 1208-13. A dry 250 mL, 1-neck round bottomed flask was charged with 4-chloro-7-methoxyquinoline (1.77 g, 9.1 mmol), and 100 mL dry dioxane. The solution was treated with 20 mL 1N HCl in $Et_2O$. The solution was occasionally swirled over a 15 minute period, and the solvent was removed in vacuo. The residue was dried at 60° C. at 0.1 mmHg for 2 h. To the flask was added a stir bar and 20 mL dry acetonitrile. The flask was fitted with a reflux condenser, and to the stirring slurry was added sodium iodide (4.1 g, 27 mmol). The solution was heated to reflux for 48 h. The solution was cooled, and the solution was filtered. The precipitate was washed with ACN (3×20 mL), and water (3×20 mL). The solid was suspended in 70% $CH_2Cl_2$-30% MeOH. To the solution was added Si-carbonate (16 g, 11 mmol). The slurry was swirled for 1 h, and filtered. The silica was washed with EtOH (3×50 mL). The solvent was removed in vacuo to afford 4-iodo-7-methoxyquinoline. $^1$H NMR (300 MHz, MeOD) δ ppm 4.00 (s, 3 H) 7.35 (dd, J=10.01, 2.48 Hz, 1 H) 7.36 (d, J=2.56 Hz, 1 H) 8.00 (d, J=9.87 Hz, 1 H) 8.01 (d, J=4.75 Hz, 1 H) 8.33 (d, J=4.90 Hz, 1 H). $^{13}$C NMR (101 MHz, MeOD) δ ppm 56.46 (s, 1 C) 107.73 (s, 1 C) 113.18 (s, 1 C) 122.61 (s, 1 C) 127.31 (s, 1 C) 132.05 (s, 1 C) 134.27 (s, 1 C) 150.18 (s, 1 C) 150.86 (s, 1 C) 163.35 (s, 1 C). MS (ESI pos. ion) m/z (MH+): 286.0, calcd for $C_{10}H_8INO+H^+$=286.0.

2-(4-Benzyl-2-fluoropyridin-3-yl)ethanol: As generally described in Molander, G. A.; Ito, T., Cross-Coupling Reactions of Potassium Alkyltrifluoroborates with Aryl and 1-Alkenyl Trifluoromethanesulfonates. *Organic Letters* 2001, 3, (3), 393-396, a 10 mL, Biotage microwave vessel was charged with cesium carbonate (0.460 g, 1.41 mmol), 1,1'-bis(diphenylphosphino)ferrocene-palladium dichloride (0.0517 g, 0.0706 mmol), potassium benzyltrifluoroborate (0.140 g, 0.706 mmol), 2-(2-fluoro-4-iodopyridin-3-yl)ethanol (0.1257 g, 0.471 mmol) and a stir bar. The vessel was sealed, and purged with Argon by piercing the septa with an Ar line and an 18-gauge needle. To the vessel was added 5 mL THF and 1 mL water. The needles were removed, and the vessel placed in a 90° C. heater block for 24 h. The solution was cooled. The THF was removed under a stream of nitrogen, and 5 mL $CH_2Cl_2$ was added. The biphasic solution was loaded onto a 10 mL Varian Chem elute CE 1005 and extracted with $CH_2Cl_2$ (5×10 mL). The solvent was removed in vacuo. The residue was passed through a 15 mL plug of $SiO_2$ conditioned with $CH_2Cl_2$, and eluted with 50 mL 10% EtOH in $CH_2Cl_2$. The solvent was removed in vacuo. The sample was purified using a Waters Spherisorb S5 column (20×250 mm, 60 Å pore, 5 μm particle size); flow=20 mL/min; A=DCE, B=EtOH; isocratic at 1% B. A band that eluted from 7.7-9.3 minutes was isolated. The solvent was removed in vacuo to afford 2-(4-benzyl-2-fluoropyridin-3-yl)ethanol. $^1$H NMR (400 MHz, CDCl$_3$) δ ppm 1.66 (br. s., 1 H) 2.95 (td, J=6.77, 0.44 Hz, 2H) 3.77 (dd, J=6.85, 6.46 Hz, 2 H) 4.12 (s, 2 H) 6.91 (d, J=5.18 Hz, 1 H) 7.07-7.16 (m, 2 H) 7.21-7.27 (m, 1 H) 7.31 (tt, J=7.29, 1.71 Hz, 2 H) 7.97 (d, J=5.09 Hz, 1 H). $^{13}$C NMR (101 MHz, CDCl$_3$) δ ppm 28.81 (s, 1 C) 38.30 (d, J=3.47 Hz, 1 C) 61.64 (s, 1 C) 119.13 (d, J=30.34 Hz, 1 C) 123.24 (d, J=3.47 Hz, 1 C) 126.79 (s, 1 C) 128.80 (s, 4 C) 138.29 (s, 1 C) 144.92 (d, J=16.04 Hz, 1 C) 154.04 (d, J=5.63 Hz, 1 C) 162.88 (d, J=237.55 Hz, 1 C). MS (ESI pos. ion) m/z (MH+): 232.1, calcd for $C_{14}H_{14}FNO+H^+$=232.1.

4-(2-(4-Benzyl-2-fluoropyridin-3-yl)ethoxy)-7-methoxyquinoline: A 10 mL, Biotage microwave vessel was charged with racemic-2-(di-t-butylphosphino)-1,1'-binaphthyl (0.093 g, 0.23 mmol), palladium(II) acetate (0.048 g, 0.21 mmol), a stir bar, and 1 mL toluene. The flask was sealed and swept with Ar by piercing the septa with an Ar inlet and an 18-gauge needle. The solution was heated to 70° C. for 20 minutes. To the solution was added cesium carbonate (0.076 g, 0.23 mmol), 4-iodo-7-methoxyquinoline (0.067 g, 0.23 mmol), and 2-(4-benzyl-2-fluoropyridin-3-yl)ethanol (0.0493 g, 0.21 mmol). The reaction was heated for 24 h at 70° C. and cooled. The solution was treated with 1 mL water, and the stirred for 20 min. The two phases were loaded onto an unbuffered, 10 mL Varian Chem elute CE 1005 (PN 12198007) and extracted with 5×5 mL $CH_2Cl_2$. The combined extracts were concentrated in vacuo. The residue was loaded onto a 30×100 mm Waters Xterra Prep C18 OBD column (100 Å pore diameter, 5 μm particle size, spherical shape, PN 186001942; Gradient: 0→5 min@35 mL/min, 25% B; 5→20 min@35 mL/min, linear gradient to 55% B; 20→24.9@35 mL/min, isocratic at 55% B, 25→29.9 min@35 mL/min, step to 100% B; 30→40 min@35 mL/min, step to 25% B; 40 min end). A=10 mM $NH_3HCO_3$ in water (pH 9.6); B=ACN. A band that eluted from 20.9-21.6 minutes was isolated. The solvent was evaporated in vacuo to afford 4-(2-(4-benzyl-2-fluoropyridin-3-yl) ethoxy)-7-methoxyquinoline. $^1$H NMR (400 MHz, CDCl$_3$) δ ppm 3.30 (t, J=6.70 Hz, 2 H) 3.94 (s, 3 H) 4.19 (s, 2 H) 4.22 (t, J=6.75 Hz, 2 H) 6.48 (d, J=5.38 Hz, 1 H) 6.99 (d, J=4.99 Hz, 1 H) 7.08-7.12 (m, 2 H) 7.14 (dd, J=9.15, 2.49 Hz, 1 H) 7.21-7.32 (m, 3 H) 7.39 (d, J=2.25 Hz, 1 H) 8.02 (d, J=9.19 Hz, 1 H) 8.05 (d, J=4.99 Hz, 1 H) 8.61 (d, J=5.48 Hz, 1 H). $^{13}$C NMR (101 MHz, CDCl$_3$) δ ppm 25.39 (s, 1 C) 38.56 (d, J=3.47 Hz, 1 C) 55.52 (s, 1 C) 66.76 (s, 1 C) 99.27 (s, 1 C) 106.74 (s, 1 C) 115.76 (s, 1 C) 118.19 (d, J=30.34 Hz, 1 C) 118.66 (s, 1 C) 123.00 (s, 1 C) 123.49 (d, J=3.90 Hz, 1 C) 126.99 (s, 1 C) 128.69 (s, 2 C) 128.95 (s, 2 C) 137.96 (s, 1 C) 145.60 (s, 1 C) 145.77 (s, 1 C) 151.12 (d, J=6.50 Hz, 1 C) 153.72 (d, J=5.20 Hz, 1 C) 161.19 (s, 1 C) 161.52 (br. s., 1 C) 163.03 (d, J=237.12 Hz, 1 C). MS (ESI pos. ion) m/z (MH+): 389.1, calcd for $C_{24}H_{21}FN_2O_2+H^+$=389.2.

4-Benzyl-3-(2-(7-methoxyquinolin-4-yloxy)ethyl)pyridin-2(1 H)-one: An NMR tube was charged with 4-(2-(4-benzyl-2-fluoropyridin-3-yl)ethoxy)-7-methoxyquinoline (0.0061 g, 0.016 mmol), 0.5 mL THF and 0.2 mL 35% HCl. The tube was heated to 70° C. for 40 h, and cooled. The solvent was removed under a stream of nitrogen, and the residue was diluted to 0.6 mL with MeOH, and treated with Si-carbonate (0.022 g, 0.016 mmol). The solution was filtered and concentrated in vacuo. A sample was scouted for prep purification using a 2.1×50 mm Xterra MS C18 column with a 3.5 μm particle size (PN 186000400); A=11 mM $NH_4HCO_3$ in water, pH adjusted to 8.5 with concentrated $NH_4OH$; B=Acetonitrile; gradient: initial@1 mL/min, 10% B; 0→5 min@1 mL/min, linear gradient to 100% B; 5→6.9 min@1 mL/min, isocratic at 100% B; 6.9→6.95 min@1 mL/min, linear gradient to 110% B, 8 min end. A major peak was observed at 3.07. The sample was purified using a 19×150 mm Waters Xterra Prep C18 OBD column (100 Å pore diameter, 5 μm particle size, spherical shape, PN 186002381; Gradient: 0→5 min@20 mL/min, 25% B; 5.0→35 min@20 mL/min, linear gradient to 55% B; 35→45@20 mL/min, isocratic at 55% B, 45→55 min@20 mL/min, step to 100% B; 55→60 min@20 mL/min, step to 25% B; 60 min end). A=11 mM $NH_4HCO_3$ in water, pH adjusted to 8.5 with concentrated $NH_4OH$; B=Acetonitrile. A band that eluted from 20.9-21.9 minutes was isolated. The solvent was removed in vacuo to afford 4-benzyl-3-(2-(7-methoxyquinolin-4-yloxy)ethyl)pyridin-2(1 H)-one. ¹H NMR (400 MHz, CDCl₃) δ ppm 3.28 (t, J=6.75 Hz, 2 H) 3.93 (s, 3 H) 4.07 (s, 2 H) 4.36 (t, J=6.65 Hz, 2 H) 6.09 (d, J=6.75 Hz, 1 H) 6.66 (d, J=5.38 Hz, 1 H) 7.08 (dd, J=9.15, 2.49 Hz, 1 H) 7.13-7.17 (m, 2 H) 7.19-7.25 (m, 2 H) 7.26-7.32 (m, 2 H) 7.34 (d, J=2.54 Hz, 1 H) 8.03 (d, J=9.19 Hz, 1 H) 8.62 (d, J=5.18 Hz, 1 H) 11.96 (br. s., 1H). ¹³C NMR (101 MHz, CDCl₃) δ ppm 26.72 (s, 1 C) 38.97 (s, 1 C) 55.43 (s, 1 C) 66.50 (s, 1 C) 99.65 (s, 1 C) 107.20 (s, 1 C) 109.62 (s, 1 C) 116.02 (s, 1 C) 118.12 (s, 1 C) 123.11 (s, 1 C) 126.28 (s, 1 C) 126.79 (s, 1 C) 128.73 (s, 2 C) 128.81 (s, 2 C) 131.53 (s, 1 C) 138.24 (s, 1 C) 151.17 (s, 1 C) 151.82 (s, 1 C) 152.21 (s, 1 C) 160.85 (s, 1 C) 161.60 (s, 1 C) 164.55 (s, 1 C). MS (ESI pos. ion) m/z (MH+): 387.2, calcd for $C_{24}H_{22}N_2O_3$+ H⁺=387.2.

EXAMPLE 71-74

Intentionally Omitted

EXAMPLE 75

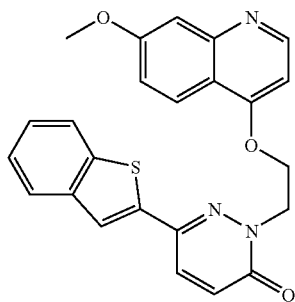

6-(Benzo[b]thiophen-2-yl)-2-(2-(7-methoxyquinolin-4-yloxy)ethyl)pyridazin-3(2 H)-one

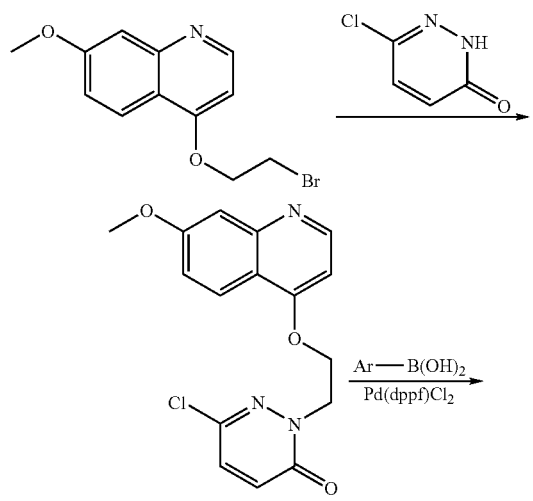

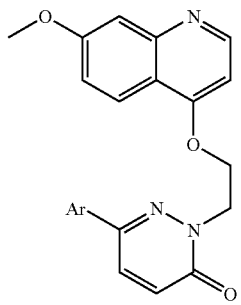

6-chloro-2-(2-(7-methoxyquinolin-4-yloxy)ethyl)pyridazin-3(2 H)-one. A mixture of 6-chloropyridazin-3(2 H)-one (3000 mg, 22983 μmol), K₂CO₃ (5000 mg, 36178 μmol), and 4-(2-bromoethoxy)-7-methoxyquinoline (6110 mg, 21656 μmol) in DMF (25 mL) was stirred at room temperature for 1.5 h. H₂O (50 mL) was added and the mixture was extracted with CH₂Cl₂ (3×50 mL). The organic layer was washed with H₂O (50 mL), dried over Na₂SO₄, and concentrated to an orange oil. The oil was diluted with ether (40 mL) and the mixture was concentrated to slurry. Hexane (20 mL) was added and the mixture was agitated at 60° C. for 50 min and cooled to room temperature. The mixture was filtered, washed with ether to give a light tan solid (3.2 g). The filtrate was concentrated and partitioned between H₂O (20 mL) and EtOAc (50 mL). The organic layer was washed with H₂O and concentrated. The residue was triturated with acetone-hexane (1:2) to give a second crop of product (1.5 g). MS (ESI pos. ion) calc'd for $C_{16}H_{14}ClN_3O_3$: 331.1; found 332.1 (MH+). ¹H NMR (400 MHz, Chloroform-d) δ ppm 3.93 (s, 3 H) 4.55 (t, J=5.28 Hz, 2 H) 4.67 (t, J=5.38 Hz, 2 H) 6.64 (s, 1 H) 6.94 (d, J=9.59 Hz, 1 H) 7.14 (dd, J=9.10, 2.45 Hz, 1 H) 7.18 (d, J=9.78 Hz, 1 H) 7.34 (d, J=2.54 Hz, 1 H) 8.05 (d, J=9.19 Hz, 1 H) 8.65 (d, J=5.28 Hz, 1 H).

6-(Benzo[b]thiophen-2-yl)-2-(2-(7-methoxyquinolin-4-yloxy)ethyl)pyridazin-3(2 H)-one. A mixture of sodium carbonate hydrate (250 mg, 2016 μmol), PdCl₂(dppf)-CH₂Cl₂ adduct (30 mg, 37 μmol), 6-chloro-2-(2-(7-methoxyquinolin-4-yloxy)ethyl)pyridazin-3(2 H)-one (220 mg, 663 μmol), and benzo[b]thiophen-2-ylboronic acid (290 mg, 1629 μmol) in DME (5 mL) and H₂O (2 mL) was heated to 80° C. under nitrogen for 18 h. The mixture was cooled to room temperature and partitioned between EtOAc (50 mL) and H₂O (20 mL). The organic phase was washed with H₂O (2×), NH₄Cl (aq), dried over Na₂SO₄, and concentrated to a brown solid. The solid was triturated with hot hexane-EtOAc-MeOH (2:1:0.1) twice and the solid was further washed with MeOH in EtOAc (1%), CH₂Cl₂ (de-colorization), and ether to give the product as an off-white solid (160 mg). MS (ESI pos. ion) calc'd for $C_{24}H_{19}N_3O_3S$: 429.11; found 430.2 (MH+). ¹H NMR (400 MHz, DMSO-d6) δ ppm 4.65 (s, 3 H) 5.46 (s, 4 H) 7.76 (d, J=4.11 Hz, 1 H) 7.81 (d, J=9.19 Hz, 1 H) 7.95 (d, J=9.39 Hz, 1 H) 8.08 (s, 1 H) 8.24 (d, J=3.33 Hz, 2 H) 8.67 (d, J=5.09 Hz, 1 H) 8.81 (d, J=8.41 Hz, 2 H) 8.88 (s, 1 H) 9.00 (d, J=9.78 Hz, 1 H) 9.44 (d, J=4.30 Hz, 1 H)

EXAMPLE 76

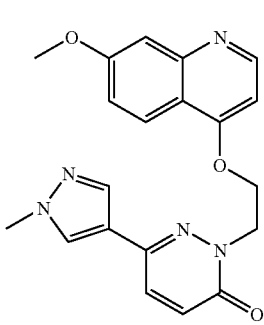

2-(2-(7-Methoxyquinolin-4-yloxy)ethyl)-6-(1-methyl-1H-pyrazol-4-yl)pyridazin-3(2H)-one This compound was prepared according to the procedure described in Example 75. MS (ESI pos. ion) m/z (MH+): 378. Calc'd exact mass for $C_{20}H_{19}N_5O_3$: 377. $^1$H NMR (400 MHz, Chloroform-d) δ ppm 3.91 (s, 3 H) 3.92 (s, 3 H) 4.61 (t, J=5.38 Hz, 2 H) 4.71 (t, J=5.28 Hz, 2 H) 6.66 (d, J=5.28 Hz, 1 H) 6.97 (d, J=9.59 Hz, 1 H) 7.03 (dd, J=9.19, 2.15 Hz, 1 H) 7.31 (d, J=2.15 Hz, 1 H) 7.39 (d, J=9.59 Hz, 1 H) 7.58 (s, 1 H) 7.78 (s, 1 H) 8.01 (d, J=9.19 Hz, 1 H) 8.63 (d, J=5.28 Hz, 1H).

EXAMPLE 77

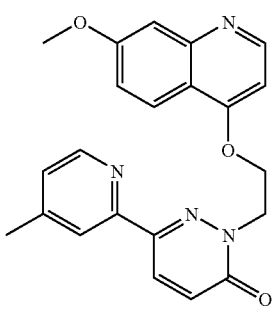

2-(2-(7-Methoxyquinolin-4-yloxy)ethyl)-6-(4-methylpyridin-2-yl)pyridazin-3(2H)-one This compound was prepared according to the procedure described in Example 75. MS (ESI pos. ion) calc'd for $C_{22}H_{20}N_4O_3$: 388.2; found 389.2 (M+1). $^1$H NMR (400 MHz, Chloroform-d) δ ppm 2.38 (s, 3 H) 3.93 (s, 3 H) 4.72 (t, J=5.28 Hz, 2 H) 4.83 (t, J=5.38 Hz, 2 H) 6.77 (d, J=5.67 Hz, 1 H) 7.02 (dd, J=9.19, 2.35 Hz, 1 H) 7.06 (d, J=9.78 Hz, 1 H) 7.14 (d, J=4.89 Hz, 1 H) 7.45 (d, J=2.35 Hz, 1 H) 7.81 (s, 1 H) 8.04 (d, J=9.19 Hz, 1 H) 8.34 (d, J=9.78 Hz, 1 H) 8.47 (d, J=5.09 Hz, 1 H) 8.72 (d, J=5.48 Hz, 1 H)

EXAMPLE 78

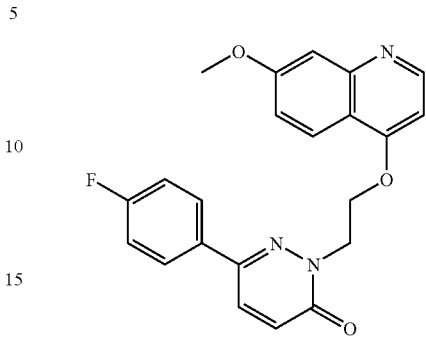

6-(4-Fluorophenyl)-2-(2-(7-methoxyquinolin-4-yloxy)ethyl)pyridazin-3(2H)-one

This compound was prepared according to the procedure described in Example 75. MS (ESI pos. ion) m/z (MH+): 392.4. Calc'd exact mass for $C_{22}H_{18}FN_3O_3$: 391.1. $^1$H NMR (300 MHz, Chloroform-d) δ ppm 3.92 (s, 3 H) 4.65 (t, J=5.33 Hz, 2 H) 4.80 (t, J=5.41 Hz, 2 H) 6.67 (d, J=5.41 Hz, 1 H) 6.99 (dd, J=9.13, 2.56 Hz, 1H) 7.05 (d, J=9.79 Hz, 1 H) 7.14 (t, J=8.70 Hz, 2 H) 7.32 (d, J=2.48 Hz, 1 H) 7.65 (d, J=9.79 Hz, 1 H) 7.72 (dd, J=8.99, 5.19 Hz, 2 H) 8.00 (d, J=9.21 Hz, 1 H) 8.65 (d, J=5.26 Hz, 1 H).

EXAMPLE 79

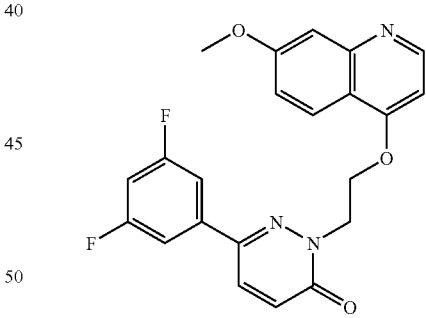

6-(3,5-Difluorophenyl)-2-(2-(7-methoxyquinolin-4-yloxy)ethyl)pyridazin-3(2H)-one This compound was prepared according to the procedure described in Example 75. MS (ESI pos. ion) m/z (MH+): 410.2. Calc'd exact mass for $C_{22}H_{17}F_2N_3O_3$: 409.1. $^1$H NMR (300 MHz, Chloroform-d) δ ppm 3.92 (s, 3 H) 4.66 (t, J=5.26 Hz, 2 H) 4.82 (t, J=5.19 Hz, 2 H) 6.68 (d, J=5.41 Hz, 1 H) 6.81-6.94 (m, 1 H) 7.00-7.11 (m, 2 H) 7.24-7.31 (m, 2 H) 7.38 (d, J=2.48 Hz, 1 H) 7.61 (d, J=9.65 Hz, 1H) 8.02 (d, J=9.21 Hz, 1 H) 8.70 (d, J=5.41 Hz, 1 H).

EXAMPLE 80

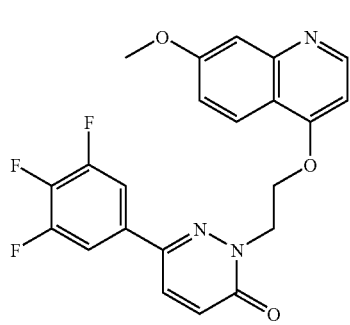

2-(2-(7-Methoxyquinolin-4-yloxy)ethyl)-6-(3,4,5-trifluorophenyl)pyridazin-3(2H)-one This compound was prepared according to the procedure described in Example 75. MS (ESI pos. ion) m/z (MH+): 428.2. Calc'd exact mass for $C_{22}H_{17}F_2N_3O_3$: 427.1. $^1$H NMR (300 MHz, Chloroform-d) δ ppm 3.92 (s, 3 H) 4.66 (t, J=5.26 Hz, 2 H) 4.82 (t, J=5.19 Hz, 2 H) 6.68 (d, J=5.41 Hz, 1 H) 6.81-6.94 (m, 1 H) 7.00-7.11 (m, 2 H) 7.24-7.31 (m, 2 H) 7.38 (d, J=2.48 Hz, 1 H) 7.61 (d, J=9.65 Hz, 1H) 8.02 (d, J=9.21 Hz, 1 H) 8.70 (d, J=5.41 Hz, 1 H).

EXAMPLE 81

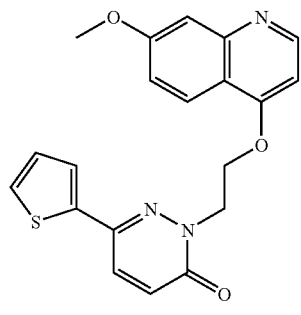

2-(2-(7-Methoxyquinolin-4-yloxy)ethyl)-6-(thiophen-2-yl)pyridazin-3(2H)-one

This compound was prepared according to the procedure described in Example 75. MS (ESI pos. ion) m/z (MH+): 380.2. Calc'd exact mass for $C_{20}H_{17}N_3O_3S$: 379.1. $^1$H NMR (300 MHz, Chloroform-d) δ ppm 3.92 (s, 3 H) 4.61 (t, J=5.33 Hz, 2 H) 4.77 (t, J=5.33 Hz, 2 H) 5.59 (none, 1 H) 6.67 (d, J=5.41 Hz, 1 H) 6.97-7.05 (m, 2 H) 7.10 (dd, J=5.04, 3.73 Hz, 1 H) 7.32 (d, J=2.48 Hz, 1 H) 7.37 (d, J=3.80 Hz, 1 H) 7.41 (d, J=5.12 Hz, 1 H) 7.62 (d, J=9.65 Hz, 1 H) 8.09 (d, J=9.21 Hz, 1H) 8.65 (d, J=5.26 Hz, 1 H).

EXAMPLE 82

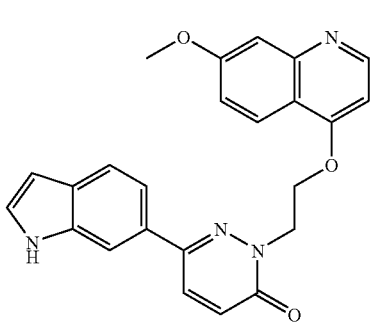

6-(1H-Indol-6-yl)-2-(2-(7-methoxyquinolin-4-yloxy)ethyl)pyridazin-3(2H)-one

This compound was prepared according to the procedure described in Example 75. MS (ESI pos. ion) m/z (MH+): 413.4. Calc'd exact mass for $C_{24}H_{20}N_4O_3$: 412.1. $^1$H NMR (300 MHz, Chloroform-d) δ ppm 6.59 (s, 1 H) 6.71 (d, J=5.26 Hz, 1 H) 6.97 (d, J=6.72 Hz, 1 H) 7.05 (d, J=9.65 Hz, 1 H) 7.31 (s, 2 H) 7.50 (d, J=8.33 Hz, 1 H) 7.60 (s, 1 H) 7.69 (d, J=8.33 Hz, 1 H) 7.75 (d, J=9.65 Hz, 1 H) 8.06 (d, J=9.06 Hz, 1 H) 8.39 (s, 1 H) 8.67 (d, J=5.26 Hz, 1 H).

EXAMPLE 83

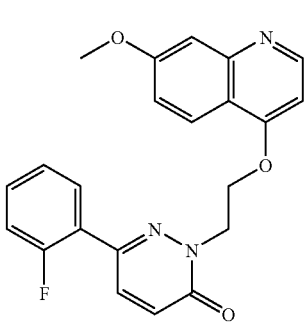

6-(2-Fluorophenyl)-2-(2-(7-methoxyquinolin-4-yloxy)ethyl)pyridazin-3(2H)-one

This compound was prepared according to the procedure described in Example 75. MS (ESI pos. ion) m/z (MH+): 392.4. Calc'd exact mass for $C_{22}H_{18}FN_3O_3$: 391.1. $^1$H NMR (300 MHz, Chloroform-d) δ ppm 3.93 (s, 3 H) 4.65 (t, J=5.41 Hz, 2 H) 4.82 (t, J=5.41 Hz, 2 H) 6.67 (d, J=5.26 Hz, 1 H) 7.02 (d, J=9.79 Hz, 2 H) 7.12-7.25 (m, 2 H) 7.33 (d, J=2.63 Hz, 1 H) 7.38-7.49 (m, 1 H) 7.61-7.72 (m, 2 H) 8.03 (d, J=9.06 Hz, 1 H) 8.65 (d, J=5.26 Hz, 1 H).

EXAMPLE 84

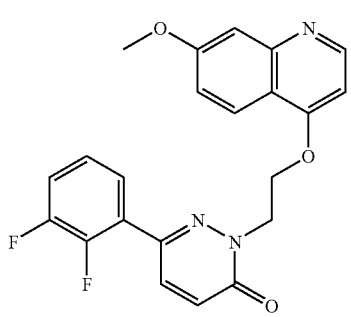

6-(2,3-Difluorophenyl)-2-(2-(7-methoxyquinolin-4-yloxy)ethyl)pyridazin-3(2H)-one This compound was prepared according to the procedure described in Example 75. MS (ESI pos. ion) m/z (MH+): 410.4. Calc'd exact mass for $C_{22}H_{17}F_2N_3O_3$: 409.1. $^1$H NMR (300 MHz, Chloroform-d) δ ppm 3.93 (s, 3 H) 4.66 (t, J=5.33 Hz, 2 H) 4.81 (t, J=5.41 Hz, 2 H) 6.67 (d, J=5.26 Hz, 1 H) 6.99-7.04 (m, 1 H) 7.04-7.07 (m, 1 H) 7.09-7.18 (m, 1 H) 7.20-7.25 (m, 1 H) 7.33 (d, J=2.48 Hz, 1 H) 7.36-7.43 (m, 1 H) 7.66 (dd, J=9.72, 2.27 Hz, 1 H) 8.02 (d, J=9.06 Hz, 1 H) 8.65 (d, J=5.26 Hz, 1 H).

EXAMPLE 85

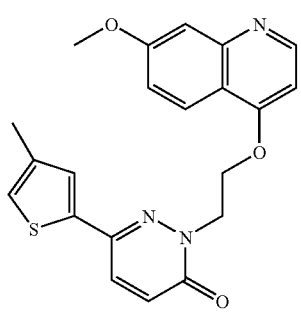

2-(2-(7-Methoxyquinolin-4-yloxy)ethyl)-6-(4-methylthiophen-2-yl)pyridazin-3(2H)-one This compound was prepared according to the procedure described in Example 75. MS (ESI pos. ion) m/z (MH+): 394.3. Calc'd exact mass for $C_{21}H_{19}N_3O_3S$: 393.1. $^1$H NMR (300 MHz, Chloroform-d) δ ppm 2.29 (s, 3 H) 3.92 (s, 3 H) 4.61 (t, J=5.41 Hz, 2 H) 4.75 (t, J=5.33 Hz, 2 H) 6.66 (d, J=5.26 Hz, 1 H) 6.93-7.01 (m, 2 H) 7.04 (dd, J=9.21, 2.48 Hz, 1 H) 7.17 (s, 1 H) 7.32 (d, J=2.48 Hz, 1 H) 7.57 (d, J=9.65 Hz, 1 H) 8.09 (d, J=9.21 Hz, 1 H) 8.65 (d, J=5.26 Hz, 1 H).

EXAMPLE 86

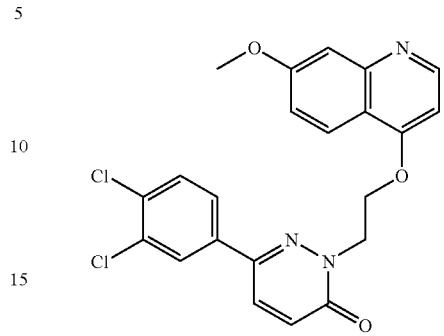

6-(3,4-Dichlorophenyl)-2-(2-(7-methoxyquinolin-4-yloxy)ethyl)pyridazin-3(2H)-one This compound was prepared according to the procedure described in Example 75. MS (ESI pos. ion) m/z (MH+): 442.4. Calc'd exact mass for $C_{22}H_{17}Cl_2N_3O_3$: 441.1. $^1$H NMR (300 MHz, Chloroform-d) δ ppm 3.92 (s, 3 H) 4.66 (t, J=5.26 Hz, 2 H) 4.81 (t, J=5.26 Hz, 2 H) 6.66 (d, J=5.26 Hz, 1 H) 6.98-7.11 (m, 2 H) 7.32 (d, J=2.48 Hz, 1 H) 7.52 (s, 2 H) 7.63 (d, J=9.65 Hz, 1 H) 7.85 (s, 1 H) 8.00 (d, J=9.21 Hz, 1 H) 8.65 (d, J=5.26 Hz, 1 H).

EXAMPLE 87

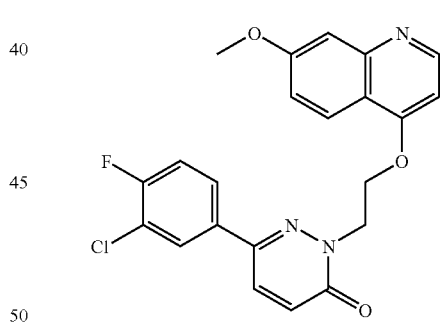

6-(3-Chloro-4-fluorophenyl)-2-(2-(7-methoxyquinolin-4-yloxy)ethyl)pyridazin-3(2H)-one This compound was prepared according to the procedure described in Example 75. MS (ESI pos. ion) m/z (MH+): 426.4. Calc'd exact mass for $C_{22}H_{17}ClFN_3O_3$: 425.1. $^1$H NMR (300 MHz, Chloroform-d) δ ppm 3.92 (s, 3 H) 4.66 (t, J=5.33 Hz, 2 H) 4.81 (t, J=5.26 Hz, 2 H) 6.67 (d, J=5.26 Hz, 1 H) 6.98-7.09 (m, 2 H) 7.21 (t, J=8.62 Hz, 1 H) 7.32 (d, J=2.48 Hz, 1 H) 7.52-7.59 (m, 1 H) 7.62 (d, J=9.79 Hz, 1 H) 7.82 (dd, J=6.87, 2.34 Hz, 1 H) 8.00 (d, 1 H) 8.65 (d, J=5.26 Hz, 1 H).

EXAMPLE 88

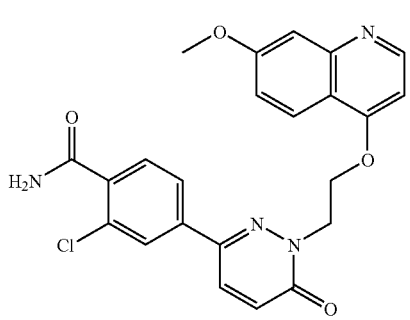

2-Chloro-4-(1-(2-(7-methoxyquinolin-4-yloxy)
ethyl)-6-oxo-1,6-dihydropyridazin-3-yl)benzamide This compound was prepared according to the procedure described in Example 75. MS (ESI pos. ion) m/z (MH+): 451.4. Calc'd exact mass for $C_{23}H_{19}ClN_4O_4$: 450.1. $^1$H NMR (300 MHz, Chloroform-d) δ ppm 3.92 (s, 3 H) 4.68 (t, J=5.19 Hz, 2 H) 4.82 (t, J=5.26 Hz, 2 H) 5.95 (s, 1 H) 6.49 (s, 1 H) 6.67 (d, J=5.26 Hz, 1 H) 7.01 (dd, J=9.13, 2.56 Hz, 1 H) 7.07 (d, J=9.65 Hz, 1 H) 7.31 (d, J=2.48 Hz, 1 H) 7.61-7.65 (m, 1 H) 7.65-7.68 (m, 1 H) 7.80 (d, J=1.61 Hz, 1 H) 7.88 (d, J=8.18 Hz, 1 H) 7.99 (d, J=9.21 Hz, 1 H) 8.65 (d, J=5.26 Hz, 1 H).

EXAMPLE 89

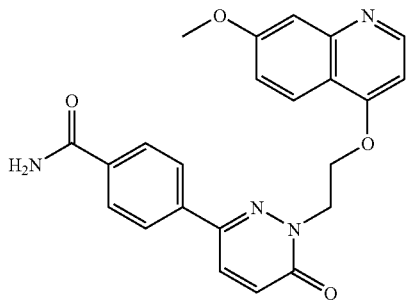

4-(1-(2-(7-Methoxyquinolin-4-yloxy)ethyl)-6-oxo-1,
6-dihydropyridazin-3-yl)benzamide This compound was prepared according to the procedure described in Example 75. MS (ESI pos. ion) m/z (MH+): 417.4. Calc'd exact mass for $C_{23}H_{20}N_4O_4$: 416.1. $^1$H NMR (300 MHz, MeOH) δ ppm 3.35 (s, 2 H) 3.88 (s, 3 H) 4.80 (dd, J=9.43, 3.73 Hz, 4 H) 6.90-6.98 (m, 2 H) 7.11 (d, J=9.79 Hz, 1 H) 7.20 (d, J=2.34 Hz, 1 H) 7.81-7.98 (m, 5 H) 8.03 (d, J=9.79 Hz, 1 H) 8.55 (d, J=5.41 Hz, 1 H).

EXAMPLE 90

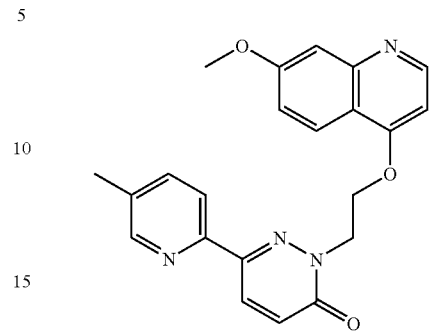

2-(2-(7-Methoxyquinolin-4-yloxy)ethyl)-6-(5-meth-
ylpyridin-2-yl)pyridazin-3(2 H)-one This compound was prepared according to the procedure described in Example 75. MS (ESI pos. ion) m/z (MH+): 389.4. Calc'd exact mass for $C_{22}H_{20}N_4O_3$: 388.1. $^1$H NMR (300 MHz, Chloroform-d) δ ppm 2.40 (s, 3 H) 3.92 (s, 3 H) 4.60-4.70 (m, 2 H) 4.81 (t, J=5.41 Hz, 2 H) 6.68 (d, J=5.26 Hz, 1 H) 6.99 (dd, J=9.13, 2.56 Hz, 1 H) 7.06 (d, J=9.79 Hz, 1 H) 7.32 (d, J=2.48 Hz, 1 H) 7.55 (d, J=8.18 Hz, 1 H) 7.95 (d, J=8.18 Hz, 1 H) 8.01 (d, J=9.06 Hz, 1 H) 8.34 (d, J=9.79 Hz, 1H) 8.45 (s, 1 H) 8.66 (d, J=5.26 Hz, 1 H).

EXAMPLE 91

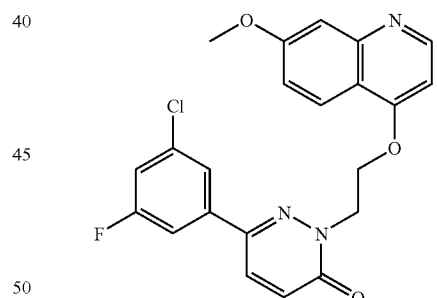

6-(3-Chloro-5-fluorophenyl)-2-(2-(7-methoxyquino-
lin-4-yloxy)ethyl)pyridazin-3(2 H)-one This compound was prepared according to the procedure described in Example 75. MS (ESI pos. ion) m/z (MH+): 426.4. Calc'd exact mass for $C_{22}H_{17}ClFN_3O_3$: 425.1. $^1$H NMR (300 MHz, Chloroform-d) δ ppm 3.92 (s, 3 H) 4.65 (t, J=5.26 Hz, 2 H) 4.81 (t, J=5.19 Hz, 2 H) 6.66 (d, J=5.41 Hz, 1 H) 7.00-7.10 (m, 2 H) 7.14-7.20 (m, 1 H) 7.32 (d, J=2.48 Hz, 1 H) 7.35 (dd, J=9.21, 1.90 Hz, 1 H) 7.54 (s, 1 H) 7.61 (d, J=9.79 Hz, 1 H) 8.01 (d, J=9.21 Hz, 1 H) 8.65 (d, J=5.26 Hz, 1 H).

EXAMPLE 92

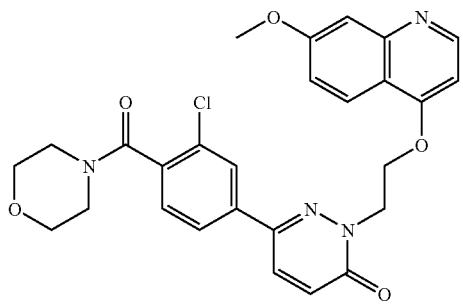

6-(3-Chloro-4-(morpholine-4-carbonyl)phenyl)-2-(2-(7-methoxyquinolin-4-yloxy)ethyl)pyridazin-3(2H)-one This compound was prepared according to the procedure described in Example 75. MS (ESI pos. ion) m/z (MH+): 521.4. Calc'd exact mass for $C_{27}H_{25}ClN_4O_5$: 520.1. $^1$H NMR (300 MHz, Chloroform-d) δ ppm 3.20-3.38 (m, 2 H) 3.56-3.67 (m, 1 H) 3.69-3.78 (m, 1 H) 3.79-3.90 (m, 4 H) 3.92 (s, 3 H) 4.66 (t, J=5.19 Hz, 2 H) 4.82 (t, J=5.26 Hz, 2 H) 6.66 (d, J=5.41 Hz, 1 H) 7.01 (dd, J=9.21, 2.48 Hz, 1 H) 7.08 (d, J=9.79 Hz, 1 H) 7.32 (d, J=2.48 Hz, 1 H) 7.38 (d, J=7.89 Hz, 1 H) 7.62-7.70 (m, 2 H) 7.83 (s, 1 H) 8.01 (d, J=9.21 Hz, 1 H) 8.65 (d, J=5.26 Hz, 1 H).

EXAMPLE 93

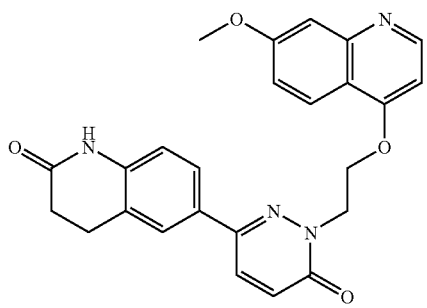

6-(1-(2-(7-Methoxyquinolin-4-yloxy)ethyl)-6-oxo-1,6-dihydropyridazin-3-yl)-3,4-dihydroquinolin-2(1H)-one This compound was prepared according to the procedure described in Example 75. MS (ESI pos. ion) m/z (MH+): 443.4. Calc'd exact mass for $C_{25}H_{22}N_4O_4$: 442.2. $^1$H NMR (400 MHz, Chloroform-d) δ ppm 2.62-2.72 (m, 2 H) 2.98 (t, J=7.53 Hz, 2 H) 3.92 (s, 3 H) 4.67 (t, J=5.28 Hz, 2 H) 4.80 (t, J=5.28 Hz, 2 H) 6.68 (d, J=5.48 Hz, 1 H) 6.80 (d, J=8.02 Hz, 1 H) 7.00 (d, J=9.19 Hz, 1 H) 7.05 (d, J=9.78 Hz, 1 H) 7.32 (s, 1 H) 7.48-7.55 (m, 2 H) 7.64 (d, J=9.78 Hz, 1 H) 7.80 (s, 1 H) 8.02 (d, J=9.19 Hz, 1 H) 8.65 (d, J=5.28 Hz, 1 H).

EXAMPLE 94

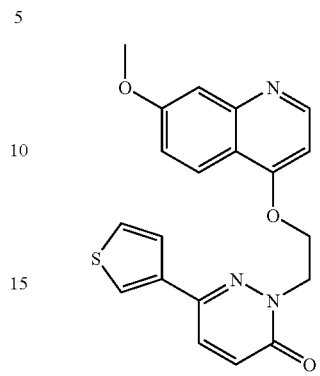

2-(2-(7-Methoxyquinolin-4-yloxy)ethyl)-6-(thiophen-3-yl)pyridazin-3(2H)-one

To a solution of 6-chloro-2-(2-(7-methoxyquinolin-4-yloxy)ethyl)pyridazin-3(2H)-one (0.090 g, 0.27 mmol) and 3-thiopheneboronic acid (0.069 g, 0.54 mmol) in 4 mL of dioxane was added 1 mL of 1N $Na_2CO_3$ followed by 30 mg of FibreCat, in a microwave vial. The reaction was heated to 120° C. for 30 minutes. The mixture was then diluted with 40 mL of $NaHCO_3$ and 60 mL of EtOAc. The organic phase was separated, washed with 30 mL of brine, dried over $Na_2SO_4$ and concentrated in vacuo. The residue was purified by a silica gel column chromatography (EtAOc to 10% MeOH/EtOAc) to give a white solid (0.074 g, 72% yield). MS (ESI pos. ion) m/z (MH+): 380.1. Calc'd Exact Mass for $C_{20}H_{17}N_3O_3S$: 379.1.

EXAMPLE 95

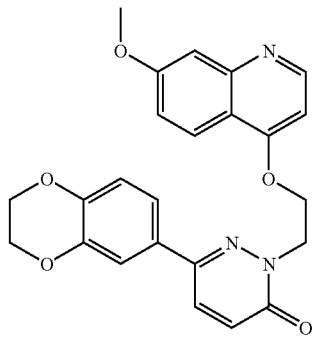

6-(2,3-Dihydrobenzo[b][1,4]dioxin-6-yl)-2-(2-(7-methoxyquinolin-4-yloxy)ethyl)pyridazin-3(2H)-one This compound was prepared according to the procedure described in Example 94. MS (ESI pos. ion) m/z (MH+): 432.1. Calc'd Exact Mass for $C_{24}H_{21}N_3O_5$: 431.15.

EXAMPLE 96

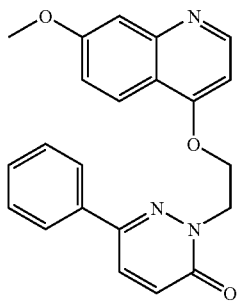

2-(2-(7-methoxyquinolin-4-yloxy)ethyl)-6-phenylpyridazin-3(2H)-one. This compound was prepared according to the procedure described in Example 94. MS (ESI pos. ion) m/z (MH+): 374. Calc'd exact mass for $C_{22}H_{19}N_3O_3$: 373. $^1$HNMR (300 MHz, CDCl$_3$): δ 8.64 (d, J=6 Hz, 1H), 8.02 (d, J=9 Hz, 1H), 7.75 (m, 2H), 7.69 (d, J=12 Hz, 1H), 7.46 (m, 3H), 7.32 (d, J=3 Hz, 1H), 7.05 (d, J=12 Hz, 1H), 6.98 (dd, J=3, 9 Hz, 1H), 6.67 (d, J=6 Hz, 1H), 4.81 (t, J=3 Hz, 2H), 4.65 (t, J=3 Hz, 2H), 3.91 (s, 3H).

EXAMPLE 97

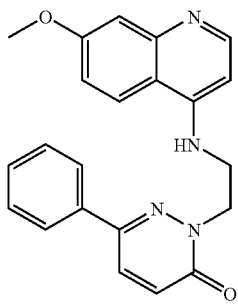

2-(2-(7-Methoxyquinolin-4-ylamino)ethyl)-6-phenylpyridazin-3(2H)-one

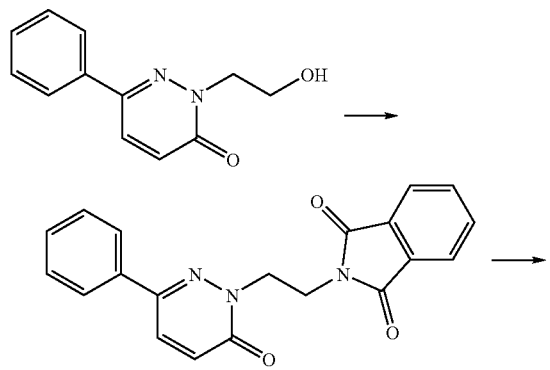

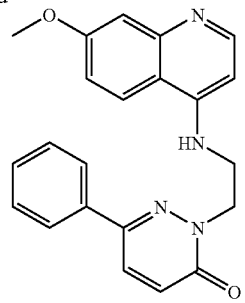

2-(2-(6-Oxo-3-phenylpyridazin-1(6H)-yl)ethyl)isoindoline-1,3-dione. To a mixture of phthalimide (1.0 g, 6.8 mmol), Ph$_3$P (1.9 g, 7.2 mmol), 2-(2-hydroxyethyl)-6-phenylpyridazin-3(2H)-one (1.2 g, 5.5 mmol) in THF (20 mL) was added diisopropyl azodicarboxylate (1.4 mL, 7.2 mmol) dropwise. The resulting hot, clear solution was stirred at room temperature. After 3 h, hexane (40 mL) was added. The slurry was filtered and the solid was washed with ether (6×15 mL) to give the product as a white (2.1 g). MS (ESI pos. ion) calc'd for $C_{20}H_{15}N_3O_3$: 345.1; found: 346.4 (MH+). $^1$H NMR (400 MHz, DMSO-d6) δ ppm 4.03 (dd, 2 H) 4.39 (t, 2 H) 6.99 (d, J=9.78 Hz, 1 H) 7.26 (t, J=7.43 Hz, 2 H) 7.34 (t, J=7.34 Hz, 1 H) 7.50 (d, J=7.24 Hz, 2 H) 7.72-7.82 (m, 4 H) 7.97 (d, J=9.78 Hz, 1 H)

2-(2-Aminoethyl)-6-phenylpyridazin-3(2H)-one. A mixture of 2-(2-(6-oxo-3-phenylpyridazin-1(6H)-yl)ethyl)isoindoline-1,3-dione (2.1 g, 6.1 mmol) and hydrazine (10 mL, 10.0 mmol) (THF) in MeOH (40 mL) was heated to 75° C. A clear solution was formed. After overnight (18 h), the slurry was cooled to room temperature and was filtered and washed with MeOH. The filtrate was concentrated and washed with 20% MeOH/CH$_2$Cl$_2$ to give a yellow solid (LCMS indicated the presence of product). The filtrate was concentrated under vacuum and was carried to next step.

2-(2-(7-Methoxyquinolin-4-ylamino)ethyl)-6-phenylpyridazin-3(2H)-one. A mixture of 2-(2-aminoethyl)-6-phenylpyridazin-3(2H)-one (60 mg, 743 μmol) and 8-chloro-3-methoxy-1,5-naphthyridine (55 mg, 282 μmol) in iPrOH (2 mL) was heated to 150° C. for 15 min under microwave. The mixture was filtered and the filtrate was chromatographed on silica with 2-5% (2N NH$_3$-MeOH) in CH$_2$Cl$_2$ to give the product as a white solid (60 mg). MS (ESI pos. ion) calc'd for $C_{21}H_{19}N_5O_2$: 373.1; found 374.2 (MH+). $^1$H NMR (400 MHz, Chloroform-d) δ ppm 3.81-3.89 (m, 2 H) 3.92 (d, J=1.37 Hz, 3 H) 4.64 (t, J=5.48 Hz, 2 H) 6.54 (dd, 1 H) 7.03 (dd, J=9.78, 1.57 Hz, 1 H) 7.10 (s, 1 H) 7.39-7.48 (m, 4 H) 7.66 (dd, J=9.59, 1.56 Hz, 1 H) 7.70-7.79 (m, 2 H) 8.38 (t, 1 H) 8.46 (dd, 1 H).

EXAMPLE 98

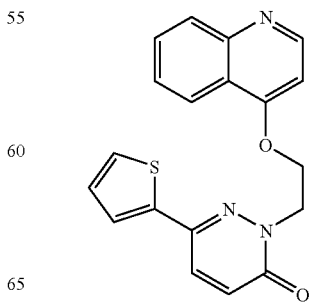

1-(2-(Quinolin-4-yloxy)ethyl)-5-(thiophen-2-yl)pyridin-2(1H)-one

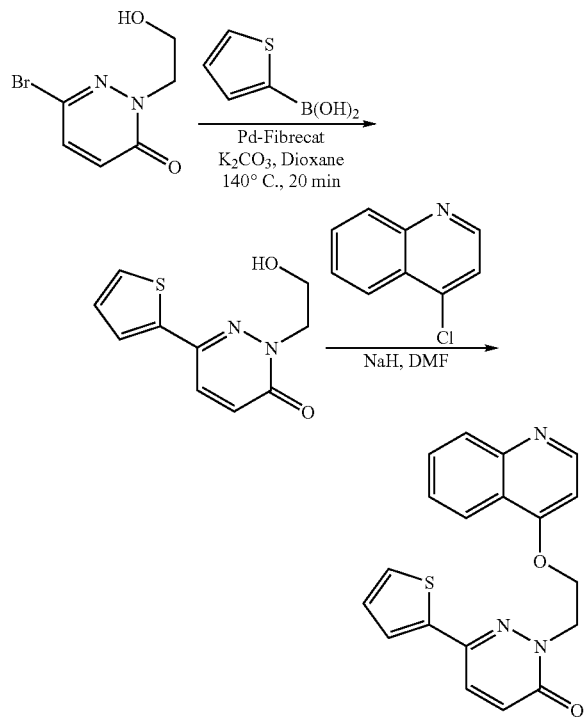

1-(2-Hydroxyethyl)-5-(thiophen-2-yl)pyridin-2(1H)-one. To a microwave vial with 5-bromo-1-(2-hydroxyethyl)pyridin-2(1H)-one (0.400 g, 2 mmol), 2-thiopheneboronic acid (0.800 g, 6 mmol), Potassium Carbonate (2 mL, 4 mmol) and 1,4-Dioxane (2.5 mL, 29 mmol) was added Palladium-Fibrecat. The vial was equipped with a stir bar and capped. The vial was placed into the CEM microwave for 20 minutes at 140° C., while 50 Watts of energy was supplied via Powermax. The progress of the reaction was monitored by LC/MS, which showed mostly desired product in the mixture. The mixture was diluted with $CH_2Cl_2$ (3 mL) and Water (2 mL). The organic layer was extracted with 3:1 $CH_2Cl_2$/MeOH (3×16 mL). Combined organics, dried over Sodium sulfate, filtered and concentrated in-vacuo. The crude was recrystallized from 5:1 $CH_2Cl_2$/MeOH and Hexanes to give the desired product as a light-yellow crystalline solid (0.280 g, 69% yield). MS (ESI pos. ion) m/z (MH+): 222. Calc'd exact mass for $C_{11}H_{11}NO_2S$: 221. $^1$H NMR (300 MHz, $CDCl_3$): 7.60 (s, 3H), 7.06 (s, 3H), 4.16 (s, 2H), 3.98 (s, 2H).

1-(2-(Quinolin-4-yloxy)ethyl)-5-(thiophen-2-yl)pyridin-2(1H)-one. To a mixture of 1-(2-hydroxyethyl)-5-(thiophen-2-yl)pyridin-2(1H)-one (0.050 g, 0.3 mmol) in DMF (1 mL, 13 mmol) was added sodium hydride (0.080 g, 3 mmol). The resulting mixture was allowed to stir 1.5 hours at ambient temperature. Then 4-chloroquinoline (0.080 g, 0.5 mmol) was added into the mixture and allowed to stir under inert atmosphere overnight. The progress of the reaction was monitored by LC/MS, which showed mostly desired product. The mixture was diluted with $CH_2Cl_2$ and water, then extracted the organic layer with $CH_2Cl_2$ (3×20 mL). The combined organics were dried over sodium sulfate, filtered and concentrated in-vacuo. The crude material was purified by Reverse-Phase HPLC. This gave the desired product as an off-white solid (0.050 g, 45% yield). MS (ESI pos. ion) m/z (MH+): 349. Calc'd exact mass for $C_{20}H_{16}N_2O_2S$: 348. $^1$H NMR (300 MHz, $CDCl_3$): 8.67 (d, J=4.82, 1H), 8.05 (d, J=8.33 Hz, 1H), 7.95 (d, J=8.33 Hz, 1H), 7.73 (s, 1H), 7.56 (d, J=9.79 Hz, 2H), 7.35 (s, 1H), 7.19 (s, 1H), 6.99 (d, J=2.34, 2H), 6.67 (d, J=4.97 Hz, 1H), 6.58 (d, J=9.35 Hz, 1H), 4.48 (s, 4H), 1.74 (s, 1H).

EXAMPLE 99

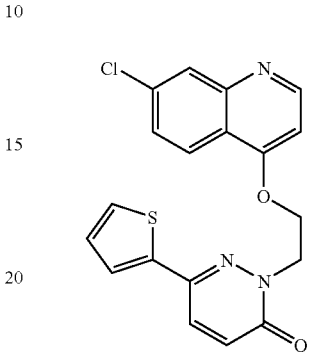

1-(2-(7-Chloroquinolin-4-yloxy)ethyl)-5-(thiophen-2-yl)pyridin-2(1H)-one This compound was prepared according to the procedure described in Example 98. MS (ESI pos. ion) m/z (MH+): 383. Calc'd exact mass for $C_{20}H_{15}ClN_2O_2S$: 382.5. $^1$H NMR (300 MHz, $CDCl_3$): 8.74 (d, J=5.12 Hz, 1H), 8.29 (d, J=2.05 Hz, 1H), 8.17 (d, J=8.77 Hz, 1H), 7.98 (d, J=1.17 Hz, 1H), 7.78 (d, J=9.35 Hz, 1H), 7.50 (s, 2H), 7.30 (s, 1H), 7.11 (d, J=4.97 Hz, 2H), 6.51 (d, J=9.50 Hz, 1H), 4.55 (s, 4H).

EXAMPLE 100

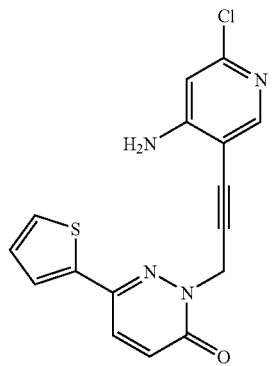

2-(3-(4-Amino-6-chloropyridin-3-yl)prop-2-ynyl)-6-(thiophen-2-yl)pyridazin-3(2H)-one

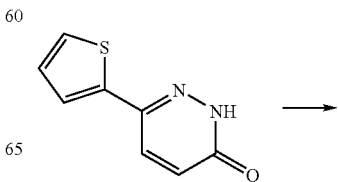

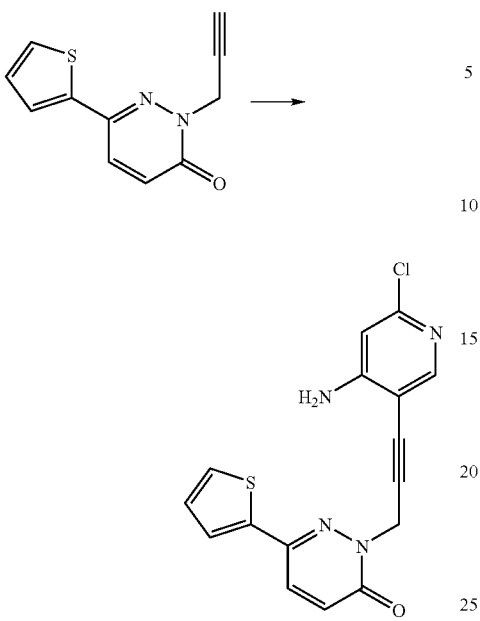

2-(Prop-2-ynyl)-6-(thiophen-2-yl)pyridazin-3(2H)-one. As generally described in Goodman, A. J.; Stanforth, S. P.; Tarbit, B. *Tetrahedron* 1999, 55, 15067: To a mixture of 6-(thiophen-2-yl)pyridazin-3-ol (634 mg, 3558 µmol) and $K_2CO_3$ (1475 mg, 10673 µmol) in DMF (6 mL) was added 3-bromoprop-1-yne (700 µl, 7856 µmol). After 1 h, EtOAc (50 mL) was added. The black mixture was washed with $H_2O$ (3×30 mL), severe emulsion was encountered. The organic phase was dried over $Na_2SO_4$ and concentrated. The material was purified on silica gel (0-5% MeOH in $CH_2Cl_2$) to give a brown oil. The oil was refluxed in hexane overnight and the yellow liquid was decanted and cooled to room temperature. This slurry was then filtered to give a yellow solid (90 mg). The filtrate and the oil from the hexane reflux were combined and was chromatographed with 1-2% MeOH in EtOAc—$CH_2Cl_2$ (1:1) to give additional product (>196 mg). MS (ESI pos. ion) calc'd for $C_{11}H_8N_2OS$: 216.1; found 217.1 (MH+). $^1H$ NMR (400 MHz, Chloroform-d) δ ppm 2.36 (t, J=2.54 Hz, 1 H) 4.95 (d, J=2.54 Hz, 2 H) 7.00 (d, J=9.78 Hz, 1 H) 7.09 (t, 1 H) 7.40 (d, J=4.30 Hz, 2 H) 7.62 (d, J=9.59 Hz, 1 H)

2-(3-(4-Amino-6-chloropyridin-3-yl)prop-2-ynyl)-6-(thiophen-2-yl)pyridazin-3(2H)-one. A mixture of $Et_3N$ (200 µl, 1435 µmol), Cu(I) (10 mg, 53 µmol), $PdCl_2(PhP_3)_2$ (20 mg, 28 µmol), 2-(prop-2-ynyl)-6-(thiophen-2-yl)pyridazin-3 (2H)-one (90 mg, 416 µmol), and 2-chloro-5-iodopyridin-4-amine (138 mg, 542 µmol) in MeCN (1.5 mL) was heated to 80° C. under nitrogen for 1 h. The mixture was cooled to room temperature, and was loaded to a silica column. Chromatography with 0.5-5% MeOH in $CH_2Cl_2$ afforded a pink solid which was triturated with EtOAc-hexane (1:2, 10 mL) to give a pink solid as the pure product (48 mg). MS (ESI pos. ion) calc'd for $C_{16}H_{11}ClN_4OS$: 342.0; found 343.1 (MH+). $^1H$ NMR (400 MHz, Chloroform-d) δ ppm 5.18 (s, 2 H) 5.75 (br. s., 2 H) 6.64 (s, 1 H) 7.03 (d, J=9.78 Hz, 1 H) 7.11 (dd, J=5.09, 3.72 Hz, 1 H) 7.37-7.48 (m, 2 H) 7.73 (d, J=9.78 Hz, 1 H) 8.03 (s, 1 H).

EXAMPLE 101

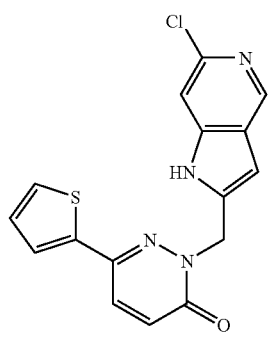

2-((6-Chloro-1H-pyrrolo[3,2-c]pyridin-2-yl)methyl)-6-(thiophen-2-yl)pyridazin-3(2H)-one When the last reaction step from Example 100 was allowed to proceed for 2 days, small amount of the title compound was isolated from HPLC. MS (ESI pos. ion): calc'd for $C_{16}H_{11}ClN_4OS$: 342.0; found 343.1 (MH+). $^1H$ NMR (400 MHz, Chloroform-d) δ ppm 5.45 (s, 2 H, $CH_2$) 6.69 (s, 1 H) 7.06 (d, J=9.59 Hz, 1 H) 7.09 (dd, J=4.99, 3.81 Hz, 1 H) 7.27 (s, 1 H) 7.39 (d, J=3.72 Hz, 1 H) 7.42 (d, J=5.09 Hz, 1 H) 7.66 (d, J=9.78 Hz, 1 H) 8.62 (s, 1 H, NH), NH: 9.62.

EXAMPLE 102

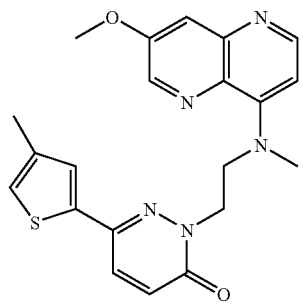

2-(2-((7-Methoxy-1,5-naphthyridin-4-yl)(methyl) amino)ethyl)-6-(4-methylthiophen-2-yl)pyridazin-3 (2H)-one

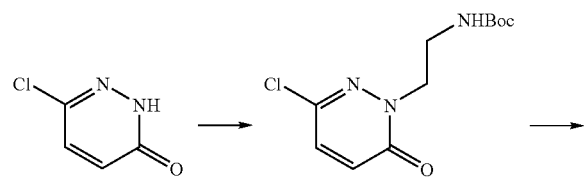

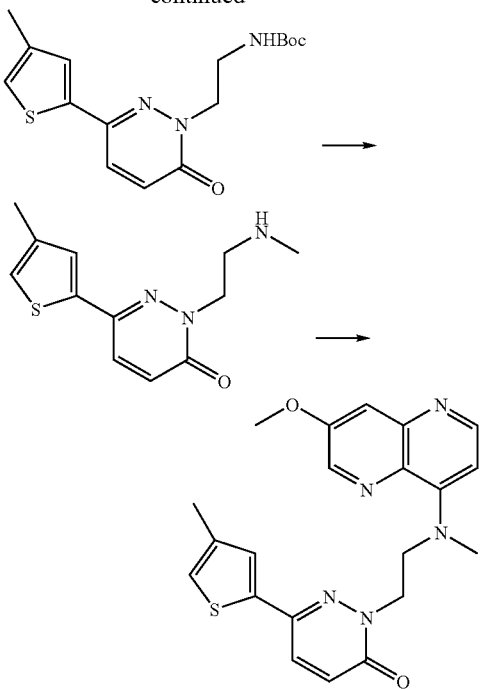

tert-Butyl 2-(3-chloro-6-oxopyridazin-1(6H)-yl)ethylcarbamate. A suspension of 6-chloropyridazin-3(2H)-one (2912 mg, 22.3 mmol), tert-butyl 2-bromoethylcarbamate (5000 mg, 22.3 μmol), and $K_2CO_3$ (9251 mg, 66.9 mmol) was stirred in DMF (40 mL) overnight at 23° C. The mixture was partioned between $CH_2Cl_2$ (200 mL) and 5% $NaHCO_3$ (50 mL). The organic layer was dried with brine and $MgSO_4$, concentrated to a solid from toluene under reduced pressure. MS (ESI pos. ion) m/z (MH+): 274 Calc'd exact mass for $C_{11}H_{16}ClN_3O_3$: 273.

tert-Butyl 2-(3-(4-methylthiophen-2-yl)-6-oxopyridazin-1(6H)-yl)ethylcarbamate. A suspension of tert-butyl 2-(3-chloro-6-oxopyridazin-1(6H)-yl)ethylcarbamate (2000 mg, 7.31 mmol), 1,1'-bis(diphenylphosphino)ferrocene-palladium dichloride (535 mg, 0.731 mmol), and 4-methylthiophen-2-ylboronic acid (2075 mg, 14.6 mmol) in DME (1.6 mL) with $Na_2CO_3$ (10.9 mL, 21.9 mmol) [2M] was sparged with argon for 1 min, then heated to 90° C. for 2 h. The mixture was partitioned between $CH_2Cl_2$ and 5% $NaHCO_3$, and the organic layer was dried over $MgSO_4$ and dried onto dry silica. The product was purified on 80 g silica eluting with 1>2.5% MeOH/$CH_2Cl_2$. MS (ESI pos. ion) m/z (MH+): 336 Calc'd exact mass for $C_{16}H_{21}N_3O_3S$: 335. $^1$H NMR (400 MHz, Chloroform-d) δ ppm 1.40 (s, 9H) 2.28 (s, 3 H) 3.61 (d, J=5.02 Hz, 2 H) 4.32 (t, J=5.27 Hz, 2 H) 5.11 (br. s., 1 H) 6.91-6.99 (m, 2 H) 7.20 (s, 1 H) 7.55 (d, J=10.04 Hz, 1 H). $^{13}$C NMR (101 MHz, Chloroform-d) δ ppm 13.71, 26.35, 37.78, 49.41, 77.33, 121.32, 125.75, 127.40, 127.95, 136.53, 139.01, 153.88, 157.97.

tert-Butyl methyl(2-(3-(4-methylthiophen-2-yl)-6-oxopyridazin-1(6H)-yl)ethyl)carbamate. A flame dried 50 mL round bottom flask was charged tert-butyl methyl(2-(3-(4-methylthiophen-2-yl)-6-oxopyridazin-1(6H)-yl)ethyl)carbamate (340 mg, 1.01 mmol) and DMF (3 mL). A nitrogen line and external ice bath was introduced, and a solution of MeI (69.7 μl, 1.11 mmol) in DMF (1 mL) added. After 4 h, the temperature was raised to 20° C. The mixture was quenched with satd. $NH_4Cl$ (10 mL), and the aqueous was extracted with $CH_2Cl_2$ (20 mL). The organic layer was dried over $MgSO_4$, and concentrated to a solid under reduced pressure from toluene. MS (ESI pos. ion) m/z (MH+): 350. Calc'd exact mass for $C_{17}H_{23}N_3O_3S$: 349.

2-(2-(Methylamino)ethyl)-6-(4-methylthiophen-2-yl)pyridazin-3(2H)-one. A solution of tert-butyl methyl(2-(3-(4-methylthiophen-2-yl)-6-oxopyridazin-1(6H)-yl)ethyl)carbamate (340 mg, 973 μmol) in $CH_2Cl_2$ (5 mL) and TFA (5 mL) was stirred for 30 min at 23° C. The solvents were removed under reduced pressure and the residue partitioned between $CH_2Cl_2$ (20 mL) and 1M NaOH (10 mL). The organic layer was dried over $MgSO_4$, concentrated and purified on silica (12 g) eluting with 0-6% (2M $NH_3$ in MeOH/$CH_2Cl_2$) to give the product as an amber oil. MS (ESI pos. ion) m/z (MH+): 250. Calc'd exact mass for $C_{12}H_{15}N_3OS$: 249. $^1$H NMR (400 MHz, Chloroform-d) δ ppm 1.60 (br. s., 2 H) 2.28 (d, J=0.78 Hz, 3 H) 2.49 (s, 3 H) 3.07 (t, J=6.06 Hz, 2 H) 4.32 (t, J=6.06 Hz, 2 H) 6.88-7.01 (m, 2 H) 7.18 (d, J=1.17 Hz, 1 H) 7.54 (d, J=9.59 Hz, 1 H).

2-(2-((7-Methoxy-1,5-naphthyridin-4-yl)(methyl)amino)ethyl)-6-(4-methylthiophen-2-yl)pyridazin-3(2H)-one. A suspension of 2-(2-(methylamino)ethyl)-6-(4-methylthiophen-2-yl)pyridazin-3(2H)-one (275 mg, 1103 μmol) and 8-chloro-3-methoxy-1,5-naphthyridine (193 mg, 993 μmol) in iPrOH (5 mL) was heated to 100° C. for 18 h in an appropriately sealed vial. The mixture was partitioned between $CH_2Cl_2$ (30 mL) and 1M NaOH (10 mL), and the organic dried over $MgSO_4$. After concentration under reduced pressure, the organic residue was dissolved in iPrOH (2 mL) and the resulting crystallized solid was washed with iPrOH (2×0.5 mL) then dried under reduced pressure. MS (ESI pos. ion) m/z (MH+): 408. Calc'd exact mass for $C_{21}H_{21}N_5O_2S$: 407. $^1$H NMR (400 MHz, Chloroform-d) δ ppm 2.26 (s, 3 H) 3.22 (s, 3 H) 3.83 (s, 3 H) 4.51 (t, J=5.77 Hz, 2 H) 4.75 (t, J=5.77 Hz, 2 H) 6.55 (d, J=5.52 Hz, 1H) 6.60 (d, J=9.54 Hz, 1 H) 6.91 (s, 1 H) 6.97 (s, 1 H) 7.19 (d, J=9.54 Hz, 1 H) 7.32 (d, J=3.01 Hz, 1 H) 8.32 (d, J=5.52 Hz, 1 H) 8.46 (d, J=2.51 Hz, 1 H).

EXAMPLE 103

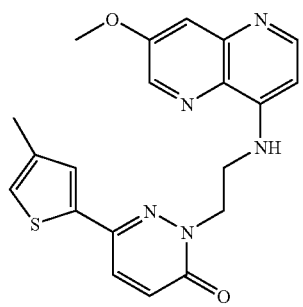

2-(2-(7-Methoxy-1,5-naphthyridin-4-ylamino)ethyl)-6-(4-methylthiophen-2-yl)pyridazin-3(2H)-one A suspension of 2-(2-aminoethyl)-6-(4-methylthiophen-2-yl)pyridazin-3(2H)-one (360 mg, 1530 μmol) and 8-chloro-3-methoxy-1,5-naphthyridine (298 mg, 1530 μmol) in iPrOH (5 mL) was heated to 100° C. in a sealed vial. After 3 h, the reaction mixture was partitioned between $CH_2Cl_2$ (30 mL) and 1M NaOH (10 mL). The organic layer was dried over $MgSO_4$, concentrated to a solid, and purified on 40 gram of silica eluting with 0-60% of 6% (2M NH₃ in MeOH)/CH₂Cl₂. The resulting oil was crystallized from ACN (0.5 mL). MS (ESI pos. ion) m/z (MH+): 394. Calc'd exact mass for $C_{20}H_{19}N_5O_2S$: 393. ¹H NMR (400 MHz, Chloroform-d) δ ppm 2.28 (s, 3 H) 3.84 (q, J=6.06 Hz, 2 H) 3.93 (s, 3 H) 4.55 (t, J=6.06 Hz, 2 H) 6.56 (d, J=5.48 Hz, 1 H) 6.93-6.98 (m, 2 H) 7.02 (t, J=5.67 Hz, 1 H) 7.16 (d, J=1.17 Hz, 1 H) 7.46 (d, J=2.74 Hz, 1 H) 7.52 (d, J=9.78 Hz, 1 H) 8.40 (d, J=2.74 Hz, 1 H) 8.46 (d, J=5.28 Hz, 1 H).

EXAMPLE 104

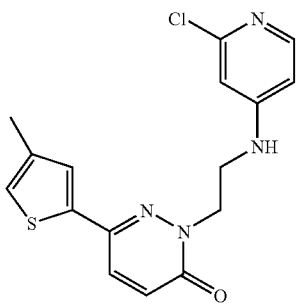

2-(2-(2-Chloropyridin-4-ylamino)ethyl)-6-(4-methylthiophen-2-yl)pyridazin-3(2H)-one A suspension of 2-chloro-4-fluoropyridine (904 mg, 6.87 mmol), 2-(2-aminoethyl)-6-(4-methylthiophen-2-yl)pyridazin-3(2H)-one (1470 mg, 6.25 mmol), and K₂CO₃ (1727 mg, 12.5 mmol) in DMF (8 mL) was stirred at 75° C. for 4 h. The mixture was partioned between CH₂Cl₂ (100 mL) and 5% NaHCO₃ (50 mL). The organic layer was dried over MgSO₄, concentrated, then purified on 40 g silica eluting with 20>60% of 2M NH₃ in MeOH/CH₂Cl₂. Product isolated as a white solid. MS (ESI pos. ion) m/z (MH+): 347. Calc'd exact mass for $C_{16}H_{15}ClN_4OS$: 346. ¹H NMR (400 MHz, Chloroform-d) δ ppm 2.29 (s, 3 H) 3.61 (q, J=5.35 Hz, 2 H) 4.44-4.51 (m, 2 H) 5.31 (br. s., 1 H) 6.46 (s, 1 H) 6.94-7.01 (m, 2 H) 7.19 (s, 1 H) 7.57 (d, J=9.54 Hz, 1 H) 7.91 (d, J=6.02 Hz, 1 H). ¹³C NMR (101 MHz, Chloroform-d) δ ppm 15.76, 42.71, 50.46, 106.06, 107.27, 123.73, 128.21, 129.82, 130.08, 138.12, 138.76, 141.69, 149.32, 152.31, 155.06, 160.44.

EXAMPLE 105

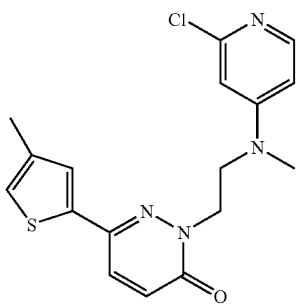

2-(2-((2-Chloropyridin-4-yl)(methyl)amino)ethyl)-6-(4-methylthiophen-2-yl)pyridazin-3(2H)-one A suspension of 2-(2-(methylamino)ethyl)-6-(4-methylthiophen-2-yl)pyridazin-3(2H)-one (200 mg, 802 μmol), 2-chloro-4-fluoropyridine (116 mg, 882 μmol), and potassium carbonate (222 mg, 1604 μmol) in DMF (1 mL) was heated to 75° C. for 90 min. The reaction mixture was partitioned between CH₂Cl₂ (50 mL) and 5% NaHCO₃ (20 mL). The organic layer was dried over MgSO₄ and concentrated to a solid from toluene under reduced pressure. The solid was triturated with toluene and dried under reduced pressure to give a white solid. MS (ESI pos. ion) m/z (MH+): 361. Calc'd exact mass for $C_{17}H_{17}ClN_4OS$: 360. ¹H NMR (400 MHz, Chloroform-d) δ ppm 2.28 (s, 3 H) 3.02 (s, 3 H) 3.83 (t, J=6.27 Hz, 2 H) 4.40 (t, J=6.27 Hz, 2 H) 6.40-6.52 (m, 2 H) 6.85 (d, J=9.54 Hz, 1 H) 6.96 (s, 1 H) 7.13 (s, 1 H) 7.46 (d, J=9.54 Hz, 1 H) 7.86 (d, J=6.02 Hz, 1 H). ¹³C NMR (101 MHz, Chloroform-d) δ ppm 15.74, 37.62, 48.39, 49.09, 105.64, 105.90, 123.48, 128.03, 129.65, 129.74, 138.18, 138.63, 141.27, 149.19, 152.43, 155.53, 159.78.

EXAMPLE 106

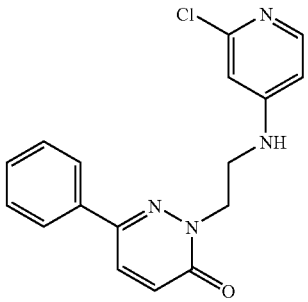

2-(2-(2-Chloropyridin-4-ylamino)ethyl)-6-phenylpyridazin-3(2H)-one

A suspension of 2-(2-aminoethyl)-6-phenylpyridazin-3(2H)-one (425 mg, 1.97 mmol), 2-chloro-4-fluoropyridine (312 mg, 2.37 mmol), and K₂CO₃ (546 mg, 3.95 mmol) in DMF (5 mL) was stirred under nitrogen at 75° C. for 3 days. The reaction mixture was partitioned between CH₂Cl₂ (40 mL) and 5% NaHCO₃ (20 mL), and the aqueous was extracted with 9:1 CHCl₃/iPrOH (3×25 mL). The combined organics was dried over MgSO₄ and concentrated to a solid from toluene. The solid was triturated with toluene (2×5 mL) and diethyl ether (10 mL) to give a white solid. MS (ESI pos. ion) m/z (MH+): 327. Calc'd exact mass for $C_{17}H_{15}ClN_4O$: 326. ¹H NMR (400 MHz, Chloroform-d) δ ppm 3.61-3.68 (m, 2 H) 4.52-4.59 (m, 2 H) 5.35 (br. s., 1 H) 6.37 (dd, J=5.77, 2.26 Hz, 1 H) 6.45 (d, J=2.01 Hz, 1 H) 7.05 (d, J=9.54 Hz, 1 H) 7.44-7.52 (m, 3 H) 7.66-7.78 (m, 3 H) 7.91 (d, J=6.02 Hz, 1 H).

EXAMPLE 107

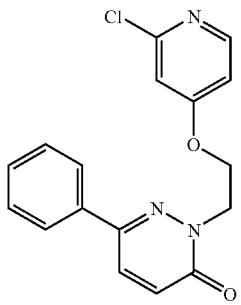

2-(2-(2-Chloropyridin-4-yloxy)ethyl)-6-phenylpyridazin-3(2H)-one

To a 15 mL round-bottomed flask was added 2-(2-hydroxyethyl)-6-phenylpyridazin-3(2H)-one (0.20 g, 0.92 mmol) and N,N-dimethylformamide (5 mL). To the mixture at 25° C. was added sodium hydride (0.039 g, 1.0 mmol, 60% dispersion in mineral oil). The solution was stirred for 5 min and then 2-chloro-4-fluoropyridine (0.17 g, 1.3 mmol) was added. After stirring for 2 hours the mixture was poured into aq. NaHCO$_3$ (100 mL) and then extracted with 50% EtOAc/hexane (3×75 mL). The combined extracts were washed with H$_2$O (3×75 mL) and brine (75 mL), dried (Na$_2$SO$_4$), and concentrated onto silica. Purification by silica gel chromatography (40 to 90% EtOAc/hexane) afforded the title compound as a white solid (0.24 g, 78% yield). MS (ESI, pos. ion.) m/z: 328 (MH+). Calc'd exact mass for C$_{17}$H$_{14}$ClN$_3$O$_2$: 327. $^1$H NMR (400 MHz, DMSO-d6) δ ppm 4.53 (t, J=5.0 Hz, 2 H), 4.61 (t, J=5.1 Hz, 2 H), 7.00 (dd, J=5.9, 2.3 Hz, 1 H), 7.08 (d, J=9.8 Hz, 1 H), 7.14 (d, J=2.2 Hz, 1 H), 7.44-7.51 (m, 3 H), 7.85-7.87 (m, 2 H), 8.06 (d, J=9.8 Hz, 1 H), 8.18 (d, J=5.9 Hz, 1 H).

EXAMPLE 108

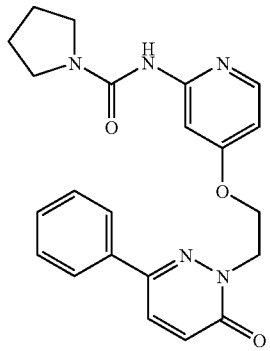

N-(4-(2-(6-Oxo-3-phenylpyridazin-1(6H)-yl)ethoxy)pyridin-2-yl)pyrrolidine-1-carboxamide This procedure was based on the method described in Antonio Abad, Consuelo Agulló, Ana Carmen Cuñat, Cristina Vilanova *Synthesis*, 2005, 915. To a 10 mL round-bottomed flask was added 2-(2-(2-chloropyridin-4-yloxy)ethyl)-6-phenylpyridazin-3(2H)-one (0.10 g, 0.31 mmol), pyrrolidine-1-carboxamide (0.038 g, 0.34 mmol) (see John E. Barry, Manuel Finkelstein, Gudrun A. Hutchins and Sidney D. Ross *Tetrahedron* 1983, 39, 2151-2156 and Charles A. Weisel, Harry S. Mosher, and F. C. Whitmore *J. Am. Chem. Soc.* 1945, 67, 1055), p-dioxane (2.5 mL), H$_2$O (0.0082 mL, 0.46 mmol) and sodium tert-butoxide (0.044 g, 0.46 mmol). The mixture was carefully evacuated and backfilled with N$_2$. This was repeated 3 times. To the mixture was added 9,9-dimethyl-4,5-bis(diphenylphosphino)xanthene (0.018 g, 0.031 mmol) and palladium(II) acetate (0.0034 g, 0.015 mmol). Once again the mixture was carefully evacuated and backfilled with N$_2$. This was repeated 3 times. The mixture was then stirred at 90° C. After 17 h, the mixture was poured into aq. NaHCO$_3$ (100 mL) and extracted with EtOAc(3×75 mL). The combined extracts were washed with water (100 mL) and brine (100 mL) and then dried (Na$_2$SO$_4$) and concentrated onto silica. Purification by silica gel chromatography (1.0 to 5.0% MeOH (2M in NH$_3$)/CH$_2$Cl$_2$) afforded N-(4-(2-(6-oxo-3-phenylpyridazin-1(6H)-yl)ethoxy)pyridin-2-yl)pyrrolidine-1-carboxamide (0.015 g, 12% yield) as a yellow solid. MS (ESI, pos. ion.) m/z: 406 (MH+). Calc'd exact mass for C$_{22}$H$_{23}$N$_5$O$_3$: 405. $^1$H NMR (400 MHz, DMSO-d6) δ ppm 1.77-1.86 (m, 4 H), 3.33-3.40 (m, 4 H), 4.46-4.55 (m, 4 H), 6.58 (dd, J=5.8, 2.4 Hz, 1 H), 7.07 (d, J=9.8 Hz, 1 H), 7.43-7.50 (m, 3H), 7.52 (d, J=2.3 Hz, 1 H), 7.84-7.89 (m, 2 H), 8.00 (d, J=5.7 Hz, 1 H), 8.05 (d, J=9.8 Hz, 1 H), 8.51 (s, 1 H).

EXAMPLE 109

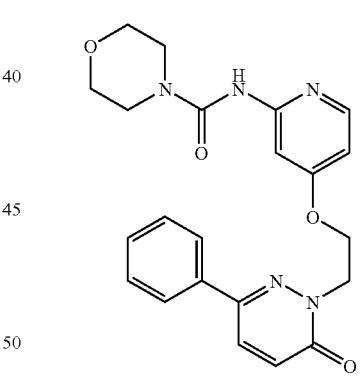

N-(4-(2-(6-Oxo-3-phenylpyridazin-1(6H)-yl)ethoxy)pyridin-2-yl)morpholine-4-carboxamide This compound was prepared according to the procedure described in Examples 107 and 108. MS (ESI, pos. ion.) m/z: 422 (MH+). Calc'd exact mass for C$_{22}$H$_{23}$N$_5$O$_4$: 421. $^1$H NMR (400 MHz, DMSO-d6) δ ppm 3.40-3.43 (m, 4 H), 3.55-3.57 (m, 4 H), 4.48 (t, J=4.7 Hz, 2 H), 4.53 (t, J=4.7 Hz, 2 H), 6.60 (dd, J=5.7, 2.3 Hz, 1 H), 7.07 (d, J=9.8 Hz, 1 H), 7.41 (d, J=2.3 Hz, 1 H), 7.44-7.50 (m, 3 H), 7.85-7.88 (m, 2 H), 8.02 (d, J=5.9 Hz, 1 H), 8.05 (d, J=9.6 Hz, 1 H), 9.11 (s, 1 H).

EXAMPLE 110

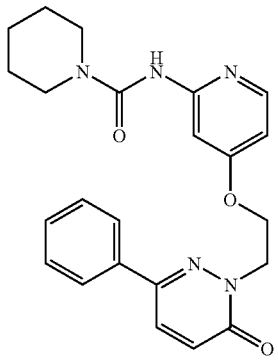

N-(4-(2-(6-oxo-3-phenylpyridazin-1(6H)-yl)ethoxy)pyridin-2-yl)piperidine-1-carboxamide This compound was prepared according to the procedure described in Examples 107 and 108. MS (ESI, pos. ion.) m/z: 420 (MH+). Calc'd exact mass for $C_{23}H_{25}N_5O_3$: 419. $^1$H NMR (400 MHz, DMSO-d6) δ ppm 1.42-1.48 (m, 4 H), 1.51-1.58 (m, 2 H), 3.37-3.42 (m, 4 H), 4.47 (t, J=4.8 Hz, 2 H), 4.53 (t, J=5.1 Hz, 2 H), 6.57 (dd, J=5.8, 2.2 Hz, 1 H), 7.07 (d, J=9.8 Hz, 1 H), 7.41 (d, J=2.2 Hz, 1 H), 7.44-7.49 (m, 3 H), 7.85-7.87 (m, 2 H), 7.99 (d, J=5.7 Hz, 1 H), 8.05 (d, J=9.8 Hz, 1 H), 8.96 (s, 1 H).

EXAMPLE 111

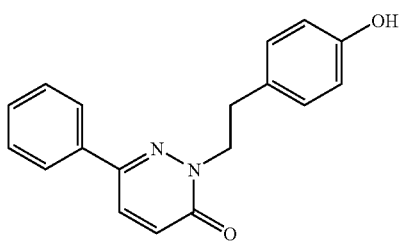

2-(4-Hydroxyphenethyl)-6-phenylpyridazin-3(2H)-one

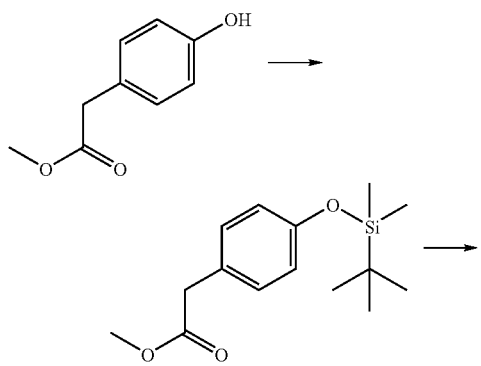

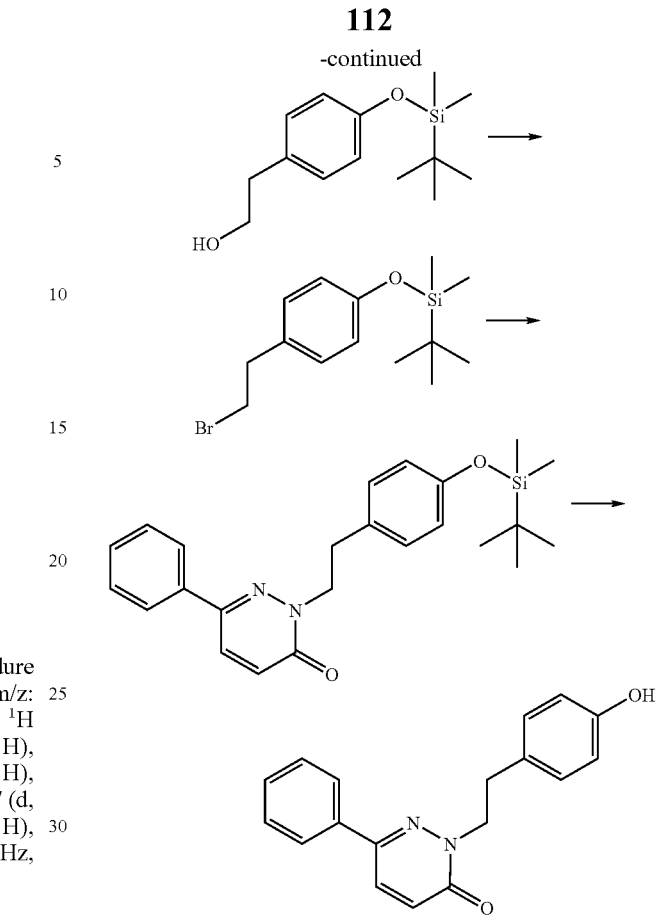

Methyl 2-(4-(tert-butyldimethylsilyloxy)phenyl)acetate. A solution of 4-hydroxyphenylacetic acid methyl ester (2000 mg, 12036 μmol), 1H-imidazole (2048 μl, 18053 μmol), and chloro-tert-butyldimethylsilane (1814 mg, 12036 μmol) in DMF (10 mL) was stirred at 23° C. for 18 h. The mixture was partitioned between EtOAc (50 mL) and 5% NaHCO$_3$ (25 mL). The organic layer was dried over MgSO$_4$ and concentrated to a colorless oil from toluene under reduced pressure. MS (ESI pos. ion) m/z (MH+): 281. Calc'd exact mass for $C_{15}H_{24}O_3Si$: 280.

2-(4-tert-Butyldimethylsilyloxy)phenyl)ethanol. To a stirring suspension of lithium aluminum hydride (893 mg, 23.5 mmol) in diethyl ether (30 mL) at 0° C. under nitrogen was added dropwise a solution of methyl 2-(4-(tert-butyldimethylsilyloxy)phenyl)acetate (3300 mg, 11767 μmol) in diethyl ether (20 mL). The mixture was stirred for 90 min, then quenched with solid sodium sulfate hexahydrate (10 g). The suspension was stirred for 45 min and the salts were removed via filtration with ether washings. The solvents were removed under reduced pressure and the residue was purified on 120 grams of silica eluting with 0-20% EtOAc/hexane to give a colorless oil. MS (ESI pos. ion) m/z (MH+): 255. Calc'd exact mass for $C_{14}H_{24}O_2Si$: 254. $^1$H NMR (400 MHz, Chloroform-d) δ ppm 0.19 (s, 6 H) 0.98 (s, 9 H) 1.39 (t, J=6.02 Hz, 1 H) 2.80 (t, J=6.53 Hz, 2 H) 3.82 (q, J=6.19 Hz, 2 H) 6.78 (d, J=8.53 Hz, 2 H) 7.08 (d, J=8.53 Hz, 2 H).

(4-(2-Bromoethyl)phenoxy)(tert-butyl)dimethylsilane. To a stirring solution of 2-(4-(tert-butyldimethylsilyloxy)phenyl)ethanol (1250 mg, 4.95 mmol) in acetonitrile (50 mL) and diethyl ether (25 mL) was sequentially added triphenylphosphine (3.44 mL, 14.8 mmol), 1H-imidazole (1011 mg, 14.8 μmol), and bromine (765 μl, 14.8 mmol). The clear solution was stirred at 23° C. for 18 h. The mixture was concentrated directly onto silica (20 g) under reduced pressure then purified on 120 grams of silica eluting with 0-5% EtOAc/Hexane. MS (ESI pos. ion) m/z (MH+): 315/317. Calc'd exact mass for $C_{14}H_{23}BrOSi$: 314. $^1H$ NMR (400 MHz, Chloroform-d) δ ppm 0.19 (s, 6 H) 0.98 (s, 9 H) 3.08 (t, J=7.78 Hz, 2 H) 3.47-3.57 (m, 2 H) 6.78 (d, J=8.53 Hz, 2 H) 7.05 (d, J=8.53 Hz, 2 H).

2-(4-(tert-Butyldimethylsilyloxy)phenethyl)-6-phenylpyridazin-3(2H)-one. A mixture of (4-(2-bromoethyl)phenoxy)(tert-butyl)dimethylsilane (142 mg, 450 µmol), 6-phenyl-3(2h)-pyridazinone (116 mg, 676 µmol), and potassium carbonate (187 mg, 1351 µmol) in DMF (1.5 mL) was stirred at 40° C. for 18 h. The mixture was partioned between $CH_2Cl_2$ (20 mL) and 5% $NaHCO_3$ (10 mL). The organic layer was dried with satd. $NH_4Cl$ and over $MgSO_4$, and dried to a film from toluene under reduced pressure. The residue was purified on 40 g silica eluting with 0>2.5% MeOH/$CH_2Cl_2$. MS (ESI pos. ion) m/z (MH+): 407 (MH+). Calc'd exact mass for $C_{24}H_{30}N_2O_2Si$: 406.

2-(4-Hydroxyphenethyl)-6-phenylpyridazin-3(2H)-one. To a stirring solution of 2-(4-(tert-butyldimethylsilyloxy)phenethyl)-6-phenylpyridazin-3(2H)-one (180 mg, 443 µmol) in ACN (3 mL) was added 70% HF-pyridine (0.25 mL) at 23° and stirred for 18 h. Solvents removed under reduced pressure and residue partioned between 9:1 $CHCl_3$/iPrOH (30 mL) and 5% $NaHCO_3$ (15 mL). The aqueous was further extracted with 9:1 $CH_3Cl$/iPrOH (3×20 mL). Combined organics dried over $MgSO_4$ then concentrated to a solid under reduced pressure from toluene. The residue was purified on 40 grams of silica eluting with 0-% EtOAc/$CH_2Cl_2$. The isolated solid was recrystallized from ACN (1 mL). MS (ESI pos. ion) m/z (MH+): 293. Calc'd exact mass for $C_{18}H_{16}N_2O_2$: 292. $^1H$ NMR (400 MHz, DMSO-d6) δ ppm 2.97 (t, J=7.28 Hz, 2 H) 3.17 (s, 1 H) 4.31 (t, J=7.53 Hz, 2 H) 6.66 (d, J=8.53 Hz, 2 H) 7.02 (t, J=8.28 Hz, 3 H) 7.39-7.54 (m, 3 H) 7.82 (d, J=8.03 Hz, 2 H) 8.01 (d, J=9.54 Hz, 1 H) 9.20 (s, 1 H).

EXAMPLE 112

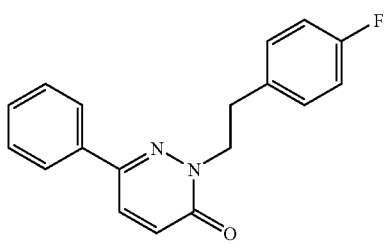

2-(4-Fluorophenethyl)-6-phenylpyridazin-3(2H)-one

A mixture of 6-phenyl-3(2h)-pyridazinone (306 mg, 1.78 mmol), 1-(2-bromo-ethyl)-4-fluoro-benzene (397 µl, 1.95 mmol), and potassium carbonate, −325 mesh (614 mg, 4.44 µmol) in DMF (5 mL) was stirred for 3 days at 23° C. The mixture was partitioned between $CH_2Cl_2$ (30 mL) and 5% $NaHCO_3$ (15 mL). The aqueous was further extracted with $CH_2Cl_2$ (2×5 mL) and the combined organics was dried over $MgSO_4$, and concentrated under reduced pressure To give a clear oil. MS (ESI pos. ion) m/z (MH+): 295. Calc'd exact mass for $C_{18}H_{15}FN_2O$: 294. $^1H$ NMR (400 MHz, Chloroform-d) δ ppm 3.16 (t, J=7.53 Hz, 2 H) 4.47 (t, J=7.78 Hz, 2 H) 6.88-7.06 (m, 3 H) 7.15-7.25 (m, 2 H) 7.35-7.53 (m, 3 H) 7.59-7.74 (m, 3 H). $^{13}C$ NMR (101 MHz, Chloroform-d) δ ppm 32.60, 52.08, 114.07, 114.28, 124.73, 127.81, 128.32, 128.89, 129.01, 129.20, 129.27, 132.63, 132.67, 133.57, 143.32, 158.60, 159.33, 161.76.

EXAMPLE 113

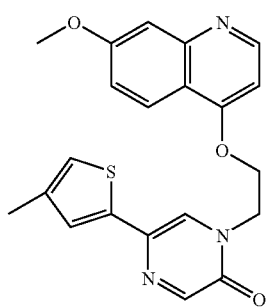

1-(2-(7-Methoxyquinolin-4-yloxy)ethyl)-5-(4-methylthiophen-2-yl)pyrazin-2(1H)-one

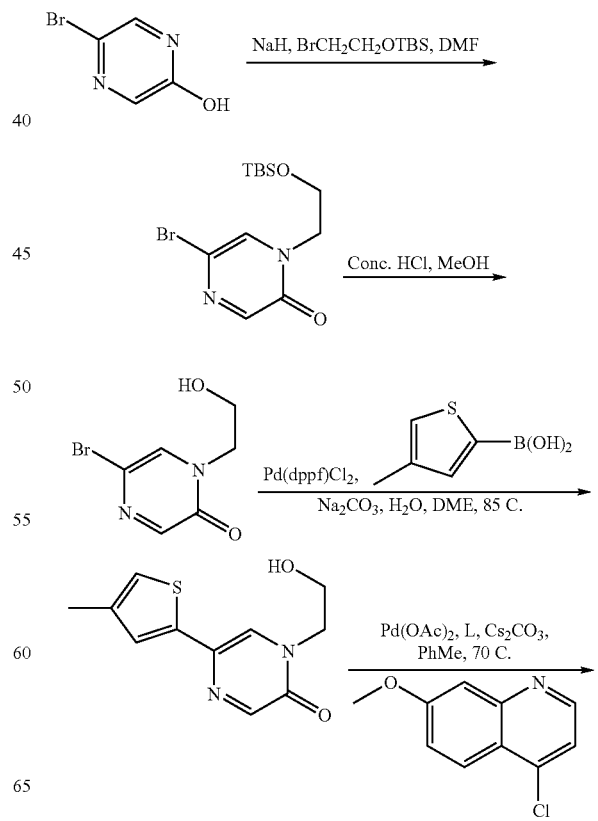

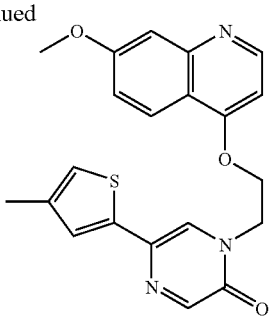

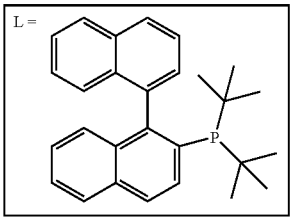

5-Bromo-1-(2-(tert-butyldimethylsilyloxy)ethyl)pyrazin-2(1H)-one. 5-Bromopyrazin-2-ol (1.209 g, 6.91 mmol) was dissolved in DMF (10.0 mL) and sodium hydride (60% in mineral, 530 mg, 13.25 mmol) was added. The reaction flask was put in a water bath and stirred under argon for 15 minutes, and then (2-bromoethoxy)(tert-butyl)dimethylsilane (1.69 mL, 7.93 mmol) was added as a solution in DMF (4.7 mL total volume), followed by a ~0.5 mL rinse with DMF. The reaction was stirred under argon at room temperature for 2 days. It was then quenched with water (50 mL) and extracted with EtOAc (3×50 mL). The organic extracts were combined, washed with water (4×50 mL) and brine (50 mL), dried over sodium sulfate, filtered, and concentrated. The material was taken on crude to the next step.

5-Bromo-1-(2-hydroxyethyl)pyrazin-2(1H)-one. The crude 5-bromo-1-(2-(tert-butyldimethylsilyloxy)ethyl)pyrazin-2(1H)-one was dissolved in MeOH (30 mL) and concentrated HCl (0.15 mL) was added, and the reaction was stirred at room temperature. After 1 hour, the reaction was quenched with saturated sodium bicarbonate (3 mL) and then concentrated. The concentrate was treated with 5:1 $CH_2Cl_2$/MeOH and filtered. The filtrate was concentrated, and put on high vacuum in water bath (50° C.). This solid was washed with hexanes (50 mL) in portions, and then put on high vacuum again to afford the desired product (870.8 mg, 3.98 mmol, 90% purity, 52% yield over two steps). MS (ESI pos. ion) m/z (MH+): 219 ($^{79}$Br), 221 ($^{81}$Br). Calc'd exact mass for $C_{18}H_{13}BrFN_3O_2$: 218 ($^{79}$Br), 220 ($^{81}$Br). $^1$H NMR (400 MHz, CDCl$_3$): 8.01 (s, 1H), 7.49 (s, 1H), 5.33 (br s, 1H), 4.08 (t, J=4.5 Hz, 2H), 3.96 (t, J=4.5 Hz, 2H).

1-(2-Hydroxyethyl)-5-(4-methylthiophen-2-yl)pyrazin-2(1H)-one. 5-Bromo-1-(2-hydroxyethyl)pyrazin-2(1H)-one (199.6 mg, 911 μmol), 1,1'-bis(diphenylphosphino)ferrocene-palladium dichloride (66.6 mg, 91 μmol), and 4-methylthiophen-2-ylboronic acid (253.7 mg, 1787 μmol) were suspended in DME (5.0 mL) and sodium carbonate (1.2 mL, 2.0 M in water, 2.4 mmol) was added. The reaction flask was fit with a reflux condensor and placed in a preheated oil bath (85° C.) and stirred under argon for 1 hour The reaction was then cooled to room temperature and quenched with saturated sodium bicarbonate (5 mL) and allowed to stand at room temperature overnight. It was then extracted with $CH_2Cl_2$ and with 10:1 $CH_2Cl_2$/MeOH, and the organic extracts were combined, dried over sodium sulfate, filtered, concentrated, and filtered through silica gel (30:1 $CH_2Cl_2$/MeOH) to afford the desired product (110.6 mg, 0.468 mmol, 51% yield). MS (ESI pos. ion) m/z (MH+): 237. Calc'd exact mass for $C_{11}H_{12}N_2O_2S$: 236. $^1$H NMR (400 MHz, CDCl$_3$): 8.21 (s, 1H), 7.53 (s, 1H), 7.12 (s, 1H), 6.88 (s, 1H), 4.14 (t, J=5.0 Hz, 2H), 4.02 (q, J=5.0 Hz, 2H), 2.33 (s, 1H, J=5.0 Hz, 1H), 2.28 (s, 3H).

1-(2-(7-Methoxyquinolin-4-yloxy)ethyl)-5-(4-methylthiophen-2-yl)pyrazin-2(1H)-one. 1-(2-hydroxyethyl)-5-(4-methylthiophen-2-yl)pyrazin-2(1H)-one (98.2 mg, 416 μmol), 4-chloro-7-methoxyquinoline (93.1 mg, 481 μmol), cesium carbonate (162 mg, 497 μmol), and palladium(II) acetate (23 mg, 102 μmol) were suspended in PhMe (2.8 mL) and racemic-2-(di-t-butylphosphino)-1,1'-binaphthyl (50 mg, 125 μmol) was added. The reaction was placed in a preheated oil bath (70° C.) and stirred under argon for 2.5 hours. The reaction was then cooled to room temperature and filtered through ~0.5 inches of silica gel with 5:1 $CH_2Cl_2$/(2 N ammonia in MeOH). The filtrate was concentrated, and washed with Et$_2$O and MeOH. The MeOH washings were combined with the solid, concentrated, and purified on HPLC (10%->95% MeCN/water with 0.1% TFA over 30 minutes) to afford the desired product (86.5 mg, 0.220 mmol, 53% yield). MS (ESI pos. ion) m/z (MH+): 394. Calc'd exact mass for $C_{21}H_{19}N_3O_3S$: 393. $^1$H NMR (400 MHz, CDCl$_3$): 8.95 (d, J=7.0 Hz, 1H), 8.29 (s, 1H), 8.10 (d, J=9.0 Hz, 1H), 7.71 (d, J=3.0 Hz, 1H), 7.59 (s, 1H), 7.30 (dd, J=9 Hz, 3 Hz, 1H), 7.20 (s, 1H), 7.03 (d, J=7.0 Hz, 1H), 6.92 (s, 1H), 4.80 (t, J=5.0 Hz, 2H), 4.57 (t, J=5.0 Hz, 2H), 4.02 (s, H), 2.30 (s, 3H).

EXAMPLE 114

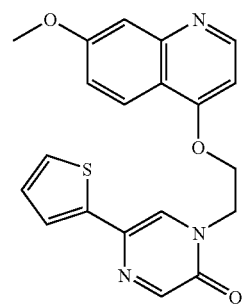

1-(2-(7-Methoxyquinolin-4-yloxy)ethyl)-5-(thiophen-2-yl)pyrazin-2(1H)-one This compound was prepared according to the procedure described in Example 113. MS (ESI pos. ion) m/z (MH+): 380. Calc'd exact mass for $C_{20}H_{17}N_3O_3S$: 379.

EXAMPLE 115

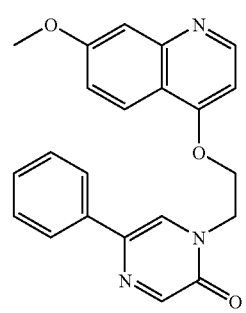

1-(2-(7-Methoxyquinolin-4-yloxy)ethyl)-5-phenylpyrazin-2(1H)-one. This compound was prepared according to the procedure described in Example 113. MS (ESI pos. ion) m/z (MH+): 374. Calc'd exact mass for $C_{22}H_{19}N_3O_3$: 373. $^1$H NMR (400 MHz, CDCl$_3$): 8.95 (d, J=7.0 Hz, 1H), 8.39 (d, J=1 Hz, 1H), 8.05 (d, J=9.0 Hz, 1H), 7.76 (dd, J=7.0 Hz, 1.0 Hz, 2H), 7.72-7.69 (m, 2H), 7.49 (t, J=7.0 Hz, 2H), 7.43 (d, J=7.0 Hz, 1H), 7.25 (dd, J=9.0 Hz, 2.0 Hz, 1H), 7.05 (d, J=7.0 Hz, 1H), 4.84 (t, J=5.0 Hz, 2H), 4.63 (t, J=5.0 Hz, 2H), 4.02 (s, 3H).

EXAMPLE 116

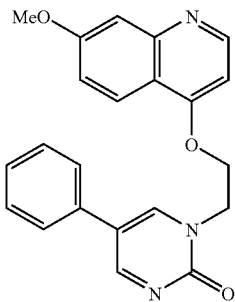

1-(2-(7-Methoxyquinolin-4-yloxy)ethyl)-5-phenylpyrimidin-2(1H)-one

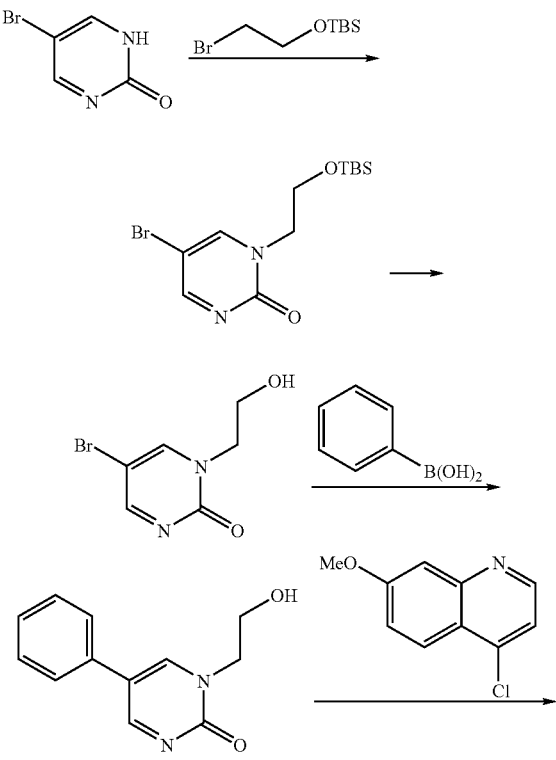

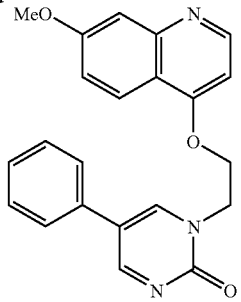

5-Bromo-1-(2-(tert-butyldimethylsilyloxy)ethyl)pyrimidin-2(1H)-one. To a solution of 5-bromo-2-pyrimidinone (5.3 g, 30 mmol) in N,N-dimethylformamide (50 mL) was added (2-bromoethoxy)(tert-butyl)dimethylsilane (8.5 mL, 39 mmol) and cesium carbonate (12 g, 36 mmol). The mixture was stirred at 25° C. for 3 days, then poured into aq. NaHCO$_3$ (500 mL) and extracted with 50% EtOAc/hexane (3×200 mL). The combined extracts were washed with H$_2$O (3×200 mL) and brine (200 mL) and then dried (Na$_2$SO$_4$) and concentrated to afford a brown solid. Recrystallization from EtOAc/hexane afforded the title compound as an off-white crystalline solid (6.0 g, 59% yield). MS (ESI, pos. ion.) m/z: 333 (MH$^+$). Calc'd exact mass for $C_{12}H_{21}BrN_2O_2Si$: 333. $^1$H NMR (400 MHz, DMSO-d6) δ ppm −0.08 (s, 6 H), 0.80 (s, 9 H), 3.81 (t, J=5.0 Hz, 2 H), 3.96 (t, J=5.0 Hz, 2 H), 8.40 (d, J=3.3 Hz, 1 H), 8.63 (d, J=3.3 Hz, 1 H).

5-Bromo-1-(2-hydroxyethyl)pyrimidin-2(1H)-one. To two 50 mL polypropylene conical tubes with caps was added 5-bromo-1-(2-(tert-butyldimethylsilyloxy)ethyl)pyrimidin-2(1H)-one (4.0 g, 12 mmol) (2 g in each tube) in tetrahydrofuran (50 mL, 12 mmol, 25 mL in each tube). To the mixture at 25° C. was added HF pyridine complex (8.0 mL, 12 mmol) (4 mL in each tube). After stirring for 30 minutes the solution was filtered through a polypropylene frit and the filtercake was washed with THF. The white filtercake was then dried in vacuo to afford the title compound as a white solid (1.6 g, 60% yield). MS (ESI, pos. ion.) m/z: 219 (MH$^+$). Calc'd exact mass for $C_6H_7BrN_2O_2$: 219. $^1$H NMR (400 MHz, DMSO-d6) δ ppm 3.64 (q, J=5.3 Hz, 2 H), 3.89 (t, J=5.2 Hz, 2 H), 4.96 (t, J=5.5 Hz, 1 H), 8.39 (d, J=3.3 Hz, 1 H), 8.61 (d, J=3.3 Hz, 1 H).

1-(2-hydroxyethyl)-5-phenylpyrimidin-2(1H)-one. To a 10 mL round bottomed flask was added 5-bromo-1-(2-hydroxyethyl)pyrimidin-2(1H)-one (0.088 g, 0.40 mmol), phenylboronic acid (0.098 g, 0.80 mmol), 1,2-dimethoxyethane (2.5 mL) and 2 M sodium carbonate (0.40 mL, 0.80 mmol). The mixture was carefully evacuated and backfilled with N$_2$. This was repeated twice. To the mixture was added dichloro [1,1'-bis(diphenylphosphino)ferrocene]palladium (II)dichloromethane adduct (0.029 g, 0.040 mmol). The mixture was again carefully evacuated and backfilled with N$_2$. This was repeated once. The mixture was then heated at 75° C. for 1.5 hours. After cooling to room temperature, the mixture was poured into water (50 mL) and then extracted with EtOAc (2×) and then with 25% iPrOH/CHCl$_3$ (3×). The combined extracts were washed with brine (1×), dried (Na$_2$SO$_4$) and concentrated onto silica. Purification by silica gel chromatography (0 to 2% MeOH (2M NH$_3$)/CH$_2$Cl$_2$) afforded 1-(2-hydroxyethyl)-5-phenylpyrimidin-2(1H)-one (0.061 g, 70% yield) as an off-white solid. MS (ESI, pos. ion.) m/z: 217 (MH+). Calc'd exact mass for $C_{12}H_{12}N_2O_2$: 216. $^1$H NMR (400 MHz, DMSO-d6) δ ppm 3.71 (q, J=5.3 Hz, 2 H), 4.00 (t, J=5.3 Hz, 2 H), 4.95 (t, J=5.6 Hz, 1 H), 7.35 (t, J=7.3 Hz, 1 H), 7.46 (t, J=7.6 Hz, 2 H), 7.61 (d, J=7.4 Hz, 2 H), 8.44 (d, J=3.3 Hz, 1 H), 8.95 (d, J=3.3 Hz, 1 H).

1-(2-(7-Methoxyquinolin-4-yloxy)ethyl)-5-phenylpyrimidin-2(1H)-one. To a 10 mL round bottomed flask was added 1-(2-hydroxyethyl)-5-phenylpyrimidin-2(1H)-one (0.043 g, 0.20 mmol), 4-chloro-7-methoxyquinoline (0.042 g, 0.22 mmol), toluene (2.0 mL) and cesium carbonate (0.071 g, 0.22 mmol). The reaction was carefully evacuated and then backfilled with $N_2$. This was repeated twice. Then racemic-2-(di-t-butylphosphino)-1,1'-binaphthyl (0.020 g, 0.050 mmol) and palladium(II) acetate (0.0089 g, 0.040 mmol) were added. The reaction was again carefully evacuated and then backfilled with $N_2$. This was repeated twice. The mixture was then heated at 80° C. for 3 h. After cooling to room temperature, the mixture was poured into aq. $NaHCO_3$ (50 mL) and extracted with EtOAc (100 mL). This produced a bad emulsion so the mixture was filtered through Celite. The Celite plug was eluted with 10% $MeOH/CH_2Cl_2$ and the aqueous phase was extracted with 25% $iPrOH/CHCl_3$. The EtOAc extract, $MeOH/CH_2Cl_2$ eluent and the $^iPrOH/CHCl_3$ extracts were combined, dried ($Na_2SO_4$) and concentrated onto silica. Purification by silica gel chromatography (0 to 1% MeOH (2M in $NH_3$)/$CH_2Cl_2$ afforded 1-(2-(7-methoxyquinolin-4-yloxy)ethyl)-5-phenylpyrimidin-2(1H)-one (0.023 g, 31% yield) as an off-white solid. MS (ESI, pos. ion.) m/z: 374 (MH+). Calc'd exact mass for $C_{22}H_{19}N_3O_3$: 373. $^1$H NMR (400 MHz, DMSO-d6) δ ppm 3.87 (s, 3 H), 4.50 (t, J=4.8 Hz, 2 H), 4.59 (t, J=4.9 Hz, 2 H), 6.93 (d, J=5.3 Hz, 1 H), 7.02 (dd, J=9.2, 2.5 Hz, 1 H), 7.29 (d, J=2.5 Hz, 1 H), 7.37 (t, J=7.3 Hz, 1 H), 7.47 (t, J=7.6 Hz, 2 H), 7.60 (d, J=7.4 Hz, 2 H), 8.00 (d, J=9.2 Hz, 1 H), 8.63 (d, J=5.1 Hz, 1 H), 8.81 (d, J=3.5 Hz, 1 H), 8.97 (d, J=3.5 Hz, 1 H).

EXAMPLE 117

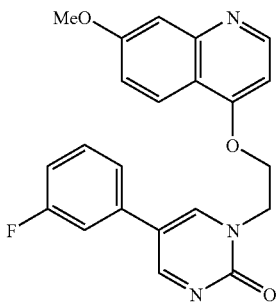

5-(3-Fluorophenyl)-1-(2-(7-methoxyquinolin-4-yloxy)ethyl)pyrimidin-2(1H)-one

This compound was prepared according to the procedure described in Example 116. MS (ESI, pos. ion.) m/z: 392 (MH+). Calc'd exact mass for $C_{22}H_{18}FN_3O_3$: 391. $^1$H NMR (400 MHz, DMSO-d6) δ ppm 3.87 (s, 3 H), 4.49 (t, J=4.9 Hz, 2 H), 4.59 (t, J=5.0 Hz, 2 H), 6.93 (d, J=5.3 Hz, 1 H), 7.01 (dd, J=9.2, 2.5 Hz, 1 H), 7.16-7.22 (m, 1 H), 7.29 (d, J=2.5 Hz, 1 H), 7.46-7.54 (m, 3 H), 8.01 (d, J=9.2 Hz, 1 H), 8.62 (d, J=5.3 Hz, 1 H), 8.88 (d, J=3.3 Hz, 1 H), 9.00 (d, J=3.3 Hz, 1 H).

EXAMPLE 118

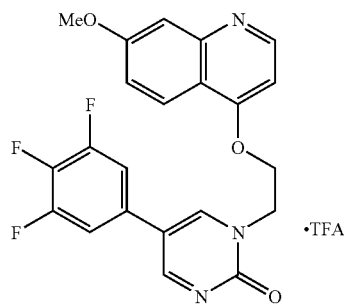

1-(2-(7-methoxyquinolin-4-yloxy)ethyl)-5-(3,4,5-trifluorophenyl)pyrimidin-2(1H)-one This compound was prepared according to the procedure described in Example 116. MS (ESI, pos. ion.) m/z: 428 (MH+). Calc'd exact mass for $C_{22}H_{16}F_3N_3O_3$: 427. $^1$H NMR (400 MHz, Chloroform-d) δ ppm 4.01 (s, 3 H), 4.64 (t, J=5.0 Hz, 2H), 4.90 (t, J=5.0 Hz, 2 H), 7.04 (dd, J=7.6, 6.3 Hz, 2 H), 7.11 (d, J=6.7 Hz, 1 H), 7.31 (dd, J=9.3, 2.2 Hz, 1 H), 7.67 (d, J=2.3 Hz, 1 H), 8.08 (d, J=9.4 Hz, 1 H), 8.11 (d, J=3.3 Hz, 1 H), 8.85-8.89 (m, 2 H).

EXAMPLE 119

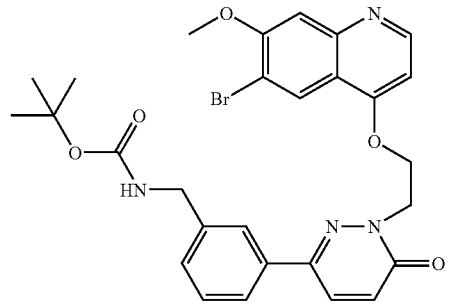

tert-Butyl (3-(1-(2-(6-bromo-7-methoxyquinolin-4-yloxy)ethyl)-6-oxo-1,6-dihydropyridazin-3-yl)phenyl)methylcarbamate

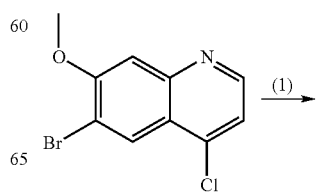

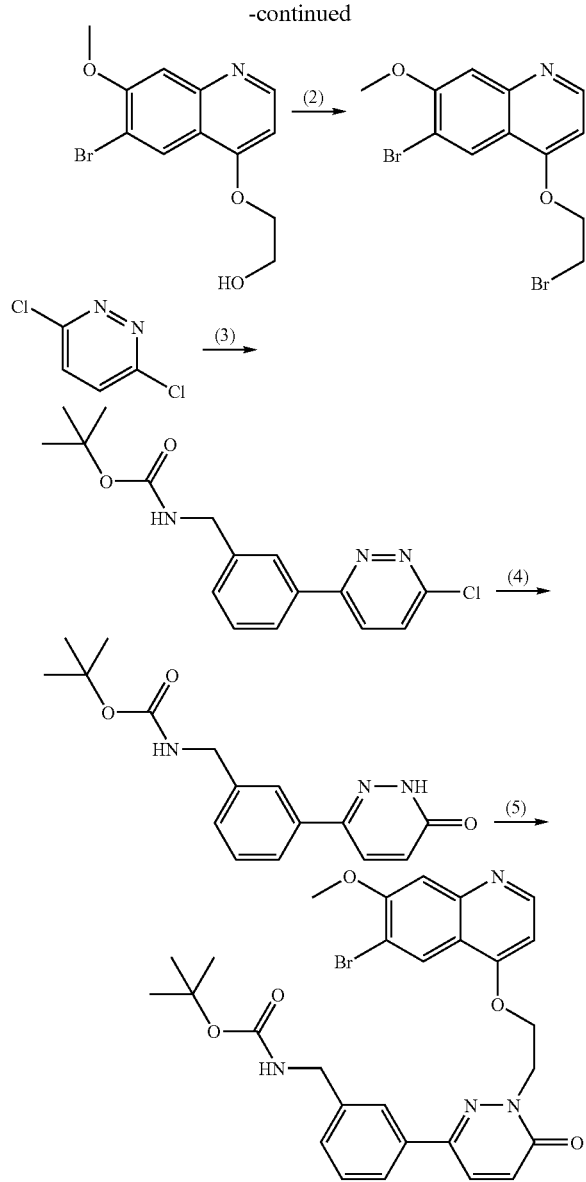

(1) A mixture of ethane-1,2-diol (20 mL, 9173 µmol) and sodium (860 mg, 37408 µmol) was heated to 80° C. under nitrogen for 10 min. To the solution was added 6-bromo-4-chloro-7-methoxyquinoline (2500 mg, 9173 µmol). After 4 h, $Cs_2CO_3$ (1 g) was added. After 30 min, the reaction mixture was diluted with $H_2O$ and was cooled to room temperature. After 2 days, the mixture was filtered and washed with $H_2O$, Some chunks of solid remained in the flask were shown to be the SM. The solid from the washing was further triturated with ether-EtOAc (2:1, 4×) to remove starting material, affording the product as brown powder. LCMS (ESI pos. ion): calc'd for $C_{12}H_{12}BrNO_3$: 297.0/299.0; found 298.0/300.0 (M+1). $^1$H NMR (400 MHz, DMSO-$d_6$) δ ppm 3.82-3.89 (m, 2 H), 4.00 (s, 3 H), 4.22 (t, J=4.60 Hz, 2 H), 5.14 (s, 1 H), 6.93 (d, J=5.28 Hz, 1 H), 7.44 (s, 1 H), 8.46 (s, 1H), 8.67 (d, J=5.28 Hz, 1 H).

(2) A mixture of 2-(6-bromo-7-methoxyquinolin-4-yloxy)ethanol (1000 mg, 3.35 mmol) and thionyl bromide (300 µl, 3.87 mmol) in DMF (5 mL) and $CH_2Cl_2$ (10 mL) was stirred at room temperature. After 1 h, more thionyl bromide (300 µl, 3.87 mmol) was added. After 1 h, the mixture was concentrated to remove the $CH_2Cl_2$. The residue was quenched with aqueous $Na_2CO_3$ until pH~14. The mixture was filtered and washed with $H_2O$ (3×3 mL) and dried in air to give a yellow powder (1.2 g). LCMS (ESI pos. ion): calcd for $C_{12}H$, $Br_2NO_2$: 358.9/360.9/362.9; found 360.0/262.0/364.0 (M+1). $^1$H NMR (400 MHz, DMSO-$d_6$) δ ppm 3.96-4.00 (m, 2 H), 4.01 (s, 3 H), 7.00 (d, J=5.48 Hz, 1 H), 7.47 (s, 1H), 8.33 (s, 1 H), 8.72 (d, J=5.28 Hz, 1 H).

(3) A mixture of $Na_2CO_3$ (1900 mg, 17926 µmol), $PdCl_2$ (dppf)-$CH_2Cl_2$ adduct (75 mg, 92 µmol), 3-((tert-butoxycarbonyl)methyl)phenylboronic acid (2200 mg, 8762 µmol), 3,6-dichloropyridazine (1100 mg, 7384 µmol) in dioxane (15 mL) and $H_2O$ (5 mL) was heated to 90° C. under nitrogen for 4 h. The mixture was taken up with $CH_2Cl_2$—$H_2O$. The organic layer was dried ($Na_2SO_4$), concentrated, and purified on silica gel (10-80% EtOAc-hexane) to give the pure product as a white solid (780 mg, 28%). LCMS (ESI pos. ion): calc'd for $C_{16}H_{18}ClN_3O_2$: 319.1; found 264.1 [(M-tBu)+1]. $^1$H NMR (400 MHz, DMSO-$d_6$) δ ppm 1.32 (s, 1H), 1.40 (s, 8 H), 4.24 (d, J=5.52 Hz, 2 H), 7.42 (d, J=7.53 Hz, 1 H), 7.45-7.57 (m, 2 H), 7.98 (d, J=7.53 Hz, 1 H), 8.02 (d, J=9.03 Hz, 1 H), 8.06 (br. s., 1 H), 8.30 (d, J=9.03 Hz, 1 H).

(4) A solution of tert-butyl 3-(6-chloropyridazin-3-yl)benzylcarbamate (700 mg, 2189 µmol) in THF (5 mL) and HCl (10 mL, 50000 µmol) was heated to 100° C. for 24 h. To this mixture was added THF (10 mL) and Boc-anhydride (0.7 mL, 3207 µmol). NaOH (5N, 10 mL) was added to adjust the pH to basic. After 5 h, the mixture was diluted with EtOAc (40 mL) and the layers were separated. The organic layer was washed with $H_2O$ twice, $NH_4Cl$ (satd.) once, dried over $Na_2SO_4$, and concentrated. The oil was purified on silica using hexane -EtOAc (1:1 to 0:1). The first fraction corresponds to the bis-Boc product, an oil. The second fraction gave the desired product as a white solid. The first fraction was dissolved in MeOH—$CH_2Cl_2$ (10 mL each) and was treated with HOAc (1.5 mL). After 1 day, MeOH was removed and $CH_2Cl_2$ (20 mL) and TFA (up to 5 mL) was added. After the bis-Boc disappeared the reaction mixture was queched with $Na_2CO_3$. The mixture was diluted with EtOAc and washed with $H_2O$, dried/$Na_2SO_4$, and concentrated to a white solid. $^1$H NMR (400 MHz, CHLOROFORM-d) δ ppm 1.47 (s, 9 H), 4.38 (d, J=5.67 Hz, 2 H), 4.92 (s, 1 H), 7.06 (d, J=9.78 Hz, 1 H), 7.31-7.40 (m, J=7.83 Hz, 1 H), 7.44 (t, J=7.63 Hz, 1 H), 7.71 (s, 1 H), 7.74 (d, J=9.98 Hz, 1 H), 10.76-10.81 (m, 1 H).

(5) A mixture of 4-(2-bromoethoxy)-7-methoxy-6-phosphinoquinoline (85 mg, 271 µmol), tert-butyl 3-(6-oxo-1,6-dihydropyridazin-3-yl)benzylcarbamate (70 mg, 232 µmol), and $K_2CO_3$ (60 mg, 434 µmol) in DMF (2 mL) was stirred at room temperature. After 1 h, more 4-(2-bromoethoxy)-7-methoxy-6-phosphinoquinoline (85 mg, 271 µmol) was added. After 16 h, the mixture was heated to 70° C. After 3 h, the mixture was diluted with EtOAc (40 mL) and washed with NaOH (2 N, 10 mL), $H_2O$ (2×5 mL), $NH_4Cl$ (satd), and dried over $MgSO_4$. The residue was purified on silica gel with MeOH in EtOAc (0-10%) to give a white foam (130 mg). LCMS (ESI pos. ion): calc'd for $C_{28}H_{29}BrN_4O_5$: 580.1/582.1; found: 581.2/583.2 (M+1). $^1$H NMR (400 MHz, CHLOROFORM-d) δ ppm 1.46 (s, 9 H), 3.99 (s, 3 H), 4.35 (d, J=5.52 Hz, 2 H), 4.67 (t, J=5.27 Hz, 2H), 4.81 (t, J=5.30 Hz, 2 H), 4.96 (br. s., 1 H), 6.70 (d, J=5.52 Hz, 1 H), 7.05 (d, J=9.54 Hz, 1 H), 7.32-7.39 (m, 2 H), 7.42 (t, J=7.78 Hz, 1 H), 7.59-7.66 (m, 2H), 7.70 (d, J=9.54 Hz, 1 H), 8.27 (s, 1 H).

EXAMPLE 120

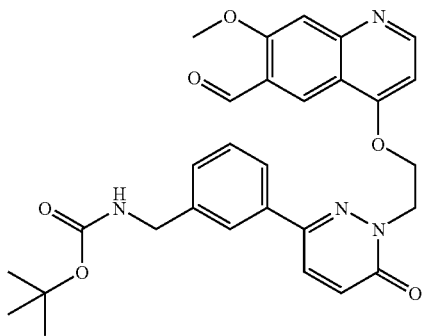

tert-Butyl (3-(1-(2-(6-formyl-7-methoxyquinolin-4-yloxy)ethyl)-6-oxo-1,6-dihydropyridazin-3-yl)phenyl)methylcarbamate

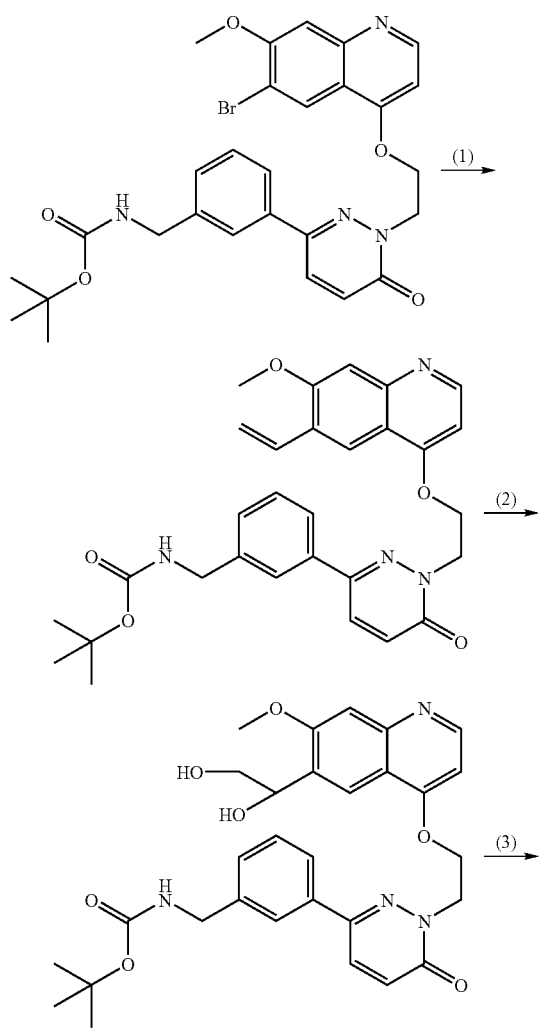

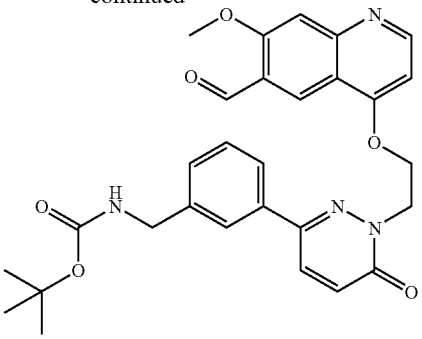

(1) In a 50 mL RBF was charged tert-butyl (3-(1-(2-(6-bromo-7-methoxyquinolin-4-yloxy)ethyl)-6-oxo-1,6-dihydropyridazin-3-yl)phenyl)methylcarbamate (330 mg, 568 µmol), 2,4,6-trivinylcyclotriboroxane pyridine complex (320 mg, 1330 µmol), Cs₂CO₃ (320 mg, 982 µmol), dioxane (10 mL), and H₂O (2 mL) under nitrogen. Pd(Ph₃P)₄ (33 mg, 28 µmol) was added and the mixture was heated to 80° C. After 4 h, more 2,4,6-trivinylcyclotriboroxane pyridine complex (320 mg, 1330 µmol) was added. After 2 hr, the combined reaction mixture (from another reaction with 50 mg of starting material) was partitioned between EtOAc (50 mL) and NH₄Cl (satd., 30 mL). The organic layer was dried over MgSO₄, concentrated, and purified on silica [0-5% (2N NH₃-MeOH) in CH₂Cl₂]. The major product fraction was collected. The foam was triturated with EtOAc-hexane (hot). Re-chromatography with MeOH in CH₂Cl₂ (0-10%) followed by a third chromatography with 5% MeOH in CH₂Cl₂ afforded a white foam (170 mg), still contaminated by satellite bands (1:8). $^1$H NMR (400 MHz, CHLOROFORM-d) δ ppm 1.46 (s, 9 H), 3.94 (s, 3 H), 4.32 (d, J=5.87 Hz, 2H), 4.67 (t, J=5.48 Hz, 2 H), 4.82 (t, J=5.38 Hz, 2 H), 4.92 (d, J=6.85 Hz, 1 H), 5.19 (d, J=12.52 Hz, 1 H), 5.70 (d, J=17.61 Hz, 1 H), 6.66 (d, J=5.28 Hz, 1 H), 6.95 (dd, J=17.80, 11.15 Hz, 1 H), 7.04 (d, J=9.78 Hz, 1 H), 7.28 (s, 1 H), 7.30-7.43 (m, 2 H), 7.56-7.64 (m, 2 H), 7.67 (d, J=9.59 Hz, 1 H), 8.11 (s, 1 H), 8.60 (d, J=5.28 Hz, 1 H).

(2) To a solution of tert-butyl (3-(1-(2-(7-methoxy-6-vinylquinolin-4-yloxy)ethyl)-6-oxo-1,6-dihydropyridazin-3-yl)phenyl)methylcarbamate (73 mg, 138 µmol) in t-BuOH (4 mL) and H₂O (1 mL) was added potassium osmate dihydrate (18 mg, 49 µmol) and NMO (32 mg, 276 µmol). After overnight, the mixture was diluted with CH₂Cl₂ (10 mL) and H₂O (25 mL) and stirred for 10 min. The organic layer was separated and the aqueous layer was extracted with CH₂Cl₂ (2×5 mL). The combined organic layer was dried over MgSO₄, and concentrated. Chromatography on silica [1-10% (2 N NH₃—MeOH) in CH₂Cl₂] afforded the product as the polar fraction, a thin film (30 mg). $^1$H NMR (400 MHz, DMSO-d₆) δ ppm 1.33-1.42 (m, 9 H), 3.55 (t, J=4.50 Hz, 2 H), 3.91 (s, 3H), 4.13 (d, J=5.67 Hz, 2 H), 4.90-4.97 (m, 1 H), 5.19 (d, J=4.30 Hz, 1 H), 6.96 (d, J=5.28 Hz, 1 H), 7.10 (d, J=9.78 Hz, 1 H), 7.23-7.32 (m, 2 H), 7.39 (t, J=7.53 Hz, 2 H), 7.59-7.70 (m, 2 H), 8.00 (d, J=9.78 Hz, 1 H), 8.10 (s, 1 H), 8.59 (d, J=5.09 Hz, 1 H).

(3) To a solution of tert-butyl (3-(1-(2-(6-(1,2-dihydroxyethyl)-7-methoxyquinolin-4-yloxy)ethyl)-6-oxo-1,6-dihydropyridazin-3-yl)phenyl)methylcarbamate (30 mg, 53 µmol) in DMSO (0.5 mL)-THF (1 mL)-MeOH (1 mL) was added a solution of NaIO₄ (80 mg, 374 µmol) in H₂O (0.5 mL). After 5 h, the mixture was diluted with aqueous Na₂SO₃ (2 mL) and CH₂Cl₂ (5 mL). The organic layer was separated, the aqueous was extracted with CH$_2$Cl$_2$ (3×5 mL). The combined organic phase was dried over MgSO$_4$, concentrated, and purified on silica (1-6% MeOH in CH$_2$Cl$_2$) to give the product as a film (24 mg). LCMS (ESI pos. ion): calc'd for C$_{29}$H$_{30}$N$_4$O$_6$: 530.1; found 531.3 (M+1). $^1$H NMR (400 MHz, CHLOROFORM-d) δ ppm 1.46 (s, 9 H), 4.02 (s, 3 H), 4.36 (d, J=5.52 Hz, 2 H), 4.70 (t, J=5.52 Hz, 2 H), 4.81 (t, J=5.27 Hz, 2 H), 5.38 (none, 1H), 5.38 (m, 1 H), 6.73 (d, J=5.02 Hz, 1 H), 7.04 (d, J=9.54 Hz, 1 H), 7.35-7.47 (m, 3 H), 7.60 (d, J=7.53 Hz, 1 H), 7.65-7.73 (m, 2 H), 8.60 (s, 1 H), 8.72 (d, J=5.02 Hz, 1 H), 10.36 (s, 1 H).

EXAMPLE 121

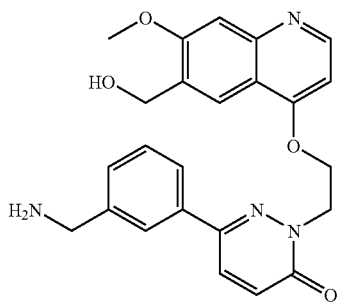

6-(3-(aminomethyl)phenyl)-2-(2-(6-(hydroxymethyl)-7-methoxyquinolin-4-yloxy)ethyl)pyridazin-3(2H)-one Sodium triacetoxyborohydride (200 mg, 944 µmol) was added to a mixture of 4-(2-(3-(3-(aminomethyl)phenyl)-6-oxopyridazin-1(6H)-yl)ethoxy)-7-methoxyquinoline-6-carbaldehyde (16 mg, 37 µmol) in CHCl$_3$ (3 mL) and MeOH (1 mL) were added (to keep solvent volume). After 19 h, K$_2$CO$_3$ (500 mg) was added. After 3 h, the mixture was filtered and concentrated. The residue was purified on silica (5% (2 N NH$_3$-MeOH) in CH$_2$Cl$_2$ to give a film (10 mg, 62%). LCMS (ESI pos. ion): calc'd for C$_{24}$H$_{24}$N$_4$O$_4$: 432.2; found 433.2 (M+1).

EXAMPLE 122

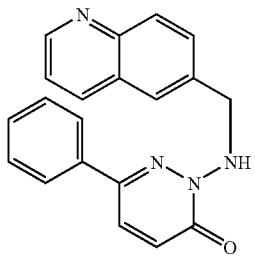

6-Phenyl-2-(quinolin-6-ylmethylamino)pyridazin-3(2H)-one A mixture of sodium triacetoxyborohydride (270 mg, 1274 µmol), quinoline-6-carbaldehyde (105 mg, 668 µmol), 2-amino-6-phenylpyridazin-3(2H)-one (160 mg, 855 µmol, prepared from 6-phenylpyridazin-3(2H)-one according to a protocol using Ph$_2$P(O)ONH$_2$: see, Y. Shen, G. K. Friestad *J. Org. Chem.* 2002, 67, 6236-6239), and a drop of HOAc in CH$_2$Cl$_2$ (10 mL) was stirred at rt for 15 h. MeOH (5 mL) and NaBH$_4$ were added. After 5 min, the mixture was concentrated and was flushed through silica gel to removing most of the inorganics. The product fraction was triturated with ether-hexane-MeOH (5:3:1) and filtered. The filtrate was concentrated and purified on silica with 1:1 acetone-hexane. The product fraction coming at the end gave a yellow film. LCMS (ESI pos. ion): calc'd for C$_{20}$H$_{16}$N$_4$O: 328.13; found: 329.2 (M+1). $^1$H NMR (400 MHz, CHLOROFORM-d) δ ppm 4.67 (d, J=6.46 Hz, 2 H) 7.04 (d, J=9.59 Hz, 1H) 7.36-7.46 (m, 4 H) 7.49 (t, J=6.55 Hz, 1 H) 7.64 (d, J=9.59 Hz, 1 H) 7.68-7.75 (m, 2 H) 7.79 (dd, J=8.71, 1.86 Hz, 1 H) 7.84 (s, 1 H) 8.10 (t, J=8.31 Hz, 2H) 8.91 (dd, J=4.11, 1.56 Hz, 1 H).

EXAMPLE 123

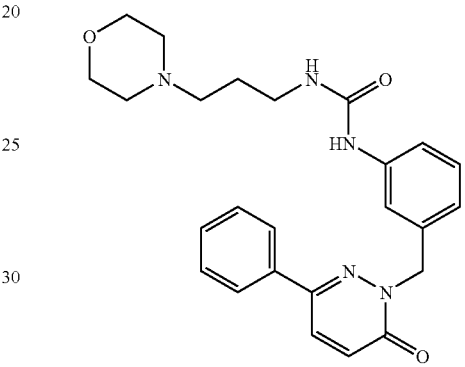

1-(3-Morpholinopropyl)-3-(3-((6-oxo-3-phenylpyridazin-1(6H)-yl)methyl)phenyl)urea

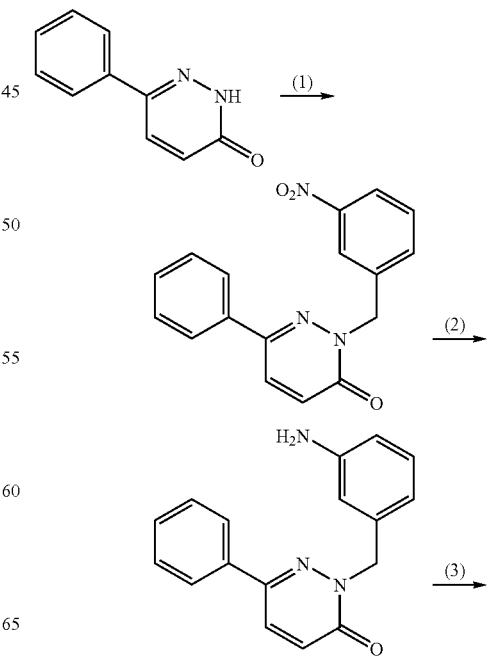

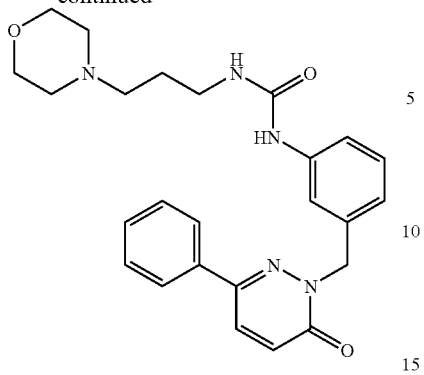

(1) A mixture of 6-phenylpyridazin-3(2H)-one (4.1 g, 24 mmol), $K_2CO_3$ (3.3 g, 24 mmol), and 1-(bromomethyl)-3-nitrobenzene (5.1 g, 24 mmol) in DMF (25 mL) was stirred at rt for 1 day. The mixture was diluted with $H_2O$ (50 mL) and stirred for 30 min. The suspension was filtered, washed with $H_2O$ and dried in air to give a white solid (6.8 g). LCMS (ESI pos. ion): calc'd for $C_{17}H_{13}N_3O_3$: 307.1; found 308.1 (M+1). $^1H$ NMR (300 MHz, CHLOROFORM-d) δ ppm 5.49 (s, 2 H) 7.05 (d, J=9.65 Hz, 1 H) 7.42-7.57 (m, 4 H) 7.71 (d, J=9.79 Hz, 1 H) 7.75-7.80 (m, 2 H) 7.83 (d, J=7.60 Hz, 1 H) 8.17 (dd, J=8.18, 2.05 Hz, 1 H) 8.35 (t, J=1.75 Hz, 1 H).

(2) A mixture of 2-(3-nitrobenzyl)-6-phenylpyridazin-3(2H)-one (5.5 g, 18 mmol) in DMF (50 mL) and $H_2O$ (5 mL) was treated with $SnCl_2$ (15 g, 79 mmol). The hot solution was stirred at rt under nitrogen for 2.5 h. The mixture was diluted with $H_2O$ (100 mL) and the resulting slurry was stirred overnight. The yellow cloudy solution was then neutralized with NaOH (7 g, 175 mmol). The slurry was filtered and washed with $H_2O$ (50 mL). The soft sludge was then stirred with iPrOH (5%) in $CHCl_3$ (5×100 mL) and the combined washes were concentrated to give a light yellow solid (5.3 g, 84%). LCMS (ESI pos. ion): calc'd for $C_{17}H_{13}N_3O_3$: 277.3; found: 278.2 (M+1). $^1H$ NMR (400 MHz, CHLOROFORM-d) δ ppm 5.32 (s, 2 H) 6.57-6.63 (m, 1 H) 6.82 (t, J=1.86 Hz, 1 H) 6.88 (d, J=7.63 Hz, 1 H) 7.02 (d, J=9.78 Hz, 1 H) 7.11 (t, J=7.73 Hz, 1 H) 7.40-7.50 (m, 3H) 7.66 (d, J=9.78 Hz, 1 H) 7.73-7.82 (m, 2 H).

(3) To a solution of 2-(3-aminobenzyl)-6-phenylpyridazin-3(2H)-one (280 mg, 1010 μmol) and 4-nitrophenyl carbonochloridate (215 mg, 1067 μmol) in $CH_2Cl_2$ (5 mL) was added pyridine (82 μl, 1010 μmol). The resulting mixture was stirred at rt overnight. A solution of 3-morpholinopropan-1-amine (170 mg, 1179 μmol) in $CH_2Cl_2$ (3 mL) was added to the mixture, resulting in a yellow solution. After 1 h, the solution was diluted with EtOAc (30 mL) and was washed with NaOH (1 N, 10 mL, 3×). The organic layer was further washed with $H_2O$ (10 mL), $NaHCO_3$ (satd., 10 mL), dried over $Na_2SO_4$ and concentrated. The yellow film was triturated with hexane-EtOAc (2:1). The oil was washed with ether, acetone in ether (10%), and pumped to a yellow foam (>110 mg). LCMS (ESI pos. ion): calc'd for $C_{25}H_{29}N_5O_3$: 447.5; found: 448.3 (M+1). $^1H$ NMR (400 MHz, CHLOROFORM-d) δ ppm 1.63-1.71 (m, 2 H) 2.32-2.43 (m, 6 H) 3.26-3.36 (m, 2 H) 3.52-3.59 (m, 4 H) 5.36 (s, 2 H) 5.51 (br. s., 1 H) 6.71 (br. s., 1 H) 7.01 (d, J=10.04 Hz, 1 H) 7.19 (d, J=7.53 Hz, 1 H) 7.24-7.31 (m, 1 H) 7.32 (s, 1 H) 7.36 (d, J=8.03 Hz, 1 H) 7.40-7.50 (m, 3 H) 7.67 (d, J=9.54 Hz, 1 H) 7.78 (d, J=7.53 Hz, 2 H).

EXAMPLE 124

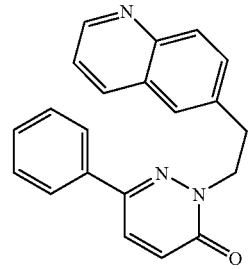

6-Phenyl-2-(2-(quinolin-6-yl)ethyl)pyridazin-3(2H)-one (1) To a 25 mL round-bottomed flask was added lithium aluminum hydride (0.057 g, 1.5 mmol, Strem Chemicals) and THF (8.0 mL). The mixture was cooled to −30° C. and methyl 2-(quinolin-6-yl)acetate (0.30 g, 1.5 mmol, Tyger) in 2 mL THF was added over 1 minute. The mixture was stirred at −30° C. for 30 min, then quenched with 0.056 mL $H_2O$. The solution was allowed to warm to rt and 0.056 mL 15% aq. NaOH and then 0.168 mL $H_2O$ were added. The mixture was stirred for 15 minutes and then filtered. The filtercake was washed with THF and the filtrate was concentrated. Purification by silica gel chromatography (0.5 to 5.0% MeOH (2 M in $NH_3$)/$CH_2Cl_2$) afforded the title compound as a yellow solid (0.22 g, 84% yield). MS (ESI pos. ion) m/z (MH+): 174. Calc'd exact mass for $C_{11}H_{11}NO$: 173. $^1H$ NMR (400 MHz, DMSO-$d_6$) δ ppm 8.83 (dd, J=4.2, 1.7 Hz, 1H), 8.28 (dd, J=8.3, 0.9 Hz, 1 H), 7.93 (d, J=8.6 Hz, 1 H), 7.77 (d, J=1.2 Hz, 1H), 7.65 (dd, J=8.6, 2.0 Hz, 1 H), 7.49 (dd, J=8.3, 4.2 Hz, 1 H), 4.73 (t, J=5.2 Hz, 1 H), 3.72 (dt, J=6.8, 5.3 Hz, 2 H), 2.92 (t, J=6.8 Hz, 2 H).

(2) (reference. J. Med. Chem. 1996, 5176). To a 15 mL round-bottomed flask was added 2-(quinolin-6-yl)ethanol (0.15 g, 0.88 mmol) and benzene (3.0 mL). To the mixture was added phosphorus tribromide (0.091 mL, 0.97 mmol) as a solution in 0.5 mL benzene. The mixture was heated at 60° C. for 45 minutes, then poured into aq. $NaHCO_3$ (10 mL) and extracted with EtOAc (2×7 mL). The combined extracts were washed with sat. $NaHCO_3$, dried ($Na_2SO_4$) and concentrated to afford the title compound as a yellow oil that was carried on without further purification.

(3) (reference: Synthesis 1981, 631). To a solution containing 6-(2-bromoethyl)quinoline (0.13 g, 0.56 mmol) in benzene (6.0 mL) was added 6-phenyl-3(2H)-pyridazinone (0.096 g, 0.56 mmol, Aldrich), tetrabutylammonium bromide (0.036 g, 0.11 mmol) and potassium hydroxide (0.094 g, 1.7 mmol). The mixture was stirred at 25° C. for 20 h, then poured into water (100 mL) and extracted with EtOAc (3×50 mL). The combined extracts were washed with brine (50 mL), dried ($Na_2SO_4$) and concentrated onto silica. Purification by silica gel chromatography (0 to 3.0% MeOH (2 M in $NH_3$)/$CH_2Cl_2$) afforded the title compound as a white solid (0.12 g, 63% yield). MS (ESI pos. ion) m/z (MH+): 328. Calc'd exact mass for $C_{21}H_{17}N_3O$: 327. $^1H$ NMR (400 MHz, DMSO-$d_6$) δ ppm 8.83 (dd, J=4.2, 1.7 Hz, 1H), 8.25 (dd, J=8.3, 0.9 Hz, 1 H), 7.98 (d, J=9.8 Hz, 1 H), 7.94 (d, J=8.6 Hz, 1 H), 7.78 (d, J=1.4 Hz, 1 H), 7.65-7.71 (m, 3H), 7.47 (dd, J=8.3, 4.2 Hz, 1

H), 7.36-7.42 (m, 3 H), 7.02 (d, J=9.8 Hz, 1 H), 4.51 (t, J=7.2 Hz, 2 H), 3.31 (t, J=7.0 Hz, 2 H).

EXAMPLE 125

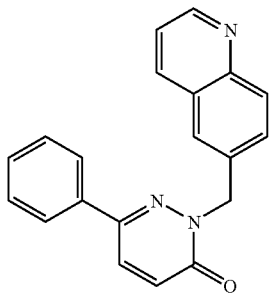

6-Phenyl-2-(quinolin-6-ylmethyl)pyridazin-3(2H)-one (1) 6-(Bromomethyl)quinoline. To a 25 mL round-bottomed flask was added 6-quinolinylmethanol (0.50 g, 3.1 mmol, Maybridge), benzene (10 mL) and phosphorus tribromide (0.33 mL, 3.5 mmol). The mixture was heated at 60° C. for 45 min, then poured into aq. NaHCO$_3$ (10 mL) and extracted with EtOAc (2×7 mL). The combined extracts were washed with brine, dried (Na$_2$SO$_4$) and concentrated to afford a yellow oil that was carried on without further purification.

(2) To a 25 mL round-bottomed flask containing 6-(bromomethyl)quinoline (0.35 g, 1.6 mmol) was added benzene (10 mL), 6-phenyl-3(2H)-pyridazinone (0.15 g, 0.87 mmol, Aldrich), tetrabutylammonium bromide (0.056 g, 0.17 mmol) and potassium hydroxide (0.15 g, 2.6 mmol). The mixture was stirred at 25° C., then poured into aq. NaHCO$_3$ (100 mL) and extracted with EtOAc (3×50 mL). The combined extracts were washed with brine (50 mL), dried (Na$_2$SO$_4$) and concentrated onto silica. Purification by silica gel chromatography (0.5 to 5.0% MeOH (2 M in NH$_3$)/CH$_2$Cl$_2$) afforded the title compound as a white solid (0.050 g, 18% yield). MS (ESI pos. ion) m/z (MH+): 314. Calc'd exact mass for C$_{20}$H$_{15}$N$_3$O: 313. $^1$H NMR (400 MHz, DMSO-d$_6$) δ ppm 8.88 (dd, J=4.2, 1.7 Hz, 1 H), 8.38 (dd, J=8.4, 0.8 Hz, 1 H), 8.11 (d, J=9.6 Hz, 1 H), 8.01 (d, J=8.6 Hz, 1 H), 7.88-7.93 (m, 3 H), 7.78 (dd, J=8.8, 2.0 Hz, 1 H), 7.43-7.54 (m, 4H), 7.13 (d, J=9.8 Hz, 1 H), 5.54 (s, 2 H).

EXAMPLE 126

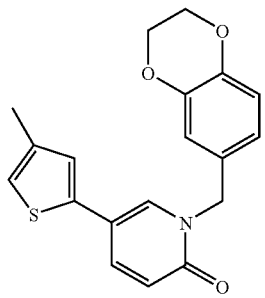

1-((2,3-dihydrobenzo[b][1,4]dioxin-6-yl)methyl)-5-(4-methylthiophen-2-yl)pyridin-2(1H)-one A 10-mL CEM vial was swept with Ar, and charged with Fibrecat 1029 (0.034 g, 0.0092 mmol), 4-methylthiophen-2-ylboronic acid (0.052 g, 0.37 mmol), a stirbar, 1-((2,3-dihydrobenzo[b][1,4]dioxin-6-yl)methyl)-5-iodopyridin-2(1H)-one (0.0340 g, 0.092 mmol) dissolved in 1 mL dry dioxane, and sodium carbonate (0.092 ml, 0.18 mmol). The Argon line was removed and the vial quickly sealed. The slurry was irradiated to 120° C. (100 W, powermax=on, ramp time=2 min, to 65° C., then from 2-7 minutes, 200 W, temp=120° C., held for 5 minutes). The solution was diluted with 5 mL DCM and loaded onto an unbuffered, 10 mL Varian Chem elute CE 1005 (PN 12198007) and extracted with DCM (3×30 mL). The combined extracts were concentrated in vacuo. The sample was purified using a 19×150 mm Waters Xterra Prep C18 OBD column (100 Å pore diameter, 5 µm particle size, spherical shape, PN 186002381; Gradient: 0→5 min@20 mL/min, 25% B; 5.0→35 min@20 mL/min, linear gradient to 55% B; 35→45@20 mL/min, isocratic at 55% B, 45→55 min@20 mL/min, step to 100% B; 55→60 min@20 mL/min, step to 25% B; 60 min end). A=10.7 mM NH$_4$HCO$_3$ in water, B=ACN. A band that eluted from 25.2-26.4 minutes was isolated. The solvent was removed in vacuo to afford 1-((2,3-dihydrobenzo[b][1,4]dioxin-6-yl)methyl)-5-(4-methylthiophen-2-yl)pyridin-2(1H)-one (0.0191 g, 61% yield). MS (ESI pos. ion) m/z (MH+): 340; calcd for C$_{19}$H$_{17}$NO$_3$S+H$^+$= 340.1). $^1$H NMR (400 MHz, CDCl$_3$) δ ppm 2.24 (d, J=1.08 Hz, 3 H) 4.23 (s, 4 H) 5.05 (s, 2 H) 6.63 (d, J=9.49 Hz, 1 H) 6.77 (t, J=1.08 Hz, 1H) 6.81-6.86 (m, 3 H) 6.84 (dd, J=2.45, 0.98 Hz, 1 H) 7.46 (d, J=2.54 Hz, 1 H) 7.53 (dd, J=9.49, 2.64 Hz, 1 H). $^{13}$C NMR (101 MHz, CDCl$_3$) δ ppm 15.75 (s, 1 C) 51.64 (s, 1 C) 64.29 (s, 2 C) 114.82 (s, 1 C) 117.12 (s, 1 C) 117.67 (s, 1 C) 119.28 (s, 1 C) 121.20 (s, 1 C) 121.32 (s, 1 C) 124.90 (s, 1 C) 129.29 (s, 1 C) 133.15 (s, 1 C) 138.48 (s, 1 C) 138.66 (s, 1 C) 139.09 (s, 1 C) 143.48 (s, 1 C) 143.71 (s, 1 C) 161.65 (s, 1 C).

EXAMPLE 127

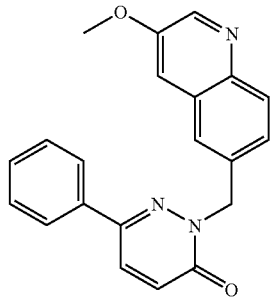

2-((3-methoxyquinolin-6-yl)methyl)-6-phenylpyridazin-3(2H)-one

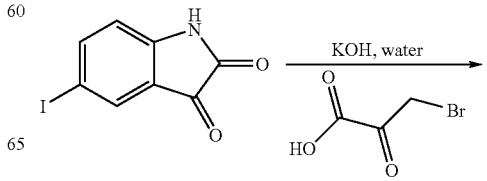

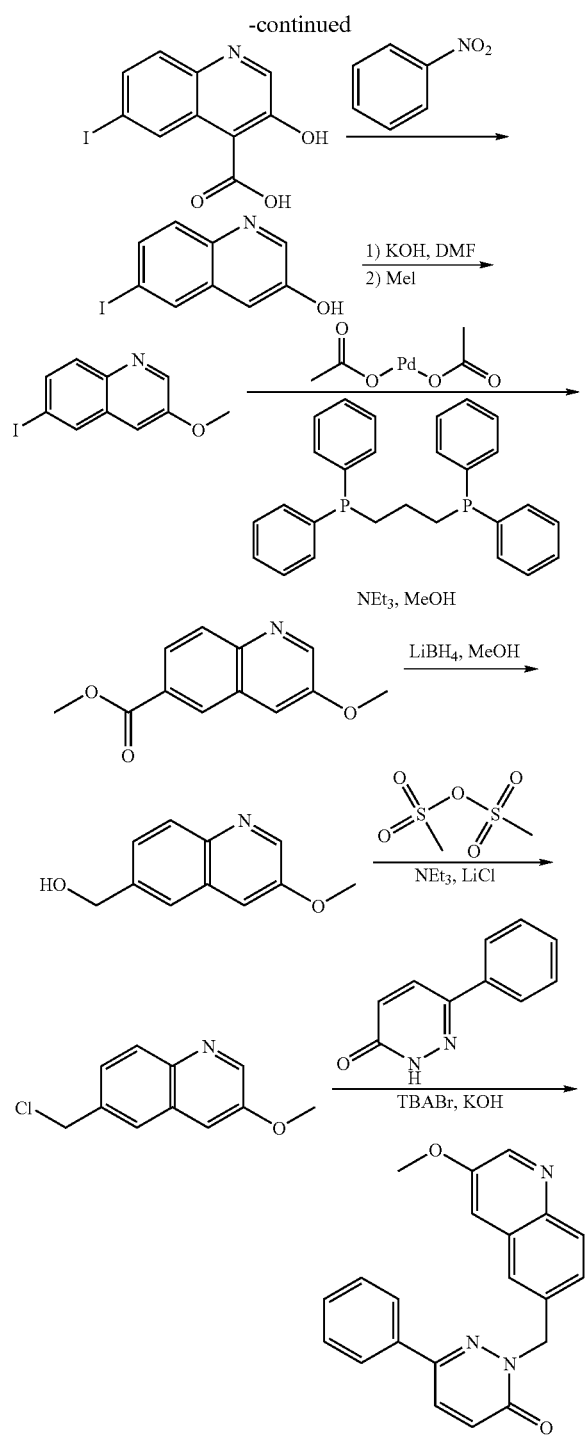

(1) 3-Hydroxy-6-iodoquinoline-4-carboxylic acid. Iodoindoline-2,3-dione (50 g, 183 mmol) was dissolved in a hot solution containing potassium hydroxide (82 g, 1465 mmol) and water (250 mL). The homogeneous solution precipitated out completely 5 min. Enough ethanol (30 mL) was added to redissolve the reaction mixture. After cooled to rt and mechanically stirred, 3-bromo-2-oxopropanoic acid hydrate (47 g, 256 mmol) was added portionwise, causing temperature to rise (>80° C.). After the addition, the reaction mixture was cooled to rt and continued to stir for 3 days. The reaction mixture was treated with saturated solution of NaHSO$_3$ (sodium bisulfite, 12 g, 115.32 mmol) in order to prevent the development of color in the product. The resulting mixture was then acidified to pH=2 using concentrated HCl. After stirred for 1 h, the yellow solid that was formed in the solution mixture was collected by filtration. The solid was washed with water and suspended in water with SO$_2$ bubbling in the solution. After 30 minutes the solid again was separated by filtration. This wet solid was suspended in water, stirred, and dissolved by gradual addition of solid Na$_2$CO$_3$. The solution was treated with a saturated solution of NaHSO$_3$ and filtered. The filtrate was acidified to pH=2 using concentrated HCl. The solid was collected by filtration and was washed with water. It was resuspended in water, and again filtered. The solid was suspended in EtOH, separated by filtration, and air dried to afford the desired product (brown solid, 22.0 g). MS (ESI pos. ion) m/z (M+1): 316.2. Calc'd exact mass for C$_{10}$H$_6$INO$_3$: 315.06. $^1$H NMR (300 MHz, DMSO-d$_6$) δ ppm 7.65-7.72 (m, 1 H) 7.75-7.84 (m, 1 H) 8.70 (s, 1 H) 8.81 (s, 1 H).

(2) 6-Iodoquinolin-3-ol. 3-hydroxy-6-iodoquinoline-4-carboxylic acid (22 g, 70 mmol) was suspended in 1-nitrobenzene (143 ml, 1397 mmol) followed by adding Hunig's base (25 mL)—the suspension was completely dissolved. The resulting mixture was heated to reflux (210° C.) for 3 h under N$_2$. The reaction mixture was cooled to rt and the solvent was removed as much as possible in vacuo. The crude product was suspended in DCM/MeOH and the solid was collected by filtration. The solid was rinsed with hexane and ether and dried as brownish solid 7.8 g. The filtrate was concentrated and purified using SiO$_2$ chromatography (Teledyne Isco RediSep®, P/N 68-2203-058, 330 g siO$_2$, solvent system: hexanes:acetone=80%:20%, Flow=100 mL/min). A peak at 35 min (product) was collected to afford the desired product as brown solid. Total product obtained was 11.2 g. MS (ESI pos. ion) m/z (M+1): 272.3. Calc'd exact mass for C$_9$H$_6$INO: 271.05. $^1$H NMR (300 MHz, MeOH) δ ppm 7.43 (d, J=2.63 Hz, 1 H) 7.60-7.70 (m, 1 H) 7.75-7.82 (m, 1 H) 8.18 (d, J=1.90 Hz, 1 H) 8.53 (d, J=2.78 Hz, 1 H).

(3) 6-Iodo-3-methoxyquinoline. To a solution of 6-iodoquinolin-3-ol (1.00 g, 4 mmol) in DMF (15 mL) was added potassium hydroxide (0.2 g, 4 mmol). After stirred for 1 h at rt, iodomethane (0.3 ml, 4 mmol) was added. The resulting mixture was continued to stir for 20 h at rt. The reaction was quenched with water and the solvent was removed in vacuo. The residue was partitioned between EtOAc/NaHCO$_3$(satd.). The aqueous layer was extracted more with EtOAc (15 mL×2). The combined organic layers were washed with water (3×10 mL), dried over MgSO$_4$ and concentrated. The crude product was purified using SiO$_2$ chromatography (Teledyne Isco RediSep®, P/N 68-2203-027, 40 g SiO$_2$, solvent system: hexanes:acetone=90%:10%, Flow=40 mL/min). A peak at 30 min was collected. The solvent was removed in vacuo to afford the desired product as light yellow solid (700.0 mg). MS (ESI pos. ion) m/z (M+1): 286.4. Calc'd exact mass for C$_{10}$H$_8$INO: 285.08. $^1$H NMR (300 MHz, CHLOROFORM-d) δ ppm 3.95 (s, 3H) 7.25 (d, J=2.78 Hz, 1 H) 7.72-7.78 (m, 1 H) 7.78-7.83 (m, 1 H) 8.14 (d, J=1.61 Hz, 1 H) 8.67 (d, J=2.92 Hz, 1 H).

(4) Methyl 3-methoxyquinoline-6-carboxylate. To a solution of 6-iodo-3-methoxyquinoline (1 g, 4 mmol) in DMSO (20 mL) under N$_2$ was added 1-((3-(diphenylphosphino)propyl)(phenyl)phosphino)benzene (0.1 g, 0.3 mmol), palladium (II) acetate (0.09 g, 0.4 mmol), triethylamine (3 ml, 21 mmol), and methanol (3 ml, 70 mmol). The reaction mixture (under N$_2$) was first bubbled with CO for a few minutes followed by evacuating—this procedure was done 3 times. After last evacuation, a CO balloon was inserted. The reaction was heated at 70° C. under CO for 2 h. The reaction mixture was partitioned between EtOAc/water. The organic layer was washed with more water (5×10 mL), dried over MgSO₄ and concentrated. The crude product was purified using SiO₂ chromatography (Teledyne Isco RediSep®, P/N 68-2203-024, 120 g SiO₂, hex:acetone=90%:10%, Flow=85 mL/min). A peak at 20 min was collected. The solvent was removed in vacuo to afford the desired product as white solid (630 mg). MS (ESI pos. ion) m/z (M+1): 218.4. Calc'd exact mass for C₁₂H₁₁NO₃: 217.22. ¹H NMR (300 MHz, CHLOROFORM-d) δ ppm 3.99 (d, J=5.26 Hz, 6 H) 7.47 (d, J=2.78 Hz, 1 H) 8.04-8.12 (m, 1 H) 8.12-8.19 (m, 1 H) 8.52 (s, 1 H) 8.77 (d, J=2.92 Hz, 1 H).

(5) (3-methoxyquinolin-6-yl)methanol. To a cooled solution (0° C.) of methyl 3-methoxyquinoline-6-carboxylate (0.15 g, 0.7 mmol) in THF (15 mL) was added methanol (0.08 ml, 2 mmol) and lithium borohydride (0.07 ml, 2 mmol). After the addition, the ice bath was removed. The reaction mixture was stirred at rt for 20 h. The reaction was quenched with water and the solvent was removed. The residue was partitioned between EtOAc/water. The organic layer was washed with water, brine, dried over MgSO₄ and concentrated. The crude product was purified using SiO₂ chromatography (Teledyne Isco RediSep®, P/N 68-2203-027, 40 g SiO₂, hex:ace=90%:10%, Flow=30 mL/min). A peak at 30 min was collected. Solvent was removed in vacuo to afford the product as yellow solid (80 mg). MS (ESI pos. ion) m/z (M+1): 190.4. Calc'd exact mass for C₁₁H₁₁NO₂: 189.22. ¹H NMR (300 MHz, CHLOROFORM-d) δ ppm 2.66 (s, 1 H) 3.96 (s, 3 H) 4.89 (s, 2H) 7.38 (d, J=2.78 Hz, 1 H) 7.54 (dd, J=8.62, 1.75 Hz, 1 H) 7.74 (s, 1 H) 8.04 (d, J=8.48 Hz, 1 H) 8.66 (d, J=2.92 Hz, 1 H).

(6) 6-(chloromethyl)-3-methoxyquinoline. To a solution of (3-methoxyquinolin-6-yl)methanol (0.17 g, 0.9 mmol) in DMF (10 mL) was added methanesulfonic anhydride (0.4 g, 2 mmol) followed by triethylamine (0.4 ml, 3 mmol). After stirred for 1 h, lithium chloride (0.08 g, 2 mmol) was added. The reaction was continued to stir at rt under N₂ for 20 h. The reaction mixture was quenched with water. The resulting mixture was partitioned between EtOAc/sat. NaHCO₃ The organic layer was washed with water, brine, dried over MgSO₄ and concentrated. The crude product was purified using SiO₂ chromatography (Teledyne Isco RediSep®, P/N 68-2203-026, 12 g SiO₂, hex:acetone=90%:10%, Flow=30 mL/min). A peak at 30 min was collected. The solvent was removed in vacuo to afford the desired product as white solid (100 mg). MS (ESI pos. ion) m/z (M+1): 208.4. Calc'd exact mass for C₁₁H₁₀ClNO: 207.66. ¹H NMR (300 MHz, CHLOROFORM-d) δ ppm 3.96 (s, 3 H) 4.76 (s, 2 H) 7.37 (d, J=2.78 Hz, 1 H) 7.58 (dd, J=8.62, 1.90 Hz, 1 H) 7.75 (s, 1 H) 8.05 (d, J=8.62 Hz, 1 H) 8.69 (d, J=2.92 Hz, 1 H).

(7) 2-((3-methoxyquinolin-6-yl)methyl)-6-phenylpyridazin-3(2H)-one. To a flame dry 25 mL round bottom flask was added 6-(chloromethyl)-3-methoxyquinoline (0.05 g, 0.2 mmol) followed by 6-phenyl-3(2h)-pyridazinone (0.06 g, 0.4 mmol), tetrabutylammonium bromide (0.02 g, 0.05 mmol), potassium hydroxide (0.04 g, 0.7 mmol), and benzene (8 mL). The reaction mixture was stirred at rt under N₂ for 20 h. Reaction was quenched with water. The resulting mixture was partitioned between EtOAc/sat. NaHCO₃. The aqueous layer was extracted more with EtOAc (2×10 mL). The combined organic layers were washed with water, brine, dried over MgSO₄ and removed solvent. The crude product was purified using SiO₂ chromatography (Teledyne Isco RediSep®, P/N 68-2203-026, 12 g SiO₂, hex:acetone=90%: 10%, Flow=30 mL/min). A peak at 30 min was collected. The solvent was removed in vacuo to afford the desired product as white solid. Wt: 70 mg. MS (ESI pos. ion) m/z: 344.4. Calc'd exact mass for C₂₁H₁₇N₃O₂: 343.38. ¹H NMR (300 MHz, CHLOROFORM-d) δ ppm 3.94 (s, 3 H) 5.58 (s, 2 H) 7.06 (d, J=9.65 Hz, 1 H) 7.38 (d, J=2.78 Hz, 1 H) 7.44-7.51 (m, 3 H) 7.70 (d, J=9.50 Hz, 2 H) 7.80 (dd, J=7.82, 1.68 Hz, 2 H) 7.84 (s, 1 H) 8.02 (d, J=8.62 Hz, 1 H) 8.65 (d, J=2.92 Hz, 1 H).

EXAMPLE 128

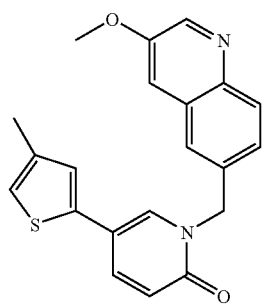

1-((3-methoxyquinolin-6-yl)methyl)-5-(4-methylthiophen-2-yl)pyridin-2(1H)-one

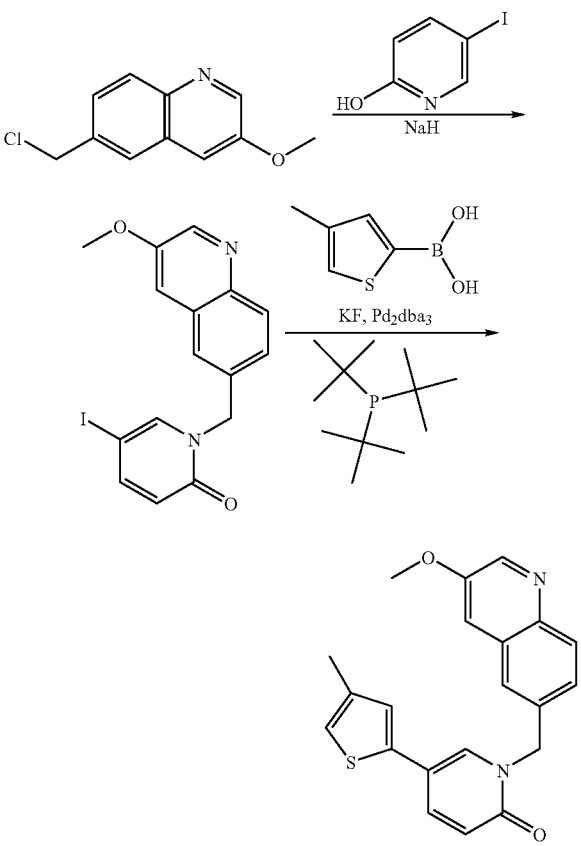

(1) 5-Iodo-1-((3-methoxyquinolin-6-yl)methyl)pyridin-2 (1H)-one. To a solution of 6-(chloromethyl)-3-methoxyquinoline (0.042 g, 0.20 mmol) in DMF (8 mL) in a flame dried 25 mL round bottom flask at 0° C. was added sodium hydroxide (0.011 g, 0.26 mmol). After stirred for 30 min, 5-iodopyridin-2-ol (0.058 g, 0.26 mmol) was added. The ice bath was removed and the reaction mixture was stirred at rt under N₂ for 20 h. The reaction was quenched with water and the resulting mixture was partitioned between EtOAc/sat. NaHCO₃. The aqueous layer was extracted with EtOAc (2×10 mL). The combined organic layers were washed with water, brine, dried over MgSO₄ and concentrated. The crude product was purified using SiO₂ chromatography (Teledyne Isco RediSep®, P/N 68-2203-026, 12 g SiO₂, isocratic 3% MeOH in DCM with 17% EtOAc, Flow=30 mL/min). A peak at 15 min was collected. The solvent was removed in vacuo to afford the desired product as white solid (42.0 mg). MS (ESI pos. ion) m/z (M+1): 393.4. Calc'd exact mass for $C_{16}H_{13}IN_2O_2$: 392.19. ¹H NMR (300 MHz, CHLOROFORM-d) δ ppm 3.95 (s, 3 H) 5.26 (s, 2 H) 6.48 (d, J=9.65 Hz, 1 H) 7.37 (d, J=2.78 Hz, 1 H) 7.41-7.51 (m, 2 H) 7.54 (d, J=2.19 Hz, 1 H) 7.65 (s, 1H) 8.04 (d, J=8.48 Hz, 1 H) 8.68 (d, J=2.92 Hz, 1 H).

(2) 1-((3-methoxyquinolin-6-yl)methyl)-5-(4-methylthiophen-2-yl)pyridin-2(1H)-one. To a dry 25 mL round bottom flask was added 5-iodo-1-((3-methoxyquinolin-6-yl)methyl)pyridin-2(1H)-one (0.04 g, 0.1 mmol) followed by 4-methylthiophen-2-ylboronic acid (0.03 g, 0.2 mmol), potassium fluoride dihydrate (0.0004 ml, 0.01 mmol), tri-tert-butylphosphine (0.005 g, 0.02 mmol), tris(dibenzylideneacetone)dipalladium (0) (0.4 g, 0.4 mmol), and DMF (8 mL). The reaction mixture was stirred at rt under N₂ for 20 h. Reaction was quenched with water. The resulting mixture was partitioned between EtOAc/sat. NaHCO₃. The aqueous layer was extracted with EtOAc (2×10 mL). The combined organic layers were washed with water, brine, dried over MgSO₄ and concentrated. The crude product was purified using SiO₂ chromatography (Teledyne Isco RediSep®, P/N 68-2203-026, 12 g SiO₂, hex:acetone=70%:30%, Flow=30 mL/min). A peak at 32 min was collected. The solvent was removed in vacuo to afford the desired product as white solid (18.0 mg). MS (ESI pos. ion) m/z (M+1): 363.5. Calc'd exact mass for $C_{21}H_{18}N_2O_2S$: 362.44. ¹H NMR (300 MHz, CHLOROFORM-d) δ ppm 2.24 (s, 3 H) 3.94 (s, 3 H) 5.35 (s, 2 H) 6.71 (d, J=9.65 Hz, 1 H) 6.78 (s, 1 H) 6.86 (s, 1 H) 7.35 (d, J=2.78 Hz, 1 H) 7.47-7.63 (m, 3 H) 7.66 (s, 1 H) 8.04 (d, J=8.62 Hz, 1 H) 8.66 (d, J=2.92 Hz, 1 H).

EXAMPLE 129

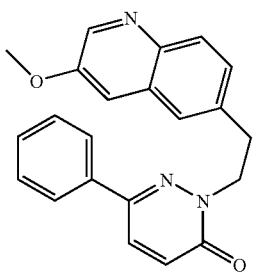

2-(2-(3-Methoxyquinolin-6-yl)ethyl)-6-phenylpyridazin-3(2H)-one

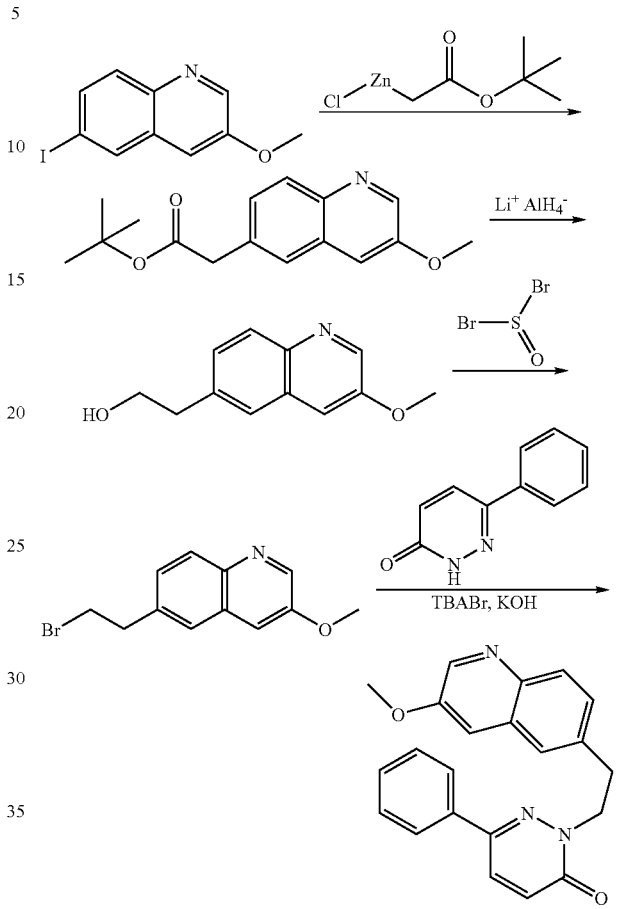

(1) tert-Butyl 2-(3-methoxyquinolin-6-yl)acetate. A stirred solution of 6-iodo-3-methoxyquinoline (2.5 g, 9 mmol) in THF (50 mL) was treated with organozinc reagent (55 ml, 28 mmol) followed by tetrakis-(triphenylphosphine)-palladium(0) (1 g, 0.9 mmol). After the addition, it was heated to reflux (75° C.) for 3 h under N₂. The reaction was cooled to rt. Solvent was removed. The residue was stirred in EtOAc/10% EDTA (50 mL/50 mL) solution mixture. After 1 h, the organic layer was separated. The aqueous layer was extracted with EtOAc (2×25 mL). The combined organic layers were washed with water, brine, dried over MgSO₄, and concentrated. The crude product was purified using SiO₂ chromatography (Teledyne Isco RediSep®, P/N 68-2203-027, 330 g SiO₂, hex:acetone=80%:20%, Flow=100 mL/min). A peak at 38 min was collected. Solvent was removed in vacuo to afford the desired product as brownish liquid and later became yellow solid (1.1 g). MS (ESI pos. ion) m/z (M+1): 274.53. Calc'd exact mass for $C_{16}H_{19}NO_3$: 273.33. ¹H NMR (300 MHz, CHLOROFORM-d) δ ppm 1.46 (s, 9 H) 3.70 (s, 2 H) 3.95 (s, 3 H) 7.35 (d, J=2.78 Hz, 1 H) 7.48 (d, J=8.62 Hz, 1 H) 7.63 (s, 1 H) 8.00 (d, J=8.62 Hz, 1 H) 8.65 (d, J=2.92 Hz, 1 H).

(2) 2-(3-Methoxyquinolin-6-yl)ethanol. To a cool solution (−78° C.) of tert-butyl 2-(3-methoxyquinolin-6-yl)acetate (0.2 g, 0.7 mmol) in THF (15 mL) was added lithium tetrahydroaluminate (2 ml, 2 mmol) dropwise via the addition funnel. After the addition, the reaction mixture was continued to stir at −78° C. under N₂ for 3 h. The reaction temperature was slowly brought up to −40° C. and stirred at that temperature for 2 h. The reaction was quenched with water. The solvent was removed. The residue was partitioned between EtOAc/sat. sodium potassium tartrate solution. The resulting mixture was stirred for 1 h. The organic layer was washed with water, brine, dried over MgSO$_4$ and concentrated (115 mg). MS (ESI pos. ion) m/z (M+1): 204.3. Calc'd exact mass for C$_{12}$H$_{13}$NO$_2$: 203.24. $^1$H NMR (300 MHz, CHLOROFORM-d) δ ppm 1.60 (s, 1 H) 3.05 (t, J=6.43 Hz, 2 H) 3.95 (s, 3 H) 3.97-4.03 (m, 2 H) 7.34 (d, J=2.78 Hz, 1 H) 7.44 (dd, J=8.62, 1.90 Hz, 1 H) 7.58 (d, J=1.32 Hz, 1 H) 7.99 (d, J=8.48 Hz, 1 H) 8.63 (d, J=2.78 Hz, 1H).

(3) 6-(2-Bromoethyl)-3-methoxyquinoline. To a stirred solution of 2-(3-methoxyquinolin-6-yl)ethanol (0.115 g, 0.566 mmol) in DCM (15 mL) was added thionyl bromide (0.219 ml, 2.83 mmol). After the addition, the reaction was continued to stir at rt under N$_2$ for 20 h. Reaction was quench with water. DCM (10 mL) was added and the resulting mixture was washed with sat. NaHCO$_3$ (gas evolved), dried over MgSO$_4$ and concentrated. The crude product was purified using SiO$_2$ chromatography (Teledyne Isco RediSep®, P/N 68-2203-026, 12 g SiO$_2$, hex:acetone=90%:10%, Flow=30 mL/min). A peak at 20 min was collected. The solvent was removed in vacuo to afford the desired product as white solid (148 mg). MS (ESI pos. ion) m/z (M+1): 267.3. Calc'd exact mass for C$_{12}$H$_{12}$BrNO: 266.13. $^1$H NMR (300 MHz, CHLOROFORM-d) δ ppm 3.35 (t, J=7.45 Hz, 2 H) 3.68 (t, J=7.38 Hz, 2 H) 3.96 (s, 3 H) 7.36 (d, J=2.78 Hz, 1 H) 7.41 (d, J=8.48 Hz, 1 H) 7.57 (s, 1 H) 8.01 (d, J=8.48 Hz, 1 H) 8.66 (d, J=2.92 Hz, 1H).

(4) 2-(2-(3-Methoxyquinolin-6-yl)ethyl)-6-phenylpyridazin-3(2H)-one. To a flame dry 25 mL round bottom flask was added 6-(2-bromoethyl)-3-methoxyquinoline (0.05 g, 0.2 mmol), 6-phenylpyridazin-3(2H)-one (0.05 g, 0.3 mmol), tetrabutylammonium bromide (0.01 g, 0.04 mmol), potassium hydroxide (0.03 g, 0.6 mmol), and benzene (8 mL). The reaction mixture was stirred at rt under N$_2$ for 20 h. Reaction was quenched with water. The resulting mixture was partitioned between EtOAc/sat. NaHCO$_3$. The aqueous layer was extracted more with EtOAc (2×10 mL). The combined organic layers were washed with water, brine, dried over MgSO$_4$ and removed solvent. The crude product was purified using SiO$_2$ chromatography (Teledyne Isco RediSep®, P/N 68-2203-026, 12 g SiO$_2$, hex:acetone=90%:10%, Flow=30 mL/min). A peak at 30 min was collected. The solvent was removed in vacuo to afford the desired product as white solid. Wt: 25.0 mg. MS (ESI pos. ion) m/z: 358.3. Calc'd exact mass for C$_{22}$H$_{19}$N$_3$O$_2$: 357.41. $^1$H NMR (300 MHz, CHLOROFORM-d) δ ppm 3.32-3.43 (m, 2 H) 3.94 (s, 3 H) 4.55-4.65 (m, 2 H) 7.03 (d, J=9.65 Hz, 1 H) 7.32 (d, J=2.78 Hz, 1 H) 7.39-7.46 (m, 3 H) 7.51 (d, J=8.62 Hz, 1 H) 7.61-7.70 (m, 4 H) 7.99 (d, J=8.62 Hz, 1 H) 8.63 (d, J=2.92 Hz, 1 H).

EXAMPLE 130

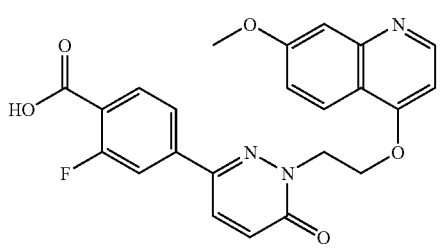

2-Fluoro-4-(1-(2-(7-methoxyquinolin-4-yloxy)ethyl)-6-oxo-1,6-dihydropyridazin-3-yl)benzoic acid To a 5 ml CEM microwave tube was added 6-chloro-2-(2-(7-methoxyquinolin-4-yloxy)ethyl)pyridazin-3(2H)-one (0.1 g, 0.3 mmol), 4-bromo-2-fluorobenzoic acid (0.08 g, 0.5 mmol), sodium carbonate (0.10 g, 0.9 mmol), dichlorobis(triphenylphosphine)-palladium(II) (30 mg, 0.05 mmol), and DMF (4 mL)-water (0.4 mL). The vial was sealed and placed in CEM microwave for 20 min at 130° C., with 100 Watts of power via Powermax. The reaction mixture was extracted with EtOAc (3×10 mL). The combined organic layers were dried over MgSO$_4$ and concentrated (toluene was added in order to removed most of DMF). The crude product was purified using SiO$_2$ chromatography (Teledyne Isco RediSep®, P/N 68-2203-026, 12 g SiO$_2$, isocratic 5% MeOH in DCM with 1% AcOH, Flow=30 mL/min). The peak at 30 min was collected to afford the desired product as white solid (85 mg). MS (ESI pos. ion) m/z (M+1): 436.2. Calc'd exact mass for C$_{23}$H$_{18}$FN$_3$O$_5$: 357.41. $^1$H NMR (300 MHz, DMSO-d$_6$) δ ppm 3.86 (s, 3 H) 4.70 (s, 4 H) 6.96-7.04 (m, 2 H) 7.13 (d, J=9.79 Hz, 1 H) 7.25-7.30 (m, 1 H) 7.69-7.73 (m, 1 H) 7.75 (s, 1 H) 7.86 (s, 1 H) 7.87-7.95 (m, 2 H) 8.12 (d, J=9.79 Hz, 1 H) 8.64 (d, J=5.26 Hz, 1 H).

EXAMPLE 131

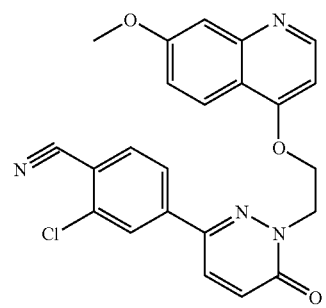

2-Chloro-4-(1-(2-(7-methoxyquinolin-4-yloxy)ethyl)-6-oxo-1,6-dihydropyridazin-3-yl)benzonitrile See example 75 for a general synthesis. To a solution of 2-chloro-4-(1-(2-(7-methoxyquinolin-4-yloxy)ethyl)-6-oxo-1,6-dihydropyridazin-3-yl)benzamide (120 mg, 266 µmol) in pyridine (10763 µL, 133075 µmol) was added thionyl chloride (194 µL, 2661 µmol). The reaction was then stirred overnight at 23° C. for 18 hours. The reaction was then chilled to 0° C., and quenched with sat. NH$_4$Cl. The organic contents were extracted with DCM (30 mL), separated, dried over MgSO$_4$, then concentrated to a solid under reduced pressure. The product was then purified on silica (12 g) eluting with 3>5% of NH$_3$ in MeOH/DCM and isolated as an off white solid. MS (ESI pos. ion) m/z: (MH+); calc'd for C$_{23}$H$_{17}$ClN$_4$O$_3$: 432. $^1$H NMR (400 MHz, CHLOROFORM-d) δ ppm 3.92 (s, 3 H) 4.67 (t, J=5.02 Hz, 2 H) 4.81 (t, J=5.27 Hz, 2 H) 6.65 (d, J=5.52 Hz, 1 H) 6.99 (dd, J=9.29, 2.26 Hz, 1 H) 7.09 (d, J=9.54 Hz, 1 H) 7.30 (s, 1 H) 7.65 (d, J=9.54 Hz, 2 H) 7.68-7.74 (m, 1 H) 7.87 (s, 1 H) 7.95 (d, J=9.54 Hz, 1 H) 8.64 (d, J=5.02 Hz, 1 H).

EXAMPLE 132

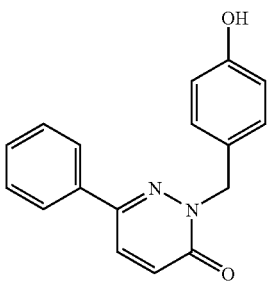

2-(4-Hydroxybenzyl)-6-phenylpyridazin-3(2H)-one (1) 2-(4-methoxybenzyl)-6-phenylpyridazin-3(2H)-one. A suspension of 6-phenyl-3(2h)-pyridazinone (517 mg, 3003 μmol), 1-(bromomethyl)-4-methoxybenzene (454 μl, 3153 μmol), and potassium carbonate, −325 mesh (1245 mg, 9008 μmol) in DMF (5 mL) was stirred at 23° C. for 28 hours. The reaction was then partitioned between EtOAc (75 mL) and 1 M NaOH (25 mL). Organic layer was then dried over $MgSO_4$, concentrated onto dry silica (20 g), then purified on 80 g silica eluting with 0>50% EtOAc/Hex. Product isolated as white crystals from ACN. MS (ESI pos. ion) m/z: 293 (MH+); calc'd for $C_{18}H_{16}N_2O_2$: 292. $^1$H NMR (400 MHz, CHLOROFORM-d) δ ppm 3.77 (s, 3 H) 5.34 (s, 2 H) 6.86 (d, J=8.80 Hz, 2 H) 6.99 (d, J=9.59 Hz, 1 H) 7.37-7.50 (m, 5 H) 7.63 (d, J=9.59 Hz, 1H) 7.77 (dd, J=8.12, 1.47 Hz, 2 H).

(2) To a stirring solution of 2-(4-methoxybenzyl)-6-phenylpyridazin-3(2H)-one (400 mg, 1368 mmol) in DCM (2.5 mL) at 0° C. under nitrogen was added boron tribromide (1294 μl, 13683 μmol) drop-wise over a 1 minute period. More DCM (10 mL) was added to the reaction to create a suspension and ice bath removed. After 3 hours, the reaction was chilled to 0° C. and quenched with methanol (5 mL). The pH was then adjusted to 14 with NaOH (1 M), then adjusted to 7 with HCl (5 M). The aqueous layer was then extracted 3× with 9:1 $CHCl_3$/IPA (50 mL). The combined organics were then dried with sat $NH_4Cl$ and $MgSO_4$. The organic was then concentrated onto dry silica (20 g) and purified on silica (40 g) eluting with 20>40% of EtOAc/DCM. Product was isolated as a white solid. MS (ESI pos. ion) calc'd for $C_{17}H_{14}N_2O_2$: 278; found 279 (MH+). $^1$H NMR (400 MHz, DMSO-$d_6$) δ ppm 5.21 (s, 2 H) 6.68-6.77 (m, 2 H) 7.06 (d, J=9.78 Hz, 1H) 7.22 (d, J=8.61 Hz, 2 H) 7.40-7.55 (m, 3 H) 7.89 (dd, J=8.22, 1.37 Hz, 2 H) 8.04 (d, J=9.78 Hz, 1 H) 9.42 (s, 1 H).

EXAMPLE 133

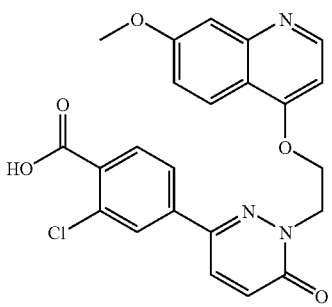

2-Chloro-4-(1-(2-(7-methoxyquinolin-4-yloxy)ethyl)-6-oxo-1,6-dihydropyridazin-3-yl)benzoic acid A suspension of 6-chloro-2-(2-(7-methoxyquinolin-4-yloxy)ethyl)pyridazin-3(2H)-one (2290 mg, 6903 μmol), 4-bromo-2-chlorobenzoic acid (2766 mg, 13805 μmol), $Na_2CO_3$ (2 M, 13805 μl, 27611 μmol), and 1,1'-bis(diphenylphosphino)ferrocene]dichloride palladium(II) complex with dichloromethane (505 mg, 690 μmol) in DME (20 mL) was sparged with argon for 10 minutes then heated to reflux for 7 hours. The reaction was then partitioned between NaOH (1 M, 75 mL) and EtOAc (25 mL). The organic layer was discarded and the aqueous layer acidified to pH 4 with HCl (2M). The resulting orange precipitate was then collected by filtration and washed with water (50 mL). MS (ESI pos. ion) m/z: 452 (MH+); calc'd for $C_{23}H_{18}ClN_3O_5$: 451. $^1$H NMR (400 MHz, DMSO-$d_6$) δ ppm 3.86 (s, 3 H) 4.68 (s, 4 H) 6.94 (d, J=4.52 Hz, 1 H) 7.02 (d, J=9.03 Hz, 1 H) 7.09 (d, J=9.54 Hz, 1 H) 7.27 (s, 1 H) 7.60 (d, J=7.03 Hz, 1 H) 7.75 (d, J=7.03 Hz, 1 H) 7.81-7.98 (m, 2 H) 8.09 (d, J=9.54 Hz, 1 H) 8.62 (d, J=4.02 Hz, 1 H).

EXAMPLE 134

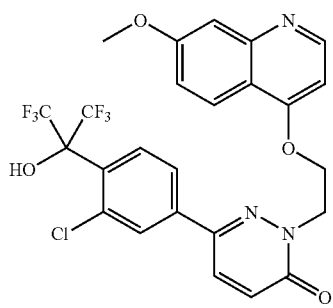

6-(3-Chloro-4-(1,1,1,3,3,3-hexafluoro-2-hydroxypropan-2-yl)phenyl)-2-(2-(7-methoxyquinolin-4-yloxy)ethyl)pyridazin-3(2H)-one A suspension of 2-chloro-4-(1-(2-(7-methoxyquinolin-4-yloxy)ethyl)-6-oxo-1,6-dihydropyridazin-3-yl)benzoic acid (205 mg, 454 μmol), HATU (173 mg, 454 μmol), and DIEA (79 μL, 454 μmol) in DMF (2 mL) was stirred for 30 minutes at 23° C. To the solution was added 2,3,4,5,6-pentafluorophenol (84 mg, 454 μmol) and the reaction was stirred for an additional 1 hour at 35° C. The reaction was then partitioned between EtOAc (20 mL) and 5% $NaHCO_3$ (10 mL). The organic layer was then dried over $MgSO_4$ then concentrated under reduced pressure. The resulting oil was then dissolved in DME (2 mL), chilled to −50° C., and (trifluoromethyl)trimethylsilane (232 μL, 1634 μmol) and tetramethylammonium fluoride (76 mg, 816 μmol) added. Once reaction warmed to 0° C., the reaction was then quenched with water (5 mL) and extracted with DCM (20 mL). The organic layer was dried over $MgSO_4$, concentrated, then purified on 40 g silica eluting product with 0>5% MeOH/DCM. Product was isolated as a tan solid from ACN. MS (ESI pos. ion) m/z: 574.1 (MH+); calc'd for $C_{25}H_{18}ClF_6N_3O_4$: 573.1. $^1$H NMR (400 MHz, CHLOROFORM-d) δ ppm 3.87 (s, 3 H) 4.66 (t, J=5.02 Hz, 2H) 4.81 (t, J=5.27 Hz, 2 H) 6.65 (d, J=5.52 Hz, 1 H) 6.98 (d, J=9.03 Hz, 1 H) 7.08 (d, J=9.54 Hz, 1 H) 7.31 (s, 1 H) 7.65 (d, J=10.04 Hz, 2 H) 7.83 (s, 2 H) 7.96 (d, J=9.54 Hz, 1 H) 8.57 (d, J=5.02 Hz, 1 H).

EXAMPLE 135

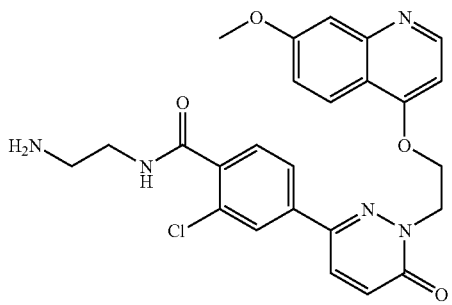

N-(2-Aminoethyl)-2-chloro-4-(1-(2-(7-methoxyquinolin-4-yloxy)ethyl)-6-oxo-1,6-dihydropyridazin-3-yl)benzamide A solution of 2-chloro-4-(1-(2-(7-methoxyquinolin-4-yloxy)ethyl)-6-oxo-1,6-dihydropyridazin-3-yl)benzoic acid (494 mg, 1093 μmol), DIEA (191 μL, 1093 μmol), and HATU (416 mg, 1093 μmol) in DMF (5 mL) was stirred at 23° C. for 15 minutes. This dark solution was then added to a second solution of ethylenediamine (730 μL, 10933 μmol) in DMF (2 mL). The reaction was then stirred overnight at 23° C. followed by a partition between 9:1 CHCl$_3$/IPA (75 mL) and NaOH (1 M, 25 mL). The organic was separated, dried over MgSO$_4$, then concentrated onto dry silica (15 g). The product was purified on silica (40 g) eluting with 10% 2 M NH$_3$ in MeOH/DCM, and isolated as a fluffy lyophilized solid from 1:1 ACN/water. MS (ESI pos. ion) m/z: 494 (MH+); calc'd for C$_{25}$H$_{24}$ClN$_5$O$_4$: 493. $^1$H NMR (400 MHz, DMSO-d$_6$) δ ppm 2.71 (t, J=6.27 Hz, 2H) 3.26 (q, J=6.02 Hz, 2 H) 3.87 (s, 3 H) 4.68 (d, J=4.52 Hz, 4 H) 6.95 (d, J=5.52 Hz, 1 H) 7.05 (dd, J=9.29, 2.26 Hz, 1 H) 7.13 (d, J=10.04 Hz, 1 H) 7.28 (d, J=2.01 Hz, 1 H) 7.51-7.58 (m, 1 H) 7.82-7.97 (m, 3 H) 8.13 (d, J=10.04 Hz, 1 H) 8.50 (t, J=5.27 Hz, 1 H) 8.62 (d, J=5.52 Hz, 1 H).

EXAMPLE 136

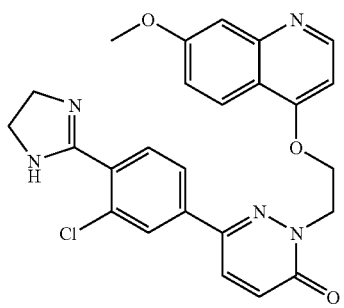

6-(3-Chloro-4-(4,5-dihydro-1H-imidazol-2-yl)phenyl)-2-(2-(7-methoxyquinolin-4-yloxy)ethyl)pyridazin-3(2H)-one A suspension of N-(2-aminoethyl)-2-chloro-4-(1-(2-(7-methoxyquinolin-4-yloxy)ethyl)-6-oxo-1,6-dihydropyridazin-3-yl)benzamide (50 mg, 101 μmol), chlorotrimethylsilane (39 μl, 304 μmol), sodium iodide (46 mg, 304 μmol), and TEA (42 μL, 304 μmol) in DCM (2 mL) was stirred for 3 hours at 40° C. in an appropriately sealed vial. The reaction was then partitioned between DCM (5 mL) and 1 M NaOH (2 mL). The organic layer was then separated and dried over MgSO$_4$, concentrated onto dry silica (2 g) then purified on silica (4 g) by washing with 5% MeOH, then eluting product with 4->10% NH$_3$ in MeOH (2M)/DCM. The product was isolated as a white solid. (ESI pos. ion) m/z: 476 (MH+); calc'd for C$_{25}$H$_{22}$ClN$_5$O$_3$: 475. $^1$H NMR (400 MHz, DMSO-d$_6$) ppm 3.65 (s, 4 H) 3.87 (s, 3 H) 4.69 (dd, J=7.34, 3.42 Hz, 4 H) 6.95 (d, J=5.28 Hz, 1 H) 7.03 (dd, J=9.10, 2.45 Hz, 1 H) 7.12 (d, J=9.78 Hz, 1 H) 7.28 (d, J=2.35 Hz, 1 H) 7.67 (d, J=8.22 Hz, 1 H) 7.83-7.92 (m, 2 H) 7.97 (d, J=1.56 Hz, 1 H) 8.13 (d, J=9.78 Hz, 1H) 8.62 (d, J=5.28 Hz, 1 H).

EXAMPLE 137

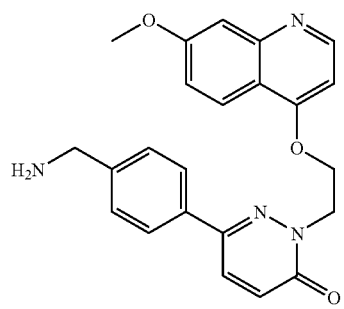

6-(4-(Aminomethyl)phenyl)-2-(2-(7-methoxyquinolin-4-yloxy)ethyl)pyridazin-3(2H)-one A suspension of 6-chloro-2-(2-(7-methoxyquinolin-4-yloxy)ethyl)pyridazin-3(2H)-one (1250 mg, 3768 μmol), (4-aminomethylphenyl)boronic acid, hydrochloride (1412 mg, 7536 μmol), Na$_2$CO$_3$ (7536 μL, 15071 μmol) [2M], and [1,1'-bis(diphenylphosphino)ferrocene]dichloride palladium (II) complex with dichloromethane (276 mg, 377 μmol) in DME (2 mL) was sparged with argon for 5 minutes then heated to 85° C. for 4 hours. The reaction was then partitioned between DCM (50 mL) and 1 M NaOH (20 mL). The organic was dried over MgSO$_4$, concentrated onto dry silica (10 g) then purified on silica (40 g) eluting with 0>5% MeOH/DCM. The product was isolated as an off white solid from ACN. MS (ESI pos. ion) m/z: 403 (MH+); calc'd for C$_{23}$H$_{22}$N$_4$O$_3$: 402. $^1$H NMR (400 MHz, DMSO-d$_6$) δ ppm 3.76 (s, 2 H) 3.87 (s, 3 H) 4.67 (s, 4 H) 6.95 (d, J=5.28 Hz, 1 H) 7.01 (dd, J=9.00, 2.54 Hz, 1 H) 7.08 (d, J=9.78 Hz, 1 H) 7.27 (d, J=2.35 Hz, 1 H) 7.41 (d, J=8.22 Hz, 2 H) 7.78 (d, J=8.41 Hz, 2 H) 7.90 (d, J=9.19 Hz, 1 H) 8.03 (d, J=9.78 Hz, 1 H) 8.62 (d, J=5.28 Hz, 1 H).

EXAMPLE 138

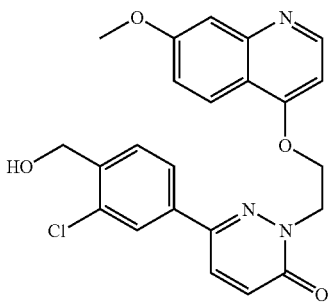

6-(3-Chloro-4-(hydroxymethyl)phenyl)-2-(2-(7-methoxyquinolin-4-yloxy)ethyl)pyridazin-3(2H)-one (1) (3-Chloro-4-(4,4,5,5-tetramethyl-1,3,2-dioxaborolan-2-yl)phenyl)methanol. A suspension of (4-bromo-3-chlorophenyl)methanol (4000 mg, 18060 µmol), bis(pinacolato) diboron (5045 mg, 19866 µmol), dichloro[1,1'bis (diphenylphoshino)ferrocene]palladium(II)dichloromethane adduct (661 mg, 903 µmol), and potassium acetate (2258 µl, 36121 µmol) in dioxane (20 mL) was sparged with argon for 10 minutes then heated to 120° C. for 2 hours in an appropriately seal vial. The reaction was then partitioned between EtOAc (100 mL) and 5% NaHCO$_3$ (50 mL). Organic then dried over MgSO$_4$, concentrate under reduced pressure, and purified on silica (120 g) eluting with 0>70% EtOAc. Product isolated as a viscous colorless oil. $^1$H NMR (400 MHz, CHLOROFORM-d) δ ppm 1.35 (s, 12 H) 1.61 (d, 1 H) 4.80 (d, J=6.02 Hz, 2 H) 7.50 (d, J=7.53 Hz, 1 H) 7.70 (d, J=7.53 Hz, 1 H) 7.78 (s, 1 H).

(2) Suzuki reaction between 6-chloro-2-(2-(7-methoxyquinolin-4-yloxy)ethyl)pyridazin-3(2H)-one and (3-chloro-4-(4,4,5,5-tetramethyl-1,3,2-dioxaborolan-2-yl)phenyl) methanol provided the desired product. MS (ESI pos. ion) m/z: 438 (MH+); calc'd for C$_{23}$H$_{20}$ClN$_3$O$_4$: 437. $^1$H NMR (400 MHz, DMSO-d$_6$) δ ppm 3.87 (s, 3 H) 4.60 (d, J=5.48 Hz, 2 H) 4.68 (s, 4 H) 5.50 (t, J=5.58 Hz, 1 H) 6.95 (d, J=5.28 Hz, 1 H) 7.00 (dd, J=9.10, 2.45 Hz, 1 H) 7.10 (d, J=9.78 Hz, 1 H) 7.27 (d, J=2.15 Hz, 1 H) 7.62 (d, J=8.02 Hz, 1 H) 7.77-7.87 (m, 2H) 7.90 (d, J=9.19 Hz, 1 H) 8.08 (d, J=9.78 Hz, 1 H) 8.62 (d, J=5.28 Hz, 1 H).

EXAMPLE 139

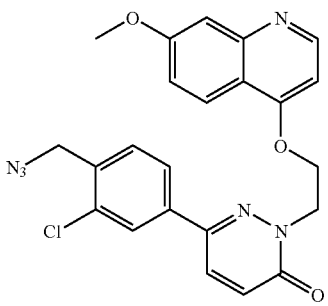

6-(4-(Azidomethyl)-3-chlorophenyl)-2-(2-(7-methoxyquinolin-4-yloxy)ethyl)pyridazin-3(2H)-one To a stirring solution of 6-(3-chloro-4-(hydroxymethyl) phenyl)-2-(2-(7-methoxyquinolin-4-yloxy)ethyl)pyridazin-3(2H)-one (1060 mg, 2421 µmol) and TEA (337 µL, 2421 µmol) in DCM (10 mL) at 0° C. under nitrogen was added methanesulfonyl chloride (187 µL, 2421 µmol) in DCM (1 mL). After 3 hours, the mixture was partitioned between DCM (25 mL) and 5% NaHCO$_3$ (25 mL). The aqueous layer was further extracted with DCM (2×10 mL). The combined organics were dried over MgSO$_4$, then concentrated to a solid. Solid was then dissolved in DMF (5 mL) and sodium azide (787 mg, 12104 µmol) in water (5 mL) was then added. The biphasic solution was then heated to 60° C. overnight. The reaction was then partitioned between DCM (25 mL) and 5% NaHCO$_3$ (25 mL). The aqueous layer was then further extracted with DCM (2×10 mL). The combined organics were then dried over MgSO$_4$, concentrated, and purified on silica (40 g) eluting with 1 to 4% of MeOH/DCM. MS (ESI pos. ion) m/z: 463 (MH+); calc'd for C$_{23}$H$_{19}$ClN$_6$O$_3$: 462.

EXAMPLE 140

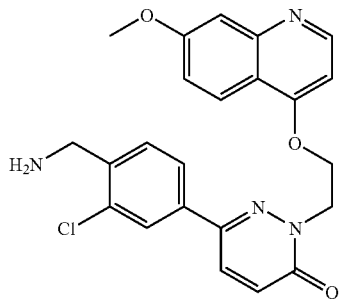

6-(4-(Aminomethyl)-3-chlorophenyl)-2-(2-(7-methoxyquinolin-4-yloxy)ethyl)pyridazin-3(2H)-one To a solution of 6-(4-(azidomethyl)-3-chlorophenyl)-2-(2-(7-methoxyquinolin-4-yloxy)ethyl)pyridazin-3(2H)-one (400 mg, 864 µmol) in THF (8 mL), MeOH (1 mL), and water (1 mL) was added sodium sulfide, nonahydrate (540 mg, 6913 µmol) and stirred overnight at 40° C. The reaction was then partitioned between DCM and 5% NaHCO$_3$. The organic layer was dried over MgSO$_4$, concentrated, then purified on silica (40 g) eluting with 0>6% of NH$_3$ in MeOH (2 M)/DCM. The product was further purified on RP-HPLC eluting with ACN/water (0.1% TFA). Desired fractions concentrated under reduced pressure then residue partitioned between DCM and NaOH (1 M). The organic was then dried over MgSO$_4$ and concentrated under reduced pressure to provide a white solid. MS (ESI pos. ion) m/z: 437 (MH+); calc'd for C$_{23}$H$_{21}$ClN$_4$O$_3$: 436. $^1$H NMR (400 MHz, CHLOROFORM-d) δ ppm 3.91 (s, 3 H) 3.99 (s, 2 H) 4.65 (t, J=5.38 Hz, 2 H) 4.80 (t, J=5.28 Hz, 2 H) 6.67 (d, J=5.48 Hz, 1 H) 6.98-7.09 (m, 2 H) 7.32 (d, J=2.35 Hz, 1 H) 7.48 (d, J=8.02 Hz, 1 H) 7.58 (dd, J=8.02, 1.76 Hz, 1 H) 7.64 (d, J=9.78 Hz, 1 H) 7.79 (d, J=1.76 Hz, 1 H) 8.02 (d, J=9.19 Hz, 1 H) 8.64 (d, J=5.28 Hz, 1 H)

EXAMPLE 141

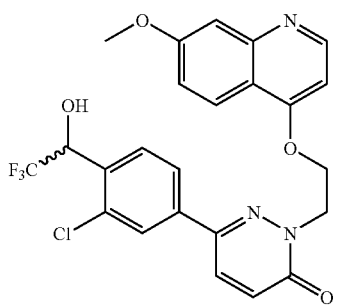

6-(3-chloro-4-(2,2,2-trifluoro-1-hydroxyethyl)phenyl)-2-(2-(7-methoxyquinolin-4-yloxy)ethyl)pyridazin-3(2H)-one (1) 2-chloro-4-(1-(2-(7-methoxyquinolin-4-yloxy)ethyl)-6-oxo-1,6-dihydropyridazin-3-yl)benzaldehyde. To a stirring solution of 6-(3-chloro-4-(hydroxymethyl)phenyl)-2-(2-(7-methoxyquinolin-4-yloxy)ethyl)pyridazin-3(2H)-one (500 mg, 1142 μmol) in DMF (7.5 mL) was added Dess-Martin periodinane (540 mg, 1.27 mmol, 1.1 eq) at 23° C. The reaction solution was stirred for 30 min, then partitioned between DCM (50 mL) and NaHCO₃ (50 mL). The aqueous layer was then further extracted with DCM (2×20 mL). The combined organics were then dried over MgSO₄, concentrated onto dried silica (10 g) and purified on silica (80 g) eluting with 2 to 5% of MeOH/DCM. ¹H NMR (400 MHz, CHLOROFORM-d) δ ppm 3.90 (s, 3 H) 4.67 (t, J=5.18 Hz, 2 H) 4.82 (t, J=5.28 Hz, 2 H) 6.66 (d, J=5.28 Hz, 1 H) 7.00 (dd, J=9.10, 2.45 Hz, 1 H) 7.08 (d, J=9.78 Hz, 1 H) 7.30 (d, J=2.35 Hz, 1 H) 7.64-7.72 (m, 2 H) 7.85 (d, J=1.76 Hz, 1 H) 7.98 (dd, J=8.71, 2.25 Hz, 2 H) 8.64 (d, J=5.28 Hz, 1 H) 10.50 (s, 1 H).

(2) To a stirring solution of 2-chloro-4-(1-(2-(7-methoxyquinolin-4-yloxy)ethyl)-6-oxo-1,6-dihydropyridazin-3-yl)benzaldehyde (370 mg, 849 μmol) and (trifluoromethyl)trimethylsilane (121 μL, 849 μmol) in DME (10 mL) at −50° C. under nitrogen was added solid tetramethylammonium fluoride (79 mg, 849 μmol). The reaction was then removed from cooling bath and slowly warmed to 0° C. The reaction was then partitioned between DCM (100 mL) and 5% NaHCO₃ (50 mL). The organic was dried over MgSO₄, concentrated under reduced pressure, then purified on silica (40 g) eluting with 2 to 3% of MeOH/DCM. Product was isolated as an off white solid. MS (ESI pos. ion) m/z: 506 (MH+); calc'd for C₂₄H₁₉ClF₃N₃O₄: 505.

¹H NMR (400 MHz, CHLOROFORM-d) δ ppm 3.81 (s, 3 H) 4.65 (t, J=5.02 Hz, 2 H) 4.71-4.86 (m, 2 H) 5.68 (q, J=6.53 Hz, 1 H) 6.65 (d, J=5.52 Hz, 1 H) 6.97 (d, J=9.54 Hz, 1 H) 7.05 (d, J=9.54 Hz, 1 H) 7.21 (s, 1 H) 7.62 (d, J=9.54 Hz, 2 H) 7.74 (s, 1 H) 7.84 (d, J=8.03 Hz, 1 H) 7.97 (d, J=9.03 Hz, 1 H) 8.53 (d, J=5.02 Hz, 1H).

EXAMPLE 142

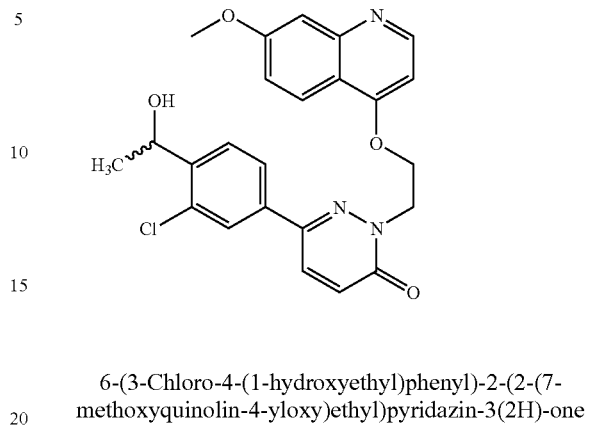

6-(3-Chloro-4-(1-hydroxyethyl)phenyl)-2-(2-(7-methoxyquinolin-4-yloxy)ethyl)pyridazin-3(2H)-one

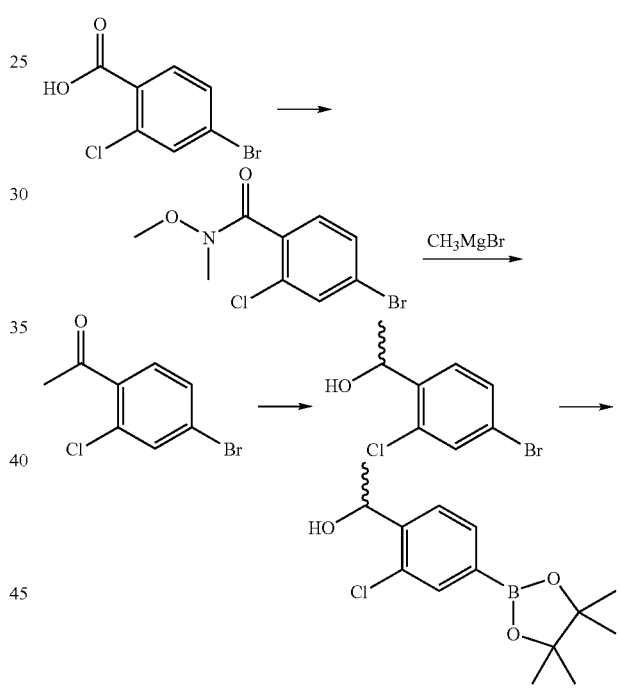

(1) 4-bromo-2-chloro-N-methoxy-N-methylbenzamide. To a stirring solution of 4-bromo-2-chlorobenzoic acid (3.45 g, 15 mmol) and DIEA (7.7 mL, 44 mmol) in DMF (30 mL) was added HATU (6.1 g, 16 mmol) at 23° C. under nitrogen. The darkened suspension was stirred for 1 hour then N,O-dimethylhydroxylamine hydrochloride (2.1 g, 22 mmol) was added. The resulting solution was stirred overnight at 23° C. then partitioned between 2.5% NaHCO₃ (250 mL) and diethyl ether (100 mL). Aqueous further extracted with ether (2×50 mL). The combined ethereal extracts were dried over MgSO₄, then concentrated an amber oil under reduced pressure. MS (ESI pos. ion) m/z: 278/280 (MH+); calc'd for C₉H₉BrClNO₂: 277/279.

(2) 1-(4-Bromo-2-chlorophenyl)ethanone. To a stirring solution of 4-bromo-2-chloro-N-methoxy-N-methylbenzamide (890 mg, 3195 μmol) in THF (10 mL) at −5° C. under nitrogen was slowly added methylmagnesium bromide in diethyl ether (3.0 M, 2.6 mL, 7.6 mmol). Cooling bath was removed and the reaction was allowed to warm to 23° C. over a 2 hour period. The reaction was then quenched with sat NH₄Cl (10 mL) and resulting white cake washed repeatedly with diethyl ether. The combined organics were then washed with water and sat. NaCl then passed through a plug of silica (10 g). The product was isolated as a colorless oil. MS (ESI pos. ion) m/z: 233/235 (MH+); calc'd for $C_8H_6BrClO$: 232/234.

(3) 1-(4-Bromo-2-chlorophenyl)ethanol. To a stirring solution of 1-(4-bromo-2-chlorophenyl)ethanone (700 mg, 2998 µmol) in THF (20 mL) was added sodium borohydride (340 mg, 8994 µmol) and methanol (5 mL). The reaction suspension was stirred overnight at 30° C. then partitioned between EtOAc (50 mL) and sat NH₄Cl (25 mL). The aqueous layer was further extracted with EtOAc (2×25 mL) and the combined organics dried over MgSO₄, concentrated, then purified on silica (40 g) eluting with 10>20% EtOAc/hexanes. Product was isolated as a colorless oil. ¹H NMR (400 MHz, CHLOROFORM-d) δ ppm 1.46 (d, J=6.46 Hz, 3H) 1.98-2.05 (m, 1 H) 5.22 (q, J=6.33 Hz, 1 H) 7.32-7.55 (m, 3 H).

(4) 1-(2-Chloro-4-(4,4,5,5-tetramethyl-1,3,2-dioxaborolan-2-yl)phenyl)ethanol. To a suspension of 1-(4-bromo-2-chlorophenyl)ethanol (600 mg, 2548 µmol), bis(pinacolato) diboron (712 mg, 2802 µmol), dichloro[1,1'bis(diphenylphoshino)ferrocene]palladium(II) dichloromethane adduct (93.2 mg, 127 µmol), potassium acetate (319 µl, 5095 µmol) in dioxane (5 mL) was sparged with argon for 5 min then heated to 120° C. in an appropriately sealed vial for 2 hours. The reaction was then partitioned between EtOAc (25 mL) and 5% NaHCO₃ (25 mL). The separated aqueous layer was further washed with EtOAc (2×20 mL). The combined organics were then dried with a combination of sat NH₄Cl and MgSO₄. After concentration of the organic under reduced pressure the product was then purified on silica (80 g) eluting with 10>35% EtOAc/Hex and isolated as a colorless oil. ¹H NMR (400 MHz, CHLOROFORM-d) δ ppm 1.34 (s, 12 H) 1.48 (d, J=6.26 Hz, 3 H) 1.74 (br. s., 1 H) 5.29 (q, J=6.33 Hz, 1 H) 7.59 (d, J=7.63 Hz, 1 H) 7.68-7.79 (m, 2 H).

(5) 6-(3-Chloro-4-(1-hydroxyethyl)phenyl)-2-(2-(7-methoxyquinolin-4-yloxy)ethyl)pyridazin-3(2H)-one. A suspension of 6-chloro-2-(2-(7-methoxyquinolin-4-yloxy)ethyl)pyridazin-3(2H)-one (130 mg, 392 µmol), 1-(2-chloro-4-(4,4,5,5-tetramethyl-1,3,2-dioxaborolan-2-yl)phenyl)ethanol (166 mg, 588 µmol), dichloro[1,1'bis(diphenylphoshino)ferrocene]palladium(II)dichloromethane adduct (29 mg, 39 µmol), cesium carbonate (511 mg, 1567 µmol) in dioxane (2 mL) and water (0.4 mL) was sparged with argon for 5 minutes then heated to 100° C. for 4 hours. The reaction was then partitioned between 9:1 CHCl₃/IPA (25 mL) and NaOH (1 M, 10 mL). The separated aqueous layer was further extracted with 9:1 CHCl₃/IPA (25 mL) and combined organics dried over MgSO₄, concentrated, then purified on silica (40 g) eluting with 1 to 4% of MeOH/DCM. The resulting material was then further purified on prep-HPLC (eluent: water/ACN (0.1% TFA). After solvents were removed the residue was dissolved in DCM (2 mL) and MeOH (2 mL) then stirred with Si-Carbonate (1 g; 0.77 mmol/g) for 30 minutes. Solids were then removed by filtration and the solvents removed under reduced pressure. Product was isolated as a white solid from ACN. MS (ESI pos. ion) m/z: 452 (MH+); calc'd for $C_{24}H_{22}ClN_3O_4$: 451. ¹H NMR (400 MHz, DMSO-d₆) δ ppm 1.33 (d, J=6.02 Hz, 3 H) 3.86 (s, 3 H) 4.67 (s, 4 H) 4.97-5.08 (m, 1 H) 5.45 (d, J=4.02 Hz, 1 H) 6.95 (d, J=5.52 Hz, 1 H) 7.00 (dd, J=9.03, 2.51 Hz, 1 H) 7.10 (d, J=10.04 Hz, 1 H) 7.27 (d, J=2.01 Hz, 1 H) 7.67 (d, J=8.03 Hz, 1 H) 7.77-7.86 (m, 2 H) 7.89 (d, J=9.03 Hz, 1 H) 8.07 (d, J=9.54 Hz, 1 H) 8.62 (d, J=5.02 Hz, 1 H).

EXAMPLE 143

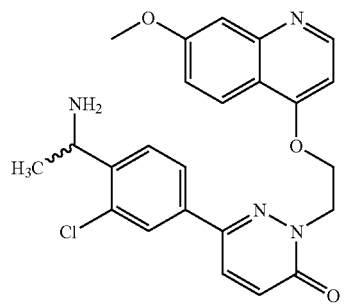

6-(4-(1-Aminoethyl)-3-chlorophenyl)-2-(2-(7-methoxyquinolin-4-yloxy)ethyl)pyridazin-3(2H)-one

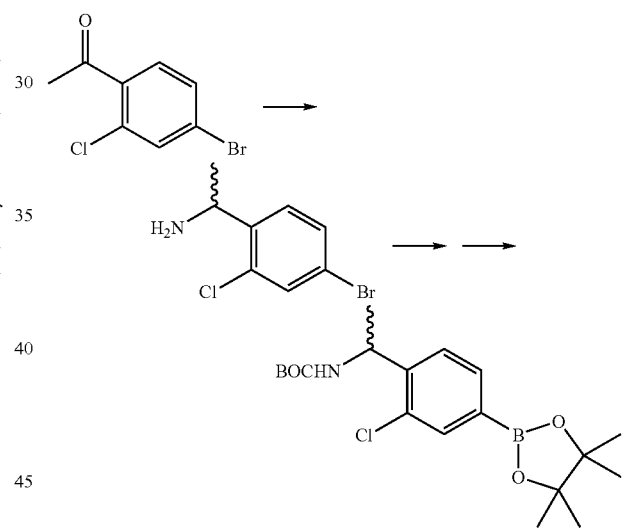

(1) 1-(4-Bromo-2-chlorophenyl)ethanamine. A solution of 1-(4-bromo-2-chlorophenyl)ethanone (2.430 g, 10 mmol), ammonia (2.0 M in MeOH; 26 ml, 52 mmol) and titanium (iv) isopropoxide (6 ml, 21 mmol) was stirred for 16 hours in an appropriately sealed vessel. The reaction was then added to a freshly prepared suspension of sodium borohydride (4 g, 104 mmol) in MeOH (20 mL). The exothermic reaction was maintained at 45° C. with an external heating bath for 45 minutes. Water (10 mL) was then added to reaction and stirred for an additional 10 minutes. The resulting white solid was then removed via filtration through Celite, and the filtrate reduced in volume under reduced pressure. The resulting suspension then partitioned between 9:1 CHCl₃/IPA (30 mL) and 1 M NaOH (10 mL). The aqueous layer was further extracted with 9:1 CHCl₃/IPA (2×10 mL). The combined organics then dried over MgSO₄, concentrated, and purified on silica (80 g) eluting with 0>5% 2 M NH₃ in MeOH/DCM isolating product as a colorless oil (45% yield). MS (ESI pos. ion) m/z: 234/236 (MH+); calc'd for $C_8H_9BrClN$: 233/235. ¹H NMR (400

MHz, CHLOROFORM-d) δ ppm 1.36 (d, J=6.65 Hz, 3 H) 1.55 (br. s., 2 H) 4.50 (q, J=6.65 Hz, 1 H) 7.37-7.47 (m, 2 H) 7.49 (d, J=1.96 Hz, 1 H).

(2) tert-Butyl 1-(2-chloro-4-(4,4,5,5-tetramethyl-1,3,2-dioxaborolan-2-yl)phenyl)ethylcarbamate. To a stirring solution of 1-(4-bromo-2-chlorophenyl)ethanamine (950 mg, 4051 μmol) in DCM (5 mL) was added BOC-anhydride (1 M in THF; 4861 μl, 4861 μmol) and reaction stirred for 18 hours at 23° C. Ethanolamine (0.25 mL) then added to the reaction and stirred for an additional 5 minutes. The reaction was then partitioned between diethyl ether (50 mL) and 5% $NaHCO_3$ (25 mL). The separated organic layer was then dried over $MgSO_4$, concentrated, and purified on silica (80 g) eluting with 0>20% EtOAc/hexanes. A suspension of tert-butyl 1-(2-chloro-4-bromo ethylcarbamate, bis(pinacolato)diboron (1132 mg, 4456 μmol), dichloro[1,1'bis(diphenylphoshino) ferrocene]palladium(ii)dichloromethane adduct (148 mg, 203 μmol), and potassium acetate (795 mg, 8102 mmol) in 1,4-dioxane (8 mL) was sparged with argon for 5 minutes then heated to 120° C. in an appropriately sealed vessel for 2 hours. The reaction was then partitioned between 9:1 $CHCl_3$/ IPA (50 mL) and sat $NH_4Cl$ (20 mL). The organic layer was then dried over $MgSO_4$, concentrated, and product purified on silica (80 g) eluting with 10>15% of EtOAc/Hex. Product isolated as a white foam. $^1$H NMR (400 MHz, CHLOROFORM-d) δ ppm 1.26 (s, 9 H) 1.33 (s, 12 H) 5.12 (br. s., 1 H) 7.33 (d, J=7.63 Hz, 1 H) 7.66 (dd, J=7.73, 0.88 Hz, 1 H) 7.77 (s, 1 H).

(3) tert-Butyl 1-(2-Chloro-4-(1-(2-(7-methoxyquinolin-4-yloxy)ethyl)-6-oxo-1,6-dihydropyridazin-3-yl)phenyl)ethylcarbamate. A suspension of tert-butyl 1-(2-chloro-4-(4,4,5,5-tetramethyl-1,3,2-dioxaborolan-2-yl)phenyl) ethylcarbamate (216 mg, 565 μmol), 6-chloro-2-(2-(7-methoxyquinolin-4-yloxy)ethyl)pyridazin-3(2H)-one (150 mg, 452 μmol), dichloro[1,1'bis(diphenylphoshino)ferrocene]palladium(II)dichloromethane adduct (33.1 mg, 45.2 μmol), cesium carbonate (589 mg, 1809 μmol) in 1,4-dioxane (2.5 mL) and water (0.25 mL) was sparged with argon for 5 minutes then heated to 100° C. with stirring for 4 hours. The reaction was then partitioned between 9:1 $CHCl_3$/IPA (50 mL) and 1 M NaOH (10 mL). The organic layer was then dried over $MgSO_4$, concentrated, and purified on silica (40 g) eluting with 2 to 4% of MeOH/DCM. Product was isolated as a colorless film. $^1$H NMR (400 MHz, CHLOROFORM-d) δ ppm 1.32-1.47 (m, 12 H) 3.91 (s, 3 H) 4.64 (t, J=5.27 Hz, 2 H) 4.80 (t, J=5.27 Hz, 2 H) 5.13 (br. s., 1 H) 6.66 (d, J=5.02 Hz, 1 H) 6.99-7.07 (m, 2 H) 7.32 (d, J=2.51 Hz, 1 H) 7.42 (d, J=8.03 Hz, 1 H) 7.60 (dd, J=16.81, 8.78 Hz, 2 H) 7.76 (s, 1 H) 8.02 (d, J=9.03 Hz, 1 H) 8.64 (d, J=5.02 Hz, 1 H).

(4) 6-(4-(1-Aminoethyl)-3-chlorophenyl)-2-(2-(7-methoxyquinolin-4-yloxy)ethyl)pyridazin-3(2H)-one. A solution of tert-butyl 1-(2-chloro-4-(1-(2-(7-methoxyquinolin-4-yloxy)ethyl)-6-oxo-1,6-dihydropyridazin-3-yl)phenyl)ethylcarbamate (140 mg, 254 μmol) in DCM (2 mL) and TFA (2 mL) was stirred for 30 minutes at 23° C. The solvents were then removed under reduced pressure and the resulting residue partitioned between 9:1 $CHCl_3$/IPA (25 mL) and 1 M NaOH (10 mL). The separated aqueous layer was then further extracted with 9:1 $CHCl_3$/IPA (2×10 mL). The combined organics were then dried over $MgSO_4$, concentrated, and purified on silica (12 g) eluting with 0>5% of 2M $NH_3$ in MeOH/DCM. Product was isolated as a white solid from ACN. MS (ESI pos. ion) m/z: 451 (MH+); calc'd for $C_{24}H_{22}ClN_4O_3$: 450. $^1$H NMR (400 MHz, DMSO-$d_6$) δ ppm 1.24 (d, J=6.53 Hz, 3 H) 1.97 (br. s., 2 H) 3.86 (s, 3 H) 4.35 (q, J=6.53 Hz, 1 H) 4.67 (s, 4 H) 6.94 (d, J=5.02 Hz, 1 H) 6.97-7.03 (m, 1H) 7.09 (d, J=10.04 Hz, 1 H) 7.27 (d, J=2.51 Hz, 1 H) 7.72-7.83 (m, 3 H) 7.89 (d, J=9.03 Hz, 1 H) 8.06 (d, J=9.54 Hz, 1 H) 8.62 (d, J=5.02 Hz, 1 H).

EXAMPLE 144

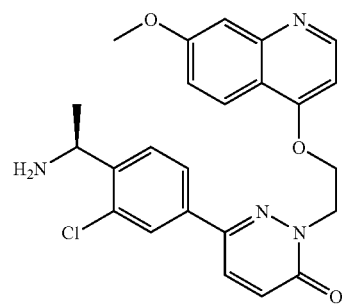

(S)-6-(4-(1-Aminoethyl)-3-chlorophenyl)-2-(2-(7-methoxyquinolin-4-yloxy)ethyl)pyridazin-3(2H)-one Chiral separation from the racemic using a Sepapak-2 (25 cm; 5 um, 6 ml/min) eluting with SPC and 55% methanol (0.2% diethylamine). There was an arbitrary assignment of chirality. MS (ESI pos. ion) m/z: 451 (MH+); calc'd for $C_{24}H_{23}ClN_4O_3$: 450. $^1$H NMR (400 MHz, -$d_6$DMSO) □ ppm 1.24 (d, J=6.46 Hz, 3H) 3.86 (s, 1 H) 4.36 (q, J=6.59 Hz, 1 H) 4.66 (br. s., 4 H) 6.94 (d, J=5.28 Hz, 1H) 6.99 (dd, J=9.19, 2.54 Hz, 1 H) 7.09 (d, J=9.78 Hz, 1 H) 7.27 (d, J=2.54 Hz, 1H) 7.72-7.82 (m, 3 H) 7.89 (d, J=9.19 Hz, 1 H) 8.05 (d, J=9.78 Hz, 1 H) 8.61 (d, J=5.28 Hz, 1 H)

EXAMPLE 145

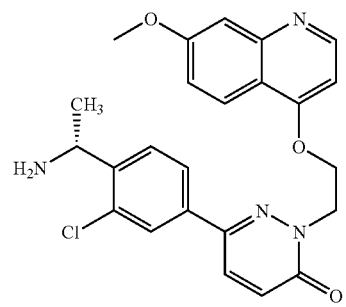

(R)-6-(4-(1-Aminoethyl)-3-chlorophenyl)-2-(2-(7-methoxyquinolin-4-yloxy)ethyl)pyridazin-3(2H)-one Chiral separation from racemic using a Sepapak-2 (25 cm; 5 um, 6 ml/min) eluting with SPC and 55% methanol (0.2% diethylamine). There was an arbitrary assignment of chirality. MS (ESI pos. ion) m/z: 451 (MH+); calc'd for $C_{24}H_{23}ClN_4O_3$: 450. $^1$H NMR (400 MHz, DMSO-$d_6$) δ ppm 1.24 (d, J=6.46 Hz, 3H) 3.31 (s, 2 H) 3.86 (s, 3 H) 4.36 (q, J=6.46 Hz, 1 H) 4.67 (s, 4 H) 6.95 (d, J=5.28 Hz, 1 H) 7.00 (dd, J=9.19, 2.54 Hz, 1 H) 7.09 (d, J=9.78 Hz, 1 H) 7.27 (d, J=2.35 Hz, 1 H) 7.72-7.84 (m, 3 H) 7.89 (d, J=9.19 Hz, 1 H) 8.07 (d, J=9.78 Hz, 1H) 8.62 (d, J=5.28 Hz, 1 H).

EXAMPLE 146

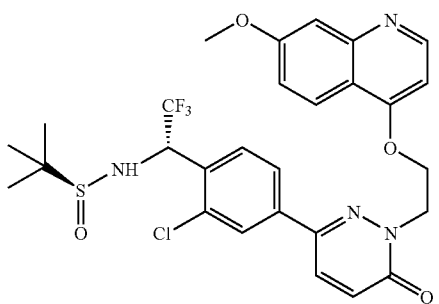

(R)-N-((S)-1-(2-Chloro-4-(1-(2-(7-methoxyquinolin-4-yloxy)ethyl)-6-oxo-1,6-dihydropyridazin-3-yl)phenyl)-2,2,2-trifluoroethyl)-2-methylpropane-2-sulfinamide

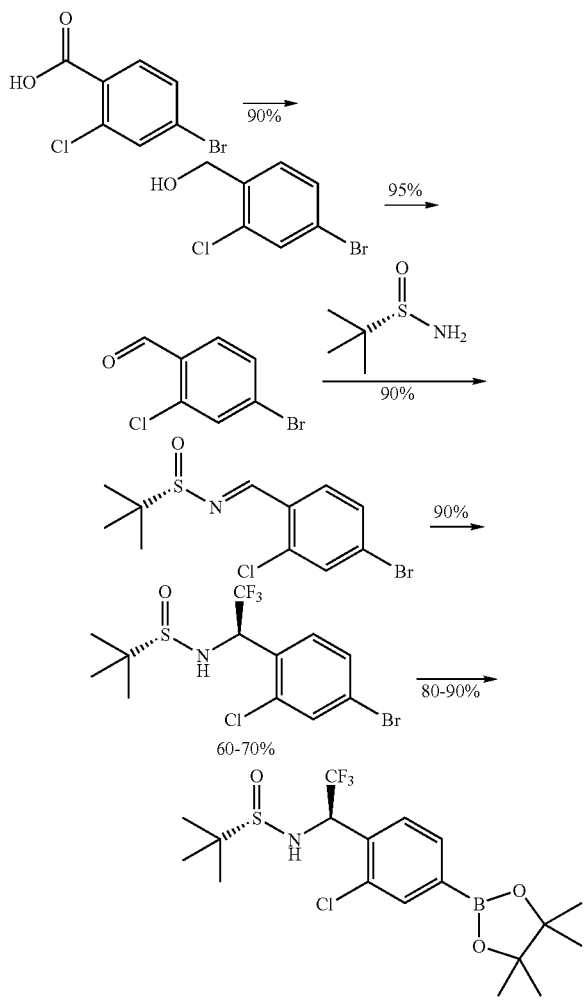

(1) (R)-N-(4-Bromo-2-chlorobenzylidene)-2-methylpropane-2-sulfinamide. A suspension of 4-bromo-2-chlorobenzaldehyde (1080 mg, 4921 μmol), (R)-2-methylpropane-2-sulfinamide (1193 mg, 9842 μmol), copper(II) sulfate (654.0 μL, 14763 μmol) in DCM (10 mL) was heated to 37° C. for 3 days. The reaction was filtered through a pad of Celite, and the solid washed repeatedly with DCM. The filtrate was then concentrated under reduced pressure and purified on silica (80 g) eluting with 0>30% of EtOAc/Hex. The product was isolated as a white solid after standing neat for 18 h (97% yield). MS (ESI pos. ion) m/z: 322/324 (MH+); calc'd for $C_{11}H_{13}BrClNOS$: 321/323. $^1$H NMR (400 MHz, CHLOROFORM-d) δ ppm 1.27 (s, 9 H) 7.49 (d, J=8.53 Hz, 1 H) 7.65 (s, 1 H) 7.93 (d, J=8.53 Hz, 1 H) 8.97 (s, 1 H).

(2) (R)-N-((S)-1-(4-Bromo-2-chlorophenyl)-2,2,2-trifluoroethyl)-2-methylpropane-2-sulfamide. (Org. Lett., 2005, 7, 2193-2196; Angew. Chem. Int. Ed. 2001, 40, p 589-590) To a stirring solution of (R,Z)-N-(4-bromo-2-chlorobenzylidene)-2-methylpropane-2-sulfinamide (1370 mg, 4246 μmol) and (trifluoromethyl)trimethylsilane (943 μl, 6369 μmol) in DMF (5 mL) was added 1,3-bis(1-adamantyl)imidazol-2-ylidene (143 mg, 425 mmol). Reaction was stirred at 35° C. for 18 hours. The reaction was then quenched with sat NH$_4$Cl (10 mL), and reaction partitioned between EtOAc (40 mL) and 5% NaHCO$_3$ (10 mL). The organic layer was dried over MgSO$_4$, concentrated under reduced pressure, then purified on silica (80 g) eluting with 20>30% EtOAc/Hex. Product was isolated as a white solid (60% yield). $^1$H NMR (400 MHz, CHLOROFORM-d) δ ppm 1.24 (s, 10H) 3.72 (d, J=7.82 Hz, 1 H) 5.37-5.48 (m, 1 H) 7.33 (d, J=8.41 Hz, 1 H) 7.48 (dd, J=8.41, 1.96 Hz, 1 H) 7.64 (d, J=1.96 Hz, 1 H). $^{19}$F NMR (377 MHz, CHLOROFORM-d) δ ppm −73.79 (d, J=6.87 Hz, 3 F) suggesting 94% de purity. $^{13}$C NMR (101 MHz, CHLOROFORM-d) δ ppm 22.29, 57.12, 57.28, 57.43, 60.41, 124.14, 129.49, 130.98, 133.05, 135.28.

(3) (R)-N-((S)-1-(2-Chloro-4-(4,4,5,5-tetramethyl-1,3,2-dioxaborolan-2-yl)phenyl)-2,2,2-trifluoroethyl)-2-methylpropane-2-sulfinamide. A suspension of (R)-N-((S)-1-(4-bromo-2-chlorophenyl)-2,2,2-trifluoroethyl)-2-methylpropane-2-sulfinamide (950 mg, 2419 μmol), bis(pinacolato)diboron (676 mg, 2661 μmol), dichloro[1,1'bis(diphenylphoshino)ferrocene]palladium(ii)dichloromethane adduct (88.5 mg, 121 μmol), and potassium acetate (475 mg, 4839 μmol) in 1,4-dioxane (6 mL) was sparged with argon for 5 minutes. The reaction was then appropriately sealed and heated to 120° C. with stirring for 1 hour. The reaction was then partitioned between EtOAc (25 mL) and 5% NaHCO$_3$ (10 mL). The organic layer was then dried over MgSO$_4$, concentrated, then purified on silica (120 g) eluting with 10>20% of EtOAc/hexanes. The product was isolated as a waxy white solid (83% yield). MS (ESI pos. ion) m/z: 440 (MH+); calc'd for $C_{18}H_{26}BClF_3NO_3S$: 439. $^1$H NMR (400 MHz, CHLOROFORM-d) δ ppm 1.24 (s, 12 H) 1.33 (s, 9 H) 3.79 (d, J=7.03 Hz, 1 H) 5.44-5.56 (m, 1 H) 7.45 (d, J=7.53 Hz, 1 H) 7.74 (d, J=8.03 Hz, 1 H) 7.88 (s, 1 H).

(4) (R)—N—((S)-1-(2-Chloro-4-(1-(2-(7-methoxyquinolin-4-yloxy)ethyl)-6-oxo-1,6-dihydropyridazin-3-yl)phenyl)-2,2,2-trifluoroethyl)-2-methylpropane-2-sulfinamide.

A suspension of 6-chloro-2-(2-(7-methoxyquinolin-4-yloxy)ethyl)pyridazin-3(2H)-one (255 mg, 769 μmol), (R)—N—((S)-1-(2-chloro-4-(4,4,5,5-tetramethyl-1,3,2-dioxaborolan-2-yl)phenyl)-2,2,2-trifluoroethyl)-2-methylpropane-2-sulfinamide (260 mg, 591 μmol), dichloro[1,1'bis(diphenylphoshino)ferrocene]palladium(II) dichloromethane adduct (43.3 mg, 59.1 μmol), cesium carbonate (771 mg, 2365 μmol) in 1,4-dioxane (3 mL) and water (0.75 mL) was sparged with argon for 5 minutes then heated to 90° C. with stirring for 2 hours The reaction was then partitioned between 9:1 CHCl$_3$/IPA (25 mL) and 5% NaHCO$_3$ (10 mL). The organic layer was then dried over MgSO$_4$, concentrated, then purified on silica (40 g) eluting with 2 to 3% MeOH/DCM. Product was isolated as an off white solid from ACN. MS (ESI pos. ion) m/z: 609 (MH+); calc'd for C$_{28}$H$_{28}$ClF$_3$N$_4$O$_4$S: 608. $^1$H NMR (400 MHz, CHLOROFORM-d) δ ppm 1.27 (s, 9 H) 3.87 (d, J=8.02 Hz, 1 H) 3.91 (s, 3 H) 4.66 (t, J=5.38 Hz, 2 H) 4.80 (t, J=5.28 Hz, 2 H) 5.46-5.56 (m, 1 H) 6.68 (d, J=5.28 Hz, 1 H) 7.00-7.09 (m, 2 H) 7.34 (d, J=2.35 Hz, 1 H) 7.52 (d, J=8.22 Hz, 1 H) 7.59-7.66 (m, 2 H) 7.84 (d, J=1.96 Hz, 1 H) 7.99 (d, J=9.19 Hz, 1 H) 8.64 (d, J=5.28 Hz, 1 H). $^{19}$F NMR (377 MHz, CHLOROFORM-d) δ ppm −73.59 (d, J=8.01 Hz, 3 F).

EXAMPLE 147

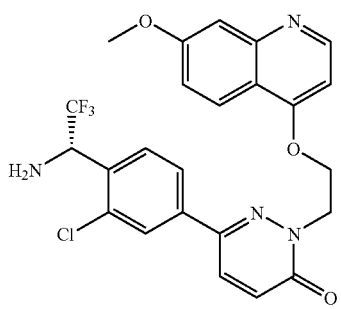

(S)-6-(4-(1-Amino-2,2,2-trifluoroethyl)-3-chlorophenyl)-2-(2-(7-methoxyquinolin-4-yloxy)ethyl)pyridazin-3(2H)-one A solution of (R)—N—((S)-1-(2-chloro-4-(1-(2-(7-methoxyquinolin-4-yloxy)ethyl)-6-oxo-1,6-dihydropyridazin-3-yl)phenyl)-2,2,2-trifluoroethyl)-2-methylpropane-2-sulfinamide (170 mg, 279 μmol) in MeOH (4 mL) was stirred with 5 N HCl (4 mL) at 23° C. for 18 hours. The solvents were then largely removed under reduced pressure and residue partitioned between 9:1 CHCl$_3$/IPA (20 mL) and aqueous pH adjusted to 14 with NaOH (5 M, 4 mL). The aqueous layer was further extracted with 9:1 CHCl$_3$/IPA (2×10 mL). The combined organics were then dried over MgSO$_4$, concentrated, and purified on silica (12 g) eluting with 0>5% NH$_3$ in MeOH (2 M)/DCM. Product was isolated as a white fluffy solid from lyophilized 50% ACN/water. MS (ESI pos. ion) m/z: 506 (MH+); calc'd for C$_{24}$H$_{20}$ClF$_3$N$_4$O$_3$: 505. $^1$H NMR (400 MHz, DMSO-d$_6$) δ ppm 3.93 (s, 3 H) 4.74 (t, J=4.27 Hz, 2 H) 4.92 (t, J=4.52 Hz, 2 H) 5.18 (q, J=7.36 Hz, 1 H) 7.14 (d, J=10.04 Hz, 1 H) 7.21-7.28 (m, 1 H) 7.40 (d, J=6.53 Hz, 1 H) 7.49 (s, 1 H) 7.87-7.96 (m, 3 H) 8.05 (d, J=9.03 Hz, 1 H) 8.14 (d, J=10.04 Hz, 1 H) 8.97 (d, J=6.02 Hz, 1 H). $^{13}$C NMR (101 MHz, DMSO-d$_6$) δ ppm 48.21, 54.49, 66.32, 99.81, 113.27, 118.38, 122.46, 123.30, 124.68, 128.27, 128.39, 129.30, 132.34, 134.84, 140.24, 145.85, 157.66, 161.35 $^{19}$F NMR (376 MHz, DMSO-d$_6$) δ ppm −73.63 (s, 3 F).

EXAMPLE 148

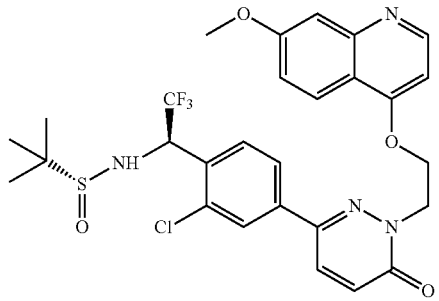

(R)—N—((R)-1-(2-Chloro-4-(1-(2-(7-methoxyquinolin-4-yloxy)ethyl)-6-oxo-1,6-dihydropyridazin-3-yl)phenyl)-2,2,2-trifluoroethyl)-2-methylpropane-2-sulfonamide MS (ESI pos. ion) m/z: 609 (MH+); calc'd for C$_{28}$H$_{28}$ClF$_3$N$_4$O$_4$S: 608. $^1$H NMR (400 MHz, CHLOROFORM-d) δ ppm 1.27 (s, 9 H) 3.86 (d, J=8.02 Hz, 1 H) 3.91 (s, 3 H) 4.67 (t, J=5.28 Hz, 2 H) 4.80 (t, J=5.38 Hz, 2 H) 5.46-5.55 (m, 1 H) 6.68 (d, J=5.28 Hz, 1 H) 7.01-7.08 (m, 2 H) 7.35 (d, J=1.96 Hz, 1 H) 7.50-7.54 (m, 1 H) 7.59-7.64 (m, 2 H) 7.84 (d, J=1.76 Hz, 1 H) 8.00 (d, J=9.19 Hz, 1 H) 8.64 (d, J=5.48 Hz, 1 H). $^{19}$F NMR (377 MHz, CHLOROFORM-d) δ ppm −73.59 (d, J=6.87 Hz, 3 F).

EXAMPLE 149

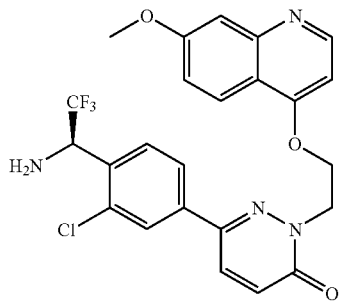

(R)-6-(4-(1-Amino-2,2,2-trifluoroethyl)-3-chlorophenyl)-2-(2-(7-methoxyquinolin-4-yloxy)ethyl)pyridazin-3(2H)-one MS (ESI pos. ion) m/z: 504 (MH+); calc'd for C$_{24}$H$_{20}$ClF$_3$N$_4$O$_3$: 505. $^1$H NMR (400 MHz, DMSO-d$_6$) δ ppm 3.94 (s, 3 H) 4.74 (t, J=4.79 Hz, 2 H) 4.93 (t, J=4.79 Hz, 2 H) 5.20 (q, J=7.43 Hz, 1 H) 7.14 (d, J=9.78 Hz, 1 H) 7.25 (dd, J=9.19, 2.35 Hz, 1 H) 7.40 (d, J=6.46 Hz, 1 H) 7.51 (d, J=2.35 Hz, 1 H) 7.88-7.96 (m, 3 H) 8.05 (d, J=9.19 Hz, 1 H) 8.14 (d, J=9.78 Hz, 1 H) 8.98 (d, J=6.46 Hz, 1 H). $^{19}$F NMR (377 MHz, DMSO-d$_6$) δ ppm −73.53 (s, 3F). $^{13}$C NMR (101 MHz, DMSO-d$_6$) δ ppm 49.65, 55.96, 67.83, 101.30, 114.72, 119.89, 123.95, 124.77, 126.15, 129.73, 129.88, 130.75, 133.82, 136.35, 141.67, 147.15, 159.11, 162.86, 165.65.

Although the pharmacological properties of the compounds of Formulas I, IA, IB, IC, ID, II, IIA, III, IV and V vary with structural change, in general, activity possessed by compounds of Formulas I, IA, IB, IC, ID, II, IIA, III, IV and V may be demonstrated in vivo. The pharmacological properties of the compounds of this invention may be confirmed by a number of pharmacological in vitro assays, such as those described below. The compounds exemplified herein have been tested in pharmacological assays and exhibit inhibition of c-Met kinase at doses less than 20 μM.

Biological Testing

The efficacy of the compounds of the invention as inhibitors of HGF related activity is demonstrated as follows.

c-Met Receptor Assay

Cloning, Expression and Purification of c-Met Kinase Domain

A PCR product covering residues 1058-1365 of c-Met (c-Met kinase domain) is generated as described in WO 06/116,713 the entirety of which is incorporated herein by reference.

Alternative Purification of Human GST-cMET from Baculovirus Cells

Baculovirus cells are broken in 5× (volume/weight) of Lysis Buffer (50 mM HEPES, pH 8.0, 0.25 M NaCl, 5 mM mercaptoethanol, 10% glycerol plus Complete Protease Inhibitors (Roche #10019600), 1 tablet per 50 mL buffer). The lysed cell suspension is centrifuged at 100,000×g (29,300 rpm) in a Beckman ultracentrifuge Ti45 rotor for 1 h. The supernatant is incubated with 10 ml of Glutathione Sepharose 4B from Amersham Biosciences (#27-4574-01). Incubation is carried out overnight in a cold room (approximately 8° C.). The resin and supernatant is poured into an appropriately sized disposable column and the flow through supernatant was collected. The resin is washed with 10 column volumes (100 mL) of Lysis Buffer. The GST-cMET is eluted with 45 mL of 10 mM Glutathione (Sigma #G-4251) in Lysis Buffer. The elution is collected as 15 mL fractions. Aliquots of the elution fractions are run on SDS PAGE (12% Tris Glycine gel, Invitrogen, #EC6005BOX). The gel is stained with 0.25% Coomassie Blue stain. Fractions with GST-cMET are concentrated with a Vivaspin 20 mL Concentrator (#VS2002; 10,00 MW cutoff) to a final volume less than 2.0 ml. The concentrated GST-cMET solution is applied to a Superdex 75 16/60 column (Amersham Biosciences #17-1068-01) equilibrated with 25 mM Tris, pH 7.5, 100 mM NaCl, 10 mM mercaptoethanol, 10% glycerol. The GST-cMET is eluted with an isocratic run of the above buffer, with the eluent collected in 1.0 mL fractions. Fractions with significant $OD_{280}$ readings are run on another 12% Tris Glycine gel. The peak tubes with GST-cMET are pooled and the $OD_{280}$ is read with the column buffer listed above as the blank buffer.

Phosphorylation of the purified GST-cMET is performed by incubating the protein for 3 h at RT with the following:

| | Final concentration |
|---|---|
| a) 100 mM ATP (Sigma #A7699) | 25 mM |
| b) 1.0 M $MgCl_2$ (Sigma #M-0250) | 100 mM |
| c) 200 mM Sodium Orthovanadate (Sigma #S-6508) | 15 mM |
| d) 1.0 M Tris-HCl, pH 7.00 (in house) | 50 mM |
| e) $H_2O$ | |
| f) GST-cMET | 0.2-0.5 mg/mL |

After incubation, the solution is concentrated in a Vivaspin 20 ml Concentrator to a volume less than 2.00 ml. The solution is applied to the same Superdex 75 16/60 column used above after re-equilibration. The GST-cMET is eluted as described above. The elution fractions corresponding to the first eluted peak on the chromatogram are run on a 12% Tris Glycine gel, as above, to identify the fractions with GST-cMET. Fractions are pooled and the $OD_{280}$ is read with the column buffer used as the blank.

A Kinase reaction Buffer is prepared as follows:

| | | | Per 1 L |
|---|---|---|---|
| 60 mM HEPES $p$H 7.4 | 1 M stock | 16.7 X | 60 mL |
| 50 mM NaCl | 5 M stock | 100 X | 10 mL |
| 20 mM $MgCl_2$ | 1 M stock | 50 X | 20 mL |
| 5 mM $MnCl_2$ | 1 M stock | 200 X | 5 mL |

When the assay is carried out, freshly add:

| 2 mM DTT | 1 M stock | 500 X |
|---|---|---|
| 0.05% BSA | 5% stock | 100 X |
| 0.1 mM $Na_3OV_4$ | 0.1 M stock | 1000 X |

The HTRF buffer contains:
50 mM Tris-HCl ($p$H 7.5), 100 mM NaCl, 0.1% BSA, 0.05% Tween 20.5 mM EDTA Fresh add SA-APC (PJ25S Phycolink Streptavidin-Allophycocyanin Conjugate, Prozyme Inc.) and Eu-PT66 (Eu-W1024 labeled anti-phosphorotyrosine antibody PT66, AD0069, Lot 168465, Perkin-Elmer Inc.) to reach the final concentration:
0.1 μM final Eu-PT66
11 nM final SA-APC Methods:
1. Dilute GST-cMet (P) enzyme in kinase buffer as follows:
Prepare 8 nM GST-cMet (P) working solution (7.32 μM to 8 nM, 915×, 10 μL to 9.15 mL). In a 96 well clear plate [Costar #3365] add 100 μL in eleven columns, in one column add 100 μL kinase reaction buffer alone.

2. Assay plate preparation:
Use Biomek FX to transfer 10 μL 8 nM GST-cMet (P) enzyme, 48.4 μL kinase reaction buffer, 1.6 μL compound (in DMSO) (Start concentration at 10 mM, 1 mM and 0.1 mM, sequential dilution 1:3 to reach 10 test points) in a 96 well costar clear plate [Costar #3365], mix several times. Then incubate the plate at RT for 30 min.

3. Prepare Gastrin and ATP working solution in kinase reaction buffer as follows:
Prepare 4 μM Gastrin and 16 μM ATP working solution

| | | Per 10 mL |
|---|---|---|
| Gastrin 4 μM stock | (500 μM to 4 μM, 125 X) | 80 μL |
| ATP 16 μM stock | (1000 μM to 16 μM, 62.5 X) | 160 μL |

Use Biomek FX to add 20 μl ATP and Gastrin working solution to the assay plate to start reaction, incubate the plate at RT for 1 h.

4. Transfer 5 μL reaction product at the end of 1 h into 80 μL HTRF buffer in black plate [Costar #3356], read on Discover after 30 min incubation.

Assay Condition Summary:

| | |
|---|---|
| $K_M$ ATP* | 6 μM |
| [ATP] | 4 μM |
| $K_M$ Gastrin/p(EY) | 3.8 μM |
| [gastrin] | 1 μM |
| [enzyme] | 1 nM |

$K_M$ ATP, $K_M$ gastrin for various enzymes were determined by HTRF/$^{33}$P labeling and HTRF methods.

c-Met Cell-based Autophosphorylation Assay

Human PC3 and mouse CT26 cells are available obtained from ATCC. The cells were cultured in a growth medium containing RPMI 1640, penicillin/streptomycin/glutamine (1×) and 5% FBS. 2×10$^4$ cells in medium were plated per well in a 96 well plate and incubated at 37° C. overnight. The cells were serum-starved by replacing the growth media with basic medium (DMEM low glucose+0.1 BSA, 120 μL per well) at 37° C. for 16 h. Compounds (either 1 mM and 0.2 mM) in 100% DMSO were serially diluted (1:3) 3333 fold on a 96 well plate, diluting 1:3 with DMSO from column 1 to 11 (columns 6 and 12 receive no compound). Compound samples (2.4 μL per well) were diluted with basic medium (240 μL) in a 96 well plate. The cells were washed once with basic medium (GIBCO, DMEM 11885-076) then compound solution was added (100 μL). The cells were incubated at 37° C. for 1 h. A (2 mg/mL) solution of CHO-HGF (7.5 μL) was diluted with 30 mL basic medium to provide a final concentration of 500 ng/mL. This HGF-containing media (120 μL) was transferred to a 96 well plate. Compounds (1.2 μL) was added to the HGF-containing media and mixed well. The mixture of media/HGF/compound (100 μL) was added to the cells (final HGF concentration ~250 ng/mL) then incubated at 37° C. for 10 min. A cell lysate buffer (20 mL) was prepared containing 1% Triton X-100, 50 mM Tris pH 8.0, 100 mM NaCl, Protease inhibitor (Sigma, #P-8340) 200 mL, Roche Protease inhibitor (Complete, #1-697-498) 2 tablets, Phosphatase Inhibitor II (Sigma, #P-5726) 200 mL, and a sodium vanadate solution (containing 900 μL PBS, 100 μL 300 mM NaVO$_3$, 6 μL H$_2$O$_2$ (30% stock) and stirred at RT for 15 min) (90 μL). The cells were washed once with ice cold 1×PBS (GIBCO, #14190-136), then lysis buffer (60 μL) was added and the cells were incubated on ice for 20 min.

The IGEN assay was performed as follows: Dynabeads M-280 streptavidin beads were pre-incubated with biotinylated anti-human HGFR (240 μL anti-human-HGFR (R&D system, BAF527 or BAF328) @ 100 μg/mL+360 mL Beads (IGEN #10029+5.4 μL buffer—PBS/1% BSA/0.1% Tween20) by rotating for 30 min at RT. Antibody beads (25 μL) were transferred to a 96 well plate. Cell lysate solution (25 μL) was transferred added and the plate was shaken at RT for 1 h. Anti-phosphotyrosine 4G10 (Upstate 05-321) (19.7 μL antibody+6 mL 1×PBS) (12.5 μL) was added to each well, then incubated for 1 h at RT. Anti-mouse IgG ORI-Tag (ORIGEN #110087) (24 μL Antibody+6 mL buffer) (12.5 μL) was added to each well, then incubated at RT for 30 min. 1×PBS (175 μL) was added to each well and the electrochemiluminescence was read by an IGEN M8. Raw data was analyzed using a 4-parameter fit equation in XLFit.

rHu-bFGF: Stock concentration of 180 ng/μL: R&D rHu-bFGF: Added 139 μL of the appropriate vehicle above to the 25 μg vial lyophilized vial. 13.3 μL of the [180 ng/μL] stock vial and added 26.6 mL of vehicle to yield a final concentration of 3.75 μM concentration.

Nitro-cellulose disk preparation: The tip of a 20-gauge needle was cut off square and beveled with emery paper to create a punch. This tip was then used to cut out≅0.5 mm diameter disks from a nitrocellulose filter paper sheet (Gelman Sciences). Prepared disks were then placed into Eppendorf microfuge tubes containing solutions of either 0.1% BSA in PBS vehicle, 10 μM rHu-VEGF (R&D Systems, Minneapolis, Minn.), or 3.75 μM rHu-bFGF (R&D Systems, Minneapolis, Minn.) and allowed to soak for 45-60 min before use. Each nitrocellulose filter disk absorbs approximately 0.1 μL of solution.

Tumor Model

A431 cells (ATCC) are expanded in culture, harvested and injected subcutaneously into 5-8 week old female nude mice (CD1 nu/nu, Charles River Labs) (n=5-15). Subsequent administration of compound by oral gavage (10-200 mpk/dose) begins anywhere from day 0 to day 29 post tumor cell challenge and generally continues either once or twice a day for the duration of the experiment. Progression of tumor growth is followed by three dimensional caliper measurements and recorded as a function of time. Initial statistical analysis is done by repeated measures analysis of variance (RMANOVA), followed by Scheffe post hoc testing for multiple comparisons. Vehicle alone (Ora-Plus, pH 2.0) is the negative control.

Tumor Models

Human glioma tumor cells (U87MG cells, ATCC) are expanded in culture, harvested and injected subcutaneously into 5-8 week old female nude mice (CD1 nu/nu, Charles River Labs) (n=10). Subsequent administration of compound by oral gavage or by IP (10-100 mpk/dose) begins anywhere from day 0 to day 29 post tumor cell challenge and generally continues either once or twice a day for the duration of the experiment. Progression of tumor growth is followed by three dimensional caliper measurements and recorded as a function of time. Initial statistical analysis is done by repeated measures analysis of variance (RMANOVA), followed by Scheffe post hoc testing for multiple comparisons. Vehicle alone (captisol, or the like) is the negative control.

Human gastric adenocarcinoma tumor cells (MKN45 cells, ATCC) are expanded in culture, harvested and injected subcutaneously into 5-8 week old female nude mice (CD1 nu/nu, Charles River Labs) (n=10). Subsequent administration of compound by oral gavage or by IP (10-100 mpk/dose) begins anywhere from day 0 to day 29 post tumor cell challenge and generally continues either once or twice a day for the duration of the experiment. Progression of tumor growth is followed by three dimensional caliper measurements and recorded as a function of time. Initial statistical analysis is done by repeated measures analysis of variance (RMANOVA), followed by Scheffe post hoc testing for multiple comparisons. Vehicle alone (captisol, or the like) is the negative control Formulations Also embraced within this invention is a class of pharmaceutical compositions comprising the active compounds of Formula I, IA, IB, IC, ID, II, IIA, III, IV and V in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, preferably from about 1 to 500 mg. A suitable daily dose for a human or other mammal may vary widely depending on the condition of the patient and other factors, but, once again, can be determined using routine methods.

The amount of compounds which are administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, preferably between about 0.01 and about 50 mg/kg, and more preferably about 0.01 and about 30 mg/kg body weight may be appropriate. The daily dose can be administered in one to four doses per day.

For therapeutic purposes, the active compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

In the case of psoriasis and other skin conditions, it may be preferable to apply a topical preparation of compounds of this invention to the affected area two to four times a day.

Formulations suitable for topical administration include liquid or semi-liquid preparations suitable for penetration through the skin (e.g., liniments, lotions, ointments, creams, or pastes) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound, which enhances absorption or penetration of the active ingredient through the skin or other affected areas. Examples of such dermal penetration enhancers include DMSO and related analogs.

The compounds of this invention can also be administered by a transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier, which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base, which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The active ingredients are preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The foregoing is merely illustrative of the invention and is not intended to limit the invention to the disclosed compounds. Variations and changes, which are obvious to one skilled in the art are intended to be within the scope and nature of the invention, which are defined, in the appended claims.

From the foregoing description, one skilled in the art can easily ascertain the essential characteristics of this invention, and without departing from the spirit and scope thereof, can make various changes and modifications of the invention to adapt it to various usages and conditions.

No unacceptable toxological effects are expected when compounds of the present invention are administered in accordance with the present invention.

All mentioned references, patents, applications and publications, are hereby incorporated by reference in their entirety, as if here written.

We claim:

1. A compound of the following Formula I

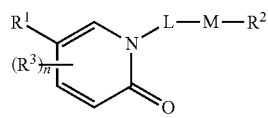

I an enantiomer, a diastereomer or a pharmaceutically acceptable salt thereof wherein n is an integer from 0 to 3;

L is $C_{1-6}$alkylene, which may be optionally independently substituted with one or more halo;

M is —O—, —$NR^6$—, —C(=O)$NR^6$—, or —$NR^6$(C=O)—;

$R^1$ is
(1) —CN, —$NR^6$—(C=O)$R^7$, —$NR^6$—(C=O)O$R^7$, —$NR^6$—(C=O)$NR^8R^9$, —(C=O)$R^7$, —S(O)$_v R^7$, —SO$_2$$NR^8R^9$, or —O$R^7$,
(2) cycloalkyl, cycloalkylalkyl, heterocyclyl, heterocyclylalkyl, aryl, arylalkyl, heteroaryl, heteroarylalkyl, $C_{2-6}$ alkenyl, or $C_{2-6}$ alkynyl any of which may be optionally independently substituted with one or more $R^{10}$ as allowed by valence;

$R^2$ is quinolinyl which may be optionally independently substituted with one or more as allowed by valence;

$R^3$ is an optional substituent independently selected at each occurrence from halo, cyano, alkyl, alkenyl, alkynyl, —(C=O)$_{0-1}$O$R^7$, —(C=O)$_{0-1}$$NR^8R^9$, —S(O)$_v R^7$, —SO$_2$$NR^8R^9$, —C=O$R^7$, —$NR^8$C=O$R^7$, —$NR^6$—C=O—$NR^8R^9$ and —$NR^8$SO$_2R^7$;

$R^6$ at each occurrence is independently
(1) H, or
(2) alkyl, alkenyl, alkynyl, cycloalkyl, heteroalkyl, heterocyclyl, aryl, heteroaryl, cycloalkylalkyl, heterocyclylalkyl, arylalkyl or heteroarylalkyl, any of which may be optionally independently substituted with one or more $R^{10}$ as allowed by valence;

$R^7$ at each occurrence is independently
(1) H, or
(2) alkyl, alkenyl, alkynyl, cycloalkyl, heteroalkyl, heterocyclyl, aryl, heteroaryl, cycloalkylalkyl, heterocyclylalkyl, arylalkyl or heteroarylalkyl any of which may be optionally independently substituted with one or more $R^{10}$ as allowed by valence;

$R^8$ and $R^9$ at each occurrence are independently
(1) H, or
(2) alkyl, cycloalkyl, heteroalkyl, heterocyclyl, aryl, heteroaryl, cycloalkylalkyl, heteroalkylalkyl, heterocyclylalkyl, arylalkyl or heteroarylalkyl any of which may be optionally independently substituted with one or more $R^{10}$ as allowed by valence;
or $R^8$ and $R^9$ together with the nitrogen atom to which they are attached may combine to form a heterocyclyl ring; and $R^{10}$ is one or more optional substituent independently selected at each occurrence as allowed by valence from halo, oxo, cyano, alkyl, haloalkyl, cycloalkyl, heterocyclyl, heteroaryl, aryl, heterocyclylalkyl, heteroarylalkyl, arylalkyl, —(CR$^4$R$^5$)$_{0-3}$O$R^7$, —(CR$^4$R$^5$)$_{0-3}$$NR^8R^9$, —(CR$^4$R$^5$)$_{0-3}$N(R$^6$)C=O$R^7$, —(CR$^4$R$^5$)$_{0-3}$N(R$^6$)(C=O)O$R^7$, —(CR$^4$R$^5$)$_{0-3}$C=O$NR^8R^9$, —(CR$^4$R$^5$)$_{0-3}$O(C=O)$NR^8R^9$, —(CR$^4$R$^5$)$_{0-3}$C=O$R^7$, —(CR$^4$R$^5$)$_{0-3}$N(R$^6$)C=O$NR^8R^9$, —(CR$^4$R$^5$)$_{0-3}$S(O)$_v R^7$, —(CR$^4$R$^5$)$_{0-3}$SO$_2$$NR^8R^9$ or —(CR$^4$R$^5$)$_{0-3}$$NR^6$SO$_2R^7$.

2. A compound of claim 1 wherein $R^1$ is
(1) —$NR^8R^9$, —$NR^6$CON$R^8R^9$, —$NR^6$COO$R^7$, —CN, or —CON$R^8R^9$; or
(2) aryl, heteroaryl, heterocyclyl, alkenyl or alkynyl any of which may be optionally independently substituted as allowed by valence with one or more $R^{10}$.

3. A compound of claim 2 wherein $R^1$ is aryl, heteroaryl or heterocyclyl any of which may be optionally independently substituted as allowed by valence with one or more $R^{10}$.

4. A compound or a pharmaceutically acceptable salt thereof selected from:
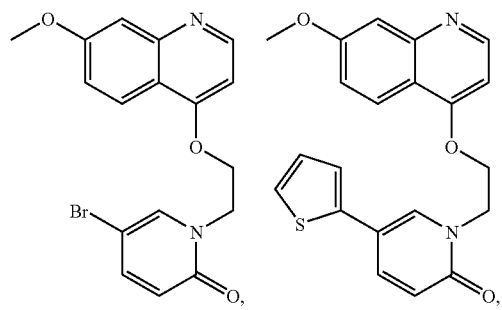
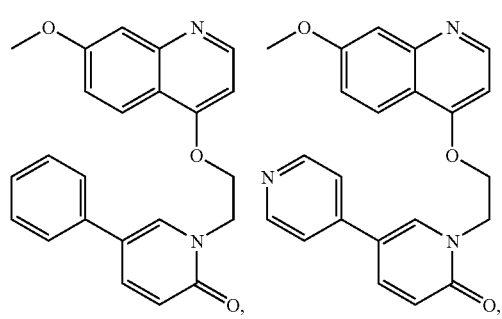
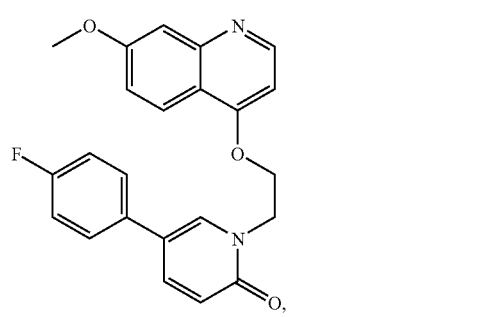
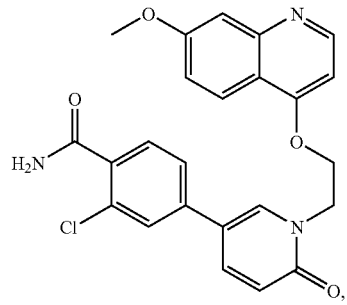
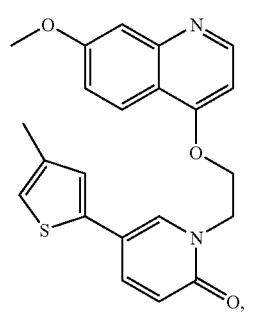
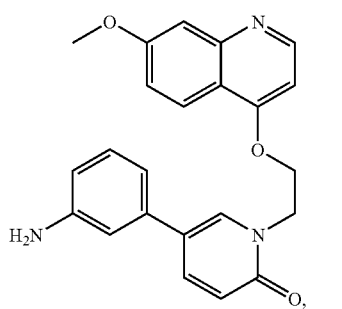
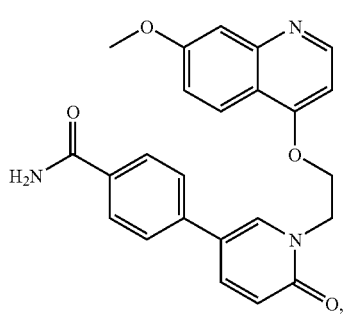
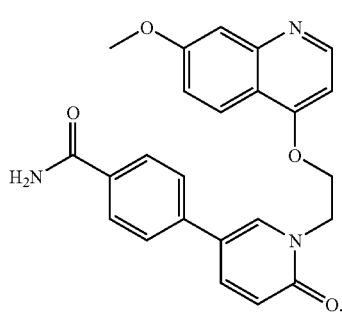
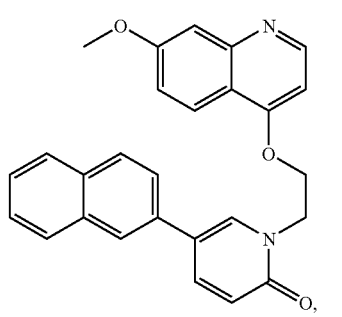
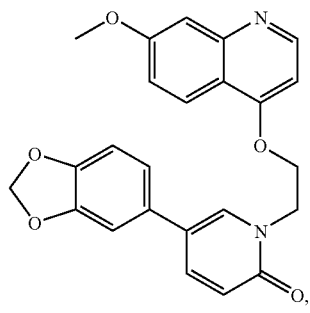

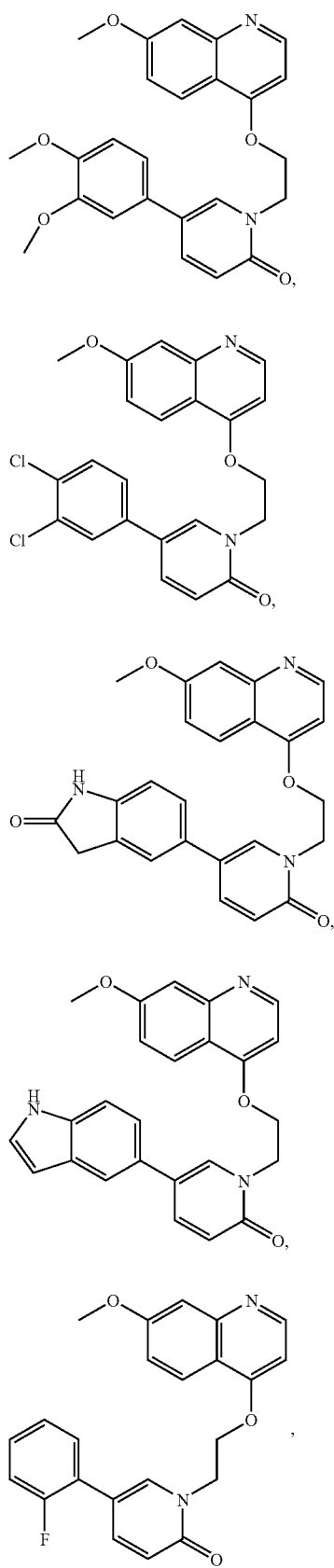
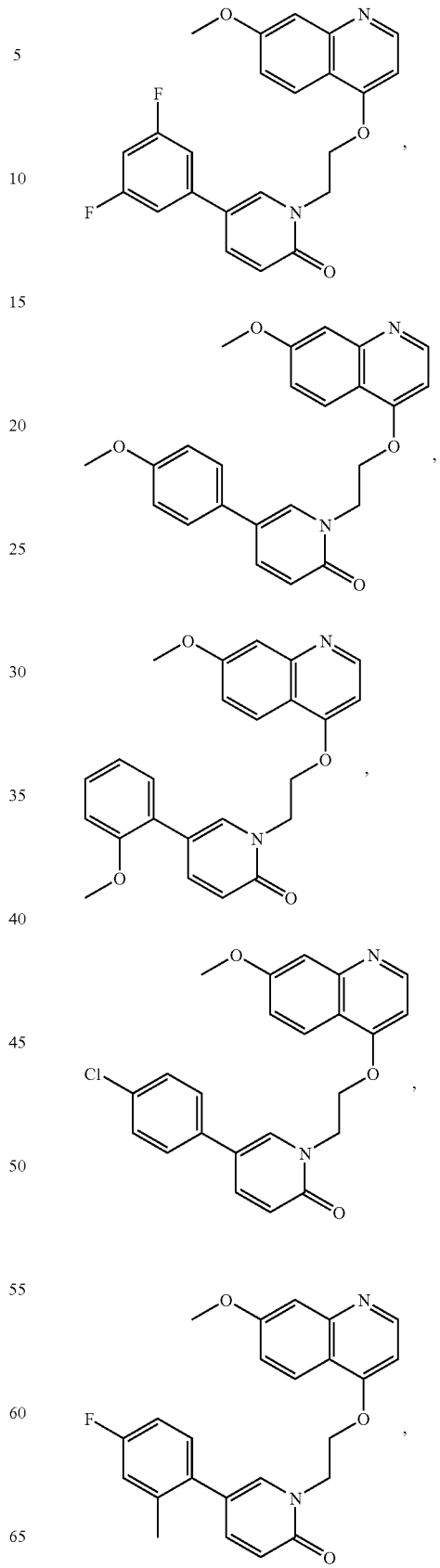

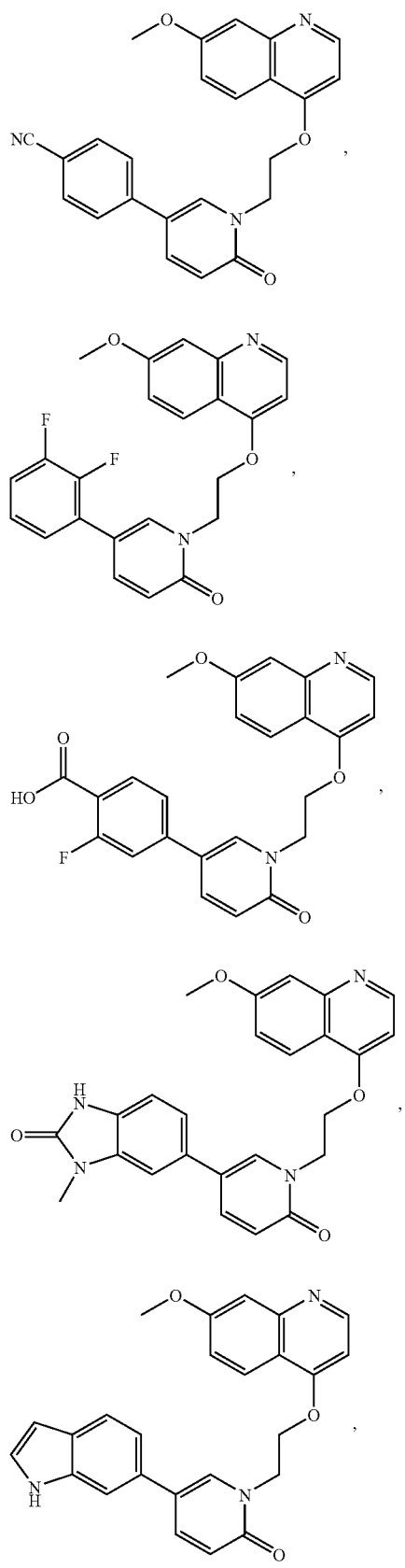
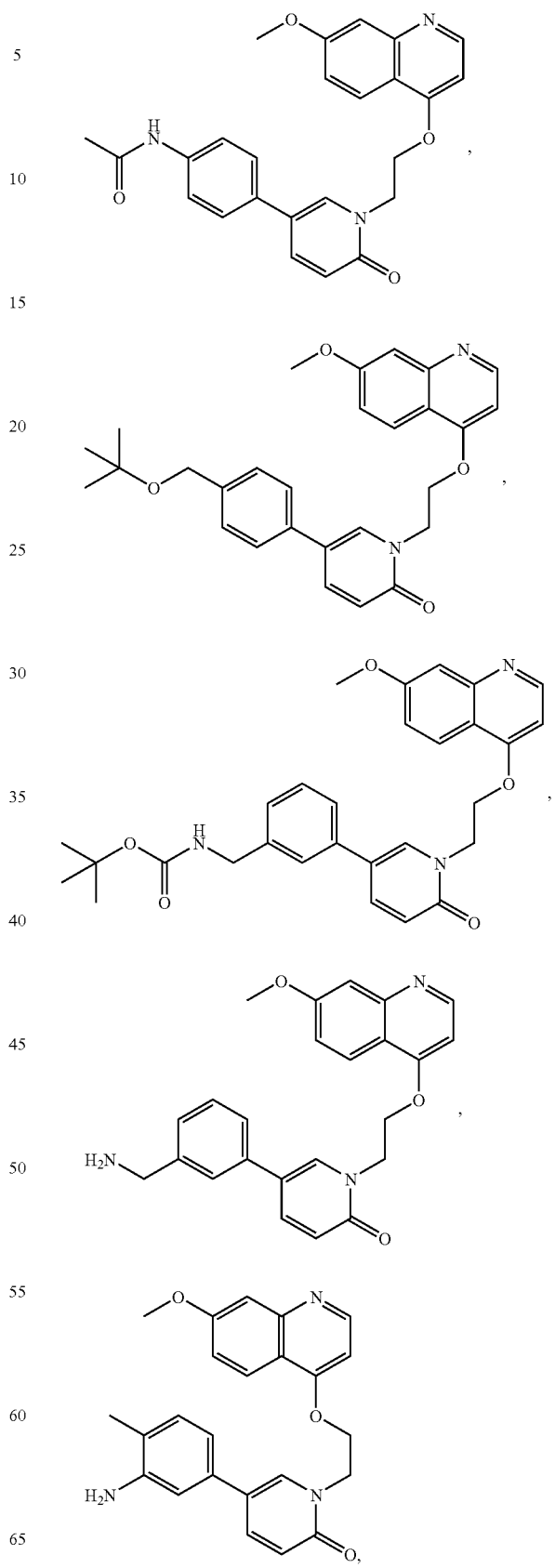

169
-continued
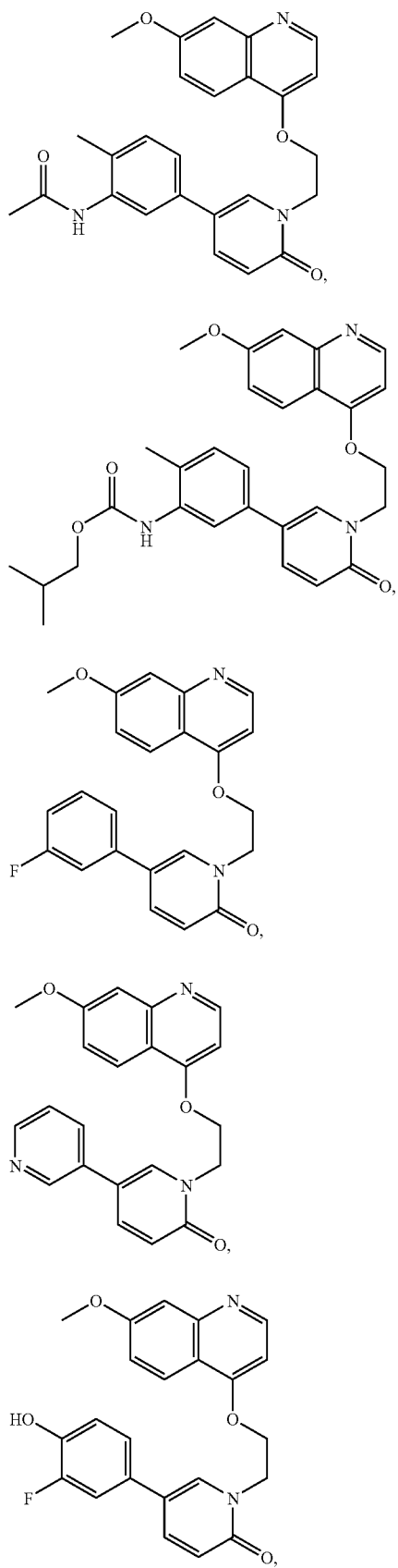
170
-continued
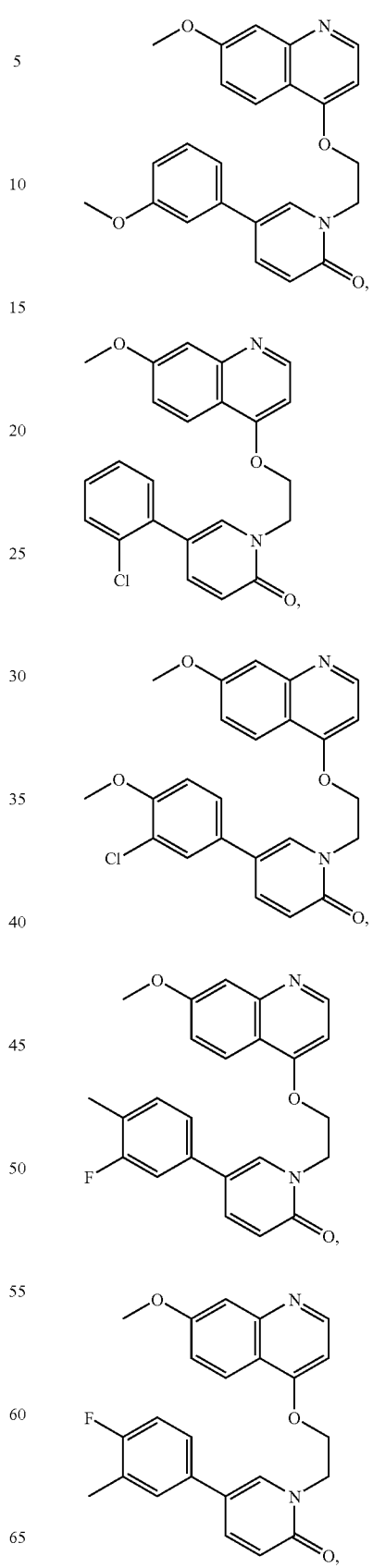

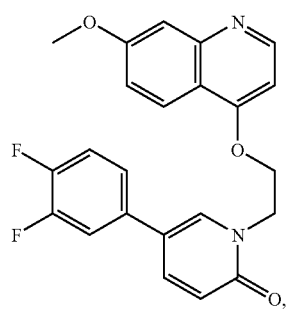
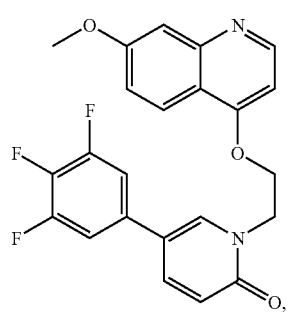
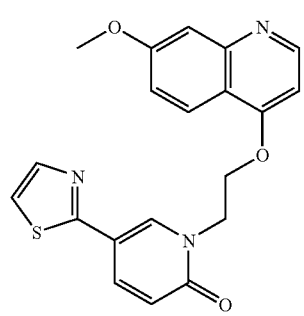
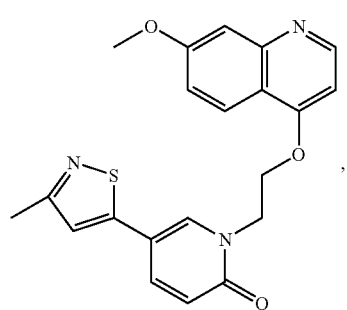
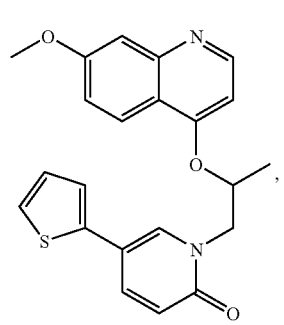
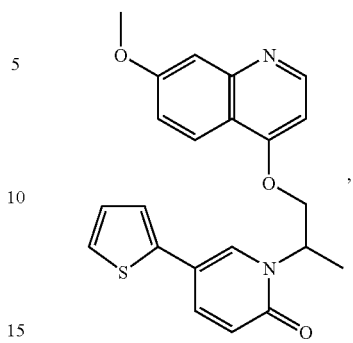
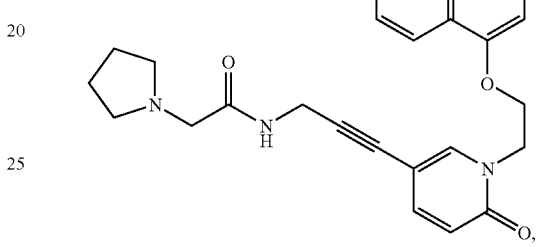
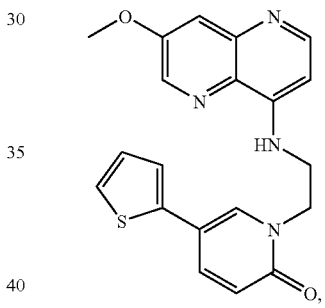
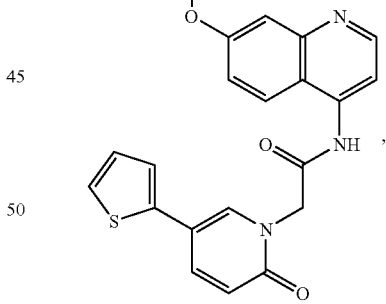
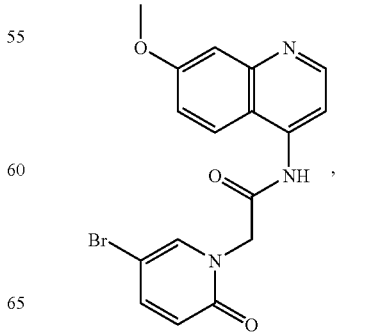

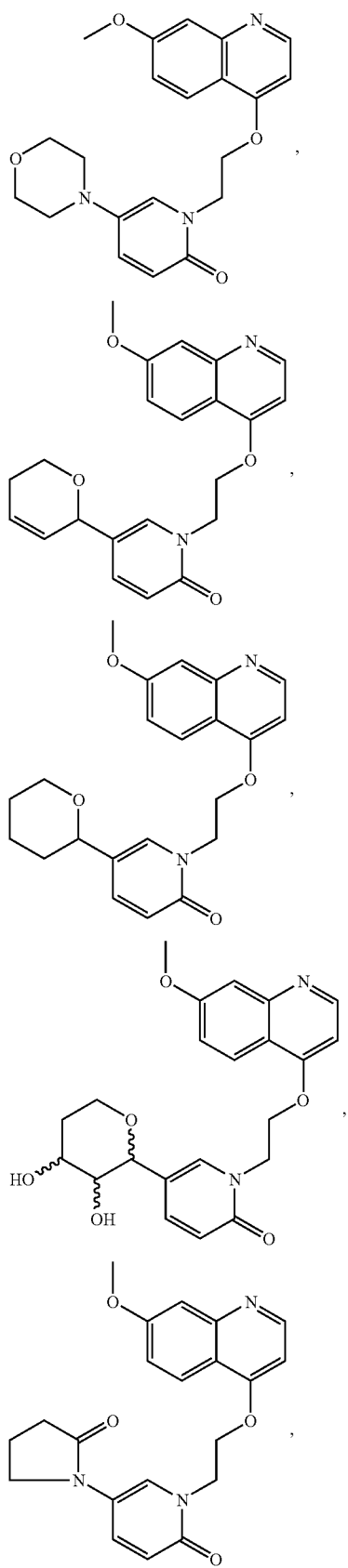
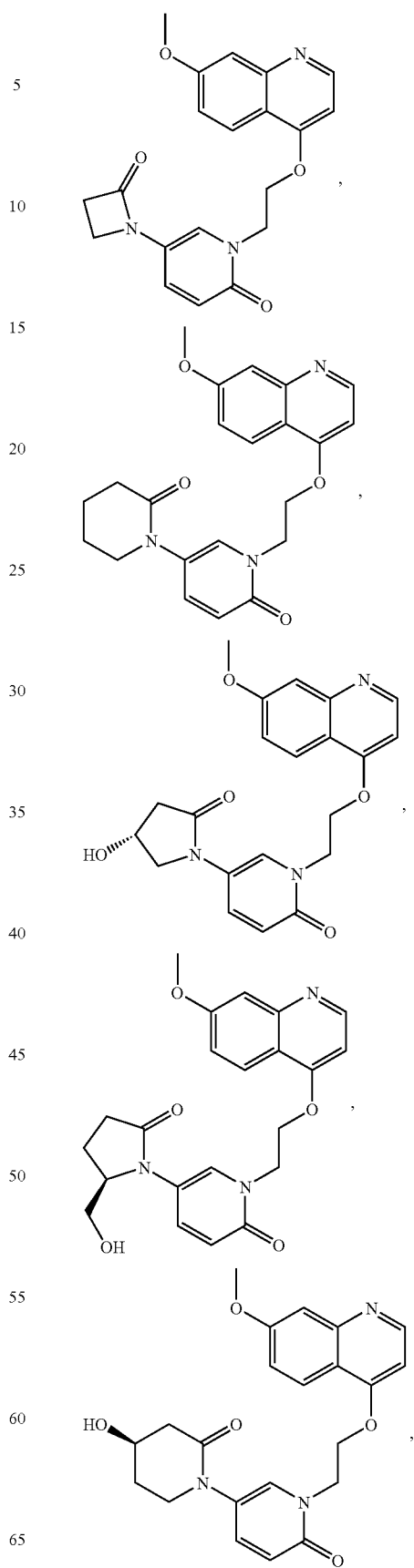

-continued

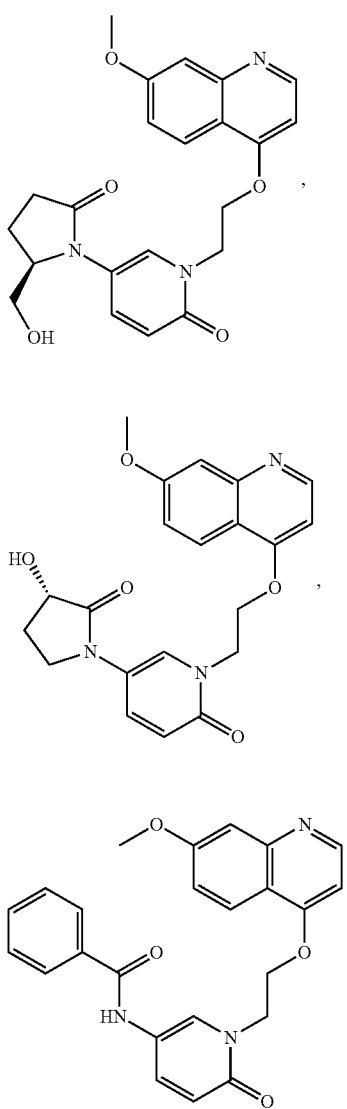

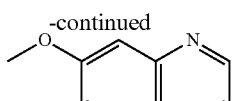

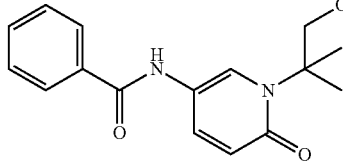

and

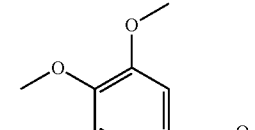

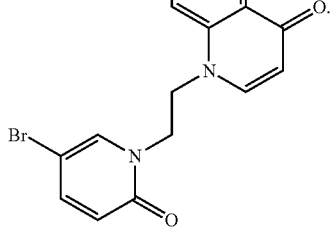

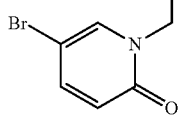

5. A pharmaceutical composition comprising a compound of any of claims 1 or 4 and a pharmaceutically-acceptable carrier.

6. A compound of claim 3 or a pharmaceutically acceptable salt thereof wherein $R^1$ is phenyl, naphthyl, naphthyridinyl, thienyl, benzothienyl, furanyl, benzofuranyl, pyridyl, pyrazinyl, pyrimidinyl, imidazolyl, triazolyl, quinoxalinyl, benzodioxolyl, benzodioxinyl dihydrobenzodioxinyl, indolinyl, indolyl, benzoimidazolyl, benzisoxazolyl, benzoisothiazolyl, benzoxazolyl, benzothiazolyl, thiazolyl, isothiazolyl, oxazolyl, isoxazolyl, morpholinyl, pyrrolidinyl, pyrazolyl, indazolyl, piperazinyl, piperadinyl, azetidinyl, pyranyl, pyridazinyl, dihydropyranyl, tetrahydropyranyl, quinolinyl, quinazolinyl, cinnolinyl, phthalazinyl, dihydroquinolinyl or isoquinolinyl any of which may be optionally independently substituted as allowed by valence with one or more $R^{10}$.

* * * * *